US009920340B2

(12) United States Patent
Roessler et al.

(10) Patent No.: US 9,920,340 B2
(45) Date of Patent: *Mar. 20, 2018

(54) ACYL-ACP THIOESTERASE GENES AND USES THEREFOR

(71) Applicant: Synthetic Genomics, Inc., La Jolla, CA (US)

(72) Inventors: Paul Gordon Roessler, San Diego, CA (US); Gena Roy, San Diego, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 27 days.

This patent is subject to a terminal disclaimer.

(21) Appl. No.: 14/608,847

(22) Filed: Jan. 29, 2015

(65) Prior Publication Data

US 2015/0147790 A1   May 28, 2015

Related U.S. Application Data

(63) Continuation of application No. 12/826,592, filed on Jun. 29, 2010, now Pat. No. 8,956,834.

(60) Provisional application No. 61/223,328, filed on Jul. 6, 2009, provisional application No. 61/221,500, filed on Jun. 29, 2009.

(51) Int. Cl.
| | |
|---|---|
| *C12N 15/55* | (2006.01) |
| *C12N 9/16* | (2006.01) |
| *C12P 7/64* | (2006.01) |
| *C12N 15/82* | (2006.01) |

(52) U.S. Cl.
CPC .............. *C12P 7/6409* (2013.01); *C12N 9/16* (2013.01); *C12N 15/8247* (2013.01); *C12P 7/6436* (2013.01); *C12P 7/6463* (2013.01); *C12Y 301/02014* (2013.01)

(58) Field of Classification Search
None
See application file for complete search history.

(56) References Cited

U.S. PATENT DOCUMENTS

| | | | |
|---|---|---|---|
| 5,298,421 A | 3/1994 | Davies et al. | |
| 5,304,481 A | 4/1994 | Davies et al. | |
| 5,344,771 A | 9/1994 | Davies et al. | |
| 5,455,167 A | 10/1995 | Voelker et al. | |
| 5,512,482 A | 4/1996 | Voelker et al. | |
| 5,530,186 A | 6/1996 | Hitz et al. | |
| 5,639,790 A | 6/1997 | Voelker et al. | |
| 5,654,495 A | 8/1997 | Voelker et al. | |
| 5,667,997 A | 9/1997 | Voelker et al. | |
| 5,723,761 A | 3/1998 | Voelker et al. | |
| 5,750,481 A | 5/1998 | Del Vecchio et al. | |
| 5,807,893 A | 9/1998 | Voelker et al. | |
| 5,850,022 A | 12/1998 | Dehesh et al. | |
| 5,910,631 A | 6/1999 | Topfer et al. | |
| 5,945,585 A | 8/1999 | Hitz et al. | |
| 5,955,329 A | 9/1999 | Yuan et al. | |
| 5,955,650 A | 9/1999 | Hitz | |
| 6,150,512 A | 11/2000 | Yuan | |
| RE37,317 E | 8/2001 | Hitz | |
| 6,331,664 B1 | 12/2001 | Rubin-Wilson et al. | |
| 6,365,802 B2 | 4/2002 | Kridl | |
| 6,380,462 B1 | 4/2002 | Kridl | |
| 7,504,563 B1 | 3/2009 | Kridl | |
| 7,622,570 B2 | 11/2009 | Oswald et al. | |
| 2006/0117414 A1 | 6/2006 | Qiu et al. | |
| 2007/0087420 A1 | 4/2007 | MaCool et al. | |
| 2009/0004715 A1 | 1/2009 | Trimbur et al. | |
| 2009/0061493 A1 | 3/2009 | Trimbur et al. | |
| 2009/0298143 A1 | 12/2009 | Roessler et al. | |

FOREIGN PATENT DOCUMENTS

| | | |
|---|---|---|
| WO | WO 91/16421 | 10/1991 |
| WO | WO 92/20236 | 11/1992 |
| WO | WO 94/10288 | 5/1994 |
| WO | WO 2007/087420 | 8/2007 |
| WO | WO2007/136762 | 11/2007 |
| WO | WO 2008/151149 | 12/2008 |
| WO | WO 2009/076559 | 6/2009 |
| WO | WO 2010/033921 | 3/2010 |
| WO | WO 2011/008565 | 1/2011 |

OTHER PUBLICATIONS

Jones, A. et al: "*Palmitoyl-Acyl Carrier Protein (ACP) Thioesterase and the Evolutionary Origin of Plant Acyl-ACP Thioesterases;*"The Plant Cell, Mar. 1995, pp. 359-371, vol. 7.
Mayer, K.M. et al: "*Identification of Amino Acid Residues Involved in Substrate Specificity of Plant Acyl-ACP Thioesterases Using a Bioinformatics-Guided Approach;*" BMC Plant Biology, Jan. 3, 2007, 11 pgs., vol. 7, No. 1.
Mayer, K.M. et al: "*A Structural Model of the Plant Acyl-Acyl Carrier Protein Thioesterase FatB Comprises Two Helix/4-Stranded Sheet Domains, the N-Terminal Domain Containing Residues that Affect Specificity and the C-Terminal Domain Containing Catalytic Residues;*" J. Biological Chemistry, Feb. 4, 2005, pp. 3621-3627, vol. 280, No. 5.
Dehesh et al.; "Two Novel Thioesterases Are Key Determinants of the Bimodal Distribution of Acyl Chain Length of *Cuphea palustris* Seed Oil", K. Plant Physiology (1996) 110:203-210.
Filichkin, S. et al., "New FATB thioesterases from a high-laurate Cuphea species: Functional and complementation analyses", European Journal of Lipid Science and Technology (2006) 108:979-990.
Grellet et al., "*Arabidopsis thaliana* systematic cDNA sequencing reveals a gene . . . thioesterase", Plant Physiol. Biochem. (1993) 31:599-602.
Guo et al., "Protein tolerance to random amino acid change", PNAS (2004) 101(25):9205-9210.

(Continued)

*Primary Examiner* — Rebecca E Prouty
(74) *Attorney, Agent, or Firm* — DLA Piper LLP (US)

(57) ABSTRACT

The present invention provides novel genes encoding Class II acyl-ACP thioesterases and variants thereof that are active on C8, C10, C12, C14, C16, and C18 acyl-ACP substrates. The thioesterases can be introduced into transgenic organisms, including microorganisms and photosynthetic organisms, for producing fatty acids and fatty acid products.

20 Claims, 23 Drawing Sheets

(56) References Cited

OTHER PUBLICATIONS

Pidugu et al., "Analysis of proteins with the 'hot dog' fold: Prediction of function and identificationof catalytic residues of hypothetical proteins", BMC Structural Biology (2009) 9:37.
Slabaugh et al., "Condensing enzymes from Cuphea wrightii associated with medium chain fatty acid biosynthesis", *The Plant Journal* (1998) 13:611-620.
Voelker and Davies, "Alteration of the Specificity and Regulation of Fatty Acid of *E. coil* by Expression of a Plant Medium-Chain Acyl-Acyl Carrier Protein Thhioesterase", *J. of Bacteriology* (1994) 176(23):7320-7327.
Witkowski et al., "Conversion of a β-Ketoacyl Synthase to a Malonyl .with Glutamine", Biochemistry (1999) 38: 11643-11650.
Yuan et al., "Modification of the substrate specificity of an acyl-acyl carrier protein thioesterase by protein engineering", *Proc. Natl. Acad. Sci. USA* (1995) 92:10639-10643.
Zhou et al., "Global analysis of gene transcription regulation in prokaryotes", *Cell. MoL Life Sci.* (2006) 63:2260-2290.
Binderup et al., "Slow-Binding Inhibition of Branching Enzyme by the Psuedooligosaccharide Bay e4609", Arch. Bloch. Biophys. (2000) 374: 73-78.
Branden et al., Introduction to Protein Structure, (1991) Garland Publishing Inc., New York, p. 247.
Cho et al., "Defective Export of a Periplasmic Enzyme Disrupts Regulation of Fatty Acid Synthesis", J. Biol. Chem. (1995) 270(9):4216-4219.
Dehesh et al., "Production of high levels of 8:0 and 10:0 fatty acids in transgenic canola by overexpression of Ch FatB2, a thioesterase cDNA from Cuphea hookeriana", K. The Plant Journal (1996) 9(2):67-172.
Dehesh et al., "Two Novel Thioesterases Are Key Determinants of the Bimodal Distribution of Acyl Chain Length of Cuphea palustris Seed Oil", K. Plant Physiology (1996) 110:203-210.
Dehesh et al., "KAS IV: a 3-ketoacyl-ACP synthase from *Cuphea sp.* Is a medium chain specific condensing enzyme", The Plant Journal (1998) 15:383-390.
Dillon and Bateman, "The Hotdog fold: wrapping up a superfamily of thioesterases and dehydratases", BMC Bioinformatics (2004) 5:109.
Dormann et al., "Characterization of two acyl-acyl carrier protein thioesterases from developing Cuphea seeds specific for medium-chain- and oleoyl-acyl carrier protein", Planta (1993) 189:425-432.
Dormann, P. et al., Cloning and Expression in *Escherichia coli* of a Novel Thioesterase from *Arabidopsis thaliana* Specific for Long-Chain Acyl-Acyl Carrier ProteinsP. et al., Archives of Biochemistry and Biophysics (1995) 316(1):612-618.
Filichkin, S. et al., "New FATB thioesterases from a high-laurate Cuphea species: Funtional and complementation analyses", European Journal of Lipid Science and Technoloy (2006) 108:979-990.

Grellet et al., "Arabidopsis thaliana systematic cDNA sequencing reveals a gene . . . thinesterase" Plant Physiol. Biochem (1993) 31:599-602.
Hawkins and Kridl, "Characterization of acyl-ACP thioesterases of mangosteen (Garcinia mangostana) seed and high levels of stearate production in transgenic canola", The Plant Journal (1998) 13(6):743-752.
Guo et al., "Protein tolerance to random amino acid change", PNAS (2004) 101(25):9205- 9210.
Ng and Henikoff, "SIFT: predicting amino acid changes that affect protein function", Nucleic Acids Research (2003) 31(13):3812-3814.
Pidugu et al., "Analysis of proteins with 'hot dog' fold: Prediction of function and identification of catalytic residues of hypothetical proteins", BMC Structural Biology (2009) 9:37.
Phippen et al., "Total Seed Oil and Fatty Acid Methyl Ester Contents of Cuphea accessions", *Industrial Crops and Products* (2006) 24:52-59.
Pierce et al., "Uptake and utilizationof inorganic carbon by cyanobacteria", Photosynthesis Research (1988) 16:141-154.
Salas and Ohlrogge, "Characterization of substrate specificity of plant FatA and FatB acyl-ACP thioesterases", Archives of Biochemistry and Biophysics (2002) 403:25-34.
Seffernick et al., "Melamine Deaminase and Atrazine Chlorohydrolase: 98 Percent Identical but Functionally Different", *J. Bacteriol.* (2001) 183(8): 2405-2410.
Slabaugh et al., "Condensing enzymes from *Cuphea wrightii* associated with medium fatty acid biosynthesis", The Plant Journal (1998) 13:611-620.
Voelker et al., "Fatty Acid Biosynthesis Redirected to Medium Chains in Transgenic Oilseed Plants", Science (1992) 257:72-74.
Voelker et al., "Plant Acyl-Acp Thioesterases: Chain-Length Determining Enzymes in Plant Fatty Acid Biosynthesis", *Science* (1992) 257:72-74.
Voelker and Davies, "Alteration of the Specificity and Regulation of Fatty Acid Synthesis of *E. coli* by Expression of a Plant Medium-Chain Acyl-Acyl Carrier Protein Thhioesterase", *J. of Bacteriology* (1994) 176(23):7320-7327.
Voelker, T. et al., "Broad-Range and Binary-Range Acyl-Acyl-Carrier-Protein . . . Production in Seeds", Plant Physiology (1997) 114: 669-677.
Witkowski et al., "Conversion of a β-Ketoacyl Synthase to a Malonyl with Glutamine", Biochemistry (1999) 38: 11643-11650.
Yuan et al., "Modification of the substrate specificity of an acyl-acyl carrier protein hioesterase by protein engineering", Proc. Natl. Acad. Sci. USA (1995) 92:10639-10643.
Zhou et all., "Global analysis of gene transcription regulation in prokaryotes", *Cell. MoL Life Sci.* (2006) 63:2260-2290.
Leonard et al., *Cuphea wrightil* thioesterases have unexpected broad specificities on saturated fatty acrds, Plant Molecular Biology 34:669-679, 1997.

(1)      VP SPGASPKPGK LGNWPSSLSP SLKPKSIPNG GFQVKANASA 1
(43)   HPKANGSAVT LKSGSLNTQE DTLSSSPPPR AFFNQLPDWS MLLTAITTVF
(1)     MANGSAVT LKSGSLNTQE DTLSSSPPPR AFFNQLPDWS MLLTAITTVF

(93)   VAPEKRWTMF DRKSKRPNML MDSFGLERVV QDGLVFRQSF SIRSYEICAD
(49)   VAPEKRWTMF DRKSKRPNML MDSFGLERVV QDGLVFRQSF SIRSYEICAD (143)  RTASLETVMN HVQETSLNQC KSIGLLDDGF GRSPEMCKRD LIWVVTRMKI
(99)   RTASLETVMN HVQETSLNQC KSIGLLDDGF GRSPEMCKRD LIWVVTRMKI 174
(193)  MVNRYPTWGD TIEVSTWLSQ SGKIGMGRDW LISDCSTGEI LVRATSVYAM
(149)  MVNRYPTWGD TIEVSTWLSQ SGKIGMGRDW LISDCSTGEI LVRATSVYAM (243)  MNQKTRRFSK LPHEVRQEFA PHFLDSPPAI EDNDGKLQKF DVKTGDSIRK
(199)  MNQKTRRFSK LPHEVRQEFA PHFLDSPPAI EDNDGKLQKF DVKTGDSIRK (293)  GLTPGWYDLD VNQHVSNVKY IGWILESMPT EVLETQELCS LTLEYRRECG
(249)  GLTPGWYDLD VNQHVSNVKY IGWILESMPT EVLETQELCS LTLEYRRECG (343)  RDSVLESVTS MDPSKVGDRF QYRHLLRLED GADIMKGRTE WRPKNAGTNG
(249)  RDSVLESVTS MDPSKVGDRF QYRHLLRLED GADIMKGRTE WRPKNAGTNG (393)  VISTGKT  (SEQ ID NO:22)
(349)  VISTGKT  (SEQ ID NO:29)

FIG. 1

| Strain # | CalFatB2 background | AA sub | C8:0 | C10:0 | C12:0 | C14:0 | C16:0 | C16:1 | C18:0 | C18:1 | Total FFAs ug/mL |
|---|---|---|---|---|---|---|---|---|---|---|---|
| 1 | CalFatB2 wt M174X | A | 13.0 | 1.0 | 0.0 | 1.2 | 0.0 | 3.1 | 0.0 | 0.0 | 18.2 |
| 2 | CalFatB2 wt M174X | A | 13.1 | 0.0 | 0.0 | 1.0 | 0.7 | 2.9 | 0.0 | 0.0 | 17.6 |
| 3 | CalFatB2 wt M174X | N | 0.0 | 0.0 | 0.0 | 0.0 | 0.0 | 2.2 | 0.0 | 0.0 | 2.2 |
| 4 | CalFatB2 wt M174X | N | 0.0 | 0.0 | 0.0 | 0.0 | 1.1 | 3.2 | 0.0 | 0.0 | 4.2 |
| 5 | CalFatB2 wt M174X | D | 0.0 | 0.0 | 0.0 | 0.7 | 0.6 | 2.9 | 0.0 | 0.0 | 4.2 |
| 6 | CalFatB2 wt M174X | D | 0.0 | 0.0 | 0.0 | 0.0 | 0.0 | 2.8 | 0.0 | 0.0 | 2.8 |
| 7 | CalFatB2 wt M174X | Q | 1.2 | 0.0 | 0.0 | 0.9 | 1.0 | 2.4 | 0.0 | 0.0 | 5.4 |
| 8 | CalFatB2 wt M174X | Q | 1.0 | 0.0 | 0.0 | 0.8 | 0.8 | 2.4 | 0.0 | 0.0 | 5.1 |
| 9 | CalFatB2 wt M174X | G | 0.0 | 0.0 | 0.0 | 0.0 | 0.0 | 7.0 | 0.0 | 0.0 | 7.0 |
| 10 | CalFatB2 wt M174X | G | 0.0 | 0.0 | 0.0 | 0.0 | 1.7 | 3.6 | 0.0 | 0.0 | 5.3 |
| 11 | CalFatB2 wt M174X | L | 122.2 | 5.1 | 0.0 | 1.2 | 0.5 | 2.3 | 0.0 | 0.0 | 131.4 |
| 12 | CalFatB2 wt M174X | L | 152.4 | 4.8 | 0.0 | 1.4 | 0.0 | 2.8 | 0.0 | 0.0 | 161.4 |
| 13 | CalFatB2 wt M174X | S | 0.9 | 0.0 | 0.0 | 0.0 | 0.0 | 3.7 | 0.0 | 0.0 | 4.6 |
| 14 | CalFatB2 wt M174X | S | 0.6 | 0.0 | 0.0 | 0.5 | 1.1 | 2.0 | 0.0 | 0.0 | 4.1 |
| 15 | CalFatB2 wt M174X | F | 130.1 | 6.7 | 0.0 | 1.5 | 0.0 | 2.9 | 0.0 | 0.0 | 141.3 |
| 16 | CalFatB2 wt M174X | F | 107.9 | 5.8 | 0.0 | 1.3 | 0.0 | 2.9 | 0.0 | 0.0 | 117.8 |
| 17 | CalFatB2 wt M174X | T | 15.1 | 1.0 | 0.0 | 0.9 | 1.1 | 2.5 | 0.0 | 0.0 | 20.6 |
| 18 | CalFatB2 wt M174X | T | 14.1 | 1.0 | 0.0 | 0.9 | 0.0 | 2.5 | 0.0 | 0.0 | 18.4 |

FIG. 2A

| Strain # | Ca1FatB2 background | AA sub | C8:0 | C10:0 | C12:0 | C14:0 | C16:0 | C16:1 | C18:0 | C18:1 | Total FFAs ug/mL |
|---|---|---|---|---|---|---|---|---|---|---|---|
| 19 | Ca1FatB2 wt M174X | W | 1.1 | 0.0 | 0.0 | 1.1 | 1.1 | 2.5 | 0.0 | 0.0 | 5.8 |
| 20 | Ca1FatB2 wt M174X | W | 1.3 | 0.0 | 0.0 | 0.7 | 1.1 | 2.7 | 0.0 | 0.0 | 5.8 |
| 21 | Ca1FatB2 wt M174X | Y | 1.9 | 0.0 | 0.0 | 1.1 | 0.7 | 2.7 | 0.0 | 0.0 | 6.3 |
| 22 | Ca1FatB2 wt M174X | Y | 2.1 | 0.0 | 0.0 | 0.7 | 0.9 | 2.9 | 0.0 | 0.0 | 6.6 |
| 23 | Ca1FatB2 wt M174X | V | 146.9 | 6.8 | 0.0 | 1.0 | 0.0 | 2.7 | 0.0 | 0.0 | 157.4 |
| 24 | Ca1FatB2 wt M174X | V | 179.6 | 6.7 | 0.0 | 1.3 | 0.0 | 2.8 | 0.0 | 0.0 | 190.4 |
| 25 | Ca1FatB2 wt M174X | E | 0.7 | 0.0 | 0.0 | 0.0 | 0.0 | 1.9 | 0.0 | 0.0 | 2.6 |
| 26 | Ca1FatB2 wt M174X | E | 0.6 | 0.0 | 0.0 | 0.0 | 0.0 | 2.3 | 0.0 | 0.0 | 2.9 |
| 27 | Ca1FatB2 wt M174X | C | 134.2 | 3.8 | 0.0 | 1.5 | 0.0 | 2.1 | 0.0 | 0.0 | 141.6 |
| 28 | Ca1FatB2 wt M174X | C | 142.9 | 4.1 | 0.0 | 1.1 | 0.0 | 1.7 | 0.0 | 0.0 | 149.7 |
| 29 | Ca1FatB2 wt M174X | H | 2.0 | 0.9 | 0.0 | 1.4 | 0.9 | 1.7 | 0.0 | 0.0 | 6.9 |
| 30 | Ca1FatB2 wt M174X | H | 1.5 | 0.0 | 0.0 | 1.3 | 0.8 | 1.6 | 0.0 | 0.0 | 5.2 |
| 31 | Ca1FatB2 wt M174X | K | 0.5 | 0.0 | 0.0 | 0.0 | 1.0 | 1.7 | 0.0 | 0.0 | 3.1 |
| 32 | Ca1FatB2 wt M174X | K | 0.5 | 0.0 | 0.0 | 0.6 | 0.7 | 2.0 | 0.0 | 0.0 | 3.8 |
| 33 | Ca1FatB2 wt M174X | M | 144.3 | 4.6 | 0.0 | 1.3 | 0.0 | 1.0 | 0.0 | 0.0 | 151.2 |
| 34 | Ca1FatB2 wt M174X | M | 161.0 | 4.8 | 0.0 | 0.0 | 0.0 | 1.7 | 0.0 | 0.0 | 167.5 |
| 35 | Ca1FatB2 wt M174X | P | 4.2 | 0.9 | 0.0 | 1.1 | 0.0 | 4.2 | 0.0 | 0.0 | 10.4 |
| 36 | Ca1FatB2 wt M174X | P | 4.1 | 0.8 | 0.0 | 1.9 | 0.8 | 1.5 | 0.0 | 0.0 | 9.2 |
| 37 | Ca1FatB2 wt M174X | – | 276.2 | 8.7 | 0.0 | 0.8 | 0.0 | 0.0 | 0.0 | 0.0 | 285.6 |
| 38 | Ca1FatB2 wt M174X | – | 243.4 | 8.2 | 0.0 | 1.2 | 0.0 | 0.0 | 0.0 | 0.0 | 252.8 |

FIG. 2B

| | Ca1FatB2 background | AA sub | C8:0 | C10:0 | C12:0 | C14:0 | C16:0 | C16:1 | C18:0 | C18:1 | Total FFAs ug/mL |
|---|---|---|---|---|---|---|---|---|---|---|---|
| 39 | Ca1FatB2 L103I, S184N, M174X | A | 51.7 | 1.6 | 0.0 | 1.1 | 0.0 | 3.4 | 0.0 | 0.0 | 57.8 |
| 40 | Ca1FatB2 L103I, S184N, M174X | A | 1.1 | 0.5 | 0.0 | 0.0 | 1.1 | 2.1 | 0.0 | 0.0 | 4.8 |
| 41 | Ca1FatB2 L103I, S184N, M174X | R | 19.3 | 1.1 | 0.0 | 0.7 | 0.0 | 2.1 | 0.0 | 0.0 | 23.2 |
| 42 | Ca1FatB2 L103I, S184N, M174X | R | 0.0 | 0.0 | 0.0 | 0.0 | 0.6 | 3.5 | 0.0 | 0.0 | 4.1 |
| 43 | Ca1FatB2 L103I, S184N, M174X | Q | 4.7 | 0.0 | 0.0 | 0.0 | 0.0 | 3.9 | 0.0 | 0.0 | 8.6 |
| 44 | Ca1FatB2 L103I, S184N, M174X | Q | 4.3 | 0.9 | 0.0 | 1.0 | 1.0 | 4.3 | 0.0 | 0.0 | 11.4 |
| 45 | Ca1FatB2 L103I, S184N, M174X | Q | 0.0 | 0.0 | 0.0 | 0.0 | 0.0 | 3.7 | 0.0 | 0.0 | 3.7 |
| 46 | Ca1FatB2 L103I, S184N, M174X | G | 0.0 | 0.0 | 0.0 | 0.4 | 0.6 | 3.7 | 0.0 | 0.0 | 4.8 |
| 47 | Ca1FatB2 L103I, S184N, M174X | G | 63.0 | 1.8 | 0.0 | 0.9 | 0.0 | 2.8 | 0.0 | 0.0 | 68.5 |
| 48 | Ca1FatB2 L103I, S184N, M174X | T | 56.4 | 0.0 | 0.0 | 0.9 | 0.0 | 2.0 | 0.0 | 0.0 | 59.3 |
| 49 | Ca1FatB2 L103I, S184N, M174X | T | 240.5 | 5.0 | 0.0 | 1.0 | 0.0 | 2.0 | 0.0 | 0.0 | 248.6 |
| 50 | Ca1FatB2 L103I, S184N, M174X | V | 216.0 | 4.6 | 0.0 | 0.7 | 0.0 | 1.2 | 0.0 | 0.0 | 222.5 |
| 51 | Ca1FatB2 L103I, S184N, M174X | V | 0.6 | 0.0 | 0.0 | 0.0 | 0.0 | 1.5 | 0.0 | 0.0 | 2.1 |
| 52 | Ca1FatB2 L103I, S184N, M174X | N | 0.6 | 0.0 | 0.0 | 0.0 | 0.0 | 1.2 | 0.0 | 0.0 | 1.8 |
| 53 | Ca1FatB2 L103I, S184N, M174X | N | 0.0 | 0.0 | 0.0 | 0.5 | 0.0 | 1.7 | 0.0 | 0.0 | 2.2 |
| 54 | Ca1FatB2 L103I, S184N, M174X | D | 0.0 | 0.0 | 0.0 | 0.0 | 0.0 | 2.1 | 0.0 | 0.0 | 2.1 |
| 55 | Ca1FatB2 L103I, S184N, M174X | D | 0.0 | 0.0 | 0.0 | 0.0 | 0.0 | 4.8 | 0.0 | 0.0 | 4.8 |
| 56 | Ca1FatB2 L103I, S184N, M174X | E | 0.0 | 0.0 | 0.0 | 0.0 | 0.0 | 1.3 | 0.0 | 0.0 | 1.3 |
| 57 | Ca1FatB2 L103I, S184N, M174X | F | 3.0 | 0.0 | 0.0 | 1.3 | 1.0 | 1.3 | 0.0 | 0.0 | 6.6 |
| 58 | Ca1FatB2 L103I, S184N, M174X | F | 3.1 | 0.8 | 0.0 | 1.5 | 0.9 | 2.6 | 0.0 | 0.0 | 8.9 |

FIG. 2C

| Strain # | Ca1FatB2 background | AA sub | C8:0 | C10:0 | C12:0 | C14:0 | C16:0 | C16:1 | C18:0 | C18:1 | Total FFAs ug/mL |
|---|---|---|---|---|---|---|---|---|---|---|---|
| 59 | Ca1FatB2 L103I, S184N, M174X | L | 174.0 | 3.9 | 0.0 | 1.3 | 0.0 | 1.8 | 0.0 | 0.0 | 181.1 |
| 60 | Ca1FatB2 L103I, S184N, M174X | L | 171.3 | 4.0 | 0.0 | 1.1 | 0.0 | 1.6 | 0.0 | 0.0 | 178.0 |
| 61 | Ca1FatB2 L103I, S184N, M174X | K | 2.4 | 0.0 | 0.0 | 0.0 | 0.0 | 1.3 | 0.0 | 0.0 | 3.6 |
| 62 | Ca1FatB2 L103I, S184N, M174X | K | 0.8 | 0.0 | 0.0 | 0.5 | 0.0 | 1.4 | 0.0 | 0.0 | 2.8 |
| 63 | Ca1FatB2 L103I, S184N, M174X | F | 198.5 | 6.6 | 0.0 | 1.1 | 0.0 | 2.6 | 0.0 | 0.0 | 208.9 |
| 64 | Ca1FatB2 L103I, S184N, M174X | F | 236.7 | 8.4 | 0.0 | 3.1 | 2.1 | 3.5 | 2.4 | 2.3 | 258.5 |
| 65 | Ca1FatB2 L103I, S184N, M174X | S | 2.9 | 0.9 | 0.0 | 0.8 | 0.0 | 5.9 | 0.0 | 0.0 | 10.5 |
| 66 | Ca1FatB2 L103I, S184N, M174X | S | 3.8 | 0.7 | 0.0 | 0.0 | 0.0 | 0.0 | 0.0 | 0.0 | 4.5 |
| 67 | Ca1FatB2 L103I, S184N, M174X | W | 4.2 | 0.0 | 0.0 | 0.0 | 0.0 | 0.0 | 0.0 | 0.0 | 4.2 |
| 68 | Ca1FatB2 L103I, S184N, M174X | W | 4.0 | 0.0 | 0.0 | 0.0 | 0.0 | 0.0 | 0.0 | 0.0 | 4.0 |
| 69 | Ca1FatB2 L103I, S184N, M174X | Y | 13.6 | 1.0 | 0.0 | 1.2 | 0.0 | 1.3 | 0.0 | 0.0 | 17.1 |
| 70 | Ca1FatB2 L103I, S184N, M174X | Y | 13.6 | 0.9 | 0.0 | 0.9 | 0.0 | 1.5 | 0.0 | 0.0 | 16.9 |
| 71 | Ca1FatB2 L103I, S184N, M174X | I | 314.9 | 6.7 | 0.0 | 1.0 | 0.0 | 0.0 | 0.0 | 0.0 | 322.7 |
| 72 | Ca1FatB2 L103I, S184N, M174X | I | 329.2 | 6.4 | 0.0 | 0.9 | 0.0 | 0.0 | 0.0 | 0.0 | 336.5 |
| 73 | empty vector | NA | 5.3 | 0.0 | 0.0 | 0.0 | 0.0 | 0.0 | 0.0 | 0.0 | 5.3 |
| 74 | empty vector | NA | 0.0 | 0.0 | 0.0 | 0.0 | 0.0 | 0.0 | 0.0 | 0.0 | 0.0 |

FIG. 2D

Normalized Values

| Strain # | CalFatB2 background | AA sub | C8:0 | C10:0 | C12:0 | C14:0 | C16:0 | C16:1 | C18:0 | C18:1 | Total FFAs ug/mL/OD | % C8: total FA |
|---|---|---|---|---|---|---|---|---|---|---|---|---|
| 1 | CalFatB2 wt M174X | A | 3.5 | 0.3 | 0.0 | 0.3 | 0.0 | 0.8 | 0.0 | 0.0 | 4.9 | 71.4 |
| 2 | CalFatB2 wt M174X | A | 3.6 | 0.0 | 0.0 | 0.3 | 0.2 | 0.8 | 0.0 | 0.0 | 4.9 | 73.5 |
| 3 | CalFatB2 wt M174X | N | 0.0 | 0.0 | 0.0 | 0.0 | 0.0 | 0.6 | 0.0 | 0.0 | 0.6 | 0 |
| 4 | CalFatB2 wt M174X | N | 0.0 | 0.0 | 0.0 | 0.0 | 0.3 | 0.8 | 0.0 | 0.0 | 1.1 | 0 |
| 5 | CalFatB2 wt M174X | D | 0.0 | 0.0 | 0.0 | 0.2 | 0.2 | 0.8 | 0.0 | 0.0 | 1.2 | 0 |
| 6 | CalFatB2 wt M174X | D | 0.0 | 0.0 | 0.0 | 0.0 | 0.0 | 0.8 | 0.0 | 0.0 | 0.8 | 0 |
| 7 | CalFatB2 wt M174X | Q | 0.3 | 0.0 | 0.0 | 0.2 | 0.3 | 0.6 | 0.0 | 0.0 | 1.5 | 20 |
| 8 | CalFatB2 wt M174X | Q | 0.3 | 0.0 | 0.0 | 0.2 | 0.2 | 0.7 | 0.0 | 0.0 | 1.5 | 20 |
| 9 | CalFatB2 wt M174X | G | 0.0 | 0.0 | 0.0 | 0.0 | 0.0 | 2.1 | 0.0 | 0.0 | 2.1 | 0 |
| 10 | CalFatB2 wt M174X | G | 0.0 | 0.0 | 0.0 | 0.0 | 0.5 | 1.0 | 0.0 | 0.0 | 1.4 | 0 |
| 11 | CalFatB2 wt M174X | L | 38.2 | 1.6 | 0.0 | 0.4 | 0.2 | 0.7 | 0.0 | 0.0 | 41.1 | 92.9 |
| 12 | CalFatB2 wt M174X | L | 44.8 | 1.4 | 0.0 | 0.4 | 0.0 | 0.8 | 0.0 | 0.0 | 47.5 | 94.3 |
| 13 | CalFatB2 wt M174X | S | 0.2 | 0.0 | 0.0 | 0.1 | 0.0 | 1.0 | 0.0 | 0.0 | 1.3 | 15.4 |
| 14 | CalFatB2 wt M174X | S | 0.1 | 0.0 | 0.0 | 0.5 | 0.3 | 0.5 | 0.0 | 0.0 | 1.0 | 10 |
| 15 | CalFatB2 wt M174X | F | 40.7 | 2.1 | 0.0 | 0.4 | 0.0 | 0.9 | 0.0 | 0.0 | 44.1 | 92.3 |
| 16 | CalFatB2 wt M174X | F | 33.7 | 1.8 | 0.0 | 0.0 | 0.0 | 0.9 | 0.0 | 0.0 | 36.8 | 91.6 |
| 17 | CalFatB2 wt M174X | T | 4.2 | 0.3 | 0.0 | 0.3 | 0.3 | 0.7 | 0.0 | 0.0 | 5.7 | 73.7 |
| 18 | CalFatB2 wt M174X | T | 3.9 | 0.3 | 0.0 | 0.2 | 0.0 | 0.7 | 0.0 | 0.0 | 5.1 | 76.5 |

FIG. 3A

Normalized Values

| Strain # | CalFatB2 background | AA sub | C8:0 | C10:0 | C12:0 | C14:0 | C16:0 | C16:1 | C18:0 | C18:1 | Total FFAs ug/mL/OD | % C8: total FA |
|---|---|---|---|---|---|---|---|---|---|---|---|---|
| 19 | CalFatB2 wt M174X | W | 0.3 | 0.0 | 0.0 | 0.3 | 0.3 | 0.7 | 0.0 | 0.0 | 1.6 | 18.8 |
| 20 | CalFatB2 wt M174X | W | 0.4 | 0.0 | 0.0 | 0.2 | 0.3 | 0.8 | 0.0 | 0.0 | 1.6 | 25 |
| 21 | CalFatB2 wt M174X | Y | 0.5 | 0.0 | 0.0 | 0.3 | 0.2 | 0.7 | 0.0 | 0.0 | 1.7 | 29.4 |
| 22 | CalFatB2 wt M174X | Y | 0.6 | 0.0 | 0.0 | 0.2 | 0.2 | 0.8 | 0.0 | 0.0 | 1.8 | 33.3 |
| 23 | CalFatB2 wt M174X | V | 52.5 | 2.4 | 0.0 | 0.4 | 0.0 | 1.0 | 0.0 | 0.0 | 56.2 | 93.4 |
| 24 | CalFatB2 wt M174X | V | 59.9 | 2.2 | 0.0 | 0.4 | 0.0 | 0.9 | 0.0 | 0.0 | 63.5 | 94.3 |
| 25 | CalFatB2 wt M174X | E | 0.2 | 0.0 | 0.0 | 0.0 | 0.0 | 0.5 | 0.0 | 0.0 | 0.7 | 28.6 |
| 26 | CalFatB2 wt M174X | E | 0.2 | 0.0 | 0.0 | 0.0 | 0.0 | 0.6 | 0.0 | 0.0 | 0.8 | 25 |
| 27 | CalFatB2 wt M174X | C | 38.4 | 1.1 | 0.0 | 0.4 | 0.0 | 0.6 | 0.0 | 0.0 | 40.5 | 94.8 |
| 28 | CalFatB2 wt M174X | C | 42.0 | 1.2 | 0.0 | 0.3 | 0.0 | 0.5 | 0.0 | 0.0 | 44.0 | 95.5 |
| 29 | CalFatB2 wt M174X | H | 0.6 | 0.3 | 0.0 | 0.4 | 0.3 | 0.5 | 0.0 | 0.0 | 2.1 | 28.6 |
| 30 | CalFatB2 wt M174X | H | 0.5 | 0.0 | 0.0 | 0.4 | 0.2 | 0.5 | 0.0 | 0.0 | 1.5 | 33.3 |
| 31 | CalFatB2 wt M174X | K | 0.1 | 0.0 | 0.0 | 0.0 | 0.3 | 0.5 | 0.0 | 0.0 | 0.9 | 11.1 |
| 32 | CalFatB2 wt M174X | K | 0.2 | 0.0 | 0.0 | 0.2 | 0.2 | 0.6 | 0.0 | 0.0 | 1.1 | 18.2 |
| 33 | CalFatB2 wt M174X | M | 40.1 | 1.3 | 0.0 | 0.4 | 0.2 | 0.3 | 0.0 | 0.0 | 42.0 | 95.5 |
| 34 | CalFatB2 wt M174X | M | 46.0 | 1.4 | 0.0 | 0.0 | 0.0 | 0.5 | 0.0 | 0.0 | 47.9 | 96 |
| 35 | CalFatB2 wt M174X | P | 1.2 | 0.2 | 0.0 | 0.3 | 0.0 | 1.2 | 0.0 | 0.0 | 3.0 | 40 |
| 36 | CalFatB2 wt M174X | P | 1.2 | 0.2 | 0.0 | 0.6 | 0.2 | 0.4 | 0.0 | 0.0 | 2.7 | 44.4 |
| 37 | CalFatB2 wt M174X | – | 86.3 | 2.7 | 0.0 | 0.2 | 0.0 | 0.0 | 0.0 | 0.0 | 89.3 | 96.6 |
| 38 | CalFatB2 wt M174X | – | 76.1 | 2.6 | 0.0 | 0.4 | 0.0 | 0.0 | 0.0 | 0.0 | 79.0 | 96.3 |

FIG. 3B

| Strain # | CalFatB2 background | AA sub | C8:0 | C10:0 | C12:0 | C14:0 | C16:0 | C16:1 | C18:0 | C18:1 | Total FFAs ug/mL/OD | % C8: total FA |
|---|---|---|---|---|---|---|---|---|---|---|---|---|
| 39 | CalFatB2 | A | 16.1 | 0.5 | 0.0 | 0.4 | 0.0 | 1.1 | 0.0 | 0.0 | 18.1 | 89 |
| 40 | CalFatB2 L103I, S184N, M174X | A | 0.3 | 0.1 | 0.0 | 0.0 | 0.3 | 0.5 | 0.0 | 0.0 | 1.2 | 25 |
| 41 | CalFatB2 L103I, S184N, M174X | R | 5.4 | 0.3 | 0.0 | 0.2 | 0.0 | 0.6 | 0.0 | 0.0 | 6.5 | 83.1 |
| 42 | CalFatB2 L103I, S184N, M174X | R | 0.0 | 0.0 | 0.0 | 0.0 | 0.2 | 1.0 | 0.0 | 0.0 | 1.2 | 0 |
| 43 | CalFatB2 L103I, S184N, M174X | Q | 1.3 | 0.3 | 0.0 | 0.0 | 0.0 | 1.1 | 0.0 | 0.0 | 2.3 | 56.5 |
| 44 | CalFatB2 L103I, S184N, M174X | Q | 1.3 | 0.3 | 0.0 | 0.3 | 0.3 | 1.3 | 0.0 | 0.0 | 3.5 | 37.1 |
| 45 | CalFatB2 L103I, S184N, M174X | G | 0.0 | 0.0 | 0.0 | 0.0 | 0.0 | 1.0 | 0.0 | 0.0 | 1.0 | 0 |
| 46 | CalFatB2 L103I, S184N, M174X | G | 0.0 | 0.0 | 0.0 | 0.1 | 0.2 | 1.0 | 0.0 | 0.0 | 1.3 | 0 |
| 47 | CalFatB2 L103I, S184N, M174X | T | 18.0 | 0.5 | 0.0 | 0.3 | 0.0 | 0.8 | 0.0 | 0.0 | 19.6 | 91.8 |
| 48 | CalFatB2 L103I, S184N, M174X | T | 17.1 | 0.0 | 0.0 | 0.3 | 0.0 | 0.6 | 0.0 | 0.0 | 18.0 | 95 |
| 49 | CalFatB2 L103I, S184N, M174X | V | 92.5 | 1.9 | 0.0 | 0.4 | 0.0 | 0.8 | 0.0 | 0.0 | 95.6 | 96.8 |
| 50 | CalFatB2 L103I, S184N, M174X | V | 83.1 | 1.8 | 0.0 | 0.3 | 0.0 | 0.5 | 0.0 | 0.0 | 85.6 | 97.1 |
| 51 | CalFatB2 L103I, S184N, M174X | N | 0.2 | 0.0 | 0.0 | 0.0 | 0.0 | 0.4 | 0.0 | 0.0 | 0.6 | 33.3 |
| 52 | CalFatB2 L103I, S184N, M174X | N | 0.2 | 0.0 | 0.0 | 0.0 | 0.0 | 0.3 | 0.0 | 0.0 | 0.5 | 40 |
| 53 | CalFatB2 L103I, S184N, M174X | D | 0.0 | 0.0 | 0.0 | 0.1 | 0.0 | 0.5 | 0.0 | 0.0 | 0.6 | 0 |
| 54 | CalFatB2 L103I, S184N, M174X | D | 0.0 | 0.0 | 0.0 | 0.0 | 0.0 | 0.5 | 0.0 | 0.0 | 0.5 | 0 |
| 55 | CalFatB2 L103I, S184N, M174X | E | 0.0 | 0.0 | 0.0 | 0.0 | 0.0 | 1.4 | 0.0 | 0.0 | 1.4 | 0 |
| 56 | CalFatB2 L103I, S184N, M174X | E | 0.0 | 0.0 | 0.0 | 0.0 | 0.3 | 0.4 | 0.0 | 0.0 | 0.4 | 0 |
| 57 | CalFatB2 L103I, S184N, M174X | F | 0.9 | 0.0 | 0.0 | 0.4 | 0.3 | 0.4 | 0.0 | 0.0 | 1.9 | 47.4 |
| 58 | CalFatB2 L103I, S184N, M174X | F | 0.9 | 0.2 | 0.0 | 0.4 | 0.3 | 0.7 | 0.0 | 0.0 | 2.5 | 36 |

FIG. 3C

Normalized Values

| Strain # | CalFatB2 background | AA sub | C8:0 | C10:0 | C12:0 | C14:0 | C16:0 | C16:1 | C18:0 | C18:1 | Total FFAs ug/mL/OD | % C8: total FA |
|---|---|---|---|---|---|---|---|---|---|---|---|---|
| 59 | CalFatB2 L103I, S184N, M174X | L | 52.7 | 1.2 | 0.0 | 0.4 | 0.0 | 0.6 | 0.0 | 0.0 | 54.9 | 96 |
| 60 | CalFatB2 L103I, S184N, M174X | L | 51.9 | 1.2 | 0.0 | 0.3 | 0.0 | 0.5 | 0.0 | 0.0 | 53.9 | 96.3 |
| 61 | CalFatB2 L103I, S184N, M174X | K | 0.6 | 0.0 | 0.0 | 0.0 | 0.0 | 0.3 | 0.0 | 0.0 | 1.0 | 60 |
| 62 | CalFatB2 L103I, S184N, M174X | K | 0.2 | 0.0 | 0.0 | 0.2 | 0.0 | 0.4 | 0.0 | 0.0 | 0.8 | 25 |
| 63 | CalFatB2 L103I, S184N, M174X | F | 60.1 | 2.0 | 0.0 | 0.3 | 0.0 | 0.8 | 0.0 | 0.0 | 63.3 | 94.9 |
| 64 | CalFatB2 L103I, S184N, M174X | F | 74.0 | 2.6 | 0.0 | 1.0 | 0.7 | 1.1 | 0.7 | 0.7 | 80.8 | 91.6 |
| 65 | CalFatB2 L103I, S184N, M174X | S | 0.8 | 0.3 | 0.0 | 0.2 | 0.0 | 1.7 | 0.0 | 0.0 | 3.0 | 26.7 |
| 66 | CalFatB2 L103I, S184N, M174X | S | 1.2 | 0.2 | 0.0 | 0.0 | 0.0 | 0.0 | 0.0 | 0.0 | 1.4 | 85.7 |
| 67 | CalFatB2 L103I, S184N, M174X | W | 1.3 | 0.0 | 0.0 | 0.0 | 0.0 | 0.0 | 0.0 | 0.0 | 1.3 | 100 |
| 68 | CalFatB2 L103I, S184N, M174X | W | 1.2 | 0.0 | 0.0 | 0.0 | 0.0 | 0.0 | 0.0 | 0.0 | 1.2 | 100 |
| 69 | CalFatB2 L103I, S184N, M174X | Y | 3.8 | 0.3 | 0.0 | 0.3 | 0.0 | 0.4 | 0.0 | 0.0 | 4.7 | 80.9 |
| 70 | CalFatB2 L103I, S184N, M174X | Y | 4.1 | 0.3 | 0.0 | 0.3 | 0.0 | 0.5 | 0.0 | 0.0 | 5.1 | 80.4 |
| 71 | CalFatB2 L103I, S184N, M174X | - | 112.5 | 2.4 | 0.0 | 0.4 | 0.0 | 0.0 | 0.0 | 0.0 | 115.2 | 97.7 |
| 72 | CalFatB2 L103I, S184N, M174X | - | 121.9 | 2.4 | 0.0 | 0.3 | 0.0 | 0.0 | 0.0 | 0.0 | 124.6 | 97.8 |
| 73 | empty vector | NA | 1.2 | 0.0 | 0.0 | 0.0 | 0.0 | 0.0 | 0.0 | 0.0 | 1.2 | |
| 74 | empty vector | NA | 0.0 | 0.0 | 0.0 | 0.0 | 0.0 | 0.0 | 0.0 | 0.0 | 0.0 | |

FIG. 3D

| Strain # | Gentoype | C8:0 | C10:0 | C12:0 | C14:0 | C16:0 | C16:1 | C18:0 | C18:1 | Total FFAs ug/mL |
|---|---|---|---|---|---|---|---|---|---|---|
| 75 | empty vector | 1.1 | 1.0 | ND | 1.2 | 1.3 | 2.3 | 0.0 | 0.0 | 6.9 |
| 76 | empty vector | 1.1 | 0.0 | ND | 0.0 | 1.0 | 1.6 | 0.0 | 0.0 | 3.7 |
| 77 | Ca1FatB2 wt | 150.6 | 5.7 | ND | 1.5 | 0.0 | 1.5 | 0.0 | 0.0 | 159.3 |
| 78 | Ca1FatB2 wt | 189.9 | 6.9 | ND | 1.5 | 0.0 | 1.4 | 0.0 | 0.0 | 199.7 |
| 79 | Ca1FatB2 L103I, M174I, S184N | 338.2 | 7.4 | ND | 1.3 | 1.0 | 1.4 | 0.0 | 0.0 | 349.2 |
| 80 | Ca1FatB2 L103I, M174II, S184N | 347.5 | 8.3 | ND | 0.9 | 0.0 | 1.1 | 0.0 | 0.0 | 357.8 |
| 81 | Ca1FatB2 M174I | 272.9 | 10.5 | ND | 1.5 | 0.0 | 1.6 | 0.0 | 0.0 | 286.5 |
| 82 | Ca1FatB2 M174I | 255.0 | 10.2 | ND | 1.0 | 0.0 | 1.4 | 0.0 | 0.0 | 267.6 |
| 83 | Ca1FatB2 L103I, M174I | 316.7 | 7.5 | ND | 0.9 | 0.0 | 1.3 | 0.0 | 0.0 | 326.3 |
| 84 | Ca1FatB2 L103I, M174I | 344.7 | 7.1 | ND | 1.0 | 0.0 | 1.3 | 0.0 | 0.0 | 354.2 |
| 85 | Ca1FatB2 M174R | 2.4 | 0.9 | ND | 0.0 | 1.0 | 2.1 | 0.0 | 0.0 | 6.4 |
| 86 | Ca1FatB2 M174R | 2.0 | 0.0 | ND | 0.0 | 0.0 | 2.8 | 0.0 | 0.0 | 4.8 |
| 87 | Ca1FatB2 L103I, M174C, S184N | 259.5 | 4.9 | ND | 1.4 | 0.0 | 2.1 | 0.0 | 0.0 | 267.7 |
| 88 | Ca1FatB2 L103I, M174C, S184N | 240.4 | 4.6 | ND | 1.1 | 0.0 | 1.6 | 0.0 | 0.0 | 247.7 |
| 89 | Ca1FatB2 L103I, M174P, S184N | 24.4 | 2.8 | ND | 0.0 | 0.0 | 1.7 | 0.0 | 0.0 | 28.9 |
| 90 | Ca1FatB2 L103I, M174P, S184N | 13.7 | 1.1 | ND | 1.3 | 0.0 | 2.6 | 0.0 | 0.0 | 18.7 |

FIG. 5A

| Strain # | Gentoype | C8:0 | C10:0 | C12:0 | C14:0 | C16:0 | C16:1 | C18:0 | C18:1 | Total FFAs ug/mL/OD | % C8/Total FA |
|---|---|---|---|---|---|---|---|---|---|---|---|
| 75 | empty vector | 0.3 | 0.3 | ND | 0.3 | 0.3 | 0.6 | 0.0 | 0.0 | 1.7 | 17.7 |
| 76 | empty vector | 0.2 | 0.0 | ND | 0.0 | 0.2 | 0.4 | 0.0 | 0.0 | 0.8 | 25 |
| 77 | Ca1FatB2 wt | 45.6 | 1.7 | ND | 0.4 | 0.0 | 0.5 | 0.0 | 0.0 | 48.3 | 94.4 |
| 78 | Ca1FatB2 wt | 61.3 | 2.2 | ND | 0.5 | 0.0 | 0.5 | 0.0 | 0.0 | 64.4 | 95.2 |
| 79 | Ca1FatB2 L103I, M174I, S184N | 120.8 | 2.6 | ND | 0.5 | 0.3 | 0.5 | 0.0 | 0.0 | 124.7 | 96.9 |
| 80 | Ca1FatB2 L103I, M174II, S184N | 128.7 | 3.1 | ND | 0.3 | 0.0 | 0.4 | 0.0 | 0.0 | 132.5 | 97.1 |
| 81 | Ca1FatB2 M174I | 91.0 | 3.5 | ND | 0.5 | 0.0 | 0.5 | 0.0 | 0.0 | 95.5 | 95.3 |
| 82 | Ca1FatB2 M174I | 87.9 | 3.5 | ND | 0.4 | 0.0 | 0.5 | 0.0 | 0.0 | 92.3 | 95.2 |
| 83 | Ca1FatB2 L103I, M174I | 121.8 | 2.9 | ND | 0.4 | 0.0 | 0.5 | 0.0 | 0.0 | 125.5 | 97.1 |
| 84 | Ca1FatB2 L103I, M174I | 132.6 | 2.7 | ND | 0.4 | 0.0 | 0.5 | 0.0 | 0.0 | 136.2 | 97.4 |
| 85 | Ca1FatB2 M174R | 0.8 | 0.3 | ND | 0.0 | 0.3 | 0.7 | 0.0 | 0.0 | 2.1 | 38.1 |
| 86 | Ca1FatB2 M174R | 0.7 | 0.0 | ND | 0.0 | 0.0 | 0.9 | 0.0 | 0.0 | 1.6 | 43.8 |
| 87 | Ca1FatB2 L103I, M174C, S184N | 89.5 | 1.7 | ND | 0.5 | 0.0 | 0.7 | 0.0 | 0.0 | 92.3 | 97 |
| 88 | Ca1FatB2 L103I, M174C, S184N | 80.1 | 1.5 | ND | 0.4 | 0.0 | 0.5 | 0.0 | 0.0 | 82.6 | 97 |
| 89 | Ca1FatB2 L103I, M174P, S184N | 7.9 | 0.9 | ND | 0.0 | 0.0 | 0.5 | 0.0 | 0.0 | 9.3 | 84.9 |
| 90 | Ca1FatB2 L103I, M174P, S184N | 4.1 | 0.3 | ND | 0.4 | 0.0 | 0.8 | 0.0 | 0.0 | 5.7 | 71.9 |

FIG. 5B

```
                          1                                  34                                  65
SEQ ID NO:29   M ANGSAVTLKSGSLNTQED  TLSSSPPPRAFFNQLPDWSMLLTAITTVFVAPEKRWTMFDRKSKRP
Ca1FatB2
                          1                                  33                                  64
SEQ ID NO:51   M ANGSAVSLKSGSLNTQED  TSSS PPPRAFINQLPDWSMLLTAITTVFVAAEKQWTMLDRKSKRS
Cc1FatB1
                          1                                  35                                  66
SEQ ID NO:55   M ANGSAVSLKSGSIETQEDKTSSSSPPPRTFINQLPVWSMLLSAVTTVFGVAEKQWPMLDRKSKRP
Ca1FatB1
                          1                                  34                                  65
SEQ ID NO:59   MGINGSSVGLKSGSLKTQED  THAT PPPRTFINQLPDWSMLLAAITTAFLAAEKQWMMLDWKPKRP
Ci1FatB1
                          1                                  34                                  65
SEQ ID NO:63   M ANGSAVSLKSDTLETQEDTSSSS PPPRTFINQLPDWSMLLSAFTNVFVAAEKQWTMLDRKYKRP
Cl1FatB1
                         53                                  84                                 115
SEQ ID NO:63   K INGSSVGLKSGSLKTQEDT PLA PPPRTFINQLPDWSMLLAAITTVFLAAERQWMMLDWKPKRP
Cl1FatB2
                          1                                  34                                  65
SEQ ID NO:69   M ANGSAVSLKDGSLETQEGTSSSSH PPRTFINQLPDWSMLLSAITTVFVAAEKQWTMLDRKSKRP
Cp1FatB1
                         53                                  84                                 115
SEQ ID NO:71   K INGSSVGLKSGSLKTQEDTPSA  PPPRTFINQLPDWSMLLAAITTVFLAAEKQWMMLDWKPKRP
Cl2FatB1
                          1                                  33                                  64
SEQ ID NO:75   M ANGSAVNLKSGSLNTQEDSSSSPS  PRAFLNQLPDWSVLLTAITTVFVAAEKQWTMLDRKSKRP
Cl2FatB2
                          1                                  34                                  65
SEQ ID NO:79   MGINGSSVGLKSGSLKTQEDTPSA  PPPRTFINQLPDWSMLLAAITTVFLAAEKQWMMLDWKPKRP
Cl3FatB1
                         55                                  85                                 116
SEQ ID NO:81   K ANGSAVNLKSGSLNTQEDSSSS  PSPRAFLNQLPDWSVLLTAITTVFVAAEKQWTMLDRKSKRP
Cl3FatB2
                          1                                  34                                  65
SEQ ID NO:85   MGINGSSVGLKSGSLKTQEDTPSS  PPPRTFINQLPDWSMLLAAITTVFLAAEKQWMMLDWKPKRP
Cd1FatB1
                          1                                  33                                  64
SEQ ID NO:89   M ANGAAVNLKSGSLNTQEDTSSS  PPPRAFLNQLPDWSMLLTAITTVFVAAEKQWTMLDRKSKRP
Cl4FatB1
                         53                                  84                                 115
SEQ ID NO:91   K INGSSVGLKSGSLKTQEDAPSA  PPPRTFINQLPDWSMLLAAITTVFLAAEKQWMMLDWKPKRP
Cl4FatB2
                         53                                  84                                 115
SEQ ID NO:93   K INGSSVGLKSGGLKTQEDAPSA  PPPRTFINQLPDWSMLLAAITTVFLAAEKQWMMLDWKPKRP
Cl4FatB3
                         53                                  84                                 115
SEQ ID NO:95   K INGHPVGLKSGGLKTQEDGPSA  PPPRTFINQLPDWSMLLAAITTVFLAAEKQWMMLDWKPKRP
Ca1FatB1
                          1                                  33                                  63
SEQ ID NO:99   M ANGSAVSLKSGSLNTQEDTSSS  PPPRTFLHQLPDWSRLLTAITTVFVKSKR PDMHDRKSKRP
Ca2FatB2
                         53                                  84                                 115
SEQ ID NO:101  K INGHPVGLKSGGLKTQEDGPSA  PPPRTFINQLPDWSMLLAAITTAFLAAEKQWMMLDWKPKRP
Ca1FatB3
```

FIG.7

ACYL-ACP THIOESTERASE GENES AND USES THEREFOR

CROSS-REFERENCE TO RELATED APPLICATIONS

This application is a continuation application of U.S. application Ser. No. 12/826,592 filed Jun. 29, 2010, now U.S. Pat. No. 8,956,834; which claims the benefit under 35 USC § 119(e) to U.S. Application Ser. No. 61/223,328 filed Jul. 6, 2009 and to U.S. Application Ser. No. 61/221,500 filed Jun. 29, 2009, both now expired. The disclosure of each of the prior applications is considered part of and is incorporated by reference in the disclosure of this application.

REFERENCE TO SEQUENCE LISTING

The instant application contains a Sequence Listing which has been submitted via EFS-Web and is hereby incorporated by reference in its entirety. Said ASCII copy, created on Jan. 26, 2015, is named SGI1230-3_ST25.txt and is 218 KB in size. The aforementioned sequence listing is hereby incorporated by reference in its entirety pursuant to 37 C.F.R. §1.52(e)(5).

BACKGROUND OF THE INVENTION

Field of the Invention

The invention relates to the production of fatty acids and fatty acid products in transgenic or genetically modified organisms, such as microorganisms and photosynthetic organisms. The invention also relates to genes encoding enzymes that function in the biosynthesis of fatty acids and related products, and in particular to acyl-ACP thioesterases.

Background Information

Plants supply most of the oils used in food products, and plant-derived lipids are also used in the manufacture of many non-dietary products, such as lubricants, soaps, detergents, cosmetics, and thickeners. In higher plants, fatty acids are synthesized in plastids and incorporated into triacylglycerols (triglycerides) in the endoplasmic reticulum (ER). In cells that store fats, such as the cells of seeds or nuts, fat droplets bud off of the ER to form lipid bodies within the cytoplasm. These reservoirs of lipids in the form of triglycerides provide an energy resource for germinating seeds.

The diversity of fatty acids produced by plant cells and incorporated into triglycerides can add to the time and cost of purification of fatty acids of particular chain lengths used for particular purposes. Medium chain fatty acids, for example, are used in the manufacture of surface disinfectants, anti-foaming agents, surfactants, lubricants, perfumes, dyes, and flavoring agents, and can be used to produce polymers and fuels. Long chain fatty acids are used in food products as well as detergents, soaps, surfactants, cosmetics, plastics, and lubricants, and can also be used in the production of fuels.

Acyl-acyl carrier protein (ACP) thioesterases are key enzymes in determining the chain lengths of fatty acids produced by a plant. Two families of acyl-ACP thioesterases are present in higher plants, the "Class I" acyl-ACP thioesterases encoded by FatA genes, and responsible for cleaving long chain (for example, C16 and C18) unsaturated fatty acids from acyl-ACP and the "Class II" acyl-ACP thioesterases encoded by FatB genes, that are active on saturated fatty acyl chains and can be specific for medium chain (C8-C14) acyl-ACPs or can be active on both medium and long chain fatty acyl-ACPs. Different acyl-ACP thioesterases have different degrees of chain length specificity, sometimes referred to as the enzyme's "preference" for cleaving a particular length of fatty acid from ACP, and thioesterases are typically most active in cleaving a particular chain length fatty acid while having lesser activity in cleaving one or more other chain length fatty acids. Some Class II (FatB) acyl-ACP thioesterases have binary activity, having a first peak of activity against a specific medium chain length acyl substrate and a second peak of activity against one or more specific long chain length acyl substrates.

The isolation of Class II acyl-ACP thioesterase genes from higher plants with medium chain specificity or having activity on both medium and long chain fatty acids has been described previously. Examples include U.S. Pat. No. 5,298,421, entitled "Plant medium-chain-preferring acyl-ACP thioesterases and related methods", which describes the isolation of an acyl-ACP thioesterase and the gene that encodes it from the immature seeds of *Umbellularia californica*. Other patents of interest include U.S. Pat. No. 5,304,481, entitled "Plant thioesterase having preferential hydrolase activity toward C12 acyl-ACP substrate", U.S. Pat. No. 5,344,771, entitled "Plant thioesterases", U.S. Pat. No. 5,455,167, entitled "Medium-chain thioesterases in plants", U.S. Pat. No. 5,512,482, entitled "Plant thioesterases", U.S. Pat. No. 5,639,790, entitled "Plant medium-chain thioesterases", U.S. Pat. No. 5,667,997, entitled "C8 and C10 medium-chain thioesterases in plants", U.S. Pat. No. 5,807,893, entitled "Plant thioesterases and use for modification of fatty acid composition in plant seed oils", U.S. Pat. No. 5,850,022, entitled "Production of myristate in plant cells", and U.S. Pat. No. 5,910,631, entitled "Middle chain-specific thioesterase genes from *Cuphea lanceolata*", U.S. Pat. No. 5,955,329, entitled "Engineering plant thioesterases for altered substrate specificity", and U.S. Pat. No. 6,150,512, entitled "Engineering plant thioesterases and disclosure of plant thioesterases having novel substrate specificity", disclose variants of plant thioesterase genes having altered chain length specificities for the encoded thioesterase enzymes.

Journal articles disclosing Class II chain acyl-ACP thioesterases include Dehesh, K. et al., "Production of high levels of 8:0 and 10:0 fatty acids in transgenic canola by overexpression of Ch FatB2, a thioesterase cDNA from *Cuphea hookeriana*", *The Plant Journal* 9:167-172 (1996), Dehesh, K. et al., "Two novel thioesterases are key determinants of the bimodal distribution of acyl chain length of *Cuphea palustris* seed oil", *Plant Physiology* 110:203-210 (1996), Dehesh, K., et al., "KAS IV: a 3-ketoacyl-ACP synthase from *Cuphea* sp. is a medium chain specific condensing enzyme", *The Plant Journal* 15:383-390 (1998), Dormann, P. et al., "Characterization of two acyl-acyl carrier protein thioesterases from developing *Cuphea* seeds specific for medium-chain and oleoyl-acyl carrier protein", *Planta* 189:425-432 (1993), Filichkin, S., et al., "New FATB thioesterases from a high-laurate *Cuphea* species: Functional and complementation analyses", *European Journal of Lipid Science and Technology* 108:979-990 (2006), Slabaugh, M., et al., "Condensing enzymes from *Cuphea wrightii* associated with medium chain fatty acid biosynthesis", *The Plant Journal* 13:611-620 (1998), Voelker, T., et al., "Fatty acid biosynthesis redirected to medium chains in transgenic oilseed plants", *Science* 257:72-74 (1992), Voelker, T., and Davies, M., "Alteration of the specificity and regulation of fatty acid synthesis of *Escherichia coli* by expression of a plant medium-chain acyl-acyl carrier protein thioesterase", *Journal of Bacteriology* 176:7320-7327 (1994).

In addition to synthesizing fatty acids for nonfuel products, microorganisms or photosynthetic organisms can be used to produce fatty acids or fatty acid products for the production of fuels and chemicals such as alcohols or hydrocarbons. In synthesizing fatty acids, these organisms can use atmospheric $CO_2$ or plant products such as starch, sugars, or cellulose that are themselves based on fixed atmospheric $CO_2$ as a source of carbon, thereby reducing the net amount of $CO_2$ generated in the production and use of the fuel or chemical. Increasing the yield and recovery of fatty acids and fatty acid products of a particular chain length from cultured microorganisms and photosynthetic organisms can improve the cost effectiveness of providing a renewable source of a variety of products, including fuel products.

SUMMARY OF THE INVENTION

The invention provides compositions and methods for producing fatty acids and fatty acid products of specific chain lengths for synthesis of a variety of intermediary or final products for various uses, for example, in foods and nutritional products, lubricants, surfactants, chemicals, plastics, soaps, and fuels. Nucleic acid molecules are provided that encode acyl-ACP thioesterases exhibiting a preference for specific acyl chain lengths, such that fatty acid preparations in which a preponderance of the isolated fatty acids are of one or more specific chain lengths can be recovered from cultures of transgenic organisms expressing the exogenous acyl-ACP thioesterase.

A first aspect of the invention provides recombinant or isolated nucleic acid molecules encoding acyl-ACP thioesterases in which the encoded thioesterases include an amino acid sequence having at least 85%, at least 90%, at least 92%, at least 95%, or at least 99% identity with the amino acid sequence from amino acid position 64 to amino acid position 361 of SEQ ID NO:51; at least 98% identity with the amino acid sequence from amino acid position 66 to amino acid position 362 of SEQ ID NO:55; at least 97% identity with the amino acid sequence from amino acid position 65 to amino acid position 360 of SEQ ID NO:59; at least 90% identity with the amino acid sequence from amino acid position 65 to amino acid position 359 of SEQ ID NO:63; at least 98% identity with the amino acid sequence from amino acid position 115 to amino acid position 410 of SEQ ID NO:65; at least 96% identity with the amino acid sequence from amino acid position 65 to amino acid position 356 of SEQ ID NO:69; at least 98% identity with the amino acid sequence from amino acid position 115 to amino acid position 410 of SEQ ID NO:71; at least 96% identity with the amino acid sequence from amino acid position 64 to amino acid position 361 of SEQ ID NO:75; at least 97% identity with the amino acid sequence from amino acid position 65 to amino acid position 360 of SEQ ID NO:79; at least 96% identity with the amino acid sequence from amino acid position 116 to amino acid position 413 of SEQ ID NO:81; at least 96% identity with the amino acid sequence from amino acid position 65 to amino acid position 362 of SEQ ID NO:85; at least 96% identity with the amino acid sequence from amino acid position 64 to amino acid position 361 of SEQ ID NO:89; at least 97% identity with the amino acid sequence from amino acid position 115 to amino acid position 394 of SEQ ID NO:91; at least 97% identity with the amino acid sequence from amino acid position 115 to amino acid position 394 of SEQ ID NO:93; at least 99% identity with the amino acid sequence from amino acid position 115 to amino acid position 394 of SEQ ID NO:95; at least 92% identity with the amino acid sequence from amino acid position 63 to amino acid position 360 of SEQ ID NO:99; or at least 98% identity with the amino acid sequence from amino acid position 115 to amino acid position 393 of SEQ ID NO:101, in which the thioesterase encoded by the isolated nucleic acid molecule has at least the level of activity as the thioesterase encoded by the reference sequence from which it is derived.

In some embodiments, the recombinant or isolated nucleic acid molecule encoding an acyl-ACP thioesterase includes an amino acid sequence having at least 85% identity with the amino acid sequence from amino acid position 33 to amino acid position 361 of SEQ ID NO:51; having at least 98% identity with the amino acid sequence from amino acid position 35 to amino acid position 362 of SEQ ID NO:55; having at least 97% identity with the amino acid sequence from amino acid position 34 to amino acid position 360 of SEQ ID NO:59; having at least 90% identity with the amino acid sequence from amino acid position 34 to amino acid position 359 of SEQ ID NO:63; having at least 98% identity with the amino acid sequence from amino acid position 84 to amino acid position 410 of SEQ ID NO:65; having at least 96% identity with the amino acid sequence from amino acid position 34 to amino acid position 356 of SEQ ID NO:69; having at least 98% identity with the amino acid sequence from amino acid position 84 to amino acid position 410 of SEQ ID NO:71; having at least 96% identity with the amino acid sequence from amino acid position 33 to amino acid position 361 of SEQ ID NO:75; having at least 97% identity with the amino acid sequence from amino acid position 34 to amino acid position 360 of SEQ ID NO:79; having at least 96% identity with the amino acid sequence from amino acid position 85 to amino acid position 413 of SEQ ID NO:81; having at least 96% identity with the amino acid sequence from amino acid position 34 to amino acid position 362 of SEQ ID NO:85; having at least 96% identity with the amino acid sequence from amino acid position 33 to amino acid position 361 of SEQ ID NO:89; having at least 97% identity with the amino acid sequence from amino acid position 84 to amino acid position 394 of SEQ ID NO:91; having at least 97% identity with the amino acid sequence from amino acid position 84 to amino acid position 394 of SEQ ID NO:93; having at least 99% identity with the amino acid sequence from amino acid position 84 to amino acid position 394 of SEQ ID NO:95; having at least 92% identity with the amino acid sequence from amino acid position 33 to amino acid position 360 of SEQ ID NO:99; or having at least 98% identity with the amino acid sequence from amino acid position 84 to amino acid position 393 of SEQ ID NO:101, and has at least the level of activity of the reference thioesterase from which the encoded thioesterase sequence is derived. In some embodiments, the encoded thioesterase shares at least 85%, at least 90%, at least 92%, at least 95%, at least 96%, at least 97%, at least 98%, at least 99%, or at least 99.5% identity with the above provided amino acid sequences, and the thioesterase encoded by the isolated nucleic acid molecule has at least the level of activity of the reference thioesterase from which the sequence is derived.

In some embodiments, the recombinant or isolated nucleic acid molecule encoding an acyl-ACP thioesterase includes an amino acid sequence having at least 85% identity with the amino acid sequence from amino acid position 1 to amino acid position 361 of SEQ ID NO:51; an amino acid sequence having at least 98% identity with the amino acid sequence from amino acid position 1 to amino acid position 362 of SEQ ID NO:55; an amino acid sequence having at least 97% identity with the amino acid sequence from amino acid position 1 to amino acid position 360 of SEQ ID NO:59; an amino acid sequence having at least 90% identity with the amino acid sequence from amino acid position 1 to amino acid position 359 of SEQ ID NO:63; an amino acid sequence having at least 98% identity with the amino acid sequence from amino acid position 53 to amino acid position 410 of SEQ ID NO:65; an amino acid sequence having at least 96% identity with the amino acid sequence from amino acid position 1 to amino acid position 356 of SEQ ID NO:69; an amino acid sequence having at least 98% identity with the amino acid sequence from amino acid position 53 to amino acid position 410 of SEQ ID NO:71; an amino acid sequence having at least 96% identity with the amino acid sequence from amino acid position 1 to amino acid position 361 of SEQ ID NO:75; an amino acid sequence having at least 97% identity with the amino acid sequence from amino acid position 1 to amino acid position 360 of SEQ ID NO:79; an amino acid sequence having at least 96% identity with the amino acid sequence from amino acid position 54 to amino acid position 413 of SEQ ID NO:81; an amino acid sequence having at least 96% identity with the amino acid sequence from amino acid position 1 to amino acid position 362 of SEQ ID NO:85; an amino acid sequence having at least 96% identity with the amino acid sequence from amino acid position 1 to amino acid position 361 of SEQ ID NO:89; an amino acid sequence having at least 97% identity with the amino acid sequence from amino acid position 53 to amino acid position 394 of SEQ ID NO:91; an amino acid sequence having at least 97% identity with the amino acid sequence from amino acid position 53 to amino acid position 394 of SEQ ID NO:93; an amino acid sequence having at least 99% identity with the amino acid sequence from amino acid position 53 to amino acid position 394 of SEQ ID NO:95; an amino acid sequence having at least 92% identity with the amino acid sequence from amino acid position 1 to amino acid position 360 of SEQ ID NO:99; or an amino acid sequence having at least 98% identity with the amino acid sequence from amino acid position 53 to amino acid position 393 of SEQ ID NO:101, and has at least the level of activity of the reference thioesterase from which the encoded thioesterase sequence is derived.

In additional aspects, the invention includes a transgenic organism that carries a recombinant nucleic acid molecule encoding any of the thioesterases provided herein, such as those having at least 85%, at least 87%, at least 90%, at least 92%, at least 93%, at least 94%, at least 95%, at least 96%, at least 97%, at least 98%, or at least 99% identity with amino acid sequences of SEQ ID NO:49, SEQ ID NO:51, SEQ ID NO:53, SEQ ID NO:55, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, or SEQ ID NO:101. The transgenic organism can be, for example, a plant, a bacterium, a fungus, a chromist, an alga, or a *cyanobacterium.*

Also included in the invention is a recombinant nucleic acid molecule encoding an acyl-ACP thioesterase that includes an amino acid sequence that has at least 99% identity to the amino acid sequence from amino acid position 65 to 355 of SEQ ID NO:29, in which expression of the thioesterase in a microorganism results in at least 60%, at least 70%, at least 80%, at least 85%, at least 90%, or at least 95% of the free fatty acid isolated from the cells or culture media have a single chain length, such as a C8 chain length. In some embodiments, the thioesterase includes an amino acid sequence that has at least 99% identity to the amino acid sequence from amino acid position 65 to 355 or from amino acid position 34 to 355 of SEQ ID NO:29, SEQ ID NO:8, SEQ ID NO:12, SEQ ID NO:26, SEQ ID NO:33, SEQ ID NO:40, SEQ ID NO:43, or SEQ ID NO:45, or from amino acid position 1 to 323 of SEQ ID NO:38. In some embodiments, the thioesterase includes an amino acid sequence that has at least 99% identity to the amino acid sequence from amino acid position 1 to 355 of SEQ ID NO:29, SEQ ID NO:8, SEQ ID NO:12, SEQ ID NO:22, SEQ ID NO:26, SEQ ID NO:33, SEQ ID NO:40, SEQ ID NO:43, or SEQ ID NO:45. In some embodiments, the thioesterase includes the amino acid sequence from amino acid position 1 to position 355 of SEQ ID NO:29.

In a further aspect, the invention includes an isolated nucleic acid molecule encoding a variant of a plant acyl-ACP thioesterase having increased activity with respect to the native thioesterase it is derived from, in which the variant comprises a mutation of the amino acid corresponding to the amino acid at position 174 of SEQ ID NO:29. In preferred embodiments, expression of the variant acyl-ACP thioesterase encoded by the isolated nucleic acid molecule in a transgenic organism increases the amount of fatty acid product produced by the organism with respect to the amount produced by the organism transformed with the gene encoding the acyl-ACP thioesterase that does not include the mutation at position 174.

In some embodiments, the acyl-ACP thioesterase gene having a mutation at position 174 encodes a variant that has increased activity toward a preferred fatty acyl substrate. In some embodiments, the acyl-ACP thioesterase gene having a mutation at position 174 encodes a variant that has increased activity toward a C8 fatty acyl substrate. In preferred embodiments, the percentage of a C8 fatty acid product to the total fatty acid product produced by a transgenic organism expressing the variant thioesterase is at least 5%, at least 10%, at least 15%, at least 20%, at least 25%, at least 30%, at least 35%, at least 40%, at least 45%, at least 50%, at least 55%, at least 65%, at least 70%, at least 75%, at least 80%, at least 85%, at least 90%, or at least 95% of the total fatty acid product produced by the organism.

In some preferred embodiments, the plant acyl-ACP thioesterase is a Class II, or "FatB" acyl-ACP thioesterase. The Class II acyl-ACP thioesterase in some embodiments comprises an amino acid sequence that is at least 65% identical, at least 70% identical, at least 75% identical, at least 80% identical, at least 85% identical, at least 90% identical, or at least 95% identical to amino acids 65 to 355 of SEQ ID NO:29. In some embodiments, a mutation in a variant of a plant acyl-ACP thioesterase changes the amino acid corresponding to position 174 of SEQ ID NO:29 to an uncharged amino acid, which in some embodiments is a branched chain aliphatic amino acid. In some embodiments, the mutation changes the amino acid at position 174 to cysteine, methionine, phenylalanine, valine, leucine, or isoleucine. In some embodiments, the mutation changes a methionine at position 174 to cysteine, phenylalanine, valine, leucine, or isoleucine. In some embodiments, the variant acyl-ACP thioesterase has one, two, three, or more mutations in addition to the mutation at position 174. In an exemplary embodiment, the isolated nucleic acid molecule encodes a variant of a plant acyl-ACP thioesterase that has an isoleucine at position 103 and comprises the mutation M174I. In some embodiments, the variant acyl-ACP thioesterase has one, two, three, or more mutations in addition to the mutation at position 174.

In some embodiments, the isolated nucleic acid molecule encodes a variant of a plant acyl-ACP thioesterase, in which the variant has at least 90% identity or at least 95% identity to the amino acid sequence from amino acid position 65 to 355 of SEQ ID NO:40, SEQ ID NO:43, or SEQ ID NO:45. In exemplary embodiments the isolated nucleic acid molecule comprises a sequence encoding the amino acid sequence from position 65 to 355 of SEQ ID NO:40, SEQ ID NO:43, or SEQ ID NO:45, or from position 34 to 355 of SEQ ID NO:40, SEQ ID NO:43, or SEQ ID NO:45. The isolated nucleic acid molecule in some embodiments comprises SEQ ID NO:39, SEQ ID NO:42, or SEQ ID NO:44.

In additional aspects, the invention includes transgenic organisms that harbor recombinant nucleic acid molecules encoding acyl-ACP thioesterase variants having increased activity as described herein, in which the variants include a mutation at the amino acid position corresponding to amino acid 174 of SEQ ID NO:29. The organisms can be transformed with or carry an exogenous gene encoding a variant acyl-ACP thioesterase that has one, two, three, or more mutations in addition to the mutation at position 174. In some preferred embodiments, a transgenic organism includes an exogenous gene encoding a variant acyl-ACP thioesterase having a mutation at position 174 and an isoleucine at position 103, for example, the transgenic organism may have an isoleucine, methionine, phenylalanine, cysteine, leucine, or valine at position 174 and an isoleucine at position 103. In an exemplary embodiment, the variant thioesterase has an isoleucine at amino acid position 103 and an isoleucine at amino acid position 174. The transgenic organism can be, for example, a plant, a bacterium, a fungus, a chromist, an alga, or a *cyanobacterium*.

Also included in the invention is a method of producing a fatty acid product (including a fatty acid), in which the method includes culturing cells of an organism having an exogenous nucleic acid molecule encoding any of the Class II acyl-ACP thioesterases disclosed herein, and isolating a fatty acid product from the organism or culture medium. In some embodiments, the organism is a photosynthetic organisms, a prokaryotic organism, a fungal species, or a chromist species (e.g., a member of the Sagenista, Oomycota, Bacillariophyta, Silicoflagellata, Chrysophyta, or Xanthophyta). In some embodiments of the methods, at least 20%, at least 25%, at least 30%, at least 35%, at least 40%, at least 45%, or at least 50% of the isolated fatty acid or fatty acid product is a fatty acid or fatty acid product of a specific chain length. In some embodiments of the methods, at least 5%, at least 10%, at least 15%, at least 20%, at least 25%, at least 30%, at least 35%, at least 40%, at least 45%, or at least 50% of the isolated fatty acids or fatty acid products are fatty acids or fatty acid products of two specific chain lengths or three specific chain lengths.

The organism carrying the exogenous acyl-ACP thioesterase gene in some embodiments is a photosynthetic organism, and in some embodiments is an alga, such as a microalga, and can be a eukaryotic alga or a *cyanobacterium*, for example. The sequence encoding the thioesterase is in some embodiments codon-optimized for expression in the host organism.

The photosynthetic organism can be cultured or grown phototrophically or mixotrophically. The fatty acid or fatty acid product can be isolated from the culture medium, from cells or tissue, or from whole culture, including both the culture medium and cells of the transgenic organism. In some embodiments, the fatty acid or fatty acid product is a triglyceride. The fatty acid or fatty acid product in alternative embodiments is a free fatty acid, a fatty aldehyde, a fatty alcohol, a fatty ester (including a wax ester) or a hydrocarbon, such as an alkane or alkene. In some embodiments, the host organism also includes one or more additional transgenes that encode enzymes used in the biosynthesis of the fatty acid product, such as, for example, an acetyl-CoA carboxylase, a ketoacyl-CoA synthase, a fatty acid elongase, an acyl-CoA synthetase, a fatty acyl-CoA reductase, a fatty aldehyde reductase, an alcohol acetyl transferase, an acyl-CoA alcohol transacylase, an acyltransferase, a wax synthase, an aldehyde decarbonylase, or a fatty acid decarboxylase.

The method can be used to produce fatty acids or fatty acid products such as triglycerides, fatty aldehydes, fatty alcohols, fatty esters, hydrocarbons, or fatty acids. In some embodiments, at least 5%, at least 10%, at least 15%, at least 20%, at least 25%, at least 30%, at least 35%, or at least 40%, at least 45%, at least 50%, at least 55%, at least 60%, at least 65%, at least 70%, at least 75%, at least 80%, at least 85%, or at least 90% of the isolated fatty acids or fatty acid products are one or more of a C8, a C10, a C12, a C14, a C16, or a C18 fatty acid or fatty acid product, such as a free fatty acid or derivative thereof.

A further aspect of the invention is a method of producing a fatty acid product, in which the method includes cultivating an organism containing an exogenous nucleic acid molecule encoding a variant plant acyl-ACP thioesterase having a mutation at the amino acid position corresponding to amino acid 174 of SEQ ID NO:29, and isolating a fatty acid product from the organism or culture medium. The transgenic organism can be, for example, a bacterium or a photosynthetic organism, such as a plant, microalga, or *cyanobacterium*. In some embodiments, for example, the transgenic organism is a prokaryote, and the method comprises isolating fatty acids from the culture medium. The sequence encoding the plant acyl-ACP thioesterase is codon-optimized for expression in the organism in some preferred embodiments.

In some preferred embodiments, the organism is a microorganism, and a fatty acid or fatty acid product is isolated from the culture medium. In some preferred embodiments, at least 10% of the fatty acid product isolated from the cells or medium is a C8 fatty acid or fatty acid product, and in some preferred embodiments, at least 30%, at least 35%, least 40%, at least 45%, at least 50%, at least 55%, at least 60%, or at least 65%, at least 70%, at least 75%, at least 80%, at least 85%, least 90%, or at least 95%, of the fatty acid or fatty acid product isolated from the cells or culture medium is a C8 fatty acid or fatty acid product. In some embodiments, the fatty acid product isolated from the cells or medium of a culture of a transgenic microorganism is octanoic acid.

Included in the method are embodiments in which the host organism carries an exogenous nucleic acid molecule that encodes a variant of a naturally-occurring medium chain length acyl-ACP thioesterase having a mutation at position 174, in which the variant has enhanced activity towards a C8 acyl substrate with respect to the naturally-occurring thioesterase. In some preferred embodiments, the variant thioesterase having enhanced activity toward a C8 acyl substrate has an isoleucine residue at the amino acid position corresponding to amino acid position 174 of SEQ ID NO:29. In an exemplary embodiment, the variant thioesterase has an isoleucine at amino acid position 103 and an isoleucine at amino acid position 174. In illustrative embodiments, the variant comprises the amino acid sequence from position 65 to amino acid 355 of SEQ ID NO:40, SEQ ID NO:43, or SEQ ID NO:45.

The method can be used to produce fatty acids or fatty acid products such as triglycerides, fatty aldehydes, fatty alcohols, fatty esters, hydrocarbons, or fatty acids. In some embodiments, fatty acids are isolated, and at least 5%, at least 10%, at least 15%, at least 20%, at least 25%, at least 30%, at least 35%, or at least 40%, at least 45%, at least 50%, at least 55%, at least 60%, at least 65%, at least 70%, at least 75%, at least 80%, at least 85%, or at least 90% of the isolated fatty acid products are a C8 fatty acid or fatty acid product, such as a C8 fatty acid or derivative thereof.

BRIEF DESCRIPTION OF THE DRAWINGS

FIG. 1 provides an alignment of the deduced amino acid sequence of the wild-type *C. aequipetala* FatB2 acyl-ACP thioesterase (Ca1FatB2) from a gene assembled by PCR of genomic DNA with the removal of intron sequences (SEQ ID NO:29) and the wild-type gene in which the N-terminal sequence was extended (SEQ ID NO:22). The methionine at position 174 is underlined.

FIGS. 2A-2D are tables showing the amount of C8, C10, C12, C14, C16, and C18 fatty acids produced by bacterial isolates which had been transformed with genes encoding variants of the Ca1FatB2 gene.

FIGS. 3A-3D are tables showing the amount of C8, C10, C12, C14, C16, and C18 fatty acids produced by strains, of bacterial isolates which had been transformed with genes encoding variants of the Ca1FatB2 gene, normalized for cell density.

FIG. 5A is a table showing the amount of C8, C10, C12, C14, C16, and C18 fatty acids produced by bacterial isolates encoding variants of the Ca1FatB2 gene mutated at position 174 (isolates 81, 82, 85, and 86); at positions 174 and 103 (isolates 83 and 84), or at positions 103, 184, and 174 (isolates 79, 80, 87, 88, 89, and 90).

FIG. 5B is a table of the bacterial isolates of FIG. 5A in which the amount of C8, C10, C12, C14, C16, and C18 fatty acids produced by the strains has been normalized for cell density.

FIG. 7 is an alignment of the translated sequence of the 5' portion of the Ca1FatB2 thioesterase genes cloned in expression constructs. Amino acid positions in the aligned thioesterases corresponding to position 33/34 and position 63/64 are shown in bold.

DETAILED DESCRIPTION OF THE INVENTION

Figure 4A:
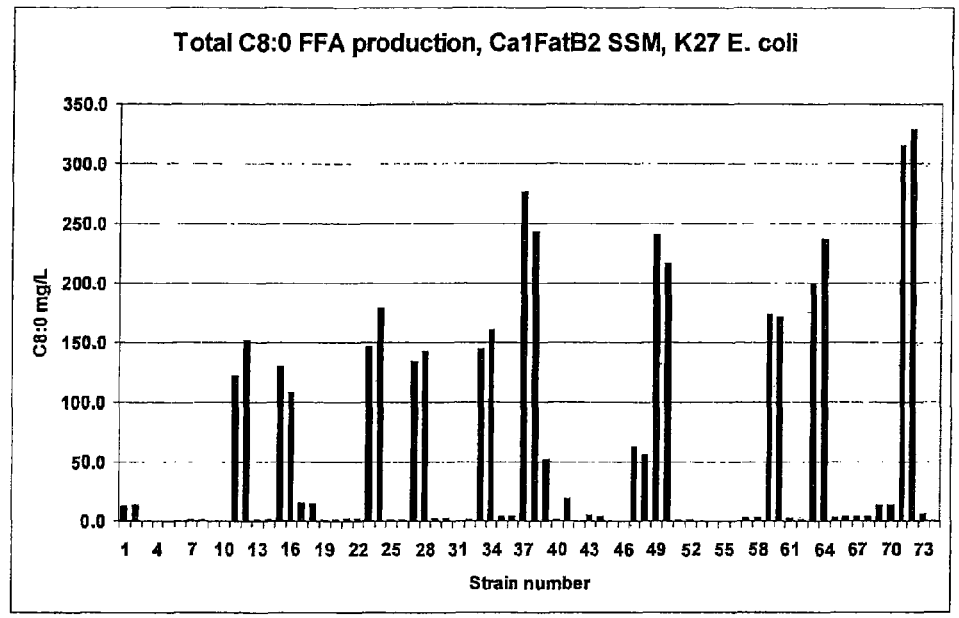
FIG. 4A depicts graphically the C8 fatty acid production of the isolates of FIGS. 2A-2D that harbor the acyl-ACP thioesterase gene mutated at position 174 (isolates 1-38) or positions 103, 184, and 174 (isolates 39-72).

Disclosed in the present application are nucleic acid molecules encoding novel plant acyl-ACP thioesterases. Such nucleic acid molecules can be used to transform organisms, such as photosynthetic organisms and prokaryotic organisms, for synthesizing fatty acids and fatty acid products such as fatty aldehydes, fatty alcohols, fatty esters, including wax esters, and hydrocarbons. Also included in the invention are organisms transformed with the nucleic acid molecules provided herein, and methods of making fatty acid products using the organisms transformed with nucleic acid molecules encoding novel acyl-ACP thioesterases.

Elements of the embodiments described herein can be combined to make additional embodiments not specifically described that are also within the scope of the invention. Headings within the application are solely for the convenience of the reader, and do not limit in any way the scope of the invention or its embodiments.

All publications and patent applications mentioned in this specification are herein incorporated by reference to the same extent as if each individual publication or patent application was specifically and individually indicated to be incorporated by reference.

Unless defined otherwise, all technical and scientific terms used herein have the same meaning as commonly understood by one of ordinary skill in the art to which this invention is related. The following terms are defined for purposes of the invention as described herein.

Accession numbers are unique identifiers for a sequence record publicly available at the National Center for Biotechnology Information internet site maintained by the United States National Institutes of Health which can be accessed at ncbi.nlm.nih.gov. The "GenInfo Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appeared in a specific GenBank record. Searching and obtaining nucleic acid or gene sequences or protein sequences based on Accession numbers and GI numbers is well known in the arts of cell biology, biochemistry, molecular biology, and molecular genetics.

The singular form "a", "an" and "the" include plural referents unless the context clearly dictates otherwise. Thus, for example, reference to "a cell" includes a plurality of cells and reference to "an antibody" includes a plurality of antibodies, etc.

As used herein, the terms "about" or "approximately" when referring to any numerical value are intended to mean a value of plus or minus 10% of the stated value. For example, "about 50 degrees C." (or "approximately 50 degrees C.") encompasses a range of temperatures from 45 degrees C. to 55 degrees C., inclusive. Similarly, "about 100 mM" (or "approximately 100 mM") encompasses a range of concentrations from 90 mM to 110 mM, inclusive. All ranges provided within the application are inclusive of the values of the upper and lower ends of the range.

An "isolated" biomolecule such as an isolated protein or nucleic acid, is a biomolecule removed from the context in which the biomolecule exist in nature. For example, an isolated protein or nucleic acid molecule is removed from the cell or organism with which it is associated in its natural state. An isolated biomolecule can be, in some instances, partially or substantially purified, for example, an isolated nucleic acid molecule can be a nucleic acid sequence that has been excised from the chromosome, genome, or episome that it is integrated into in nature.

A recombinant or "engineered" nucleic acid molecule is a nucleic acid molecule that has been altered through human manipulation. As nonlimiting examples, a recombinant nucleic acid molecule: 1) includes conjoined nucleotide sequences that are not conjoined in nature, 2) has been engineered using molecular cloning techniques such that it lacks one or more nucleotides with respect to the naturally occurring nucleic acid molecule sequence, or 3) has been manipulated using molecular cloning techniques such that it has one or more sequence changes or rearrangements with respect to the naturally occurring nucleic acid sequence. As nonlimiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

A "homolog" of a gene or protein refers to its functional equivalent in another species.

A "variant" of a gene or nucleic acid sequence is a sequence having at least 65% identity with the referenced gene or nucleic acid sequence, and can include one or more base deletions, additions, or substitutions with respect to the referenced sequence. Variants also include chimeric genes that include sequences from two or more sources. A variant can be a naturally-occurring variant or the result of a spontaneous or induced mutation. Induced mutations can be created using methods known in the art for mutagenesis of organisms or cells (for example, using gamma or UV irradiation or chemical mutagens such as 5-bromo deoxyuridine, ethyl methane sulfonate (EMS), methyl methane sulfonate (MMS), diethylsulfate (DES), nitrosoguanidine (NTG), ICR compounds, etc., or can be introduced using genetic engineering techniques, such as gene synthesis, in vivo single strand repair techniques, polymerase-based amplification at error-permissive temperature and/or polymerase-based amplification using primers that incorporate base changes.

A "variant" of a peptide or protein is a peptide or protein sequence that varies at one or more amino acid positions with respect to the reference peptide or protein. A variant can be a naturally-occurring variant or can be the result of spontaneous, induced, or genetically engineered mutation(s) to the nucleic acid molecule encoding the variant peptide or protein. A variant peptide can also be a chemically synthesized variant.

As used herein "thioesterase" includes wild-type thioesterase proteins as well as variants thereof, and "thioesterase gene" refers to any nucleotide sequence encoding a thioesterase, which can be a wild-type thioesterase or a variant thioesterase.

"Exogenous" in the context of a gene or protein is a gene or protein that is not derived from the host organism species.

A "heterologous" gene or nucleic acid sequence is a gene or sequence from a different source than the host organism it is introduced into, or from a different source than another nucleic acid sequence with which is juxtaposed in a nucleic acid construct. For example, a gene of one species introduced into another species may be referred to as a heterologous gene. A promoter linked to a gene not operably linked to the promoter in its natural state in the organism may be referred to as a heterologous promoter.

A gene that is "codon-optimized" for expression in an organism is a gene whose nucleotide sequence has been altered with respect to the original nucleotide sequence, such that one or more codons of the nucleotide sequence has been changed to a different codon that encodes the same amino acid, in which the new codon is used more frequently in genes of the organism of interest than the original codon. The degeneracy of the genetic code provides that all amino acids except for methionine and tryptophan are encoded by more than one codon. For example, arginine, leucine, and serine are encoded by different six different codons; glycine, alanine, valine, threonine, and proline are encoded by four different codons. Many organisms use certain codons to encode a particular amino acid more frequently than others. Without limiting any aspects of the invention to any particular mechanism, it is believed that some tRNAs for a given amino acid are more prevalent than others within a particular organism, and genes requiring a rare tRNA for translation of the encoded protein may be expressed at a low level due in part to a limiting amount of the rare tRNA. Thus, for adequate or optimal levels of expression of an encoded protein, a gene may be "codon-optimized" to change one or more codons to new codons ("preferred codons") that are among those used more frequently in the genes of the host organism (referred to as the "codon preference" of the organism). As used in the context of the invention, a "codon-optimized" gene or nucleic acid molecule of the invention need not have every codon altered to conform to the codon preference of the intended host organism, nor is it required that altered codons of a "codon-optimized" gene or nucleic acid molecule be changed to the most prevalent codon used by the organism of interest. For example, a codon-optimized gene may have one or more codons changed to codons that are used more frequently that the original codon(s), whether or not they are used most frequently in the organism to encode a particular amino acid.

"Photosynthetic organisms" are any prokaryotic or eukaryotic organisms that can perform photosynthesis. Photosynthetic organisms include higher plants (i.e., vascular plants), *bryophytes*, algae, and photosynthetic bacteria. The term "algae" includes cyanobacteria (Cyanophyceae), green algae (Chlorophyceae), yellow-green algae (Xanthophyceae), golden algae (Chrysophyceae), brown algae (Phaeophyceae), red algae (Rhodophyceae), diatoms (Bacillariophyceae), and "pico-plankton" (Prasinophyceae and Eustigmatophyceae). Also included in the term algae are members of the taxonomic classes Dinophyceae, Cryptophyceae, Euglenophyceae, Glaucophyceae, and Prymnesiophyceae. Microalgae are unicellular or colonial algae that can be seen as single organisms only with the aid of a microscope. Microalgae include both eukaryotic and prokaryotic algae (e.g., cyanobacteria). Photosynthetic bacteria include cyanobacteria, green sulfur bacteria, purple sulfur bacteria, purple nonsulfur bacteria, and green nonsulfur bacteria.

A "plant acyl-ACP thioesterase" is an acyl-ACP thioesterase derived from a plant species, which includes species of higher plants, ferns, and mosses, for example, *bryophyte, pteridophyte, cycadophyte, ginkgophyte, pinophyte, gnetophyte*, and *magnoliophyte* species.

A "fatty acid product" includes a fatty acid, a fatty aldehyde, a fatty alcohol, a fatty ester (including a wax ester), a triglyceride, a hydrocarbon, or any other fatty acid derivatives.

A "C8 fatty acid" or a "C8 fatty acid product" is a fatty acid or a fatty acid product having an acyl chain of 8 carbons. An example of a saturated C8 fatty acid is octanoic acid, also called caprylic acid.

A "C10 fatty acid" or a "C10 fatty acid product" is a fatty acid or a fatty acid product having an acyl chain of 10 carbons. An example of a C10 fatty acid is decanoic acid, also known as capric acid.

A "C12 fatty acid" or a "C12 fatty acid product" is a fatty acid or a fatty acid product having an acyl chain of 12 carbons. An example of a C12 fatty acid is dodecanoic acid, also known as lauric acid.

A "C14 fatty acid" or a "C14 fatty acid product" is a fatty acid or a fatty acid product having an acyl chain of 14 carbons. An example of a C14 fatty acid is tetradecanoic acid, also known as myristic acid.

A "C16 fatty acid" or a "C16 fatty acid product" is a fatty acid or a fatty acid product having an acyl chain of 16 carbons. An example of a C14 fatty acid is hexadecanoic acid, also known as palmitic acid.

A "C18 fatty acid" or a "C18 fatty acid product" is a fatty acid or a fatty acid product having an acyl chain of 18 carbons. An example of a C18 fatty acid is octadecanoic acid, also known as stearic acid.

A "C8 preferring" acyl-ACP thioesterase is an acyl-ACP thioesterase having higher activity on a C8 acyl-ACP substrate (e.g., octanoyl-ACP) than on any other chain length substrate. Analogously, a "C10 preferring" acyl-ACP thioesterase is an acyl-ACP thioesterase having higher activity on a C10 acyl-ACP substrate (e.g., decanoyl-ACP) than on any other chain length substrate, a "C12 preferring" acyl-ACP thioesterase is an acyl-ACP thioesterase having higher activity on a C12 acyl-ACP substrate (e.g., dodecanoyl-ACP) than on any other chain length substrate, a "C14 preferring" acyl-ACP thioesterase is an acyl-ACP thioesterase having higher activity on a C14 acyl-ACP substrate (e.g., tetradecanoyl-ACP) than on any other chain length substrate, a "C16 preferring" acyl-ACP thioesterase is an acyl-ACP thioesterase having higher activity on a C16 acyl-ACP substrate (e.g., hexadecanoyl-ACP) than on any other chain length substrate, and a "C18 preferring" acyl-ACP thioesterase is an acyl-ACP thioesterase having higher activity on a C18 acyl-ACP substrate (e.g., octadecanoyl-ACP) than on any other chain length substrate.

An acyl-ACP thioesterase with "binary activity" is a thioesterase that has a preference for one or more medium chain length acyl-ACP substrates as well as a preference for one or more long chain length acyl-ACP substrates.

A "medium chain length" fatty acid or fatty acid product is a fatty acid or fatty acid product having an acyl chain length of from 8-14 carbons.

A "long chain length" fatty acid or fatty acid product is a fatty acid or fatty acid product having an acyl chain length of greater than 14 carbons.

The degree of amino acid or nucleic acid sequence identity can be determined by various computer programs for aligning the sequences to be compared based on designated program parameters. For example, sequences can be aligned and compared using the local homology algorithm of Smith & Waterman, *Adv. Appl. Math.* 2:482 (1981), the homology alignment algorithm of Needleman & Wunsch, *J. Mol. Biol.* 48:443 (1970), or the search for similarity method of Pearson & Lipman, *Proc. Nat'l. Acad. Sci. USA* 85:2444 (1988), and can be aligned and compared based on visual inspection or can use computer programs for the analysis (for example, GAP, BESTFIT, FASTA, and TFASTA in the Wisconsin Genetics Software Package, Genetics Computer Group, 575 Science Dr., Madison, Wis.).

The BLAST algorithm, described in Altschul et al., *J. Mol. Biol.* 215:403-410 (1990), is publicly available through software provided by the National Center for Biotechnology Information (at the web address www.ncbi.nlm.nih.gov). This algorithm identifies high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra.). Initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below due to the accumulation of one or more negative-scoring residue alignments; or the end of either sequence is reached. For determining the percent identity of an amino acid sequence or nucleic acid sequence, the default parameters of the BLAST programs can be used. For analysis of amino acid sequences, the BLASTP defaults are: word length (W), 3; expectation (E), 10; and the BLOSUM62 scoring matrix. For analysis of nucleic acid sequences, the BLASTN program defaults are word length (W), 11; expectation (E), 10; M=5; N=−4; and a comparison of both strands. The TBLASTN program (using a protein sequence to query nucleotide sequence databases) uses as defaults a word length (W) of 3, an expectation (E) of 10, and a BLOSUM 62 scoring matrix. (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). The smallest sum probability (P(N)), provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, preferably less than about 0.01, and more preferably less than about 0.001.

Nucleic Acid Molecules Encoding Class II Thioesterases

Provided herein are new thioesterase FatB genes from various *Cuphea* species. As detailed in the examples, the native or wild-type FatB genes Ca1FatB2 (SEQ ID NO:21), Cc1FatB1 (SEQ ID NO:48), Ca1FatB1 (SEQ ID NO:52), Ci1FatB1 (SEQ ID NO:56), Cl1FatB1 (SEQ ID NO:60), Cl1FatB2 (SEQ ID NO:64), Cp1FatB1 (SEQ ID NO:66), Cl2FatB1 (SEQ ID NO:70), Cl2FatB2 (SEQ ID NO:72), Cl3FatB1 (SEQ ID NO:76), Cl3FatB2 (SEQ ID NO:80), Cd1FatB1 (SEQ ID NO:82), Cl4FatB1 (SEQ ID NO:86), Cl4FatB2 (SEQ ID NO:90), Cl4FatB3 (SEQ ID NO:92), Ca2FatB1 (SEQ ID NO:94), Ca2FatB2 (SEQ ID NO:96), and Ca2FatB3 (SEQ ID NO:100), have been reconstructed using primer-based amplification (i.e., polymerase chain reaction, or PCR) and gene walking such that, based on homology with other plant thioesterases, it is estimated that all of the protein-encoding sequence except for sequences encoding approximately ten to fifteen amino acids of the N-terminuses have been determined. The deduced amino acid sequences of the encoded proteins are provided as SEQ ID NO:22 (Ca1FatB2), SEQ ID NO:49 (Cc1FatB1), SEQ ID NO:53 (Ca1FatB1), SEQ ID NO:57 (Ci1FatB1), SEQ ID NO:61 (Cl1FatB1), SEQ ID NO:65 (Cl1FatB2), SEQ ID NO:67 (Cp1FatB), SEQ ID NO:71 (Cl2FatB1), SEQ ID NO:73 (Cl2FatB2), SEQ ID NO:77 (Cl3FatB1), SEQ ID NO:81 (Cl3FatB2), SEQ ID NO:83 (Cd1FatB1), SEQ ID NO:87 (Cl4FatB1), SEQ ID NO:91 (Cl4FatB2), SEQ ID NO:93 (Cl4FatB3), SEQ ID NO:95 (Ca2FatB1), SEQ ID NO:97 (Ca2FatB2), and SEQ ID NO:101 (Ca2FatB3). Protein-encoding sequences of gene constructs for the expression of thioesterases based on some of these genes and the deduced amino acid sequences are provided in Table 4. The nucleotide and amino acid sequences disclosed herein are reference sequences when referring to variants based on those sequences. A reference thioesterase is a thioesterase having the sequence of the reference sequence.

The invention includes isolated or recombinant nucleic acid molecules encoding Class II thioesterases having at least at least 85%, at least 90%, at least 95%, or at least 99% identity with the amino acid sequence from amino acid position 1 to amino acid position 361 of SEQ ID NO:51; an amino acid sequence having at least 98% identity with the amino acid sequence from amino acid position 1 to amino acid position 362 of SEQ ID NO:55; an amino acid sequence having at least 97% identity with the amino acid sequence from amino acid position 1 to amino acid position 360 of SEQ ID NO:59; an amino acid sequence having at least 90% identity with the amino acid sequence from amino acid position 1 to amino acid position 359 of SEQ ID NO:63; an amino acid sequence having at least 98% identity with the amino acid sequence from amino acid position 53 to amino acid position 410 of SEQ ID NO:65; an amino acid sequence having at least 96% identity with the amino acid sequence from amino acid position 1 to amino acid position 356 of SEQ ID NO:69; an amino acid sequence having at least 98% identity with the amino acid sequence from amino acid position 53 to amino acid position 410 of SEQ ID NO:71; an amino acid sequence having at least 96% identity with the amino acid sequence from amino acid position 1 to amino acid position 361 of SEQ ID NO:75; an amino acid sequence having at least 97% identity with the amino acid sequence from amino acid position 1 to amino acid position 360 of SEQ ID NO:79; an amino acid sequence having at least 96% identity with the amino acid sequence from amino acid position 54 to amino acid position 413 of SEQ ID NO:81; an amino acid sequence having at least 96% identity with the amino acid sequence from amino acid position 1 to amino acid position 362 of SEQ ID NO:85; an amino acid sequence having at least 96% identity with the amino acid sequence from amino acid position 1 to amino acid position 361 of SEQ ID NO:89; an amino acid sequence having at least 97% identity with the amino acid sequence from amino acid position 53 to amino acid position 394 of SEQ ID NO:91; an amino acid sequence having at least 97% identity with the amino acid sequence from amino acid position 53 to amino acid position 394 of SEQ ID NO:93; an amino acid sequence having at least 99% identity with the amino acid sequence from amino acid position 53 to amino acid position 394 of SEQ ID NO:95; an amino acid sequence having at least 92% identity with the amino acid sequence from amino acid position 1 to amino acid position 360 of SEQ ID NO:99; or an amino acid sequence having at least 98% identity with the amino acid sequence from amino acid position 53 to amino acid position 393 of SEQ ID NO:101, in which the expressed protein encoded by the nucleic acid molecule has thioesterase activity. In some embodiments, the expressed thioesterase has at least the level of activity against an acyl-ACP substrate as the reference thioesterase from which the encoded thioesterase sequence is derived.

Also contemplated are nucleic acid molecules encoding acyl-ACP thioesterases with mature polypeptide sequences having at least 85%, 87%, 90%, 92%, 93%, 94%, 95%, 96%, 97%, 98%, or 99% identity to the sequences of a mature thioesterase as disclosed herein, in which the thioesterases have N-terminal sequences that differ from the wild-type thioesterases from which they are derived. Thioesterase genes from plants such as *Cuphea* encode transit peptides. The cleavage site for removal of the transit peptide upon import of thioesterases into chloroplasts is hypothesized to be between positions 33 and 34 of SEQ ID NO:29 (Mayer and Shanklin BMC Plant Biology 7:1 (2007); see FIG. 1 and FIG. 7). As the transit peptide of plant thioesterases for import of the enzymes into plastids is not necessary for the activity of a thioesterase expressed in a prokaryotic organism, in many embodiments thioesterase genes designed for expression in prokaryotes, as exemplified in the Examples herein, do not encode all or a portion of a transit peptide.

In some embodiments, the recombinant or isolated nucleic acid molecule encoding an acyl-ACP thioesterase includes an amino acid sequence having at least 85%, at least 90%, at least 95%, or at least 99% identity with the amino acid sequence from amino acid position 33 to amino acid position 361 of SEQ ID NO:51; having at least 98% identity with the amino acid sequence from amino acid position 35 to amino acid position 362 of SEQ ID NO:55; having at least 97% identity with the amino acid sequence from amino acid position 34 to amino acid position 360 of SEQ ID NO:59; having at least 90% identity with the amino acid sequence from amino acid position 34 to amino acid position 359 of SEQ ID NO:63; having at least 98% identity with the amino acid sequence from amino acid position 84 to amino acid position 410 of SEQ ID NO:65; having at least 96% identity with the amino acid sequence from amino acid position 34 to amino acid position 356 of SEQ ID NO:69; having at least 98% identity with the amino acid sequence from amino acid position 84 to amino acid position 410 of SEQ ID NO:71; having at least 96% identity with the amino acid sequence from amino acid position 33 to amino acid position 361 of SEQ ID NO:75; having at least 97% identity with the amino acid sequence from amino acid position 34 to amino acid position 360 of SEQ ID NO:79; having at least 96% identity with the amino acid sequence from amino acid position 85 to amino acid position 413 of SEQ ID NO:81; having at least 96% identity with the amino acid sequence from amino acid position 34 to amino acid position 362 of SEQ ID NO:85; having at least 96% identity with the amino acid sequence from amino acid position 33 to amino acid position 361 of SEQ ID NO:89; having at least 97% identity with the amino acid sequence from amino acid position 84 to amino acid position 394 of SEQ ID NO:91; having at least 97% identity with the amino acid sequence from amino acid position 84 to amino acid position 394 of SEQ ID NO:93; having at least 99% identity with the amino acid sequence from amino acid position 84 to amino acid position 394 of SEQ ID NO:95; having at least 92% identity with the amino acid sequence from amino acid position 33 to amino acid position 360 of SEQ ID NO:99; or having at least 98% identity with the amino acid sequence from amino acid position 84 to amino acid position 393 of SEQ ID NO:101, and has at least the level of activity of the reference thioesterase from which the encoded thioesterase sequence is derived. In some embodiments, the encoded thioesterase shares at least 85%, at least 90%, at least 92%, at least 95%, at least 96%, at least 97%, at least 98%, at least 99%, or at least 99.5% identity with the above provided amino acid sequences, and the thioesterase encoded by the isolated nucleic acid molecule has at least the level of activity of the reference thioesterase from which the sequence is derived.

In some embodiments of the invention, a nucleic acid molecule may encode acyl-ACP thioesterases having a transit peptide sequence derived from one or more different acyl-ACP thioesterases, or from one or more proteins other than thioesterases that are imported into plastids. For example, in some embodiments in which a thioesterase gene is transformed into a eukaryotic photosynthetic organism for the production of a fatty acid product, the acyl-ACP thioesterase gene can encode a thioesterase that is at least 85%, at least 90%, at least 92%, at least 95%, at least 96%, at least 97%, at least 98%, at least 99%, or at least 99.5% identical to a thioesterase disclosed herein, while optionally including a sequence encoding any functional plastid transit peptide, such as a chloroplast transit peptide having an amino acid sequence that is less than 95% identical, less than 90% identical, less than 80% identical, less than 70% identical, less than 60% identical, less than 50% identical, less than 40% identical, less than 30% identical or less than 20% identical to sequences of the reference thioesterase precursor transit peptide. The transit peptide operably linked to the mature acyl-ACP thioesterase protein is in some embodiments from a chloroplast-directed protein from the species to be used as a transgenic host in the methods of the invention.

Furthermore, plant Class II thioesterases having deletions of the N-terminal amino acids extending to and including the amino acid corresponding to amino acid 65 of SEQ ID NO:29 (see FIG. 7), in which the thioesterase encoded by the isolated nucleic acid molecule has thioesterase activity. In preferred embodiments the encoded thioesterase has at least the level of activity as the reference thioesterase.

The invention includes, in exemplary embodiments, nucleic acid molecules encoding a thioesterase comprising an amino acid sequences having at least 96% identity to the amino acid sequence of SEQ ID NO:75, or from amino acid 64 to amino acid 361 of SEQ ID NO:75; or at least 92% identity to the amino acid sequence of SEQ ID NO:99 or from amino acid 64 to amino acid 361 of SEQ ID NO:99, in which the encoded thioesterase has a C10 acyl substrate preference, a C16 acyl substrate preference, or a binary preference for C10 and C16 acyl substrates. In illustrative examples expression of nucleic acid molecules encoding a thioesterase in a transgenic prokaryotic organism results in at least 20%, at least 30%, at least 35%, at least 40%, at least 45%, at least 50%, or at least 60% of the free fatty acids produced by or isolated from the prokaryotic organism being C10 and/or C16 fatty acids. In some embodiments, a nucleic acid molecule has at least 96% identity to the amino acid sequence of SEQ ID NO:75, or from amino acid 64 to amino acid 361 of SEQ ID NO:75; or at least 92% identity to the amino acid sequence of SEQ ID NO:99 or from amino acid 64 to amino acid 361 of SEQ ID NO:99, and expression of the thioesterase in a transgenic photosynthetic organism results in at least 20%, at least 30%, or at least 40%, of the free fatty acids produced by or isolated from the prokaryotic organism being C10 fatty acids.

In some embodiments, a nucleic acid molecule encodes a thioesterase having binary substrate preference, for example, the encoded thioesterase having at least 96% identity to SEQ ID NO:75 or at least 92% identity to SEQ ID NO:99, or a portion thereof, in some embodiments has a preference for one or more C10 substrates and one or more C16 substrates.

In another example, the invention includes nucleic acid molecules encoding a thioesterase comprising an amino acid sequences having at least 92% identity to from amino acid 63 to amino acid 360 of SEQ ID NO:99 or at least 99% identity to from amino acid 65 to amino acid 360 of SEQ ID NO:29, and the encoded thioesterase has a C8 acyl substrate preference. In some embodiments, a nucleic acid molecule encodes a thioesterase comprising an amino acid sequences having at least 92% identity to from amino acid 63 to amino acid 360 of SEQ ID NO:95 and expression of the thioesterase in a transgenic prokaryotic organism results in at least 20%, at least 30%, at least 35%, at least 40%, at least 45%, or at least 50% of the free fatty acids produced by or isolated from the prokaryotic organism being C8 and/or C10 fatty acids. In some embodiments, a nucleic acid molecule has at least 92% identity to from amino acid 63 to amino acid 360 of SEQ ID NO:99 or at least 99% identity to from amino acid 65 to amino acid 360 of SEQ ID NO:29, and expression of the thioesterase in a transgenic photosynthetic organism results in at least 20%, at least 30%, at least 35%, at least 40%, at least 45%, or at least 50% of the free fatty acids produced by or isolated from the prokaryotic organism being C8 fatty acids.

In other examples, the invention includes nucleic acid molecules encoding a thioesterase comprising an amino acid sequences having at least 85%, at least 90%, at least 92%, at least 95%, or at least 99% identity with the amino acid sequence from amino acid position 64 to amino acid position 361 of SEQ ID NO:51; at least 98% identity with the amino acid sequence from amino acid position 66 to amino acid position 362 of SEQ ID NO:55; at least 97% identity with the amino acid sequence from amino acid position 65 to amino acid position 360 of SEQ ID NO:59; at least 90% identity with the amino acid sequence from amino acid position 65 to amino acid position 359 of SEQ ID NO:63; at least 98% identity with the amino acid sequence from amino acid position 115 to amino acid position 410 of SEQ ID NO:65; at least 96% identity with the amino acid sequence from amino acid position 65 to amino acid position 356 of SEQ ID NO:69; at least 98% identity with the amino acid sequence from amino acid position 115 to amino acid position 410 of SEQ ID NO:71; at least 96% identity with the amino acid sequence from amino acid position 64 to amino acid position 361 of SEQ ID NO:75; at least 97% identity with the amino acid sequence from amino acid position 65 to amino acid position 360 of SEQ ID NO:79; at least 96% identity with the amino acid sequence from amino acid position 116 to amino acid position 413 of SEQ ID NO:81; at least 96% identity with the amino acid sequence from amino acid position 65 to amino acid position 362 of SEQ ID NO:85; at least 96% identity with the amino acid sequence from amino acid position 64 to amino acid position 361 of SEQ ID NO:89; at least 97% identity with the amino acid sequence from amino acid position 115 to amino acid position 394 of SEQ ID NO:91; at least 97% identity with the amino acid sequence from amino acid position 115 to amino acid position 394 of SEQ ID NO:93; at least 99% identity with the amino acid sequence from amino acid position 115 to amino acid position 394 of SEQ ID NO:95; at least 92% identity with the amino acid sequence from amino acid position 63 to amino acid position 360 of SEQ ID NO:99; or at least 98% identity with the amino acid sequence from amino acid position 115 to amino acid position 393 of SEQ ID NO:101, in which the encoded thioesterase has a C12, C14, and/or C16 acyl substrate preference. In some examples, the encoded acyl-ACP thioesterase has a C14 and/or C16 substrate preference. In illustrative examples expression of nucleic acid molecules encoding a thioesterase in a transgenic prokaryotic organism results in at least 20%, at least 30%, at least 35%, at least 40%, at least 45%, at least 50%, or at least 60% of the free fatty acids produced by or isolated from the prokaryotic organism being C12, C14 and/or C16 fatty acids.

An acyl-ACP thioesterase, such any of those disclosed herein, can be tested for its ability to direct synthesis of fatty acids or fatty acid products that are produced by transgenic organisms transformed with the nucleic acid molecules. Provided in the examples are descriptions of transforming host organisms with recombinant nucleic acid molecules encoding acyl-ACP thioesterases and recovering fatty acid products to determine the amount of fatty acid products of different chain lengths produced by the transgenic host.

Assays of a thioesterase can also be performed using lysates of transgenic organisms such as *E. coli* that are transformed with expression constructs that include the acyl-ACP thioesterase gene. Such assays can use labeled acyl substrates (see, for example, U.S. Pat. No. 5,667,997, incorporated herein by reference). An acyl-ACP thioesterase can also be partially or substantially purified prior to performing an assay; for example, the thioesterase can be expressed with an affinity tag (for example, a His tag) for affinity purification prior to performing the assay (Dehesh et al. *Plant Physiol* 110: 203-210 (1996), incorporated herein by reference).

The nucleic acid molecules encoding acyl-ACP thioesterases can be used to transform prokaryotic organisms or photosynthetic organisms, such as plants or algae, for the production of fatty acid products in the organisms. In some preferred embodiments, the sequence encoding the Class II thioesterase is codon-optimized for expression in the host organism. Codons can be optimized by methods such as those provided in U.S. Pat. No. 7,135,290, incorporated herein by reference. A codon usage database is available at the world wide web site kazusa.or.jp/codon/. Preferred codon usage can also be determined by a practitioner based on gene sequences entered in databases such as Genbank (ncbi.nlm.nih.gov/GenBank/), or a subset of genes of the organism (for example, highly expressed genes).

In some embodiments, the transgenic organism that includes a thioesterase gene of the invention is a bacterium, such as, but not limited to, an *Acetobacter, Acinetobacter, Arthrobacter, Bacillus, Brevibacterium, Chromatium, Chlorobium, Clostridium, Corynebacterium, Deinococcus, Delftia, Desulfovibrio, Enterococcus, Escherichia, Kineococcus, Klebsiella, Lactobacillus, Lactococcus, Micrococcus, Mycobacterium, Jeotgalicoccus, Paenibacillus, Propionibacter, Pseudomonas, Rhodopseudomonas, Rhodobacter, Rhodococcus, Rhodospirillium, Rhodomicrobium, Salmonella, Serratia, Shewanella, Stenotrophomonas, Streptomyces, Streptococcus, Vibrio,* or *Zymomonas* species.

A photosynthetic organism transformed with the nucleic acid molecule that encodes a thioesterase gene can be a plant, such as but not limited to a higher plant, or can be an alga. Higher plants considered for use in the invention include, without limitation, *Arabidopsis thaliana, Arachis hypogaea, Avena sativa, Brassica* species (e.g., *Brassica napus, Brassica campestris, Brassica juncea*), *Camelina sativa, Carthamus tinctorius, Cocos nucifera, Crambe abyssinica, Cuphea* species, *Elaeis* species (e.g., *Elaeis guineensis, Elaeis oleifera*), *Gossypium hirsutum, Glycine max, Helianthus annuulus, Jatropha* species, *Cucurbita pepo, Oryza satvia, Sesamum indicum, Simmondsia chinensis, Theobroma cacao, Ricinus communis,* and *Zea mays*.

Algae that can be used in the methods of the invention can be any algae, and can include microalgae, such as but not limited to, *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Platymonas, Pleurochrysis, Pleurococcus, Prototheca, Pseudochlorella, Pyramimonas, Pyrobotrys, Scenedesmus, Schizochytrium, Skeletonema, Spyrogyra, Stichococcus, Tetraselmis, Thraustochytrium, Viridiella,* or *Volvox* species.

In some embodiments, photosynthetic bacteria, including for example, green sulfur bacteria, purple sulfur bacteria, green nonsulfur bacteria, purple nonsulfur bacteria, or cyanobacteria are used for producing a fatty acid product. Cyanobacterial species that can be used for production of fatty acid products include, without limitation, *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema,* or *Xenococcus* species.

In addition to photosynthetic microorganisms, non-photosynthetic microorganisms such as fungi, and nonalgal stamenophiles can be transformed with one or more thioesterase genes as disclosed herein for producing fatty acid products. For example, oleaginous yeasts, including but not limited to *Aspergillus niger, Yarrowia lypolytica, Cryptococcus curvatus, Cryptococcus terricolus, Candida* species, *Lipomyces starkeyi, Lipomyces lipofer, Endomycopsis vernalis, Rhodotorula glutinis*, and *Rhodotorula gracilis* can also be hosts transformed with thioesterase genes as disclosed herein. Other fungi, including but not limited to species of *Aspergillus, Trichoderma, Neurospora, Fusarium, Humicola, Rhizomucor, Kluyveromyces, Pichia, Mucor, Myceliophtora, Penicillium, Phanerochaete, Chrysosporium, Saccharomyces*, and *Schizosaccharomyces*, are also considered as transgenic hosts expressing thioesterase genes as disclosed herein for use in making fatty acid products. *Labyrinthulomycete* species (e.g., *Thraustichytrium, Ulkenia*, and *Schizochytrium* species) can also be transformed with a thioesterase gene in the practice of the invention.

Production of Fatty Acid Products

In another aspect, the invention provides a method of producing a fatty acid or a fatty acid product, in which the method includes cultivating an organism having an exogenous nucleic acid molecule that includes a sequence encoding an acyl-ACP thioesterase as disclosed herein, and isolating a fatty acid or a fatty acid product from the organism or culture medium. The transgenic host organism can be a bacterium, alga, cyanobacterium, or plant as provided herein, and the sequence encoding the plant acyl-ACP thioesterase in some embodiments is codon-optimized for expression in the host organism.

The methods can be used for the production and isolation of a fatty acid product such as a triglyceride, a fatty aldehyde, a fatty alcohol, a fatty ester, or a hydrocarbon such as an alkene or alkane. In some embodiments, the methods include isolation of fatty acid products that include one or more of a C8, C10, C12, C14, C16, or C18 fatty acid product. In some embodiments, the methods include isolation of fatty acid products that include one or more of a C8 or C10 fatty acid product. In some exemplary embodiments, one or more fatty acids (free fatty acids) are isolated using the methods of the invention, such as, for example, one or more of a C8 fatty acid or a C10 fatty acid.

In some preferred embodiments expression of an acyl-ACP thioesterase gene as provided herein in a transgenic organism results in at least 20%, at least 25%, at least 30%, at least 35%, at least 40%, or at least 45%, at least 50%, at least 55%, at least 60%, at least 65%, at least 70%, at least 75%, at least 80%, at least 85%, at least 90%, or at least 95% of the isolated fatty acid products isolated from the organism and/or culture medium being a single chain length fatty acid product. For example, in some embodiments, at least 20%, at least 25%, at least 30%, at least 35%, at least 40%, or at least 45%, at least 50%, at least 55%, at least 60%, at least 65%, at least 70%, at least 75%, at least 80%, at least 85%, at least 90%, or at least 95% of the isolated fatty acid products from an organism expressing an exogenous acyl-ACP thioesterase of the invention is a C8, a C10, a C12, a C14, a C16, or a C18 fatty acid product. In some preferred embodiments, the isolated fatty acid products are fatty acids, and at least 20%, at least 25%, at least 30%, at least 35%, at least 40%, or at least 45%, at least 50%, at least 55%, at least 60%, at least 65%, at least 70%, at least 75%, at least 80%, at least 85%, at least 90%, or at least 95% of the fatty acids isolated from the organism and/or the growth medium is a C8 or a C10 free fatty acid.

In some embodiments, at least 20%, at least 25%, at least 30%, at least 35%, at least 40%, or at least 45%, at least 50%, at least 55%, at least 60%, at least 65%, at least 70%, at least 75%, at least 80%, at least 85%, at least 90%, or at least 95% of the isolated fatty acid products from an organism expressing an exogenous acyl-ACP thioesterase of the invention are fatty acid products or two or more chain lengths, such as two or more of a C8, a C10, a C12, a C14, a C16, or a C18 fatty acid product. In some preferred embodiments, the fatty acid products are fatty acids, and at least 20%, at least 25%, at least 30%, at least 35%, at least 40%, or at least 45%, at least 50%, at least 55%, at least 60%, at least 65%, at least 70%, at least 75%, at least 80%, at least 85%, at least 90%, or at least 95% of the fatty acids isolated from the organism and/or the growth medium are fatty acids of a specific chain length, such as two or more of C8, C10, C12, C14, C16, or C18 fatty acids.

In some embodiments, at least 20%, at least 25%, at least 30%, at least 35%, at least 40%, or at least 45%, at least 50%, at least 55%, at least 60%, at least 65%, at least 70%, at least 75%, at least 80%, at least 85%, at least 90%, or at least 95% of the isolated fatty acid products from an organism expressing an exogenous acyl-ACP thioesterase of the invention are fatty acid products or two or more chain lengths, such as two or more of a C12, a C14, a C16, or a C18 fatty acid product. In some preferred embodiments, the fatty acid products are fatty acids, and at least 20%, at least 25%, at least 30%, at least 35%, at least 40%, or at least 45%, at least 50%, at least 55%, at least 60%, at least 65%, at least 70%, at least 75%, at least 80%, at least 85%, at least 90%, or at least 95% of the fatty acids isolated from the organism and/or the growth medium are fatty acids of a specific chain length, such as two or more of C12, C14, C16, or C18 fatty acids. In some preferred embodiments, the fatty acid products are fatty acids, and at least 20%, at least 25%, at least 30%, at least 35%, at least 40%, or at least 45%, at least 50%, at least 55%, at least 60%, at least 65%, at least 70%, at least 75%, at least 80%, at least 85%, at least 90%, or at least 95% of the fatty acids isolated from the organism and/or the growth medium are fatty acids of a specific chain length, such as C14 and C16 fatty acids.

Nucleic acid molecules used in the methods of the invention include those disclosed herein.

In some embodiments of the invention, the transgenic organism is transformed with a nucleic acid molecule that encodes a thioesterase having 96% or greater identity with amino acids 64 to 361 of SEQ ID NO:75 or 92% or greater identity with amino acids 64 to 361 of SEQ ID NO:99, and at least 20%, at least 25%, at least 30%, at least 35%, at least 40%, or at least 45%, at least 50%, at least 55%, at least 60%, at least 65%, at least 70%, at least 75%, at least 80%, at least 85%, at least 90%, or at least 95% of the fatty acid products isolated from the transgenic organism and/or medium from culturing of a transgenic organism are C10 fatty acid products, such as but not limited to a C10 fatty acid, C10 fatty aldehyde, or C10 fatty alcohol, or a wax ester, alkene, or alkane.

In some embodiments of the invention, the transgenic organism is transformed with a nucleic acid molecule that encodes a thioesterase having 96% or greater identity with amino acids 64 to 361 of SEQ ID NO:75, or to amino acids 64 to 361 of SEQ ID NO:99, and at least 20%, at least 25%, at least 30%, at least 35%, at least 40%, or at least 45%, at least 50%, at least 55%, at least 60%, at least 65%, at least 70%, at least 75%, at least 80%, at least 85%, at least 90%, or at least 95% of the fatty acid products isolated from the transgenic organism and/or medium from culturing of a transgenic organism are C16 fatty acid products, such as but not limited to a C16 fatty acid, C16 fatty aldehyde, or C16 fatty alcohol, or a wax ester, alkene, or alkane.

In some examples, a transgenic organism is transformed with a nucleic acid molecule that encodes a thioesterase having 92% or greater identity with amino acid 63 to amino acid 360 of SEQ ID NO:99, and at least 20%, at least 25%, at least 30%, at least 35%, at least 40%, or at least 45%, at least 50%, at least 55%, at least 60%, at least 65%, at least 70%, at least 75%, at least 80%, at least 85%, at least 90%, or at least 95% of the isolated fatty acid products are a C8 and/or a C10 fatty acid product. In some examples, a transgenic organism is transformed with a nucleic acid molecule that encodes a thioesterase having 92% or greater identity with amino acid 63 to amino acid 360 of SEQ ID NO:99, and at least 20%, at least 25%, at least 30%, at least 35%, at least 40%, or at least 45%, at least 50%, at least 55%, at least 60%, at least 65%, at least 70%, at least 75%, at least 80%, at least 85%, at least 90%, or at least 95% of the isolated fatty acid products are a C8 fatty acid product, such as but not limited to a C8 fatty acid, C8 fatty aldehyde, or C8 fatty alcohol, or a wax ester, alkene, or alkane.

In further examples, a transgenic organism is transformed with a nucleic acid molecule that encodes a thioesterase having at least 85%, at least 90%, at least 92%, at least 95%, or at least 99% identity with the amino acid sequence from amino acid position 64 to amino acid position 361 of SEQ ID NO:51; at least 98% identity with the amino acid sequence from amino acid position 66 to amino acid position 362 of SEQ ID NO:55; at least 97% identity with the amino acid sequence from amino acid position 65 to amino acid position 360 of SEQ ID NO:59; at least 90% identity with the amino acid sequence from amino acid position 65 to amino acid position 359 of SEQ ID NO:63; at least 98% identity with the amino acid sequence from amino acid position 115 to amino acid position 410 of SEQ ID NO:65; at least 96% identity with the amino acid sequence from amino acid position 65 to amino acid position 356 of SEQ ID NO:69; at least 98% identity with the amino acid sequence from amino acid position 115 to amino acid position 410 of SEQ ID NO:71; at least 96% identity with the amino acid sequence from amino acid position 64 to amino acid position 361 of SEQ ID NO:75; at least 97% identity with the amino acid sequence from amino acid position 65 to amino acid position 360 of SEQ ID NO:79; at least 96% identity with the amino acid sequence from amino acid position 116 to amino acid position 413 of SEQ ID NO:81; at least 96% identity with the amino acid sequence from amino acid position 65 to amino acid position 362 of SEQ ID NO:85; at least 96% identity with the amino acid sequence from amino acid position 64 to amino acid position 361 of SEQ ID NO:89; at least 97% identity with the amino acid sequence from amino acid position 115 to amino acid position 394 of SEQ ID NO:91; at least 97% identity with the amino acid sequence from amino acid position 115 to amino acid position 394 of SEQ ID NO:93; at least 99% identity with the amino acid sequence from amino acid position 115 to amino acid position 394 of SEQ ID NO:95; at least 92% identity with the amino acid sequence from amino acid position 63 to amino acid position 360 of SEQ ID NO:99; or at least 98% identity with the amino acid sequence from amino acid position 115 to amino acid position 393 of SEQ ID NO:101, and at least 20%, at least 25%, at least 30%, at least 35%, at least 40%, or at least 45%, at least 50%, at least 55%, at least 60%, at least 65%, at least 70%, at least 75%, at least 80%, at least 85%, at least 90%, or at least 95% of the isolated fatty acid products are a C12, C14, C16 and/or a C18 fatty acid product. In some examples, a transgenic organism is transformed with a nucleic acid molecule that encodes a thioesterase and at least 20%, at least 25%, at least 30%, at least 35%, at least 40%, or at least 45%, at least 50%, at least 55%, at least 60%, at least 65%, at least 70%, at least 75%, at least 80%, at least 85%, at least 90%, or at least 95% of the isolated fatty acid products are a C12, a C14, a C16, or a C18 fatty acid product, such as but not limited to a fatty acid, fatty aldehyde, or fatty alcohol, or a wax ester, alkene, or alkane. For example, the isolated fatty acid products from culturing a transgenic organism may be at least 50%, at least 60%, at least 70%, at least 80%, or at least 90% C14 and/or C16 fatty acid products.

The transgenic organism is in some embodiments a photosynthetic organism, such as, for example, a microalga. In some embodiments, the transgenic organism is a prokaryote.

In some illustrative embodiments, the method includes isolating fatty acid products from the culture medium, in which at least 20%, at least 25%, at least 30%, at least 35%, at least 40%, or at least 45%, at least 50%, at least 55%, at least 60%, at least 65%, at least 70%, at least 75%, at least 80%, at least 85%, at least 90%, or at least 95% of the fatty acid products isolated from the organism or the growth medium are fatty acid products of a specific chain length.

Production of Medium Chain Fatty Acid Products

As set forth in the Examples, a new Class II thioesterase gene from *Cuphea aequipetala*, denoted Ca1FatB2, has been isolated. The sequence of the putative mature form of the enzyme is provided in FIG. 1 as SEQ ID NO:29. The invention provides a method of producing a C8 fatty acid product in which the method includes culturing a photosynthetic organism that includes an exogenous nucleic acid molecule encoding a medium chain length acyl-ACP thioesterase that is at least 90% identical to amino acids 65 to 355 of SEQ ID NO:29 and isolating a fatty acid product from the organism or culture medium, in which at least 5% of the isolated fatty acid product is a C8 fatty acid product. The method includes the use of transgenic host organisms that include an exogenous nucleic acid molecule encoding a medium chain acyl-ACP thioesterase that is at least 90% identical to amino acids 34 to 355 of SEQ ID NO:29. A nucleic acid molecule used in these methods encodes a Class II medium chain plant acyl-ACP thioesterase or a variant thereof.

Nucleic acid molecules used in the methods of the invention encode acyl-ACP thioesterases having at least 90% identity to amino acids 65 to 355 of SEQ ID NO:29, in which expression of the thioesterase-encoding sequences in a photosynthetic transgenic organism results in production of a population of fatty acid products in the cells or growth media in which at least 5% of the fatty acid products isolated from the cells or growth media is a C8 fatty acid product. In some embodiments, a nucleic acid molecule used in the methods of the invention encodes an acyl-ACP thioesterase having at least 90% identity to amino acids 34 to 355 of SEQ ID NO:29. Using the methods of the invention, the percentage of a C8 fatty acid product, such as, for example, octanoic acid, in the recovered fatty acids is, for example, 5% or greater, 10% or greater, 15% or greater, 20% or greater, 25% or greater, 30% or greater, 35% or greater, 40% or greater, 45% or greater, 50% or greater, 55% or greater, 60% or greater, 65% or greater, 70% or greater, 75% or greater, or 80% or greater. In some preferred embodiments, the percentage of octanoic acid or another C8 fatty acid product in the fatty acids or fatty acid products recovered from the cultured cells and/or the culture medium is 85% or greater, such as 86%, 87%, between 87% and 90%, between 90% and 93%, between 93% and 95%, between 95% and 97%, between 97% and 98%, between 98% and 99%, or between 99% and 100%.

As detailed in Example 3, the *Cuphea aequipetala* FatB2 coding sequence has been reconstructed using PCR and gene walking such that, based on homology with other plant thioesterases, it is estimated that all but approximately ten to fifteen amino acids of the N-terminus have been determined. This sequence of the *C. aequipetala* FatB2 coding sequence (SEQ ID NO:22) is provided in FIG. 1. As evident in the figure, SEQ ID NO:22 and SEQ ID NO:29 are identical from amino acid position 2 to amino acid position 355. (SEQ ID NO:22 includes additional amino acids –43 to –1, considered to be amino acids included in the chloroplast transit peptide, that are not present in SEQ ID NO:29.) Thus, reference to any amino acid sequences between amino acid position 2 and amino acid 355 of SEQ ID NO:22 are interchangeable with the same sequences of SEQ ID NO:29 and vice versa.

The acyl-ACP thioesterase variants encoded by the nucleic acid molecules carried by transgenic host organisms may have N-terminal or C-terminal regions that differ from the wild-type thioesterase from which they are derived. With regard to the N-terminus, it is noted that acyl-ACP thioesterases of higher plants, such as the acyl-ACP thioesterase of *C. aequipetala*, are synthesized as precursor proteins that are transported into plastids, where the enzymes function in fatty acid biosynthesis. The site within the precursor protein sequence at which cleavage of the N-terminal transit peptide occurs has not been empirically determined.

The examples provided herein confirm that the transit peptide (including amino acids -43 through -1 of SEQ ID NO:22 in FIG. 1) is not necessary for the activity of a thioesterase expressed in a prokaryotic organism. Example 4 further demonstrates that thioesterase activity is not reduced by additional deletion of amino acids 1 to 33 of the putative mature thioesterase (SEQ ID NO:29). Plant medium chain thioesterases having deletions of the N-terminal amino acids extending to the amino acid corresponding to amino acid 64 of SEQ ID NO:22 have been shown to be active (see, for example, U.S. Pat. No. 5,667,997). Thus, the invention recognizes that N-terminal deletions of up to amino acid 64 (referencing SEQ ID NO:22 and SEQ ID NO:29, FIG. 1) of a medium chain acyl-ACP thioesterase are useful in the methods of the invention. The invention therefore includes methods of producing a fatty acid product in which a transgenic organism used to synthesize the fatty acid product is transformed with a gene encoding an acyl-ACP thioesterase having a deletion in its N-terminal region, in which the acyl-ACP thioesterase is at least 90% identical to amino acids 65-355 of SEQ ID NO:29.

In some embodiments of the invention, a nucleic acid molecule may encode acyl-ACP thioesterases having a transit peptide sequence derived from a different acyl-ACP thioesterase, or from a protein other than a thioesterase that is imported into plastids. For example, in some embodiments in which a thioesterase gene is transformed into a eukaryotic photosynthetic organism for the production of a fatty acid product, the acyl-ACP thioesterase gene can encode a thioesterase that is at least 90% identical to amino acids 65 to 355 of SEQ ID NO:29, while including a sequence encoding a transit peptide having an amino acid sequence that is less than 90% identical, less than 80% identical, less than 70% identical, less than 60% identical, less than 50% identical, less than 40% identical or less than 30% identical to sequences of the thioesterase precursor of SEQ ID NO:22. The transit peptide operably linked to the mature acyl-ACP thioesterase protein is in some embodiments from a chloroplast-directed protein from the species to be used as a transgenic host in the methods of the invention.

Also demonstrated in examples herein is the ability to introduce variations into the sequence of the C-terminal portion of a medium chain acyl-ACP thioesterase without significant loss of activity (see Example 2). Thus the invention includes variants of acyl-ACP thioesterases that terminate at amino acid 355, that include a C-terminal sequence of a different acyl-ACP thioesterase, or that have one or more amino acids that differ from any known acyl-ACP thioesterase, so long as there is no substantial detrimental effect on the activity of the thioesterase with regard to its C8 specificity and activity level.

The examples further disclose genes encoding variant acyl-ACP thioesterases having one, two, or three mutations with respect to the wild-type sequence (SEQ ID NO:29), in which the mutants retain the C8 specificity of the wild-type molecule, and where expression of a variant results in recovery of as great or a greater amount of C8 fatty acid from the culture as results from expression of the wild-type thioesterase. In some embodiments, then, a nucleic acid molecule used in the methods of the invention encodes an acyl-ACP thioesterase having between 90% and 95% identity, between 95% and 97% identity, between 97% and 98% identity, between 98% and 99% identity, between 99% and 99.5% identity, or between 99.5% and 100% identity to amino acids 65 to 355 of SEQ ID NO:29, while retaining at least the level of activity toward a C8 acyl substrate of the thioesterase of SEQ ID NO:29. In some embodiments of the methods a nucleic acid molecule encodes an acyl-ACP thioesterase having between 90% and 95% identity, between 95% and 97% identity, between 97% and 98% identity, between 98% and 99% identity, between 99% and 99.5% identity, or between 99.5% and 100% identity to amino acids 34 to 355 of SEQ ID NO:29, while retaining at least the level of activity toward a C8 acyl substrate of the thioesterase of SEQ ID NO:29.

In some embodiments, a nucleic acid molecule used in the methods of the invention encodes an acyl-ACP thioesterase having between 90% and 95% identity, between 95% and 98% identity, between 98% and 99% identity, between 99% and 99.5% identity, or between 99.5% and 100% identity to amino acids 65 to 355 of SEQ ID NO:29, in which expression of the acyl-ACP thioesterase in a transgenic organism results in production of at least the level of a C8 fatty acid produced by the transgenic organism expressing the thioesterase of SEQ ID NO:29. In some embodiments of the methods a nucleic acid molecule encodes an acyl-ACP thioesterase having between 90% and 95% identity, between 95% and 97% identity, between 97% and 98% identity, between 98% and 99% identity, between 99% and 99.5% identity, or between 99.5% and 100% identity to amino acids 34 to 355 of SEQ ID NO:29, and expression of the acyl-ACP thioesterase in a transgenic organism results in production of at least the level of a C8 fatty acid produced by the transgenic organism expressing the thioesterase of SEQ ID NO:29.

For any variants of an acyl-ACP thioesterase, such as variants of the acyl-ACP thioesterase of SEQ ID NO:22 or SEQ ID NO:29, the nucleic acid molecule encoding a variant acyl-ACP thioesterase can be tested for its ability to direct synthesis of a high proportion of C8 fatty acids or C8 fatty acid products, that are produced by the organisms and can be isolated from higher plants or cultures of algae transformed with the nucleic acid molecules. Provided in the examples are descriptions of transforming host organisms with recombinant nucleic acid molecules encoding acyl-ACP thioesterases and recovering fatty acid products to determine the amount of fatty acid products of different chain lengths produced by the transgenic host.

Assays of a thioesterase can also be performed using lysates of transgenic organisms such as *E. coli* that are transformed with expression constructs that include the acyl-ACP thioesterase gene and its activity determined using labeled acyl substrates (see, for example, U.S. Pat. No. 5,667,997, incorporated herein by reference). An acyl-ACP thioesterase variant can also be partially or substantially purified prior to performing an assay; for example, the thioesterase or thioesterase variant can be expressed with an affinity tag (for example, a His tag) for affinity purification prior to performing the assay (Dehesh et al. *Plant Physiol* 110: 203-210 (1996), incorporated herein by reference).

In some preferred embodiments, a nucleic acid molecule used in the methods of the invention encodes a plant B-type acyl-ACP thioesterase or a variant thereof, in which the encoded B-type acyl-ACP thioesterase comprises an amino acid sequence that is at least 95%, at least 97%, at least 98%, at least 99%, or at least 99.5% identical to amino acids 65 to 355 of SEQ ID NO:29. In some embodiments, the nucleic acid molecule encodes SEQ ID NO:8, SEQ ID NO:12, SEQ ID NO:22, SEQ ID NO:26, SEQ ID NO:33, SEQ ID NO:40, SEQ ID NO:43, or SEQ ID NO:45, or a thioesterase having any combination of the mutations provided in Table 2, the table provided in FIGS. 3A-3D, or the table provided in FIGS. 5A-5B. In some embodiments, the nucleic acid molecule comprises a sequence that encodes at least amino acids 65-355 of SEQ ID NO:29. In some preferred embodiments, a nucleic acid molecule according to the invention encodes a plant B-type acyl-ACP thioesterase or a variant thereof, in which the encoded B-type acyl-ACP thioesterase comprises an amino acid sequence that is at least 95%, at least 97%, at least 98%, at least 99%, or at least 99.5% identical to amino acids 34 to 355 of SEQ ID NO:29. In some embodiments, the nucleic acid molecule encodes SEQ ID NO:8, SEQ ID NO:12, SEQ ID NO:22, SEQ ID NO:26, SEQ ID NO:33, SEQ ID NO:40, SEQ ID NO:43, or SEQ ID NO:45, or a thioesterase having any combination of the mutations provided in Table 2, the table provided in FIGS. 3A-3D, or the table provided in FIGS. 5A-5B. In some embodiments, the nucleic acid molecule comprises a sequence that encodes at least amino acids 34-355 SEQ ID NO:29. In some embodiments, the nucleic acid molecule comprises a sequence that encodes SEQ ID NO:29.

The nucleic acid molecules encoding acyl-ACP thioesterases can be used to transform photosynthetic organisms, such as plants or algae, for the production of C8-enriched fatty acid products in the organisms. In some preferred embodiments, the sequence encoding the medium chain length fatty acid is codon-optimized for expression in the host organism. Codons can be optimized by methods such as those provided in U.S. Pat. No. 7,135,290, incorporated herein by reference. A codon usage database is available at the world wide web site kazusa.or.jp/codon/. Preferred codon usage can also be determined by a practitioner based on gene sequences entered in databases such as Genbank (ncbi.nlm.nih.gov/GenBank/), or a subset of genes of the organism (for example, highly expressed genes).

A photosynthetic organism transformed with the nucleic acid molecule that encodes a thioesterase gene can be a plant, such as but not limited to a higher plant, or can be an alga. Higher plants considered for use in the invention include, without limitation, *Arabidopsis thaliana, Arachis hypogaea, Avena sativa, Brassica* species (e.g., *Brassica napus, Brassica campestris, Brassica juncea*), *Camelina sativa, Carthamus tinctorius, Cocos nucifera, Crambe abyssinica, Cuphea* species, *Elaeis* species (e.g., *Elaeis guineensis, Elaeis oleifera*), *Gossypium hirsutum, Glycine max, Helianthus annuulus, Jatropha* species, *Cucurbita pepo, Oryza satvia, Sesamum indicum, Simmondsia chinensis, Theobroma cacao, Ricinus communis*, and *Zea mays*.

Algae that can be used in the methods of the invention can be any algae, and can include microalgae, such as but not limited to, *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Platymonas, Pleurochrysis, Pleurococcus, Prototheca, Pseudochlorella, Pyramimonas, Pyrobotrys, Scenedesmus, Schizochytrium, Skeletonema, Spyrogyra, Stichococcus, Tetraselmis, Thalassiosira, Viridiella*, or *Volvox* species.

In some embodiments, photosynthetic bacteria, including for example, green sulfur bacteria, purple sulfur bacteria, green nonsulfur bacteria, purple nonsulfur bacteria, or cyanobacteria are used for producing a C8 fatty acid product. Cyanobacterial species that can be used for production of C8 fatty acid products include, without limitation, *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema*, or *Xenococcus* species.

In another aspect the invention provides an isolated nucleic acid molecule that encodes a variant of a plant acyl-ACP thioesterase, in which the variant has a mutation at the amino acid corresponding to amino acid position 174 of SEQ ID NO:29 in which the variant has activity as high as or higher than the thioesterase from which the variant was derived. For example, in preferred embodiments, culturing of a transgenic organism that carries the variant gene in some embodiments allows isolation of as great or a greater amount of a fatty acid product of a specific chain length than does culturing of a transgenic organism that carries the native thioesterase gene. In preferred embodiments, expression of the variant in a transgenic host organism allows for isolation of fatty acid products of a specific chain length, in which the percentage of fatty acid products of a specific chain length to total fatty acid products isolated is at least as high as the percentage of fatty acid products of a specific chain length to total fatty acid products isolated from a host organism carrying the native gene.

In some preferred embodiments of the invention, the percentage of octanoic acid present in the population of fatty acids secreted by a prokaryotic organism transformed with a nucleic acid molecule encoding a variant of SEQ ID NO:29 having a mutation at position 174 is 55% or greater, 60% or greater, 65% or greater, 70% or greater, 75% or greater, or 80% or greater. In some preferred embodiments of the invention, the percentage of octanoic acid present in the population of fatty acids secreted by a prokaryotic organism transformed with a nucleic acid molecule encoding a variant of SEQ ID NO:29 having a mutation at position 174 is 85% or greater, such as 86%, 87%, between 87% and 90%, between 90% and 93%, between 93% and 95%, between 95% and 100%, between 95% and 97%, or between 97% and 100%. For example, in some embodiments expression of a variant of the acyl-ACP thioesterase of SEQ ID NO:29 in a bacterium or cyanobacterium results in secretion of a population of fatty acids enriched for octanoic acid.

The amino acid position corresponding to amino acid 174 of SEQ ID NO:29 refers to the amino acid position of an acyl-ACP thioesterase amino acid sequence that would align with amino acid 174 of SEQ ID NO:29 if the sequence of interest and SEQ ID NO:29 were aligned for maximum homology. Such alignments of Class II thioesterase sequences can be seen, for example, in U.S. Pat. No. 6,150,512 at FIG. 1. The terms "amino acid position 174", "position 174", or "consensus position 174" or similar nomenclature all refer to the consensus position for an acyl-ACP thioesterase corresponding to amino acid position 174 of SEQ ID NO:29 (and of SEQ ID NO:22, see FIG. 1) when the sequence is aligned with SEQ ID NO:29 (and, optionally, the sequences of other plant acyl-ACP thioesterases) for maximal sequence matches. Analogously, references to other amino acid positions, such as but not limited to, position 34, 35, 64, 65, 67, 103, 184, 355, etc., refer to numbered positions of the thioesterase sequences provided herein, including SEQ ID NO:22 and SEQ ID NO:29 (FIG. 1). These positions can be translated to numbered positions of other thioesterase genes as provided in patents, patent applications, publications, and gene and protein databases by aligning the sequence of SEQ ID NO:22 or SEQ ID NO:29 with the published, documented, or discovered thioesterase sequence for maximum homology.

In contrast to other acyl-ACP thioesterse mutants that have been isolated, the variants described in Examples 4-7 having an amino acid substitution at position 174 have increased activity while the chain length preference of the thioesterase has not been shifted from one acyl chain length to another acyl chain length. Isolation of a variant having a mutation at position 174 having increased activity was surprising not only because no previously identified acyl-ACP thioesterase mutants have exhibited increased activity, but also because the active site for Class II acyl-ACP thioesterases had been identified as being located more than 100 amino acids away from position 174, using SEQ ID NO:29 reference numbering (see FIG. 1), in the area of amino acid residues 293-297 and 304 (see, for example, U.S. Pat. No. 6,150,512).

A mutation at consensus position 174 can be a mutation that changes the amino acid of the naturally-occurring or wild-type gene at that consensus position to any other amino acid. In some embodiments, in which the naturally-occurring or wild-type gene has a methionine residue at amino acid position 174, the mutation can change M174 to any other amino acid, for example, glycine, proline, alanine, valine, leucine, isoleucine, phenylalanine, tyrosine, tryptophan, cysteine, serine, threonine, glutamine, asparagine, lysine, arginine, histidine, glutamate, or aspartate. In some embodiments, a mutation at position 174 changes the amino acid at position 174 of an acyl-ACP thioesterase to an uncharged amino acid, which can be, for example, any of glycine, proline, alanine, valine, leucine, isoleucine, phenylalamine, tyrosine, tryptophan, cysteine, methionine, serine, threonine, glutamine, or asparagine. In some embodiments, the mutation changes the amino acid at position 174 to methionine, leucine, phenylalanine, valine, cysteine, or isoleucine. In some embodiments, the mutation changes the amino acid at position 174 to valine or isoleucine.

Alignment of native plant Class II (FatB-encoded) acyl ACP thioesterases reveals that the amino acid at the position that corresponds to amino acid position 174 of SEQ ID NO:29 is typically a methionine residue. (This position is most often designated as a position between about residue 220 and about residue 250 for thioesterase amino acid sequences that number the first residue of the precursor protein as residue 1.) For example, plant acyl-ACP thioesterases having a methionine at the position corresponding to position 174 of SEQ ID NO:29 include FatB-encoded thioesterases of Cuphea species, such as but not limited to those encoded by Cuphea calophylla FatB genes (e.g., ABB71579, ABB71580, and ABB71581), Cuphea hookeriana FatB1 (Q39513), Cuphea hookeriana FatB1-1 (AAC72882), Cuphea hookeriana FatB2 (AAC49269), Cuphea hookeriana FatB3 (AAC72881), the Cuphea hookeriana 16:0-ACP thioesterase (AAC48990), Cuphea palustris FatB1(AAC49179 and 2208474A), Cuphea palustris FatB2 (AAC49180 and 2208474B), Cuphea wrightii FatB1 (AAC49783) and Cuphea wrightii FatB2 (AAC49784), and Cuphea lanceolata Class II thioesterases (e.g., AAE24875, CAA02760, CAA02766, CAA02765, CAA54060, CAC19934, and CAC19933). Also included are the Class II thioesterases of Diploknema butyracea (e.g., AAX51636), Brassica napus (e.g., ABH11710) and Brassica juncea (e.g., ABI18986). Other Class II thioesterases having a methionine at position 174 are those of Camellia oleifera (e.g., ACQ57190, ACQ63293, ACQ57188, ACQ57189, and ACQ57187), Helianthus annuus (e.g., AAB88824, AAQ08202, AAX19387, AAX19386, AAX19385, AAX19384, AAX19383, AAX19382, AAX19381, AAX19380, AAX19379, AAX19378, AAX19377, CAC80371, and CAC80370), and Jatropha curcas (e.g., ABU96744), as well as Madhuca longifolia FatB (AAX51637), Myristica fragrans FatB2 (AAB71729), Populus tomentosa FatB (ABC47311), Ricinus communis FatB genes (e.g., ABV54795, EEF47013, EEF51750, and EEF36100), Umbellularia califonica FatB genes (M941159, AAC49001, and Q41635), Ulmus Americana FatB (AAB71731), and thioesterases of Arabidopsis thaliana (e.g, AAF22899 and CAA85388). The numbers in parentheses are Genbank accession numbers of representative protein sequences. This list is not intended to be exhaustive, but nonetheless demonstrates that a large number of Class II acyl-ACP thioesterases have a methionine at the amino acid position corresponding to amino acid position 174 of SEQ ID NO:29, indicating that the residue is highly conserved among Class II acyl-ACP thioesterases, and strongly suggesting that its functional role is also conserved.

The invention includes plant FatB acyl-ACP thioesterase genes encoding variant thioesterases, in which the methionine residue corresponding to position 174 of SEQ ID NO:29 is mutated to an uncharged amino acid. In these embodiments, the variant thioesterases preferably have higher activity against an acyl-ACP substrate than the thioesterases encoded by the wild-type genes. The encoded FatB acyl-ACP thioesterases can be of any chain length specificity, such as, for example, C8, C10, C12, C14, C16, or C18. Included in the invention is a plant FatB acyl-ACP thioesterase gene encoding a variant thioesterase in which the methionine at position 174 in the wild-type thioesterase is mutated to leucine, phenylalanine, valine, cysteine, or isoleucine. In some embodiments, a variant plant acyl-ACP thioesterase comprises the mutation M174I, wherein the methionine at position 174 is replaced with isoleucine.

In these embodiments variant thioesterase genes having an M174I mutation may be variants of any plant FatB (Class II) acyl-ACP thioesterase gene that encodes a methionine at the position corresponding to position 174 of SEQ ID NO:29, including but not limited to genes of any of the Class II thioesterases listed above, including variants thereof having at least 85% identity to the amino acid sequence from about position 65 to about position 355 (using the numbering of SEQ ID NO:29 as a reference) of the thioesterase amino acid sequence of Class II thioesterase genes. The thioesterase genes can have any acyl chain length specificity. Illustrative examples of such thioesterase genes include, for example, an *Arabidopsis thaliana* FatB thioesterase gene, a *Cuphea aequipetala* FatB thioesterase gene, a *Cuphea calophylla* FatB thioesterase gene, a *Cuphea hookeriana* FatB thioesterase gene, a *Cuphea lanceolata* FatB thioesterase gene, a *Cuphea palustris* FatB thioesterase gene, a *Cuphea wrightii* FatB thioesterase gene, a *Diploknema butyracea* FatB thioesterase gene, a *Brassica napus* or *Brassica juncea* FatB thioesterase gene, a *Camellia oleifera* FatB thioesterase gene, a *Helianthus annuus* FatB thioesterase gene, a *Jatropha curcas* FatB thioesterase gene, a *Madhuca longifolia* FatB gene, a *Myristica fragrans* FatB2, a *Populus tomentosa* FatB gene, a *Ricinus communis* FatB gene, an *Umbellularia californica* FatB gene, and an *Umbellularia californica* FatB gene. The variants having an M174I mutation can have one or more additional amino acid substitutions with respect to the wild type genes from which they are derived, or can be N-terminally deleted or have variant carboxy termini, provided that the variants have a higher thioesterase activity than the wild-type sequence from which they are derived. The variants having an M174I mutation in some embodiments are between 80% and 85% identical, between 85% and 90% identical, between 90 and 95% identical, between 95% and 97% identical, between 97% and 99% identical, or between 99% and 100% identical to the wild type mature acyl-ACP thioesterase sequence at the amino acid level from about the amino acid position corresponding to position 65 of SEQ ID NO:29 to about the amino acid position corresponding to position 355 of SEQ ID NO:29. A variant acyl-ACP encoded by a nucleic acid molecule of the invention in some embodiments includes an isoleucine at the amino acid position corresponding to amino acid 103 of SEQ ID NO:29 in addition to the M174I mutation.

In other embodiments, a variant acyl-ACP thioesterase has an isoleucine at position 103 and the amino acid at position 174 is phenylalanine, cysteine, leucine, or valine.

The invention includes an isolated nucleic acid molecule that encodes a variant plant Class II acyl-ACP thioesterase having at least 80%, at least 85%, at least 90%, or at least 95% identity to the amino acid sequence from position 65 to amino acid 355 of SEQ ID NO:40, SEQ ID NO:43, or SEQ ID NO:45, in which the variant includes a M174I mutation and has enhanced activity with respect to the plant acyl-ACP thioesterase lacking the mutation at consensus position 174.

In some embodiments of the invention, an isolated nucleic acid encoding a variant acyl-ACP thioesterase having an M174I mutation comprises a sequence encoding the amino acid sequence from position 65 to 355 of SEQ ID NO:40, SEQ ID NO:43, or SEQ ID NO:45.

Also included in the invention is an isolated nucleic acid molecule that encodes a variant plant Class II acyl-ACP thioesterase having at least 80%, at least 85%, at least 90%, or at least 95% identity to the amino acid sequence from position 34 to amino acid 355 of SEQ ID NO:40, SEQ ID NO:43, or SEQ ID NO:45, in which the variant has enhanced activity with respect to the plant acyl-ACP thioesterase lacking the mutation at consensus position 174. In some embodiments of the invention, an isolated nucleic acid encoding a variant acyl-ACP thioesterase having an M174I mutation comprises a sequence encoding the amino acid sequence from position 34 to 355 of SEQ ID NO:40, SEQ ID NO:43, or SEQ ID NO:45. The isolated nucleic acid molecule in some embodiments comprises a sequence encoding the amino acid sequence of SEQ ID NO:40, SEQ ID NO:43, or SEQ ID NO:45. In some embodiments, the nucleic acid molecule comprises SEQ ID NO:39, SEQ ID NO:42, or SEQ ID NO:44.

A further aspect of the invention is a transgenic organism that includes an exogenous nucleic acid molecule that encodes a variant plant acyl-ACP thioesterase, in which the variant thioesterase has a mutation at the amino acid position corresponding to amino acid position 174 of SEQ ID NO:29 and exhibits increased thioesterase activity. Specifically included are transgenic organisms that include genes encoding any of the aforementioned variants having a mutation at amino acid position 174, including, for example, variants having an isoleucine, methionine, valine, leucine, cysteine, or phenylalanine at positions 174. In some embodiments, the transgenic organism has an exogenous nucleic acid molecule encoding a thioesterase having an isoleucine, valine, leucine, cysteine, or phenylalanine at position 174 and an isoleucine at position 103. In an exemplary embodiment, a transgenic organism has an exogenous gene encoding a thioesterase having an isoleucine at position 174 and an isoleucine at position 103. A transgenic organism is in various embodiments a plant, an alga, or a prokaryote.

For example, in some embodiments, the transgenic organism is a bacterium, such as, but not limited to, an *Acetobacter, Acinetobacter, Arthrobacter, Bacillus, Brevibacterium, Chromatium, Chlorobium, Clostridium, Corynebacterium, Deinococcus, Delftia, Desulfovibrio, Enterococcus, Escherichia, Kineococcus, Klebsiella, Lactobacillus, Lactococcus, Micrococcus, Mycobacterium, Jeotgalicoccus, Paenibacillus, Propionibacter, Pseudomonas, Rhodopseudomonas, Rhodobacter, Rhodococcus, Rhodospirillium, Rhodomicrobium, Salmonella, Serratia, Stenotrophomonas, Streptococcus, Vibrio*, or *Zymomonas* species.

In other embodiments, a transgenic organism harboring an acyl-ACP variant having a mutation at amino acid residue 174 is an alga, for example, a microalga such as an *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas,*

*Oedogonium, Oocystis, Ostreococcus, Pavlova, Parachlorella, Pascheria, Phaeodactylum, Phagus, Platymonas, Pleurochrysis, Pleurococcus, Prototheca, Pseudochlorella, Pyramimonas, Pyrobotrys, Scenedesmus, Schizochytrium, Skeletonema, Spyrogyra, Stichococcus, Tetraselmis, Thalassiosira, Viridiella,* or *Volvox* species. In some embodiments, a transgenic organism is a *cyanobacterium*, such as an *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema,* or *Xenococcus* species.

A transgenic organism transformed with a nucleic acid molecule encoding a variant acyl-ACP thioesterase having a mutation at position 174 is in some embodiments a higher plant, such as, for example, *Arabidopsis thatliana, Arachis hypogaea, Avena sativa, Brassica* species (e.g., *Brassica napus, Brassica campestris, Brassica juncea*), *Camelina sativa, Carthamus tinctorius, Cocos nucifera, Crambe abyssinica, Cuphea* species, an *Elaeis* species (e.g., *Elaeis guineensis, Elaeis oleifera*), *Gossypium hirsutum, Glycine max, Helianthus annulus,* a *Jatropha* species, *Cucurbita pepo, Oryza satvia, Sesamum indicum, Simmondsia chinensis, Theobroma cacao, Ricinus communis,* or *Zea mays.*

In yet another aspect, the invention provides a method of producing a fatty acid or a fatty acid product, in which the method includes cultivating an organism having an exogenous nucleic acid molecule that includes a sequence encoding a variant acyl-ACP thioesterase having a mutation at the amino acid position corresponding to position 174 of SEQ ID NO:29, and isolating a fatty acid or a fatty acid product from the organism or culture medium. The variant acyl-ACP thioesterase in some embodiments has an isoleucine at position 103 and an isoleucine at position 174. The transgenic host organism can be a bacterium, alga, *cyanobacterium,* or plant as provided herein, and the sequence encoding the plant acyl-ACP thioesterase in some embodiments is codon-optimized for expression in the host organism. In some preferred embodiments, the nucleic acid molecule encodes a variant of a naturally-occurring medium chain length acyl-ACP thioesterase having a mutation at the amino acid position corresponding to amino acid position 174 in SEQ ID NO:29, in which the variant has enhanced activity towards a C8 acyl substrate with respect to the wild type thioesterase.

The methods can be used for the production and isolation of a fatty acid product such as a triglyceride, a fatty aldehyde, a fatty alcohol, a fatty ester, or a hydrocarbon such as an alkene or alkane. In some embodiments, the fatty acid product is a fatty acid. In exemplary embodiments, the fatty acid product is a C8 fatty acid.

In some preferred embodiments expression of a variant acyl-ACP thioesterase gene as provided herein in a transgenic organism results in an increased percentage of a specific chain length fatty acid product being recovered from the organism and/or culture medium. In some embodiments, at least 5%, at least 10%, at least 15%, at least 20%, at least 25%, at least 30%, at least 35%, at least 40%, or at least 45%, at least 50%, at least 55%, at least 60%, at least 65%, at least 70%, at least 75%, at least 80%, at least 85%, at least 90%, or at least 95% of the isolated fatty acid products from an organism and/or medium from culturing of an organism having an exogenous nucleic acid molecule encoding a variant acyl-ACP thioesterase of the invention are fatty acid products of a specific chain length. For example, in some embodiments, at least 5%, at least 10%, at least 15%, at least 20%, at least 25%, at least 30%, at least 35%, at least 40%, or at least 45%, at least 50%, at least 55%, at least 60%, at least 65%, at least 70%, at least 75%, at least 80%, at least 85%, at least 90%, or at least 95% of the isolated fatty acid products from an organism expressing an exogenous variant acyl-ACP thioesterase of the invention are C8 fatty acid products. In some preferred embodiments, the fatty acid product is a C8 fatty acid, and at least 5%, at least 10%, at least 15%, at least 20%, at least 25%, at least 30%, at least 35%, at least 40%, or at least 45%, at least 50%, at least 55%, at least 60%, at least 65%, at least 70%, at least 75%, at least 80%, at least 85%, at least 90%, or at least 95% of the fatty acids isolated from the organism and/or the growth medium is a C8 fatty acid, such as octanoic acid.

In some illustrative embodiments, the transgenic organism is a prokaryote, such as a bacterium or a *cyanobacterium,* and the method includes isolating fatty acid products from the culture medium, in which at least 5%, at least 10%, at least 15%, at least 20%, at least 25%, at least 30%, at least 35%, at least 40%, or at least 45%, at least 50%, at least 55%, at least 60%, at least 65%, at least 70%, at least 75%, at least 80%, at least 85%, at least 90%, or at least 95% of the fatty acid products isolated from the organism or the growth medium are fatty acid products of a specific chain length. For example, in some embodiments, at least 5%, at least 10%, at least 15%, at least 20%, at least 25%, at least 30%, at least 35%, at least 40%, or at least 45%, at least 50%, at least 55%, at least 60%, at least 65%, at least 70%, at least 75%, at least 80%, at least 85%, at least 90%, or at least 95% of the fatty acid products isolated from the culture medium of a prokaryotic organism transformed with a variant acyl-ACP thioesterase of the invention are C8 fatty acid products. In an illustrative embodiment, at least 5%, at least 10%, at least 15%, at least 20%, at least 25%, at least 30%, at least 35%, at least 40%, or at least 45%, at least 50%, at least 55%, at least 60%, at least 65%, at least 70%, at least 75%, at least 80%, at least 85%, at least 90%, or at least 95% of the fatty acid products isolated from the culture medium of a prokaryotic organism transformed with a variant acyl-ACP thioesterase of the invention are C8 fatty acid products, such as octanoic acid.

Nucleic acid molecules encoding variant acyl-ACP thioesterases mutated at position 174 that can be expressed in a transgenic host organism can be any disclosed herein. For example, in some embodiments, the variant has a mutation that changes the amino acid at position 174 to an uncharged amino acid. In some embodiments, the amino acid position corresponding to amino acid position 174 of SEQ ID NO:29 is mutated from methionine to any of phenylalanine, cysteine, leucine, valine, or isoleucine. In some embodiments, the variant thioesterase has an isoleucine at position 103, and the amino acid at position 174 is phenylalanine, cysteine, valine, leucine, or isoleucine. In some embodiments, the amino acid position corresponding to amino acid position 103 of SEQ ID NO:29 is isoleucine and the amino acid corresponding to amino acid position 174 of SEQ ID NO:29 is isoleucine. The thioesterase from which the variant sequence is derived can be any plant acyl-ACP thioesterase, such as a plant Class II acyl-ACP thioesterase. In some embodiments, the thioesterase encoded by the exogenous nucleic acid molecule comprises an amino acid sequence having at least 80%, at least 85%, at least 90%, at least 95%, at least 97%, at least 98%, or at least 99% identity to amino acids 65 to 355 of SEQ ID NO:40, SEQ ID NO:43, or SEQ ID NO:45. In some embodiments, the thioesterase encoded by the exogenous nucleic acid molecule comprises amino acids 65 to 355 of SEQ ID NO:40, SEQ ID NO:43, or SEQ ID NO:45. In some embodiments, the thioesterase encoded by the exogenous nucleic acid molecule comprises amino acids 34 to 355 of SEQ ID NO:40, SEQ ID NO:43, or SEQ ID NO:45.

Additional Genes Encoding Enzymes for Synthesizing Fatty Acid Products

Also included in the invention are transgenic host organisms and methods of using transgenic host organisms that include an exogenous acyl-ACP thioesterase as disclosed herein, and further include one or more exogenous genes encoding enzymes that participate in the synthesis of fatty aldehydes, fatty alcohols, fatty esters, or hydrocarbons (e.g., alkanes, alkenes) such as, for example, an acetyl CoA carboxylase, an acyl-CoA synthetase, a ketoacyl-CoA synthase, a fatty acyl-CoA/aldehyde reductase, a fatty acid elongase, a fatty acyl-CoA reductase, a fatty aldehyde reductase, an alcohol acetyl transferase, an acyl-CoA alcohol transacylase, an acyltransferase, a wax synthase, a fatty aldehyde decarbonylase, or a fatty acid decarboxylase.

In some embodiments, genes encoding a fatty acyl-ACP thioesterase and one or more genes encoding other hydrocarbon modification enzymes are transformed into a host organism, and the organism is used for the production of a fatty aldehyde, a fatty alcohol, a fatty ester (including a wax-ester), or a hydrocarbon.

Genes encoding fatty acyl-CoA/aldehyde reductases that can be used include, without limitation, those having Genbank accession numbers AAC45217, YP_047869, BAB85476, YP_001086217, YP_580344, YP_001280274, YP_264583, YP_436109, YP_959769, ZP_01736962, ZP_01900335, ZP_01892096, ZP_01103974, ZP_01915077, YP_924106, YP_130411, ZP_01222731, YP_550815, YP_983712, YP_001019688, YP_524762, YP_856798, ZP_01115500, YP_001141848, NP_336047, NP_216059, YP_882409, YP_706156, YP_001136150, YP_952365, ZP_01221833, YP_130076, NP_567936, AAR88762, ABK28586, NP_197634, CAD30694, NP_001063962, BAD46254, NP_001030809, EAZ10132, EAZ43639, EAZ07989, NP_001062488, CAB88537, NP_001052541, CAH66597, CAE02214, CAH66590, CAB88538, EAZ39844, AAZ06658, CAA68190, CAA52019, and BAC84377. Also included are genes encoding variants of these and other naturally-occurring fatty acyl-CoA/aldehyde reductases having at least 65% identity to the referenced or naturally occurring proteins, in which the activity of the enzyme is not substantially reduced with respect to the wild-type or above referenced enzyme.

Genes encoding fatty acyl-CoA reductases can include genes that encode, without limitation, the fatty acyl-CoA reductases having GenBank accession numbers NP_187805, ABO14927, NP_001049083, CAN83375, NP_191229, EAZ42242, EAZ06453, CAD30696, BAD31814, NP_190040, AAD38039, CAD30692, CAN81280, NP_197642, NP_190041, AAL15288, and NP_190042. Also included are genes encoding variants of these and other naturally-occurring fatty acyl-CoA reductases having at least 65% identity to the referenced or naturally occurring proteins, in which the activity of the enzyme is not substantially reduced with respect to the wild-type or above referenced enzyme.

Genes encoding fatty aldehyde decarbonylases that can be transformed into an organism harboring an exogenous gene that encodes a plant acyl-ACP thioesterase as disclosed herein include genes that encode the fatty aldehyde decarbonylases listed by GenBank accession numbers. NP_850932, ABN07985, CAN60676, AAC23640, CAA65199, AAC24373, CAE03390, ABD28319, NP_181306, EAZ31322, CAN63491, EAY94825, EAY86731, CAL55686, XP_001420263, EAZ23849, NP_200588, NP_001063227, CAN83072, AAR90847, and AAR97643. Also included are genes encoding variants of these and other naturally-occurring fatty aldehyde decarbonylases having at least 65% identity to the referenced or naturally occurring proteins, in which the activity of the enzyme is not substantially reduced with respect to the wild-type or above referenced enzyme.

In particular embodiments, organisms of the present invention are genetically engineered to express a fatty acyl-ACP thioesterase as provided herein, and one or more of an acyl-CoA synthetase, a fatty acyl-CoA/aldehyde reductase, a fatty acyl-CoA reductase, a fatty aldehyde reductase, a fatty aldehyde decarbonylase, or a fatty acid decarboxylase. Suitable expression methods are described below with respect to the thioesterase gene, including, among other methods, inducible expression and tissue-specific expression.

The enzymes described directly above may have a specificity for acting on a substrate having an acyl chain of a specific length. In some embodiments the transgenic host used for producing a fatty acid product contains an acyl-ACP thioesterase as described herein, and one or more exogenous genes that encode enzymes with specificity for substrates of the same acyl chain length. The enzymatic specificity can, in various embodiments, be for a substrate having from 8 to 34 carbon atoms, preferably from 8 to 18 carbon atoms. For example, the nucleic acid molecules introduced into a transgenic host can encode enzymes that have specificity for substrates having 8, 10, 12, 14, 16, or 18 carbon atoms in the acyl chain.

Also included in the invention are embodiments in which a transgenic organism expresses, in addition to a heterologous acyl-ACP thioesterase, a ketoacyl synthase (KAS). In some embodiments, the gene that encodes a β-ketoacyl synthase (KAS) that preferentially produces acyl-ACPs having medium chain lengths. Such KAS enzymes have been described from several plants, including various species of *Cuphea* (Dehesh et al., 1998; Slabaugh et al., 1998), and would serve to increase the availability of acyl-ACP molecules of the proper length for recognition and cleavage by the heterologous acyl-ACP thioesterase.

Additional embodiments of this invention include transgenic hosts expressing an exogenous plant acyl-ACP thioesterase as provided herein, and optionally one or more additional genes encoding enzymes that function in the synthesis of fatty acid products, in which one or more host genes that encode beta-oxidation pathway enzymes have been inactivated or downregulated. Inactivation of a beta-oxidation enzyme can prevent the degradation of fatty acids released from acyl-ACPs, thus enhancing the yield of accumulated or secreted fatty acids. For example, in cases where the desired products are medium chain fatty acids, the inactivation or downregulation of genes that encode medium chain-specific acyl-CoA synthetase and/or medium chain-specific acyl-CoA oxidase enzymes would be beneficial.

Mutations in the genes encoding medium chain-specific acyl-CoA synthetase and/or medium chain-specific acyl-CoA oxidase enzymes such that the activity of the enzymes is diminished would also be effective in increasing the yield of accumulated or secreted fatty acids. Mutations in the genes can be introduced either by recombinant or non-recombinant methods.

Transformation of Host Organisms

Plants for use in the methods of the invention can be transformed by any feasible means, including, without limitation, the use of *Agrobacterium*, particle gun-mediated transformation, laser-mediated transformation, or electroporation. Algae and photosynthetic bacteria can be transformed by any suitable methods, including, as nonlimiting examples, natural DNA uptake (Chung et al. (1998) *FEMS Microbiol. Lett.* 164: 353-361; Frigaard et al. (2004) *Methods Mol. Biol.* 274: 325-40; Zang et al. (2007) *J. Microbiol.* 45: 241-245), conjugation, transduction, glass bead transformation (Kindle et al. (1989) *J. Cell Biol.* 109: 2589-601; Feng et al. (2009) *Mol. Biol. Rep.* 36: 1433-9; U.S. Pat. No. 5,661,017), silicon carbide whisker transformation (Dunahay et al. (1997) *Methods Mol. Biol.* (1997) 62: 503-9), biolistics (Dawson et al. (1997) *Curr. Microbiol.* 35: 356-62; Hallmann et al. (1997) *Proc. Natl. Acad. USA* 94: 7469-7474; Jakobiak et al. (2004) *Protist* 155:381-93; Tan et al. (2005) *J. Microbiol.* 43: 361-365; Steinbrenner et al. (2006) *Appl Environ. Microbiol.* 72: 7477-7484; Kroth (2007) *Methods Mol. Biol.* 390: 257-267; U.S. Pat. No. 5,661,017) electroporation (Kjaerulff et al. (1994) *Photosynth. Res.* 41: 277-283; Iwai et al. (2004) *Plant Cell Physiol.* 45: 171-5; Ravindran et al. (2006) *J. Microbiol. Methods* 66: 174-6; Sun et al. (2006) *Gene* 377: 140-149; Wang et al. (2007) *Appl. Microbiol. Biotechnol.* 76: 651-657; Chaurasia et al. (2008) *J. Microbiol. Methods* 73: 133-141; Ludwig et al. (2008) *Appl. Microbiol. Biotechnol.* 78: 729-35), laser-mediated transformation, or incubation with DNA in the presence of or after pre-treatment with any of poly(amidoamine) dendrimers (Pasupathy et al. (2008) *Biotechnol. J.* 3: 1078-82), polyethylene glycol (Ohnuma et al. (2008) *Plant Cell Physiol.* 49: 117-120), cationic lipids (Muradawa et al. (2008) *J. Biosci. Bioeng.* 105: 77-80), dextran, calcium phosphate, or calcium chloride (Mendez-Alvarez et al. (1994) *J. Bacteriol.* 176: 7395-7397), optionally after treatment of the cells with cell wall-degrading enzymes (Perrone et al. (1998) *Mol. Biol. Cell* 9: 3351-3365). *Agrobacterium*-mediated transformation can also be performed on algal cells, for example after removing or wounding the algal cell wall (e.g., WO 2000/62601; Kumar et al. (2004) *Plant Sci.* 166: 731-738). Biolistic methods are particularly successful for transformation of the chloroplasts of plant and eukaryotic algal species (see, for example, Ramesh et al. (2004) *Methods Mol. Biol.* 274: 355-307; Doestch et al. (2001) *Curr. Genet.* 39: 49-60; U.S. Pat. No. 7,294,506; WO 2003/091413; WO 2005/005643; and WO 2007/133558, all incorporated herein by reference in their entireties).

In some preferred embodiments of the invention, an acyl-ACP thioesterase gene (such as a gene as disclosed herein), is cloned into an expression vector for transformation into a plant, alga, or photosynthetic or nonphotosynthetic bacterium. The vector includes sequences that promote expression of the transgene of interest, e.g., an exogenous acyl-ACP thioesterase gene, such as a promoter, and may optionally include a transit peptide-encoding sequence for directing the expressed thioesterase to the chloroplast of transformed eukaryotic cells, an intron sequence, a sequence having a polyadenylation signal, etc. Alternatively, if the vector does not contain a promoter in operable linkage with the gene of interest, the gene can be transformed into the cells such that it becomes operably linked to an endogenous promoter by homologous recombination or vector integration.

In some embodiments, a vector is designed for integration of the acyl-ACP thioesterase gene into the host genome. For example, vectors used for higher plant transformation include but are not limited to *Agrobacterium*-based vectors that are designed for integrating transgenes (exogenous genes transformed into the host plant) into the genome of the plant. In other embodiments, vectors can be: 1) targeted for integration into a plant or algal chromosome by including flanking sequences that enable homologous recombination into the chromosome, 2) targeted for integration into endogenous host plasmids by including flanking sequences that enable homologous recombination into the endogenous plasmids, or 3) designed such that the expression vectors replicate within the chosen host.

Artificial chromosome vectors can also be used for the transformation of higher plants, for example, vector constructs that include a centromere sequence and an origin of replication so that the vector and its integrated sequences can be maintained in the plant (see, for example, U.S. Pat. No. 7,456,013 incorporated by reference herein in its entirety). Artificial chromosomes can accommodate more transgenes than can other types of vectors such as, for example, *Agrobacterium*-based vectors, and therefore can be used in higher plant or algal systems when more than one gene that encodes an enzyme that participates in the synthesis of a fatty acid product is transformed into an organism.

In some cases in which it may be advantageous to transform the chloroplast of a higher plant or alga, vectors can be designed to have regions of sequences flanking the transgene (e.g., the acyl-ACP thioesterase gene or another gene for synthesis of a fatty acid product) that are homologous to chloroplast sequences to promote homologous recombination and integration of the sequence of interest. In these embodiments, the vector preferably includes a promoter for expressing the transgene, in which the promoter functions in the chloroplast.

Vectors that include gene regulatory sequences for transformation of higher plants are well known in the art. Seed specific or inducible promoters can optionally be used in the vectors and constructs transformed into higher plants engineered for synthesis of fatty acid products (for example, U.S. Pat. Nos. 5,421,034; 5,608,152; and 6,642,437).

Vectors designed for expression of a gene in microalgae can in some embodiments include a promoter active in microalgae operably linked to the exogenous gene being introduced. A variety of gene promoters and terminators that function in green algae can be utilized in expression vectors, including, but not limited to promoters and terminators from *Chlamydomonas* and other algae (see, for example, *Plant Cell Physiol* 49: 625-632 (2008)), promoters and terminators from viruses, and synthetic promoters and terminators.

For transformation of diatoms, a variety of gene promoters that function in diatoms can be utilized in these expression vectors, including, but not limited to: 1) promoters from *Thalassiosira* and other heterokont algae, promoters from viruses, and synthetic promoters. Promoters from *Thalassiosira pseudonana* that would be suitable for use in expression vectors include an alpha-tubulin promoter, a beta-tubulin promoter, and an actin promoter. Promoters from *Phaeodactylum tricornutum* that would be suitable for use in expression vectors include an alpha-tubulin promoter, a beta-tubulin promoter, and an actin promoter. The terminators associated with these genes, other diatom genes, or particular heterologous genes can be used to stop transcription and provide the appropriate signal for polyadenylation.

In some instances it can be advantageous to express a heterologous enzyme, such as but not limited to a thioesterase, at a certain point during the growth of the transgenic host to minimize any deleterious effects on the growth of the transgenic organism and/or to maximize production of the fatty acid product of interest. In these instances one or more exogenous genes introduced into the transgenic organism can be operably linked to an inducible promoter. The promoter can be a lac promoter, a tet promoter (e.g., U.S. Pat. No. 5,851,796), a hybrid promoter that includes either or both of portions of a tet or lac promoter, a hormone-responsive promoter (e.g., an ecdysone-responsive promoter, e.g., U.S. Pat. No. 6,379,945) a metallothionien promoter (U.S. Pat. No. 6,410,828), or a pathogenesis-related (PR) promoter that can be responsive to a chemical such as, for example, salicylic acid, ethylene, thiamine, or BTH (U.S. Pat. No. 5,689,044). An inducible promoter can also be responsive to light or dark (U.S. Pat. Nos. 5,750,385, and 5,639,952) or temperature (U.S. Pat. No. 5,447,858; Abe et al., *Plant Cell Physiol.* 49: 625-632 (2008); Shroda et al. *Plant J.* 21: 121-131 (2000)). The foregoing list is exemplary and not limiting. The promoter sequences can be from any organism, provided that they are functional in the host organism. Inducible promoters as used in the constructs of the present invention can use one or more portions or one or more domains of the aforementioned promoters or other inducible promoters fused to at least a portion of a different promoter that operates in the host organism to confer inducibility on a promoter that operates in the host species.

A variety of gene promoters that function in cyanobacteria can be utilized in expression vectors, including, but not limited to: 1) the lac, tac, and trc promoters that are inducible by the addition of isopropyl β-D-1-thiogalactopyranoside (IPTG), 2) promoters that are naturally associated with transposon- or bacterial chromosome-borne antibiotic resistance genes (neomycin phosphotransferase, chloramphenicol acetyltrasferase, spectinomycin adenyltransferase, etc.), 3) promoters of various heterologous bacterial and native cyanobacterial genes, 4) promoters from viruses and phages, and 5) synthetic promoters. Promoters isolated from cyanobacteria that have been used successfully include the following:

secA (secretion; controlled by the redox state of the cell)
  rbc (Rubisco operon)
  psaAB—(PS I reaction center proteins; light regulated)
  psbA—(D1 protein of PSII; light-inducible)

Likewise, a wide variety of transcriptional terminators can be used for expression vector construction. Examples of possible terminators include, but are not limited to, psbA, psaAB, rbc, secA, and T7 coat protein.

Transformation vectors preferably also include a selectable marker, such as but not limited to a drug resistance gene, an herbicide resistance gene, a metabolic enzyme or factor required for survival of the host (for example, an auxotrophic marker), etc. Transformed cells can be optionally selected based upon the ability to grow in the presence of the antibiotic or other selectable marker under conditions in which cells lacking the resistance cassette or auxotrophic marker would not grow. In some embodiments a non-selectable marker may be present on a vector, such as a gene encoding a fluorescent protein or enzyme that generates a detectable reaction product. In an alternative transformation strategy, selectable or non-selectable markers can be provided on a separate construct, where both the gene-of-interest construct and the selectable marker construct are used together in transformation protocols, and selected transformants are analyzed for co-transformation of the construct that includes the gene-of-interest (see, for example, Kindle (1990) *Proc. Natl. Acad. Sci. USA* 87: 1228-32; Jakobiak et al. (2004) *Protist* 155:381-93).

Growth of Transformed Organisms

Plants can be grown on or in culture media or in soil, and can be grown in a greenhouse or growth chamber, or outdoors. Algae and photosynthetic bacteria can be cultured phototrophically, in the absence of a fixed carbon source, or mixotrophically, where the cultures are supplied with light for at least part of the day, and also supplied with a reduced carbon source, such as a (e.g., glucose, fructose, galactose, mannose, rhamnose, arabinose, xylose, lactose, sucrose, maltose), an organic acid (e.g., actetate, citrate, succinate), or glycerol. The photosynthetic organism in some embodiments is cultured mixotrophically, in which the organism is grown in the presence of light for at least a part of the day, and also provided with one or more sources of reduced carbon. A photosynthetic organism can be grown mixotrophically for a period of time, followed by a period of phototrophic growth, or vice versa.

Media for phototrophic or mixotrophic growth of algae are well known, and media can be optimized to enhance growth or production of fatty acid products for a particular species. Artificial light sources can be used as the sole light source or to enhance or extend natural light.

In some embodiments, a transgenic organism contains an exogenous gene for an acyl-ACP thioesterase as described herein (and, optionally one or more additional exogenous genes) that is under the control of an inducible promoter, as described above, and the transgenic organism is grown or cultured for a period of time while the transgene(s) is/are not induced. At a point during the growth period, which can be empirically determined based on production levels of the fatty acid product, the gene can be induced, for example, by a period of dark or light, raising or lowering of the temperature, or addition of one or more nutrients or chemicals to the culture medium. The transgenic organism can be maintained under inducing conditions for any feasible amount of time for production of protein(s) encoded by the transgene(s).

Growth of algae can be in open areas, such as, for example, ponds, canals, channels, raceways, or tanks, or can be in bioreactors. Bioreactors are preferred for mixotrophic growth, and can also be used for phototrophic growth. The bioreactors can be of any sizes and form, and can include inlets for providing nutrients, additives, or gases, such as but not limited to air or $CO_2$. A bioreactor preferably also has an outlet for sampling of the culture. A bioreactor can be configured such that the algal culture is mixed during the growth period, for example, by stirring, rocking, shaking, inverting, bubbling of gases through the culture, etc. Outdoor ponds, raceways, tanks, canals, etc. can also be designed for mixing of cultures through, for example, paddles, pumps, hoses or jets for circulation of the culture media, or tubes, hoses or inlets for supplying air or $CO_2$ to the culture.

Production of Fatty Acid Products

Where cultures of algae or photosynthetic bacteria are employed in the methods, the fatty acid products can be isolated from the culture medium, from the cells, or from whole culture (culture medium plus cells). In some embodiments the fatty acid products include a C8 fatty acid product, such as octanoic acid, triglycerides that include octanoic acid, or a fatty aldehyde, fatty alcohol, fatty ester, or hydrocarbon derived from octanoic acid. In some embodiments the fatty acid products include a C10 fatty acid product, such as decanoic acid, triglycerides that include decanoic acid, or a fatty aldehyde, fatty alcohol, fatty ester, or hydrocarbon derived from decanoic acid.

In embodiments in which a fatty acid product such as a triglyceride, a fatty aldehyde, a fatty alcohol, a fatty ester, or a hydrocarbon are produced by the transgenic organism, the transgenic organism optionally includes an additional exogenous gene, in which the additional transgene encodes another enzyme that functions in the synthesis of a fatty acid product. In embodiments in which the fatty acid product is a fatty aldehyde, for example, a C8 fatty aldehyde or a C10 fatty aldehyde, the transgenic host organism can further comprise an exogenous nucleic acid molecule that encodes an acyl-CoA reductase. Where the isolated fatty acid product is a fatty alcohol, the transgenic photosynthetic organism in some embodiments comprises, in addition to the transgene that encodes a C8-preferring or a C10-preferring acyl-ACP thioesterase, an exogenous nucleic acid molecule encoding an acyl-CoA reductase. In embodiments in which the fatty acid product is a fatty ester, such as a wax ester, the transgenic organism used for production of the wax ester can include a fatty acyl-CoA reductase and an exogenous nucleic acid molecule encoding a wax ester synthase (which may or may not also have diacylglycerol acyltransferase activity). Nucleic acid molecules encoding additional enzymes for the synthesis of fatty acid products can be provided in expression constructs. The genes can be codon-optimized for expression in the host.

In embodiments in which a fatty acid is isolated or separated from the cells and/or culture medium, the isolated or separated fatty acid can be converted to one or more of a fatty aldehyde, fatty alcohol, fatty ester, or hydrocarbon through chemical or enzymatic methods.

In some preferred embodiments, the method includes culturing a photosynthetic organism transformed with a nucleic acid molecule encoding a Class II acyl-ACP thioesterase, and isolating one or more fatty acid products of specific chain length(s) from the culture. In preferred embodiments, at least 20%, at least 25%, at least 30%, at least 35%, at least 40%, at least 45%, or at least 50% of the fatty acid product isolated from the culture is a fatty acid product of a specific chain length. In some preferred embodiments, between 50% and 55%, between 55% and 60%, between 60% and 65%, between 65% and 70%, between 70% and 75%, between 75% and 80%, between 80 and 85%, between 85% and 90%, between 90% and 95%, between 95% and 97%, between 97% and 99%, or between 99% and 100% of the fatty acid product isolated from the culture is one or more fatty acids of specific chain length(s). In some embodiments of these methods, a prokaryotic photosynthetic organism transformed with a nucleic acid molecule encoding an acyl-ACP thioesterase is grown in culture, and one or more fatty acids is isolated from the culture media, where at least 50%, at least 55%, at least 60%, at least 65%, at least 70%, at least 75%, at least 80%, between 80% and 85%, between 85% and 90%, between 90% and 95%, between 95% and 97%, between 97% and 99%, or between 99% and 100% of the fatty acids isolated from the culture are fatty acids of specific chain lengths.

Isolation of Fatty Acid Products

Fatty acids and fatty acid products can be extracted from the seeds, fruit, or nuts of higher plants by grinding, crushing, or pressing the seeds, fruit or nuts. In some preferred embodiments, the seeds, nuts, or fruit are heated prior to or during the extraction process to soften plant tissues and improve solubility of the fatty acid product. Algae that produce fatty acid products can also be subject to extraction procedures in which the cells are ground, sonicated, or otherwise disrupted and pressed to separate the oil and other liquids from solid cell or tissue components. Fatty acids can be extracted with an organic solvent, for example, triglycerides and fatty acids can be extracted with hexane.

Extracellular hydrocarbons can also be extracted from living microalgae cells which are then returned to a bioreactor by exposure of the cells, in an otherwise sterile environment, to a non-toxic extraction solvent, followed by separation of the living cells and the hydrophobic fraction of extraction solvent and hydrocarbons, in which the separated living cells are then returned to a culture container such as a stainless steel fermentor or photobioreactor (see Biotechnol Bioeng. 2004 Dec. 5; 88(5):593-600 and Biotechnol Bioeng. 2004 Mar. 5; 85(5):475-81).

Fatty acid products (e.g., lipids, fatty acids, aldehydes, alcohols, alkenes, and alkanes) produced by cells of the invention can be harvested, or otherwise collected, by any convenient means. For example, hydrocarbons secreted from cells can be centrifuged to separate the hydrocarbons in a hydrophobic layer from contaminants in an aqueous layer and optionally from any solid materials as a precipitate in after centrifugation. Material containing cell or cell fractions can be treated with proteases to degrade contaminating proteins before or after centrifugation. In some instances the contaminating proteins are associated, possibly covalently, to hydrocarbons or hydrocarbon precursors which form hydrocarbons upon removal of the protein. In other instances the hydrocarbon molecules are in a preparation that also contains proteins. Proteases can be added to hydrocarbon preparations containing proteins to degrade proteins (for example, the protease from Streptomyces griseus can be used (SigmaAldrich catalog number P5147). After digestion, the hydrocarbons are preferably purified from residual proteins, peptide fragments, and amino acids. This purification can be accomplished, for example, by methods listed above such as centrifugation and filtration.

In some embodiments, fatty acid products are isolated from algal cells or whole culture that includes cells by generating a cell lysate. The cells are first disrupted, for example, by heat, treatment with an acid or base, treatment with enzymes, osmotic shock, mechanical disruption, sonication, freeze-thaw, etc., and then intracellular and cell membrane/cell wall-associated fatty acids can be collected from the lysed cells.

The fatty acid products can be extracted with a hydrophobic solvent such as hexane (see Frenz et al. 1989, *Enzyme Microb. Technol.,* 11:717) or by liquefaction (see for example Sawayama et al. 1999, *Biomass and Bioenergy* 17:33-39 and Inoue et al. 1993, *Biomass Bioenergy* 6(4): 269-274); oil liquefaction (see for example Minowa et al. 1995, *Fuel* 74(12):1735-1738); or supercritical $CO_2$ extraction (see for example Mendes et al. 2003, *Inorganica Chimica Acta* 356:328-334). Cells can also be freeze dried and pulverized followed by extraction with n-hexane (Miao and Wu, *Biosource Technology* (2006) 97:841-846).

In embodiments in which algae or microorganisms secrete fatty acid products, the cells can be removed from the culture medium, for example, by centrifugation, sedimentation, flocculation, or filtering, and the culture medium can be extracted with a solvent such as hexane.

Capture and recovery of fatty acids or fatty acid products that are secreted into the culture medium by recombinant bacteria and algae, such as cyanobacteria, as described above, can also be performed by adsorbing the fatty acids secreted into the culture medium to small, easily harvested objects. In this method, small objects that are able to bind free fatty acids and other lipids, referred to for purposes of this specification as "fat adsorbing objects," are circulated in the culture medium for an appropriate amount of time and then collected by physical separation. The fatty acids are then eluted from the fat adsorbing objects by the use of an appropriate non-polar solvent. Evaporation of the solvent, followed by further processing of the isolated fatty acids and lipids can then be carried out to yield chemicals and fuels that can be used for a variety of commercial purposes.

The fat adsorbing objects (for example, spheres ranging from 1 mm to 30 mm) can be manufactured from various materials including, but not limited to, polymers including, for example, polyethylene and derivatives, polystyrene and derivatives, polyamide and derivatives, polyester and derivatives, polyurethane and derivatives, polyacrylates and derivatives, silicone and derivatives, and polysaccharide and derivatives. Certain glass and ceramic materials can also be used as the solid support component of the fat adsorbing objects. The surfaces of the fat adsorbing objects are modified so that they are able to bind fatty acids and lipids. An example of such modification is the introduction of ether-linked alkyl groups having various chain lengths, preferably 10-30 carbons. In another example, acyl chains of various lengths can be attached to the surface of the fat adsorbing objects via ester, thioester, or amide linkages.

In another embodiment of this invention, the fat adsorbing objects are coated with inorganic compounds known to bind fatty acids and lipids. Examples of such compounds include but are not limited to aluminum hydroxide, graphite, anthracite, and silica.

To capture secreted fatty acids from the culture medium used to cultivate the photosynthetic microorganisms, the fat adsorbing objects are circulated in the culture medium for an appropriate period of time, and then removed from the culture by the use of filters or screens or other physical separation devices. Alternatively, the fat absorbing objects can be provided in a column or tube through which the algal culture can be passed.

The fatty acids bound to the fat adsorbing objects are then eluted by the use of an appropriate non-polar solvent such as hexane, after which the fat adsorbing objects can be dried and returned to the culture medium so that more fatty acids can be bound and removed. The hexane containing the dissolved fatty acids is then evaporated, leaving the fatty acids in a purified state for further conversion to chemicals and fuels. The fat adsorbing objects can be designed to be neutrally buoyant or positively buoyant to enhance circulation in the culture medium. It is anticipated that a continuous cycle of fatty acid removal and recovery using the fat adsorbing objects can be implemented by utilizing the steps outlined above.

The following examples are offered to illustrate but not to limit the invention.

EXAMPLE 1

Isolation of a Gene that Encodes a Novel Acyl-ACP Thioesterase (CalFatB2) from *Cuphea Aequipetala*

To isolate a gene encoding a medium chain acyl-ACP thioesterase, seeds of *Cuphea aequipetala* (Accession No. PI561477) were obtained from the USDA National Plant Germplasm System through the North Central Regional Plant Introduction Station in Ames, Iowa. Genomic DNA was isolated from the seeds as follows: 50 seeds were transferred to a microfuge tube and incubated for one hour at 50-55° C. in 0.35 mL of Extraction Buffer (200 mM Tris-HCl pH 8.0, 200 mM NaCl, 25 mM EDTA, 0.5% SDS, and 20 mg/mL proteinase K). The hydrated and lysed seeds were then ground using a plastic pestle. 0.35 mL of CTAB solution (2% w/v CTAB, 100 mM Tris-HCl, pH 8.0, 20 mM EDTA, 1.4 M NaCl, 1% PVP) was added and incubated at room temperature for one hour. The mixture was then centrifuged at 14000×g for 5 minutes and the supernatant solution was transferred to a Phase Lock Gel tube (5 Prime, Inc.). DNA was extracted with one volume of phenol: chloroform (1:1) and the aqueous phase was transferred to a new tube; this step was repeated twice. DNA was precipitated in 1/10 volume of 3 M sodium acetate, pH 5.5, and 0.8 volumes of isopropanol. The pellet was rinsed with 70% ethanol and the genomic DNA was resuspended in water.

A nested polymerase chain reaction (PCR) approach was used to amplify a large portion of the CalFatB2 gene using degenerate oligonucleotide primers. The primary PCR was performed with primers 'fatB degen1 2F' (SEQ ID NO:1) and 'fatB degen6 1R' (SEQ ID NO:2). The secondary PCR was performed with primers 'fatB degen7 1F' (SEQ ID NO:3) and 'fatB degen8 1R' (SEQ ID NO:4) that were nested inside the 'fatB degen1 2F' and 'fatB degen6 1R' primer sequences. A mixture of Phusion DNA polymerase (New England Biolabs, Ipswich, Mass.) plus RedTaq DNA polymerase (Sigma, St. Louis, Mo.) was used for both PCR reactions under the following thermocycler conditions: 94° C. for 5 min; 40 cycles of (94° C. for 30 s; 55° C. for 30 s; 72° C. for 4 min); 72° C. for 5 min. After electrophoresis through 1% agarose gels, 1.7- to 3-kbp amplicons from the secondary PCR were excised and purified using the ZYMO-CLEAN™ Gel DNA Recovery Kit (Zymo Research, Orange, Calif.). The isolated DNA was subsequently incubated for 15 min at 72° C. with Taq DNA polymerase and dNTPs, followed by insertion into the pCR4-TOPO vector (Invitrogen, Carlsbad, Calif.), which was used to transform chemically competent *E. coli* TOP10 cells (Invitrogen). Transformants were colony-screened using the primers 'fatB degen7 1F' (SEQ ID NO:3) and 'fatB seq2 R' (SEQ ID NO:5) to confirm the presence of the CalFatB2 gene. Positive clones were then sequenced.

The sequence of the isolated *Cuphea aequipetala* FatB2 genomic fragment is provided as SEQ ID NO:6. The first 22 and last 21 nucleotides of SEQ ID NO:6 correspond to the amplification primer sequences that were based on homology to other acyl-ACP thioesterases. Intron locations were predicted by comparison of the translated sequences from all three reading frames with known FatB protein sequences along with examination for consensus intron/exon boundaries, allowing the coding regions of the gene and deduced amino acid sequence of the encoded protein to be determined. The sequence was found to be highly homologous at the amino acid level to FatB genes of other *Cuphea* species, and the corresponding gene was designated "CalFatB2". The cloned region lacked sequences encoding the complete chloroplast transit peptide and the carboxy terminus since the primers used to isolate the sequence annealed to sequences within the coding region.

EXAMPLE 2

Expression of a Synthetic CalFatB2 Gene in *E. Coli*

A synthetic acyl-ACP thioesterase gene based on the coding sequences of the isolated CalFatB2 genomic clone was constructed for expression studies. The nucleotide sequence of this synthetic version of the CalFatB2 gene is indicated as SEQ ID NO:7, and the amino acid sequence derived from this synthetic gene is indicated as SEQ ID NO:8. The plasmid containing the synthetic gene is referred to as pJ201:24592.

The synthetic gene was truncated at the 5' end to eliminate sequences encoding the putative chloroplast transit peptide. Although the site of processing of plant acyl-ACP thioesterase precursors is not known with certainty, it is believed that the truncation of the synthetic gene excludes all or most of the plastid transit peptide-encoding region at the amino-terminus of the CalFatB2 thioesterase. Furthermore, as the gene sequence obtained by PCR lacked a carboxy-terminus-encoding region, a consensus carboxy-terminus sequence was designed based on published acyl-ACP thioesterase sequences in order to complete the 3' region of the gene (amino acid positions 356-362 of SEQ ID NO:8). The gene was synthesized using the codon usage preference of *Synechocystis* for functional testing of the gene product via expression in *E. coli* and *Synechocystis* 6803 (kazusa.or.jp/codon/cgi-bin/showcodon.cgi?species=1148).

In order to produce an expression vector, the synthetic CalFatB2 gene was amplified from pJ201:24592 using primers 'fatB GLA162 SYopt NT F' (SEQ ID NO:9) and 'fatB GLA162 SYopt R' (SEQ ID NO:10), and the IN-FUSION™ Dry-Down PCR Cloning Kit (Clontech, Mountain View, Calif.) was used to insert the gene into pTrcHisB (Invitrogen, Carlsbad, Calif.) having the TrcE promoter, which was then introduced into TOP10 *E. coli* cells to create plasmid GLA256 in strain PE-0284. Plasmid GLA256 was then transformed into the *E. coli* strain K27, which has a mutation in the fadD (acyl-CoA synthetase) gene (Overath et al., *Eur. J. Biochem.* 7:559-574), to create strain PE-0285. During the cloning process, an inadvertent elongation of the 3' consensus sequence by 15 nucleotides occurred, such that the last 2 amino acids (IS, i.e., isoleucine and serine) were replaced by KLGCFGG (SEQ ID NO: 11). The substrate preference and protein function of this thioesterase having a variant C-terminus (SEQ ID NO:12) were not significantly altered by this change in the carboxy-terminus when compared to the native sequence (the activity of the native sequence is shown as "Variant I" in Table 2 of Example 4). The *Synechocystis* codon-optimized nucleic acid sequence encoding this carboxy terminus variant is provided as SEQ ID NO:13.

Transformed *E. coli* K27 cells were inoculated into 4 mL of LB medium at $OD_{600}$=0.2 and induced with 0.5 mM IPTG during log phase; *E. coli* Top10 strains did not require induction. The cells were cultured in 15 mL Falcon round-bottom tubes for 24 hours and assayed for free fatty acid (FFA) production and secretion into the medium by the use of gas chromatography as follows: Cultures were centrifuged at 3,000×g and the supernatant solutions were filtered through 0.7 μm WHATMAN™ glass microfiber filters using a Millipore vacuum filter manifold. Two mL of the filtrate were transferred to glass tubes with Teflon-lined caps. Each 2-mL sample was extracted with a mixture of 40 μinternal standard solution (C11:0, 2 mg/mL), 50 μphosphoric acid (1 M), 100 μNaCl (5 M) and 2 mL hexane. After incubation for one hour with gentle rocking at room temperature, the organic phase was transferred to a GC vial. A 1 μL sample was injected into an Agilent Model 7890A gas chromatograph using a 40:1 split ratio onto a DB-FFAP column (J&W Scientific, 15 m×250 μm×0.25 μm), with a temperature profile starting at 150° C. for 0.5 min, then heating at 15° C./min to 230° C. and holding for 7.1 min (1.1 mL/min He). As shown in Table 1, octanoic acid was the predominant fatty acid secreted into the medium by the *E. coli* cells containing the CalFatB2 gene. No fatty acids were detected in the media of control cells lacking the CalFatB2 gene (but containing plasmid pTrcHisB).

TABLE 1

Production and Secretion of FFAs in *E. coli* Cells Expressing a Synthetic CalFatB2 Gene

| Strain ID | Plasmid | FFA levels (mg/L) | | | | | | | |
|---|---|---|---|---|---|---|---|---|---|
| | | 8:0 | 10:0 | 12:0 | 14:0 | 16:0 | 16:1 | 18:0 | 18:1 |
| CalFatB2 in *E. coli* Top 10 cells (Strain PE-0284) | GLA256 | 9.3 | 0.2 | 0.0 | 0.0 | 0.0 | 0.0 | 0.0 | 0.0 |
| CalFatB2 in *E. coli* K27 cells (Strain PE-0285) | GLA256 | 39.8 | 1.8 | 1.2 | 0.0 | 0.0 | 0.0 | 0.0 | 0.0 |
| Empty vector control (Strain PE-0286) | pTrcHisB | 0.0 | 0.0 | 0.0 | 0.0 | 0.0 | 0.0 | 0.0 | 0.0 |

EXAMPLE 3

Completion of the 3' End of the Native CalFatB2 Gene

Genome walking was performed to determine the complete actual sequence at the 3' end of the CalFatB2 coding region. An adaptor 'GW ad' was constructed by annealing oligos 'GW adL' (SEQ ID NO:14) and 'GW adS' (SEQ ID NO:15) at a final concentration of 100 mM each in 1× DNA ligase buffer (Invitrogen Corp., Carlsbad, Calif.). The GW adS oligomer was phosphorylated at the 5' end and included a 3' amino modifier. The following incubation conditions were used: 95° C. for 3 min; followed by 55° C. for 3 min; 45° C. for 3 min; 35° C. for 3 min; 25° C. for 3 min; 15° C. for 3 min; and then 4° C. hold. Single endonuclease digests were performed on *C. aequipetala* genomic DNA (gDNA) with PmlI, SnaBI, MscI, and StuI (New England Biolabs, Ipswich, Mass.) with overnight incubation at 37° C. The reactions were heat inactivated at 80° C. and the DNA was purified by standard phenol/chloroform procedures. Adaptor 'GW ad' was then ligated to the digested gDNA at 16° C. overnight with T4 DNA ligase (Invitrogen Corp., Carlsbad, Calif.). A nested PCR approach was used to amplify the 3' end of CalFatB2 gene. The primary PCR was performed with primers 'adP1' (SEQ ID NO:16) and 'GLA162-1F' (SEQ ID NO:17). The secondary PCR was performed with 'adP2' (SEQ ID NO:18) and 'GLA162-2BF' (SEQ ID NO:19). Phusion DNA polymerase (New England Biolabs, Ipswich, Mass.) was used for both PCRs using the following thermocycler conditions: 98° C. for 3 min; 10 cycles (98° C. for 10 sec; 67° C. for 30 sec; 72° C. for 4 min); 30 cycles (98° C. for 10 sec; 70° C. for 30 sec; 72° C. for 4 min); 72° C. for 5 min; 4° C. hold. dNTPs were added to the secondary amplicons and incubated with Taq polymerase at 72° C. for 5 min. The PCR products were cloned into the pCR4-TOPO vector by use of the TOPO TA Cloning kit (Invitrogen Corp., Carlsbad, Calif.) and sequenced. Sequence alignments were performed with Sequencher (Gene Codes Corp., Ann Arbor, Mich.).

The sequence of the resulting isolated *Cuphea aequipetala* FatB2 genomic DNA fragment is provided as SEQ ID NO:20. The predicted native Ca1FatB2 coding nucleotide sequence is indicated as SEQ ID NO:21. A small portion of the region of the gene that encodes the plastid transit peptide is not included in this sequence, although the entire sequence could be obtained by additional 5' genome walking The deduced protein sequence that is encoded by this Ca1FatB2 gene, assembled by PCR of genomic DNA with primers designed to hybridize within the coding region of a Class II acyl-ACP thioesterase followed by removal of intron sequences and gene walking to obtain sequences C-terminal sequences downstream of the amplified region of the gene is indicated as SEQ ID NO:22 (FIG. 1).

In order to confirm the absence of a chimeric assembly in the gene sequence extended by genome walking, a one-piece amplicon was obtained using primers 'GLA162 seq1F' (SEQ ID NO:23) and 'GLA162-290R' (SEQ ID NO:24). The 2.1 kb amplicon was gel purified and TOPO cloned into the pCRII-Blunt vector (Invitrogen Corp., Carlsbad, Calif.). The one-piece amplicon differed slightly within the coding regions of the version originally amplified from the seed DNA at two residues: M67I (methionine at residue 67 replaced by isoleucine) and L103I (leucine at residue 103 replaced by isoleucine). These amino acid substitutions were incorporated as a variant of the gene. These amino acid changes are present in "Variant III"; the nucleotide sequence of this variant is provided as SEQ ID NO:25 and the protein translation is provided as SEQ ID NO:26. The protein functionality of Variant III was not found to be affected to a significant extent (see Example 4).

EXAMPLE 4

Production of Ca1FatB2 Gene Variants and Expression in *E. Coli*

As described above, genome walking was performed to determine the 3' DNA sequence of the native Ca1FatB2 gene. The region encoding the hybrid carboxy-terminus consensus sequence present in plasmid GLA256 was replaced by a codon-optimized version of the native 3' end of the Ca1FatB2 gene using primers 'fatB GLA162 SYopt NT F' (SEQ ID NO:9) and 'fatB GLA162 SYopt 2R' (SEQ ID NO:27). The resulting amplicon (SEQ ID NO:28) encoded the protein indicated as SEQ ID NO:29 ("Variant I") and was inserted into the *Synechocystis* expression vector pSGI-YC28 using the InFusion system to create plasmid PR2B. pSGI-YC28 contains the TrcE promoter from pTrcHisA (Invitrogen Corp) the lacI$^q$ gene, and the homology arms that enable integration of the expression cassette into the "RS1" site of the *Synechocystis* PCC 6803 genome (Williams, *Methods Enzymol.* 167:766-778). This vector replicates autonomously in *E. coli* and allows gene expression in both *E. coli* and *Synechocystis* sp. PR2B was transformed into *E. coli* K27 to create strain PE-0238.

As described below, additional variants of the Ca1FatB2 gene were produced in order to assess potential structure-function relationships. Results of expression analyses normalized to optical density at 600 nm (OD600) are provided in Table 2.

Variant II: The encoded gene product has an isoleucine at amino acid position 103 rather than a leucine. The gene was produced from the Variant I gene via overlap PCR using the primers 'fatB GLA162 SYopt NT F' (SEQ ID NO:9), 'GLA162 SYopt mut2 R' (SEQ ID NO:68), 'GLA162SYopt mut2 F' (SEQ ID NO:69), and 'fatB GLA162 SYopt 2R' (SEQ ID NO:65). The nucleotide sequence of the Variant II gene product is given as SEQ ID NO:70, and the amino acid sequence of the Variant II gene product is given as SEQ ID NO:71.

Variant III: The encoded gene product has an isoleucine at amino acid position 103 rather than a leucine and an isoleucine at amino acid position 67 rather than a methionine. The gene was produced from the Variant II gene via overlap PCR using the primers 'fatB GLA162 SYopt NT F' (SEQ ID NO:9), 'GLA162SYopt mut3 R' (SEQ ID NO:30), 'GLA162SYopt mut3 F' (SEQ ID NO:31), and 'fatB GLA162 SYopt 2R' (SEQ ID NO:27). The nucleotide sequence of the Variant III gene is given as SEQ ID NO:25, and the amino acid sequence of the Variant III gene product is given as SEQ ID NO:26.

Variant IV: The encoded gene product has an isoleucine at amino acid position 103 rather than a leucine. In addition, the amino-terminus of the gene product was truncated by an additional 33 amino acids. The gene was produced from Variant II via PCR using the primers 'fatB GLA162 SYopt NT2 F' (SEQ ID NO:36) and 'fatB GLA162 SYopt 2R' (SEQ ID NO:27). The nucleotide sequence of Variant IV is provided as SEQ ID NO:37, and the amino acid sequence of the Variant IV gene product is given as SEQ ID NO:38.

Variant V: The encoded gene product has an isoleucine at amino acid position 103 rather than a leucine, an asparagine at amino acid position 184 rather than a serine, and an isoleucine at amino acid position 174 rather than a methionine. The gene was produced from Variant II via PCR. The nucleotide sequence of Variant V is provided as SEQ ID NO:39, and the amino acid sequence of the Variant V gene product is given as SEQ ID NO:40. This variant unexpectedly led to a much higher rate of octanoic acid secretion compared to the other variants and produced a higher proportion of octanoic acid. This result was surprising not only because mutants demonstrating increased activity toward the enzyme's preferred substrate have been unattainable until now, but also because other researchers have identified the active site of the enzyme as encompassing amino acids at least 100 residues away from the region of the protein exhibiting these mutations (see for example, U.S. Pat. No. 6,150,512, identifying amino acids YRREC (SEQ ID NO:41) as being at the active site (corresponding to amino acids 293-297 of SEQ ID NO:29 (FIG. 1)).

TABLE 2

Production and Secretion of FFAs in *E. coli* K27-Derived Cells Expressing Variants of a Synthetic Ca1FatB2 Gene

| Variant | Encoded protein | Vector | Strain ID | % total FFA | | | Production mg |
| | | | | C8:0 | C10:0 | C12:0 | C8:0/L/OD600 |
|---|---|---|---|---|---|---|---|
| I (native) SEQ ID NO: 28 | Original sequence of CaFatB1 mature protein SEQ ID NO: 29 | PR2B | PE-0238 | 87 | 6 | 3 | 15 |
| II SEQ ID NO: 32 | L103I SEQ ID NO: 33 | GLA518 | PE-0288 | 87 | 6 | 3 | 19 |
| III SEQ ID NO: 25 | M67I, L103I SEQ ID NO: 26 | GLA700 | PE-0295 | 92 | 6 | 2 | 19 |
| IV SEQ ID NO: 37 | L103I 96-bp 5' deletion SEQ ID NO: 38 | GLA513 | PE-0292 | 89 | 5 | 2 | 19 |
| V SEQ ID NO: 39 | S184N, L103I, M174I SEQ ID NO: 40 | GLA648 | PE-0049 | 95 | 4 | 1 | 65 |

EXAMPLE 5

Synthesis and Assay of Additional Thioesterase Variants

Based on the above results, additional variants of the FatB acyl-ACP thioesterase were constructed by overlap PCR amplification in which the mutations were incorporated into primer sequences. A first set of mutants is based on the wild-type *C. aequipetala* sequence, in which the mutants have various substitutions at amino acid position 174. A second set of mutants was constructed in which the mutants had substitutions at position 174, in addition to the mutations L103I and S184N. Two isolates of each variant were selected for determining the level of production and secretion of various chain length fatty acids in *E. coli* K27 according to the methods provided in Example 2. The results are provided in the tables of FIGS. 2A-2D and FIGS. 3A-3D, and depicted graphically in FIGS. 4A-4B).

Figure 4B:
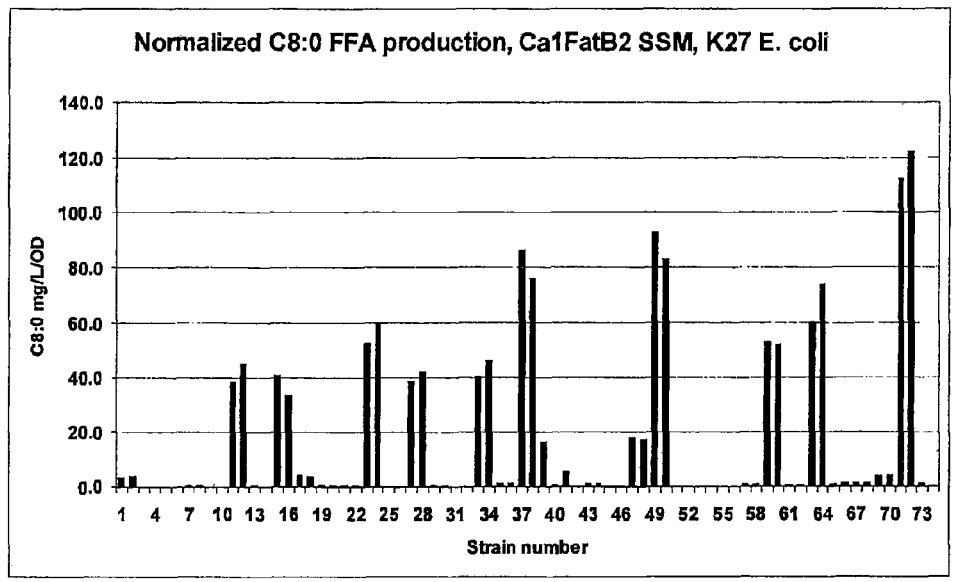
FIG. 4B depicts graphically the data from FIGS. 3A-3D of C8 fatty acid production normalized to cell density of the same isolates overnight growth.

Results of the fatty acid determination of samples from single amino acid position mutants indicate that isoleucine at position 174 results in the highest levels of production of C8 fatty acid. The M174I mutant (isolates 37 and 38 in FIGS. 2A-2D and FIGS. 3A-3D, having the nucleotide sequence provided as SEQ ID NO:42 and the amino acid sequence provided as SEQ ID NO:43) produces more than twice the octanoic acid produced by the isolates having the wild type gene (isolates 33 and 34 in FIGS. 2A-2D and FIG. 3A-3D). A mutant having valine at position 174 (isolates 23 and 24) also produced higher than wild-type levels of C8 fatty acid, and mutants having phenylalanine (isolates 15 and 16), cysteine (isolates 27 and 28), or leucine (isolates 11 and 12) at position 174 produced high levels and high percentages of octanoic acid as well. This was true for the cultures as a whole (FIG. 4A) and when the values were normalized for cell density (FIG. 4B).

The production of octanoic acid was enhanced even further when additional mutations were combined with the mutations at position 174. The highest producing isolates, isolates 71 and 72, which included the S184N and L103I mutations in addition to the M174I mutation, yielded almost three-fold the amount of octanoic acid as did the wild-type strain (isolates 33 and 34), confirming the results shown in Table 2, in which the S184N, L103I, M174I mutant ("Variant V" having the nucleotide sequence SEQ ID NO:39, encoding amino acid sequence of SEQ ID NO:40) produced about four-fold the amount of octanoic acid as did the native *C. aequipetala* sequence ("Variant I"). Mutations of M174 to valine, phenylalanine, or leucine in combination with the L103I and S184N mutations (variants 49 and 50, 63 and 64, and 59 and 60, respectively) also showed enhancement of C8 fatty acid production with respect to transformants expressing the M174V, M174F, and M174L mutations on their own (isolates 23 and 24, 15 and 16, and 11 and 12, respectively).

EXAMPLE 6

Synthesis and Assay of Additional Thioesterase Variants

To complete the set of single site mutants having different substitutions at position 174 that was provided in Example 5, the single site mutant M174R was constructed. The triple site mutants L103I, M174C, S184N and L103, M174P, S184N were also constructed to determine the effect of the L103I and S184N substitutions on a moderately high-producing mutant (M174C, having activity comparable to wild-type) and a low-producing mutant (M174P). Finally, to elucidate the relative contribution of the mutations at positions 103 and 184 to the increased activity of the L103I, M174I, S184N triple site mutant over the M174I single site mutant, the double mutant L103I, M174I was also constructed by PCR amplification.

*E. coli* K27 cells were transformed with each of the constructs, and as a control, cells were transformed with empty vector. Additional isolates of cells transformed with constructs containing the M174I thioesterase mutant gene and triple L103I, M174I, S184N thioesterase mutant gene used in the experiments of Example 5 were also obtained for comparison of the results to previous experiments. Two isolates were obtained for each of the mutants and the empty vector control. The sequences of the thioesterase constructs in isolated TOP10 *E. coli* transformants were confirmed by sequencing prior to transforming the constructs into the K27 expression strain.

The thioesterase mutant-containing cells and empty vector-containing cells were cultured and induced for thioesterase expression, and fatty acids were isolated from the media after culturing the isolates overnight and assayed as provided in Example 5. Due to co-eluting contaminating peaks, C12 fatty acid amounts could not be determined; however, based on Example 2, the amount of C12 fatty acid in the samples was likely to be less than 3% of the total fatty acids in the samples.

Figure 6:
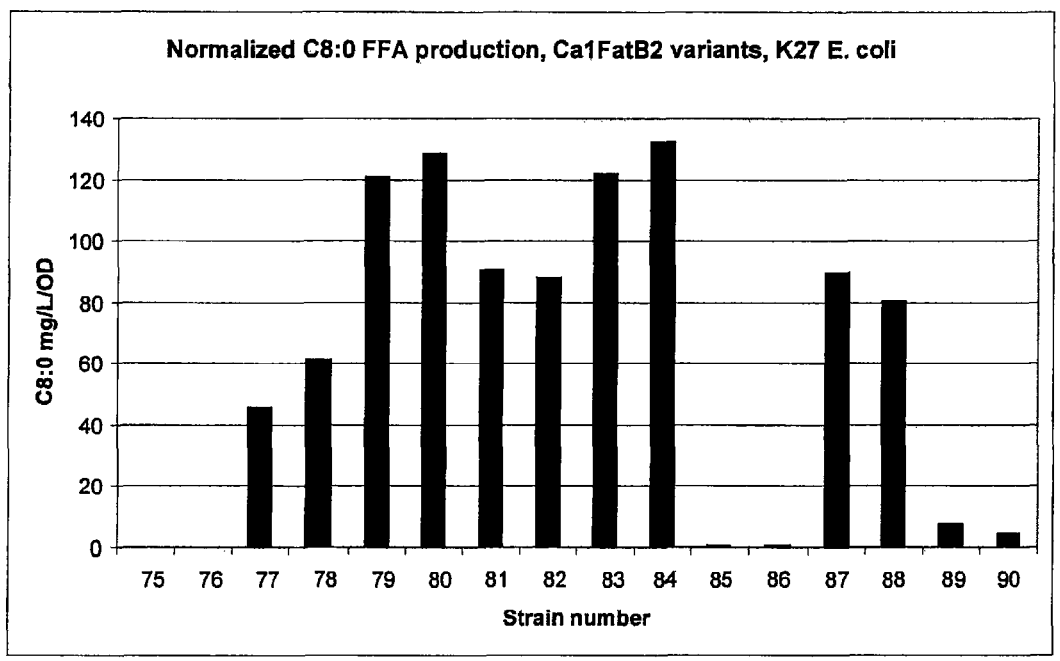
FIG. 6 depicts graphically the C8 fatty acid production, normalized for cell density, of the isolates of FIGS. 5A-5B.

The data presented in the table of FIG. 5A shows that the amounts of C8 and total fatty acids produced by the wild-type, M174I mutant, and L103I, M174I, S184N mutant were comparable to the levels seen in FIGS. 2A-2D (compare isolates 37, 38, 71, and 72 of FIGS. 2A-2D with isolates of 81, 82, 79, and 80 of FIGS. 5A-5B), demonstrating the reproducibility of the results. Isolates 83 and 84 of FIG. 5 (nucleotide and amino acid sequences provided as SEQ ID NO:44 and SEQ ID NO:45, respectively), which include the L103I and M174I mutations (but lack the S184N mutation), produce levels of C8 fatty acid and total fatty acid that are essentially the same as that of the triple mutant L103I, M174I, S184N, indicating that a mutant thioesterase that includes the L103I mutation in addition to the M174I mutation has enhanced fatty acid production with respect to a mutant thioesterase that includes only the M174I mutation, while the S184N mutation has no discernible affect on fatty acid production. Normalized fatty acid production is provided in the table of FIG. 5B and presented graphically in FIG. 6.

This result also indicates that the mutation of position M174, alone or in combination with a mutation at position 103, is tolerant of at least some mutations at other amino acid positions in the protein, as the S184N mutation did not affect the yield.

The data also demonstrate that modifying the gene such that an isoleucine is encoded at position 103 (here, in combination with S184N) increases the activity of a thioesterase mutant having a C or P at position 174 (comparing the higher production levels of isolates 87-90 of FIGS. 5A-5B with those of isolates 27, 28, 35, and 36 of FIGS. 2A-2D). A variant having isoleucine at position 103 and cysteine at position 174 also showed enhancement of C8 fatty acid production with respect to wild-type bearing isolates.

EXAMPLE 7

Expression of the Ca1FatB2 Gene in the Cyanobacterium Synechocystis Sp.

Plasmid PR2B of Example 4 was also transformed into Synechocystis sp. PCC 6803 to create strain PH-0094. The transformation protocol used was essentially as described by Zang et al. (*Microbiology* 45:241-245). To test for the production of free fatty acids in phototrophically grown Synechocystis, the Ca1FatB2-containing cells were pre-cultivated in 100 mL of BG-11 medium supplied with kanamycin (20 mg/L) to late-log phase ($OD_{730\ nm}$=1.0) on a rotary shaker (150 rpm) at 30° C. with constant illumination (60 $\mu E \cdot m^{-2} \cdot sec^{-1}$). Cultures were then subcultured at initial $OD_{730\ nm}$=0.4-0.5 in BG-11 and cultivated overnight to $OD_{730\ nm}$=0.7-0.9. For time-course studies, 50-mL aliquots of the culture were transferred into 250-mL flasks and induced by adding IPTG (final conc.=1 mM). Cultures were sampled at various time points after IPTG induction and then filtered through WHATMAN™ GF/B glass microfiber filters using a MILLIPORE® vacuum filter manifold (Millipore, Billerica, Mass.). Filtrates were collected in screw top culture tubes for gas chromatographic (GC) analysis. Free fatty acids (FFA) were separated from the filtered culture supernatant solutions by liquid-liquid extraction. For each sample, 2 mL filtered culture was extracted with a mixture of 40 µL internal standard solution (C11:0, 2 mg/mL), 50 µl phosphoric acid (1 M), 100 µl NaCl (5 M) and 2 mL hexane. A 1 µl sample was injected using a 40:1 split ratio on to a DB-FFAP column (J&W Scientific, 15 m×250 µm×0.25 µm), with a temperature profile starting at 150° C. for 0.5 min, then heating at 15° C./min to 230° C. and holding for 7.1 min (1.1 mL/min He). The level of secreted FFAs in the medium 10 days after IPTG induction is provided in Table 3. The results demonstrate that the high activity thioesterase variants also result in higher fatty acid production by a photosynthetic organism.

TABLE 3

Production and Secretion of FFAs in Synechocystis Cells Expressing a Synthetic Ca1FatB2 Gene

| Strain ID | Plasmid | C8:0 | C10:0 | C12:0 | C14:0 | C16:0 | C16:1 | C18:0 | C18:1 | Total FFA (mg/L) |
|---|---|---|---|---|---|---|---|---|---|---|
| Vector control (Strain PH-0019) | YC27 | 0.0 | 0.0 | 0.0 | 0.0 | 0.0 | 0.0 | 0.0 | 0.0 | 0.0 |
| Ca1FatB2 native gene (Strain PH-0094) | PR2B | 54.8 | 6.4 | 0.0 | 0.0 | 0.0 | 0.0 | 0.0 | 0.0 | 61.2 |
| Ca1FatB2 S184N, L103I, M174I gene (Strain PH-0095) | GLA648 | 156.4 | 11.4 | 0.2 | 0.0 | 0.0 | 0.0 | 0.0 | 0.0 | 167.8 |

EXAMPLE 8

Isolation of Additional Novel Acyl-ACP Thioesterase (FatB) Genes from Various *Cuphea* Species An additional seventeen novel FatB genes, listed in Table 4, were also isolated from *Cuphea* samples by extracting genomic DNA from *Cuphea* seeds or vegetative tissues. Nested degenerate primers were used to clone individual FatB genes from the DNA samples. This approach results in gene sequences lacking complete 5' and 3' ends of the genes. The genes obtained by amplification of genomic DNA provided sequences that started from within the plastid transit peptide, therefore it was unnecessary to complete the terminal 5' nucleotide sequence in order to obtain a functional gene. (The activity of the thioesterase is unaffected by the presence or the absence of this transit peptide (Jones et al. (1995) *The Plant Cell* 7: 359-371; Voelker et al. (1992) *Science* 257:72-74).) The 3' ends of many of the novel thioesterase genes were completed via genome walking For those genes whose 3' ends were not determined, a consensus hybrid sequence was appended based on known *Cuphea* FatB protein sequences prior to expressing the genes in vivo. We have found that altering the 3' sequence does not significantly modify substrate preference or function of FatB genes.

Genomic DNA Isolation from *Cuphea* Samples

Genomic DNA was isolated from *Cuphea avigera*, *Cuphea carthagenesis*, *Cuphea decandra*, *Cuphea inflate*, *Cuphea paucipetala*, and *Cuphea leptopoda* tissues as follows: 2 cm stem and leaf cuttings (*Cuphea avigera*) or 40-50 seeds (other species) from each *Cuphea* sample were transferred to separate microfuge tubes and incubated for one hour at 55° C. in 350 μl of Extraction Buffer (200 mM Tris-HCl pH 8.0, 200 mM NaCl, 25 mM EDTA, 0.5% SDS, and 20 mg/ml proteinase K). The hydrated and lysed tissues were then ground using a plastic pestle. 350 μl of CTAB solution (2% w/v CTAB, 100 mM Tris-Cl, pH 8.0, 20 mM EDTA, 1.4 M NaCl, 1% PVP) were added and incubated at room temperature for one hour. The mixture was then centrifuged at 14000×g for 5 minutes and the supernatant solution was transferred to a Phase Lock Gel tube (5 Prime, Inc., Gaithersburg, Md.). DNA was extracted with one volume of phenol:chloroform (1:1) and the aqueous phase was transferred to a new tube; this step was repeated 2-3 times. DNA was precipitated in 1/10 volume of 3 M sodium acetate, pH 5.5, and 0.8 volumes of isopropanol. The pellet was rinsed with 70% ethanol and the genomic DNA was resuspended in water.

Gene Isolation and Cloning

A nested PCR approach was employed to amplify FatB genes using degenerate primers as described below. The primary PCR was performed with primers fatB degen1 2F (5'-ATGGTGGCTRCYGMWGCAAG; SEQ ID NO:1) and fatB degen6 1R (5'-CTAAGAKAYMGAGTYTCCAKKT-SARGTC; SEQ ID NO:2). The secondary PCR was performed with primers fatB degen7 1F (5'-GCAGCAAGT-TCHGCATKCTTCC; SEQ ID NO:3) and fatB degen8 1R (5'-CAKTCTTSGGYCKCCACTCAG; SEQ ID NO:4). A mixture of Phusion DNA polymerase (New England Biolabs, Ipswich, Mass.) plus RedTaq (Sigma, St. Louis, Mo.) was used for both PCRs under the following thermocycler conditions: 94° C. for 5 min; 40 cycles (94° C. for 30 s; 55° C. for 30 s; 72° C. for 4 min); 72° C. for 5 min. 1.7- to 3-kbp amplicons from the secondary PCR were excised and purified after electrophoresis through 1% agarose gels (Bio-Rad, Hercules, Calif.). The isolated DNA was subsequently incubated for 15 min at 72° C. with Taq DNA polymerase and dNTPs, followed by cloning into the pCR4-TOPO vector (Invitrogen, Carlsbad, Calif.) and transformed into chemically competent *E. coli* TOP10 cells (Invitrogen). Selected *E. coli* clones that were positive for gene insertions were then sequenced. Intron locations were predicted by comparison of the translated sequences from all three reading frames with known FatB protein sequences, allowing the coding regions of the genes and deduced amino acid sequences of the encoded proteins to be determined.

Genome Walking to Determine 3' Carboxy Terminus Coding Sequence

Genome walking was performed on the Cc1FatB1, Ci1FatB1, Cl1FatB1, Cl3FatB1, Cd1FatB1, Cl4FatB1 and Ca2FatB2 genes to complete the sequences at the 3' ends of the coding regions. An adaptor 'GW ad' was constructed by annealing oligos 'GW adL' (GTAATACGACTCAC-TATAGGGCACGCGTGGTCGACGGCCCGGGCT GGTT; SEQ ID NO:14) and 'GW adS' (AACCAGCCCG; SEQ ID NO:15) at a final concentration of 100 μM each in 1× ligase buffer (Invitrogen Corp.). The following thermocycler conditions were used: 95° C. for 3 min; 55° C. for 3 min; 45° C. for 3 min; 35° C. for 3 min; 25° C. for 3 min; 15° C. for 3 min; 4° C. hold. Single endonuclease digests were performed on the *Cuphea* genomic DNAs with PmlI, SnaBI, MscI, EcoRV, and/or StuI (Fermentas, Glen Burnies, Md.; New England Biolabs, Ipswich, Mass.) with overnight incubation at 37° C. The reactions were heat inactivated at 80° C. and were followed by standard phenol/chloroform cleanup. Adaptor 'GW ad' was then ligated to the digested genomic DNA at 16° C. overnight with T4 DNA ligase (Invitrogen). A nested PCR approach was used to amplify the genomic 3' ends of the FatB genes. Phusion DNA polymerase (New England Biolabs) was used for both PCRs using the following thermocycler conditions: 98° C. for 3 min; 10 cycles (98° C. for 10 sec; 67° C. for 30 sec; 72° C. for 4 min); 30 cycles (98° C. for 10 sec; 70° C. for 30 sec; 72° C. for 4 min); 72° C. for 5 min; 4° C. hold. dNTPs were added to the secondary amplicons and incubated with Taq at 72° C. for 5 min. The PCR products were cloned into the pCR4 vector (Invitrogen Corp.) and sequenced (Bio Applied Technologies Joint, Inc., San Diego, Calif.). Alignments were performed with the Sequencher program (Gene Codes Corp., Ann Arbor, Mich.).

Cloning of Codon-Optimized Synthetic FatB Genes

The *Synechocystis* sp. PCC 6803 codon usage table was utilized to codon optimize the coding regions for most of the novel thioesterase genes. Gene constructs encoding the sequences of SEQ ID NO:55 was synthesized to include the carboxy-terminus consensus sequence ANGAISTGK-TSNGNSIS (SEQ ID NO:46), gene constructs encoding the sequences of SEQ ID NO:30 and SEQ ID NO:36 were synthesized to include the carboxy-terminus consensus sequence TNGAISTTKTSPGNSVS (SEQ ID NO:47), and genes encoding the sequences of SEQ ID NO:51, SEQ ID NO:59, SEQ ID NO:63, SEQ ID NO:79, SEQ ID NO:85, SEQ ID NO:89, and SEQ ID NO:99 were cloned with the native 3' sequences that were determined by genome walking Both consensus sequences were based on published acyl-ACP thioesterase 3' DNA sequences. The synthetic gene constructs for expression were made with a truncation of the 5' end to exclude the predicted plastid transit peptide-encoding region at the amino-terminus.

References to the disclosed sequences (SEQ ID NOs) of these synthetic genes are indicated in Table 4. The CiFatB1 gene was synthesized by Integrated DNA Technologies (Coralville, Iowa); all other genes were synthesized by DNA 2.0 (Menlo Park, Calif.). All genes were cloned into a *Synechocystis* sp. PCC 6803 integration vector pSGI-YC28 with the exception of Ca1FatB1, which was cloned into the pTrcHisB vector (Invitrogen), and Cl3FatB1 and Ca2FatB2, which were cloned into the pJexpress plasmid at the time of synthesis. pSGI-YC28 contains the "TrcE" trc promoter from pTrcHisA, the lacI$^q$ gene, and the homology arms that enable integration of the expression cassette into the "RS1" site of the *Synechocystis* PCC 6803 genome (Williams, *Methods Enzymol.* 167:766-778). This vector replicates autonomously in *E. coli* and allows gene expression in both *E. coli* and *Synechocystis* sp. 6803. pJexpress is an *E. coli* expression system developed at DNA2.0 in which a modified inducible T5 promoter drives gene expression. Gene inserts were either cloned using the InFusion system (Clontech, Mountainview, Calif.) or double-digested with BamHI and NcoI (New England Biolabs) and ligated with T4 DNA ligase (New England Biolabs). An alignment of the amino terminal regions of the proteins encoded by the expression constructs is provided as FIG. 7.

TABLE 4

Novel FatB Genes Isolated from Various *Cuphea* Species

| NGPR Acc. Number | *Cuphea* Species | Gene | Isolated genomic DNA sequence | Isolated gene, amino acid sequence | Codon-optimized gene sequence, expression constructs | Amino acid Sequence, Expression constructs |
|---|---|---|---|---|---|---|
| PI 534673 | C. carthagenensis | Cc1FatB1 | SEQ ID NO: 48 | SEQ ID NO: 49 | SEQ ID NO: 50 | SEQ ID NO: 51 |
| PI 561477 | C. aequipetala | Ca1FatB1 | SEQ ID NO: 52 | SEQ ID NO: 53 | SEQ ID NO: 54 | SEQ ID NO: 55 |
| PI 534687 | C. inflata | Ci1FatB1 | SEQ ID NO: 56 | SEQ ID NO: 57 | SEQ ID NO: 58 | SEQ ID NO: 59 |
| PI 534694 | C. leptopoda | Cl1FatB1 | SEQ ID NO: 60 | SEQ ID NO: 61 | SEQ ID NO: 62 | SEQ ID NO: 63 |
| PI 534694 | C. leptopoda | Cl1FatB2 | SEQ ID NO: 64 | SEQ ID NO: 65 | | |
| PI 561495 | C. paucipetala | Cp1FatB1 | SEQ ID NO: 66 | SEQ ID NO: 67 | SEQ ID NO: 68 | SEQ ID NO: 69 |
| PI 561487 | C. leptopoda | Cl2FatB1 | SEQ ID NO: 70 | SEQ ID NO: 71 | | |
| PI 561487 | C. leptopoda | Cl2FatB2 | SEQ ID NO: 72 | SEQ ID NO: 73 | SEQ ID NO: 74 | SEQ ID NO: 75 |
| PI 578175 | C. leptopoda | Cl3FatB1 | SEQ ID NO: 76 | SEQ ID NO: 77 | SEQ ID NO: 78 | SEQ ID NO: 79 |
| PI 578175 | C. leptopoda | Cl3FatB2 | SEQ ID NO: 80 | SEQ ID NO: 81 | | |
| PI 594928 | C. decandra | Cd1FatB1 | SEQ ID NO: 82 | SEQ ID NO: 83 | SEQ ID NO: 84 | SEQ ID NO: 85 |
| PI 650910 | C. leptopoda | Cl4FatB1 | SEQ ID NO: 86 | SEQ ID NO: 87 | SEQ ID NO: 88 | SEQ ID NO: 89 |
| PI 650910 | C. leptopoda | Cl4FatB2 | SEQ ID NO: 90 | SEQ ID NO: 91 | | |
| PI 650910 | C. leptopoda | Cl4FatB3 | SEQ ID NO: 92 | SEQ ID NO: 93 | | |
| Ames 17868 | C. avigera | Ca2FatB1 | SEQ ID NO: 94 | SEQ ID NO: 95 | | |
| Ames 17868 | C. avigera | Ca2FatB2 | SEQ ID NO: 96 | SEQ ID NO: 97 | SEQ ID NO: 98 | SEQ ID NO: 99 |
| Ames 17868 | C. avigera | Ca2FatB3 | SEQ ID NO: 100 | SEQ ID NO: 101 | | |

EXAMPLE 9

Expression of FatB Thioesterases in *E. Coli* and Analysis Of FFA Products

Constructs of Example 8 were transformed into *E. coli* strain K27, which has a mutation in the fadD (acyl-CoA synthetase) gene (Overath et al., *Eur. J. Biochem.* 7:559-574), to create the indicated strains. Ca2FatB2 and Cl3FatB1 were under the control of the inducible T5 promoter; all other thioesterase genes were driven by the inducible pTrcE promoter. These strains were inoculated into 10 mL of LB medium supplemented with 50 mg/L kanamycin at $OD_{600}$=0.2 and induced with 0.5 mM IPTG during log phase.

The cultures were grown in 25 mL glass vials for 24 hours and assayed for free fatty acid (FFA) production and secretion into the medium by the use of gas chromatography as follows: Extractions were performed on 7.2 mL whole culture with a mixture of 40 µl internal standard solution (C9:0, C13:0, and C17:0, final concentration of 50 µg/mL), 0.6 mL of 50% sulfuric acid, 1.2 mL NaCl (5 M), and 10.8 mL hexane. Samples were vortexed vigorously to emulsify, incubated at room temperature for one hour, and vortexed again. The mixture was spun at 1800 rpm for 5 minutes, and the organic phase was transferred to a GC vial. A 1 µL sample was injected into an Agilent Model 7890A gas chromatograph using a 40:1 split ratio onto a DB-FFAP column (J&W Scientific, 15 m×250 µm×0.25 µm), with a temperature profile starting at 180° C. for 0.5 minute, then heated at a rate of 30° C. per minute to 230° C., and holding for 3.9. minutes (1.8 mL/min He). Free fatty acid peaks were detected on an FID instrument.

Table 5 shows the predominant fatty acids produced by the various strains.

The *E. coli* strain transformed with the Ca2FatB2 thioesterase predominantly synthesized C8 free fatty acids, which made up 40% of the C8-C18 free fatty acids produced by the strain.

The *E. coli* strains transformed with the Cl2FatB2 and Cl4FatB1 thioesterases predominantly synthesized C10 free fatty acids, which made up 42.6% and 37.7% of the total C8-C18 free fatty acids produced by Cl2FatB2 and Cl4FatB1 strains, respectively, but the transformed strains also made a significant amount of C16 fatty acids, which made up 25.4% and 27.7% of the total C8-C16 free fatty acids produced by Cl2FatB2 and Cl4FatB1 strains, respectively.

Figure 8:
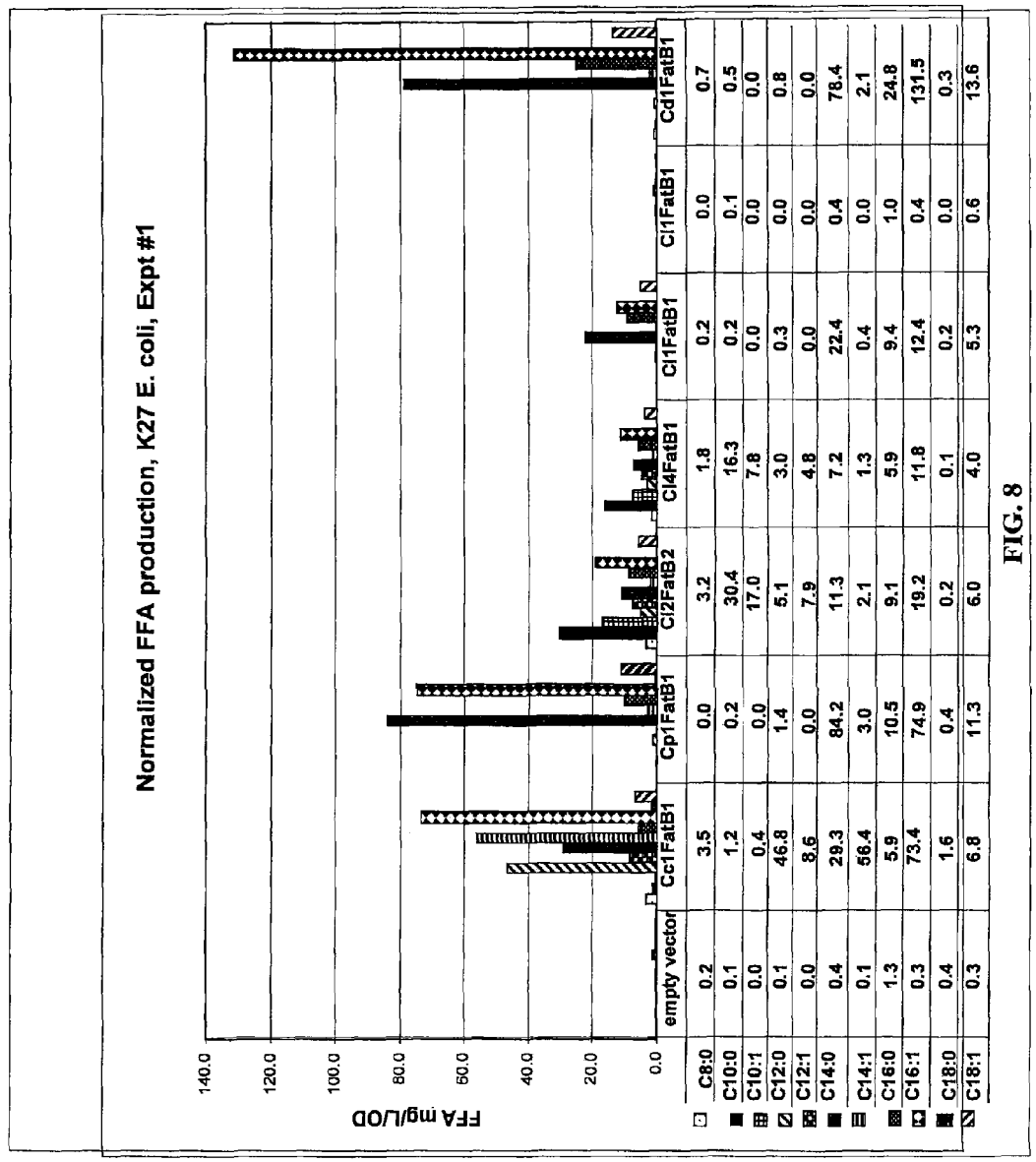
FIG. 8 provides a graph showing the amount of C8:0, C10:0, C10:1, C12:0, C12:1, C14:0, C14:1, C16:0, C16:1, C18:0, and C18:1 free fatty acids, normalized to cell density, isolated from cultures of *E. coli* transformed with various *Cuphea* FatB thioesterase genes.
Figure 9:
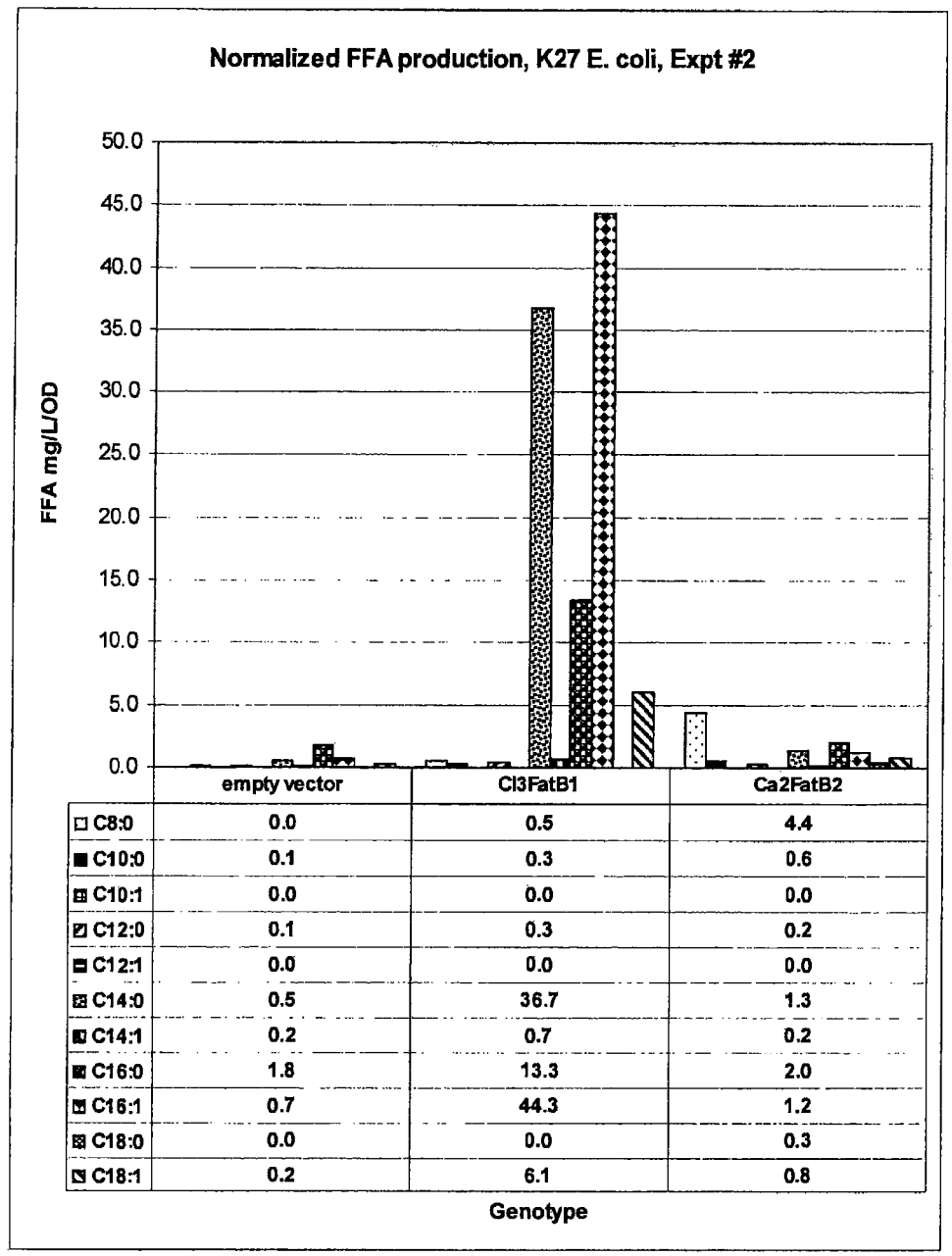
FIG. 9 provides a graph showing the amount of C8:0, C10:0, C10:1, C12:0, C12:1, C14:0, C14:1, C16:0, C16:1, C18:0, and C18:1 free fatty acids, normalized to cell density, isolated from cultures of *E. coli* transformed with various *Cuphea* FatB thioesterase genes.
Figure 10:
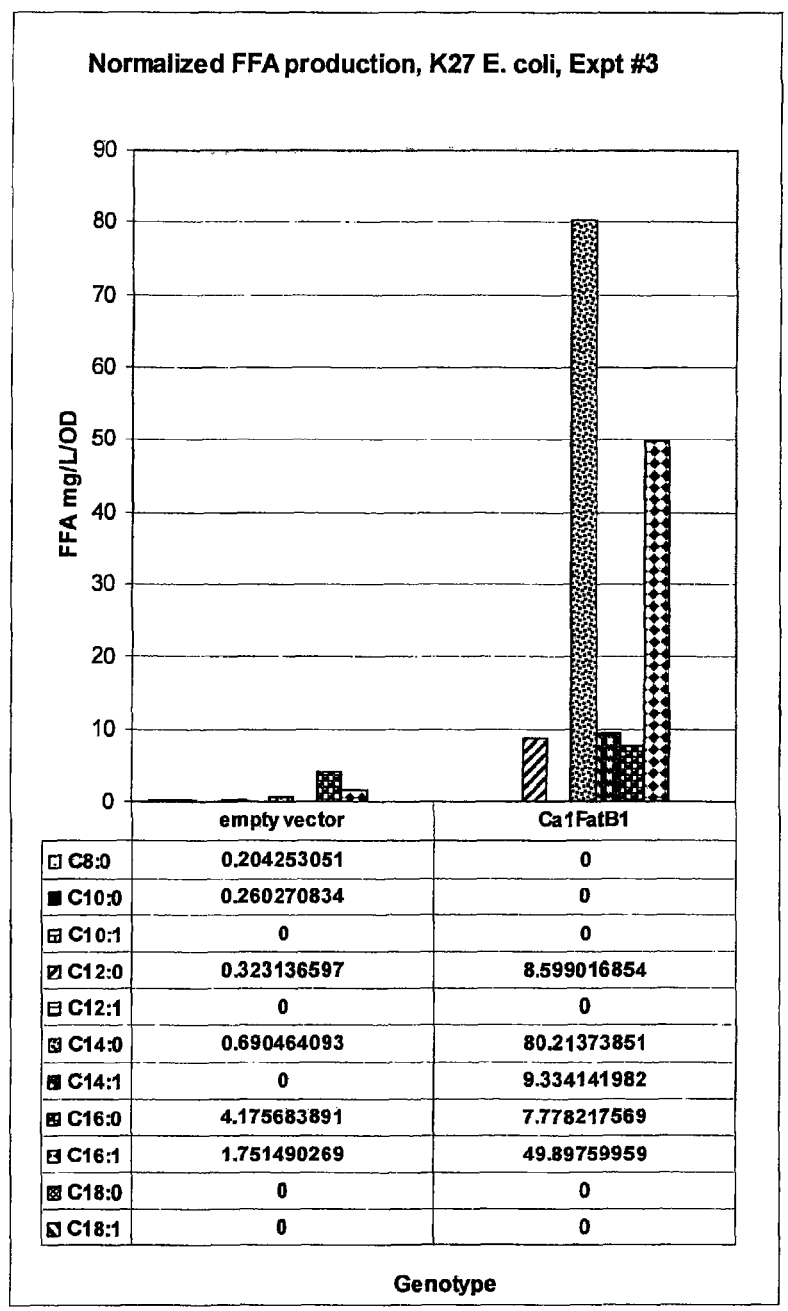
FIG. 10 provides a graph showing the amount of C8:0, C10:0, C12:0, C14:0, C16:0, C16:1, C18:0, and C18:1 free fatty acids, normalized to cell density, isolated from cultures of *E. coli* transformed with the Ca1FatB1 thioesterase gene.
Figure 11:
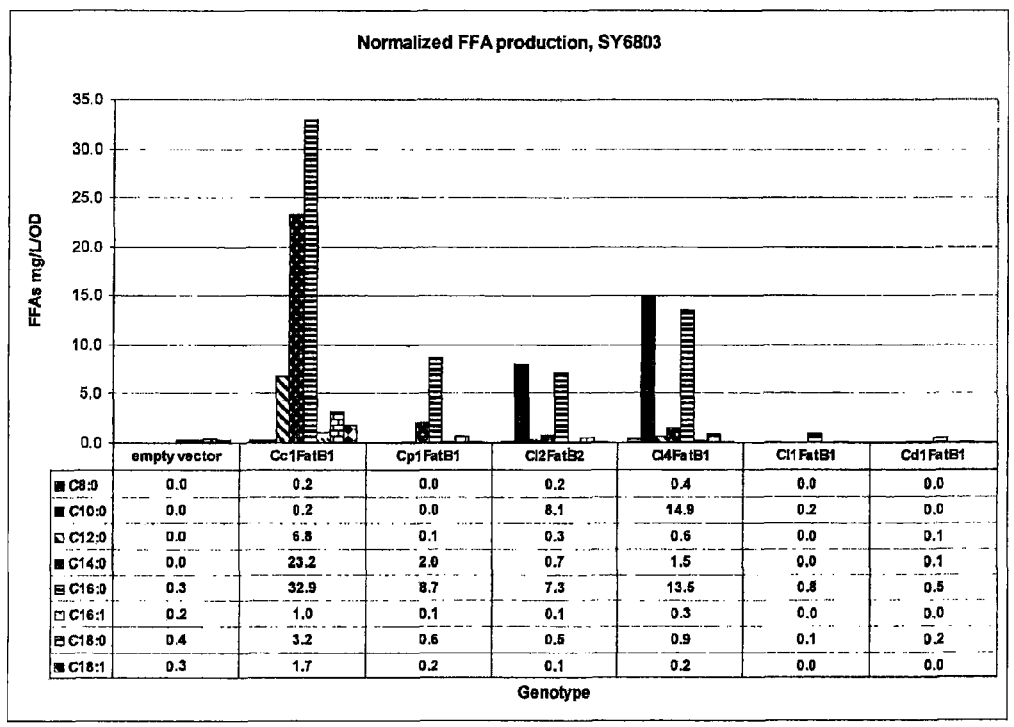
FIG. 11 provides a graph showing the amount of C8:0, C10:0, C12:0, C14:0, C16:0, C16:1, C18:0, and C18:1 free fatty acids, normalized to cell density, isolated from cultures of *Synechocystis* transformed with various *Cuphea* FatB thioesterase genes.
Figure 12:
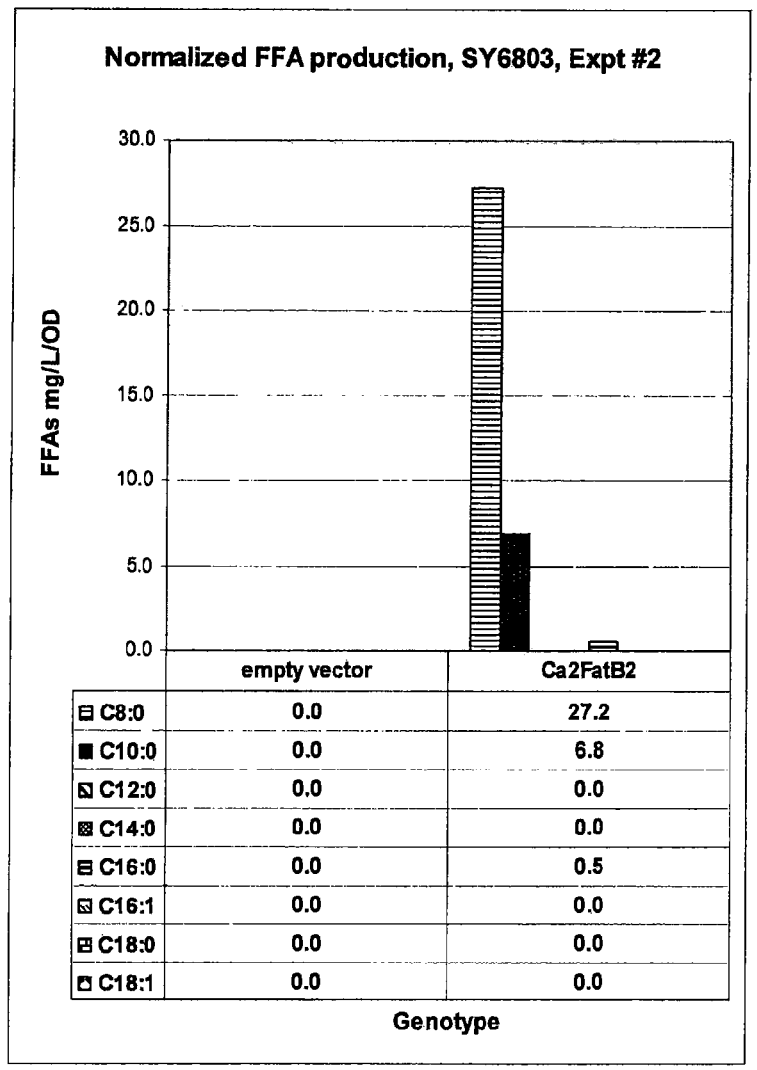
FIG. 12 provides a graph showing the amount of C8:0, C10:0, C12:0, C14:0, C16:0, C16:1, C18:0, and C18:1 free fatty acids, normalized to cell density, isolated from a culture of *Synechocystis* transformed with the Ca2FatB2 thioesterase gene.
Figure 13A:
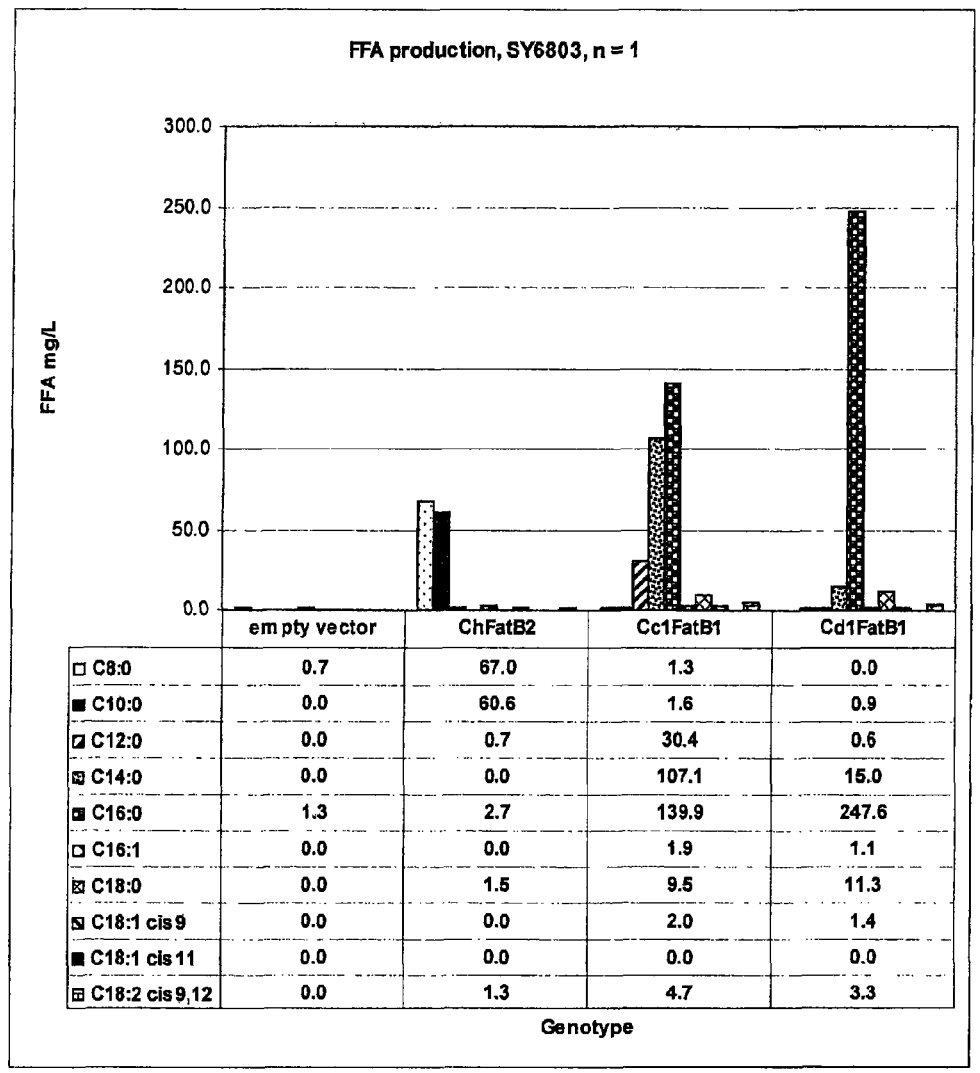
FIG. 13A provides a graph showing the amount of C8:0, C10:0, C12:0, C14:0, C16:0, C16:1, C18:0, and C18:1 free fatty acids isolated from cultures of *Synechocystis* transformed with various *Cuphea* FatB thioesterase genes.
Figure 13B:
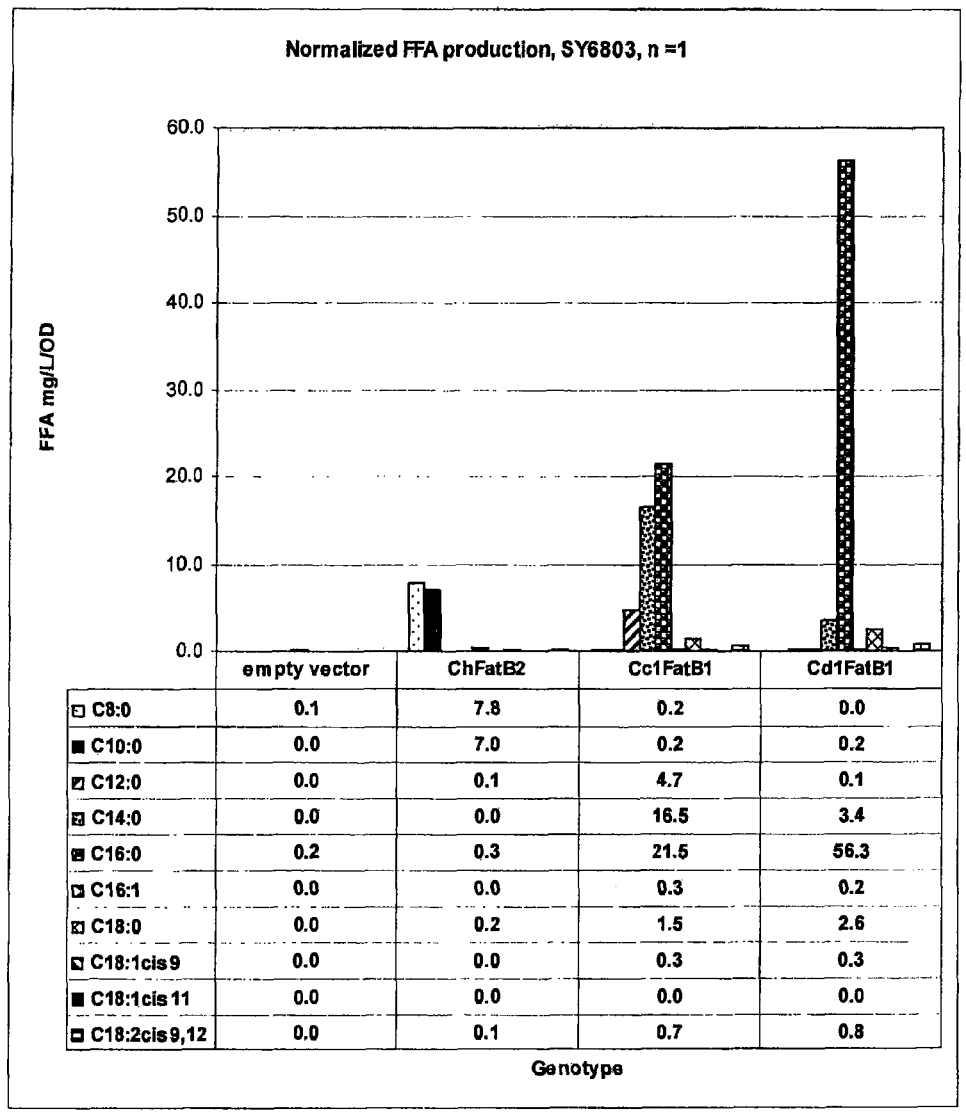
FIG. 13B provides a graph of the same data, in which the production values were normalized for cell density.

The Cc1FatB1-containing *E. coli* strain produced mainly C12, C14, and C16 free fatty acids, with a greater percentage of C14 and C16 free fatty acids that C12 free fatty acids being produced by the *E. coli* host. Cp1FatB1, Cl1FatB1, Cd1FatB1, and Cl3FatB1-containing strains produced predominantly C14 and C16 free fatty acids, with 80% to greater than 90% of the free fatty acids being produced being C14 or C16 fatty acids. Although more than 50% of the free fatty acids produced by the Ci1FatB1-carrying strain were C16 fatty acids, this strain also produces some C18 fatty acids (>20% of the fatty acids produced). The results are depicted graphically in FIG. 8, FIG. 9, and FIG. 10.

TABLE 5

Production and Secretion of Free Fatty Acids by *E. coli* Expressing FatB Genes

| Genotype | OD 600 | C8:0 | C10:0 | C10:1 | C12:0 | C12:1 | C14:0 | C14:1 | C16:0 | C16:1 | C18:0 | C18:1 | Total FFAs mg/L/OD |
|---|---|---|---|---|---|---|---|---|---|---|---|---|---|
| Experiment #1 | | | | | | | | | | | | | |
| empty vector | 4.8 | 0.2 | 0.1 | 0.0 | 0.1 | 0.0 | 0.4 | 0.1 | 1.3 | 0.3 | 0.4 | 0.3 | 3.2 |
| Cc1FatB1 | 1.3 | 3.5 | 1.2 | 0.4 | 46.8 | 8.6 | 29.3 | 56.4 | 5.9 | 73.4 | 1.6 | 6.8 | 234.1 |
| Cp1FatB1 | 2.3 | 0.0 | 0.2 | 0.0 | 1.4 | 0.0 | 84.2 | 3.0 | 10.5 | 74.9 | 0.4 | 11.3 | 185.9 |
| Cl2FatB2 | 3.2 | 3.2 | 30.4 | 17.0 | 5.1 | 7.9 | 11.3 | 2.1 | 9.1 | 19.2 | 0.2 | 6.0 | 111.4 |
| Cl4FatB1 | 3.9 | 1.8 | 16.3 | 7.8 | 3.0 | 4.8 | 7.2 | 1.3 | 5.9 | 11.8 | 0.1 | 4.0 | 63.9 |

TABLE 5-continued

Production and Secretion of Free Fatty Acids by E. coli Expressing FatB Genes

| Genotype | OD 600 | C8:0 | C10:0 | C10:1 | C12:0 | C12:1 | C14:0 | C14:1 | C16:0 | C16:1 | C18:0 | C18:1 | Total FFAs mg/L/OD |
|---|---|---|---|---|---|---|---|---|---|---|---|---|---|
| Cl1FatB1 | 3.6 | 0.2 | 0.2 | 0.0 | 0.3 | 0.0 | 22.4 | 0.4 | 9.4 | 12.4 | 0.2 | 5.3 | 50.6 |
| Ci1FatB1 | 4.5 | 0.0 | 0.1 | 0.0 | 0.0 | 0.0 | 0.4 | 0.0 | 1.0 | 0.4 | 0.0 | 0.6 | 2.6 |
| Cd1FatB1 | 1.1 | 0.7 | 0.5 | 0.0 | 0.8 | 0.0 | 78.4 | 2.1 | 24.8 | 131.5 | 0.3 | 13.6 | 252.6 |
| Experiment #2 | | | | | | | | | | | | | |
| empty vector | 4.3 | 0.0 | 0.1 | 0.0 | 0.1 | 0.0 | 0.5 | 0.2 | 1.8 | 0.7 | 0.0 | 0.2 | 3.6 |
| Cl3FatB1 | 2.1 | 0.5 | 0.3 | 0.0 | 0.3 | 0.0 | 36.7 | 0.7 | 13.3 | 44.3 | 0.0 | 6.1 | 102.3 |
| Ca2FatB2 | 4.1 | 4.4 | 0.6 | 0.0 | 0.2 | 0.0 | 1.3 | 0.2 | 2.0 | 1.2 | 0.3 | 0.8 | 11.0 |
| Experiment #3 | | | | | | | | | | | | | |
| empty vector | 3.3 | 0.2 | 0.3 | 0.0 | 0.3 | 0.0 | 0.7 | 0.0 | 4.2 | 1.8 | 0.0 | 0.0 | 7.4 |
| Ca1FatB1 | 0.9 | 0.0 | 0.0 | 0.0 | 8.6 | 0.0 | 80.2 | 9.3 | 7.8 | 49.9 | 0.0 | 0.0 | 155.8 |

EXAMPLE 10

Expression of FatB Thioesterases in the Cyanobacterium Synechocystis Sp.

The plasmid constructs were also transformed into Synechocystis sp. PCC 6803. The transformation protocol used was essentially as described by Zang et al. (Microbiology 45:241-245). To test for the production of free fatty acids in the various cyanobacterial isolates, the strains were pre-cultivated in 30 mL of BG-11 medium supplemented with kanamycin (20 mg/L) to late-log phase ($OD_{730\ nm}$=1.0) on a rotary shaker (150 rpm) at 30° C. with constant illumination (60 $\mu E \cdot m^{-2} \cdot sec^{-1}$). Cultures were then subcultured into 125 mL glass flasks with silicone stoppers at initial $OD_{730\ nm}$=0.4-0.5 in BG-11 and cultivated overnight to $OD_{730\ nm}$=0.7-0.9, and induced by addition of IPTG (final concentration, 1 mM).

Free fatty acid (FFA) analyses were performed on extractions of 20 mL whole cell culture with a mixture of internal standard solution (C9:0, C13:0, and C17:0, final concentration of 50 µg/mL), 1.7 mL 50% sulfuric acid, 3.4 mL NaCl (5M), and 30 mL hexane. Samples were vortexed vigorously to emulsify, incubated at room temperature for one hour, and vortexed again. The mixture was transferred to 50 mL glass centrifuge tubes and spun at 1800 rpm for 5 minutes, and the organic phase was transferred to a GC vial. A 1 ul sample was injected into an Agilent model 7890A gas chromatograph using a 40:1 split ration onto a DB-FFAP column (J&W Scientific, 15 m×250 µm×0.25 µm), with a temperature profile starting at 180° C. for 0.5 minute, then heating at 30° C./minute to 230° C. and holding for 3.9 minutes (1.8 mL/min He). Free fatty acid peaks were detected on an FID instrument.

The levels of secreted FFAs produced six days after IPTG induction are provided in Table 6 and Table 7, and depicted graphically in FIG. 11, FIG. 12, and FIGS. 13A-13B). The Synechocystis isolate transformed with Cd1FatB1, depicted in FIG. 11, produced essentially no free fatty acids and was later found by DNA sequencing to have incurred a premature stop codon within the reading frame. An alternate Cd1FatB1-carrying Synechocystis isolate, was found to be one of the highest free fatty acid producers tested, as shown in Table 7 and depicted in FIGS. 13A-13B.

TABLE 6

Production and Secretion of Free Fatty Acids by Synechocystis Expressing FatB Genes

| Genotype | OD 730 | C8:0 | C10:0 | C12:0 | C14:0 | C16:0 | C16:1 | C18:0 | C18:1 | Total FFAs mg/L/OD |
|---|---|---|---|---|---|---|---|---|---|---|
| Experiment #1 | | | | | | | | | | |
| empty vector | 6.2 | 0.0 | 0.0 | 0.0 | 0.0 | 0.3 | 0.2 | 0.4 | 0.3 | 1.3 |
| Cc1FatB1 | 4.5 | 0.2 | 0.2 | 6.8 | 23.2 | 32.9 | 1.0 | 3.2 | 1.7 | 69.4 |
| Cp1FatB1 | 6.8 | 0.0 | 0.0 | 0.1 | 2.0 | 8.7 | 0.1 | 0.6 | 0.2 | 11.7 |
| Cl2FatB2 | 6.8 | 0.2 | 8.1 | 0.3 | 0.7 | 7.3 | 0.1 | 0.5 | 0.1 | 17.3 |
| Cl4FatB1 | 6.4 | 0.4 | 14.9 | 0.6 | 1.5 | 13.5 | 0.3 | 0.9 | 0.2 | 32.3 |
| Cl1FatB1 | 6.5 | 0.0 | 0.2 | 0.0 | 0.0 | 0.8 | 0.0 | 0.1 | 0.0 | 1.1 |
| Cd1FatB1 | 8.0 | 0.0 | 0.0 | 0.1 | 0.1 | 0.5 | 0.0 | 0.2 | 0.0 | 0.9 |
| Experiment #2 | | | | | | | | | | |
| empty vector | 5.2 | 0.0 | 0.0 | 0.0 | 0.0 | 0.0 | 0.0 | 0.0 | 0.0 | 0.0 |
| Ca2FatB2 | 4.1 | 27.2 | 6.8 | 0.0 | 0.0 | 0.5 | 0.0 | 0.0 | 0.0 | 34.5 |

TABLE 7

Production and Secretion of Free Fatty Acids by *Synechocystis* Expressing FatB Genes

| Genotype | OD 730 | C8:0 | C10:0 | C12:0 | C14:0 | C16:0 | C16:1 | C18:0 | C18:1 cis9 | C18:1 cis11 | C18:2 cis9, 12 | Total FFAs mg/L |
|---|---|---|---|---|---|---|---|---|---|---|---|---|
| empty vector | 7.3 | 0.7 | 0.0 | 0.0 | 0.0 | 1.3 | 0.0 | 0.0 | 0.0 | 0.0 | 0.0 | 1.9 |
| ChFatB2 | 8.6 | 67.0 | 60.6 | 0.7 | 0.0 | 2.7 | 0.0 | 1.5 | 0.0 | 0.0 | 1.3 | 133.7 |
| Cc1FatB1 | 6.5 | 1.3 | 1.6 | 30.4 | 107.1 | 139.9 | 1.9 | 9.5 | 2.0 | 0.0 | 4.7 | 298.3 |
| Cd1FatB1 | 4.4 | 0.0 | 0.9 | 0.6 | 15.0 | 247.6 | 1.1 | 11.3 | 1.4 | 0.0 | 3.3 | 281.2 |

| Genotype | OD 730 | C8:0 | C10:0 | C12:0 | C14:0 | C16:0 | C16:1 | C18:0 | C18:1 cis9 | C18:1 cis11 | C18:2 cis9, 12 | Total FFAs mg/L/OD |
|---|---|---|---|---|---|---|---|---|---|---|---|---|
| empty vector | 7.3 | 0.1 | 0.0 | 0.0 | 0.0 | 0.2 | 0.0 | 0.0 | 0.0 | 0.0 | 0.0 | 0.3 |
| ChFatB2 | 8.6 | 7.8 | 7.0 | 0.1 | 0.0 | 0.3 | 0.0 | 0.2 | 0.0 | 0.0 | 0.1 | 15.6 |
| Cc1FatB1 | 6.5 | 0.2 | 0.2 | 4.7 | 16.5 | 21.5 | 0.3 | 1.5 | 0.3 | 0.0 | 0.7 | 45.9 |
| Cd1FatB1 | 4.4 | 0.0 | 0.2 | 0.1 | 3.4 | 56.3 | 0.2 | 2.6 | 0.3 | 0.0 | 0.8 | 63.9 |

As seen in Table 6 and Table 7, *Synechocystis* transformed with the Ca2FatB2 thioesterase gene makes predominantly C8 free fatty acids, and also produces some C10 free fatty acids: 78.84% of the free fatty acids secreted into the media are C8 free fatty acids, and 19.71% are C10 free fatty acids. *Synechocystis* transformed with the Cl2FatB2 thioesterase gene and *Synechocystis* transformed with the Cl4FatB1 thioesterase gene synthesize predominantly C10 and C16 fatty acids, with slightly more C10 than C16 being produced: The Cl2FatB2 strain produced 46.8% C10 FFAs and 42.7% C16 FFAs, and the Cl4FatB1 strain produced 46.8% C10 FFAs and 42.1% C16 FFAs. *Synechocystis* cyanobacterial cells transformed with the Cp1FatB1 gene, the Cl1FatB1 gene, the Ci1FatB1 gene, the Cd1FatB1 gene, the Cl3FatB1 gene, and the Ca1FatB1 gene produced predominantly C14 and C16 free fatty acids, while *Synechocystis* transformed with Cc1FatB1 produced a majority of C14 and C16 fatty acids along with some C12 fatty acids.

EXAMPLE 11

Production of Wax Ester by *E. Coli* Expressing *Cuphea* Acyl-ACP Thioesterases

To demonstrate that a microorganism transformed with one of the *Cuphea* thioesterases disclosed herein could produce a fatty acid product derived from one or more fatty acids, *E. coli* cells were transformed with a construct containing three exogenous genes: a *Cuphea thioesterase (either the C8 and C10-preferring Cuphea hookeriana* Ch1FatB2 gene (Dehesh, K. et al., *The Plant Journal* 9:167-172 (1996)) or the Cc1FatB1 gene (SEQ ID NO:51) disclosed herein), a *Mus musculus* wax synthase gene (NCBI Genbank GI:49854217) and an *Arabidopsis thaliana* fatty acyl-CoA reductase gene, FAR6 (NCBI Genbank GI:67633703). All three genes were cloned on the same expression plasmid, in which all three genes were driven by separate trc promoters.

The FAR6 gene did not appear to be active in *E. coli*, probably due to the presence of the chloroplast transit peptide in the expressed protein, which likely interfered with enzyme activity. However, the cells did produce esters when provided with 5 mM decanol in the culture medium.

To test for wax ester formation, *E. coli* cells were grown at 30° C. with shaking until they reached an OD 600 of 0.7 to 0.9, at which time the transgenes were induced by the addition of 0.5 mM IPTG. At the same time IPTG was added, decanol was added to a final concentration of 5 mM, and the cultures were incubated overnight. The cells were then harvested, washed once with PBS and then resuspended in water and transferred to a glass vial. An equal volume of 2:1 chloroform:methanol was added to each sample, and the suspension was vortexed vigorously and then centrifuged to separate the phases. The organic layer was transferred to a 2 mL glass GC vial and the contents were evaporated under nitrogen. The residue was resuspended in chloroform:methanol for GC analysis.

Figure 14A:
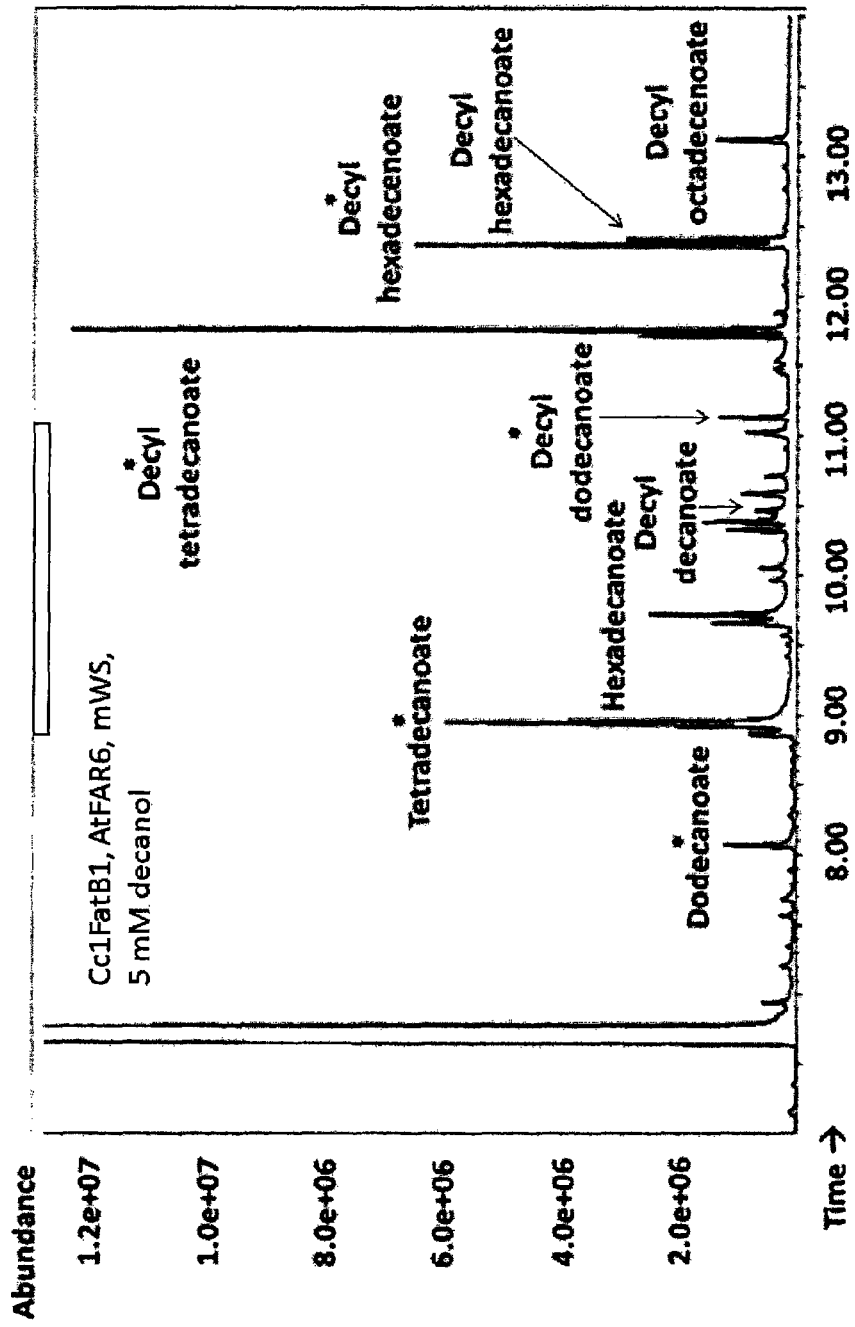
FIG. 14A depicts the results of gas chromatography analysis of wax ester products extracted from *E. coli* cells transformed with the *Mus musculus* wax synthase gene and the Cc1FatB1 thioesterase gene and supplied with decanol.
Figure 14B:
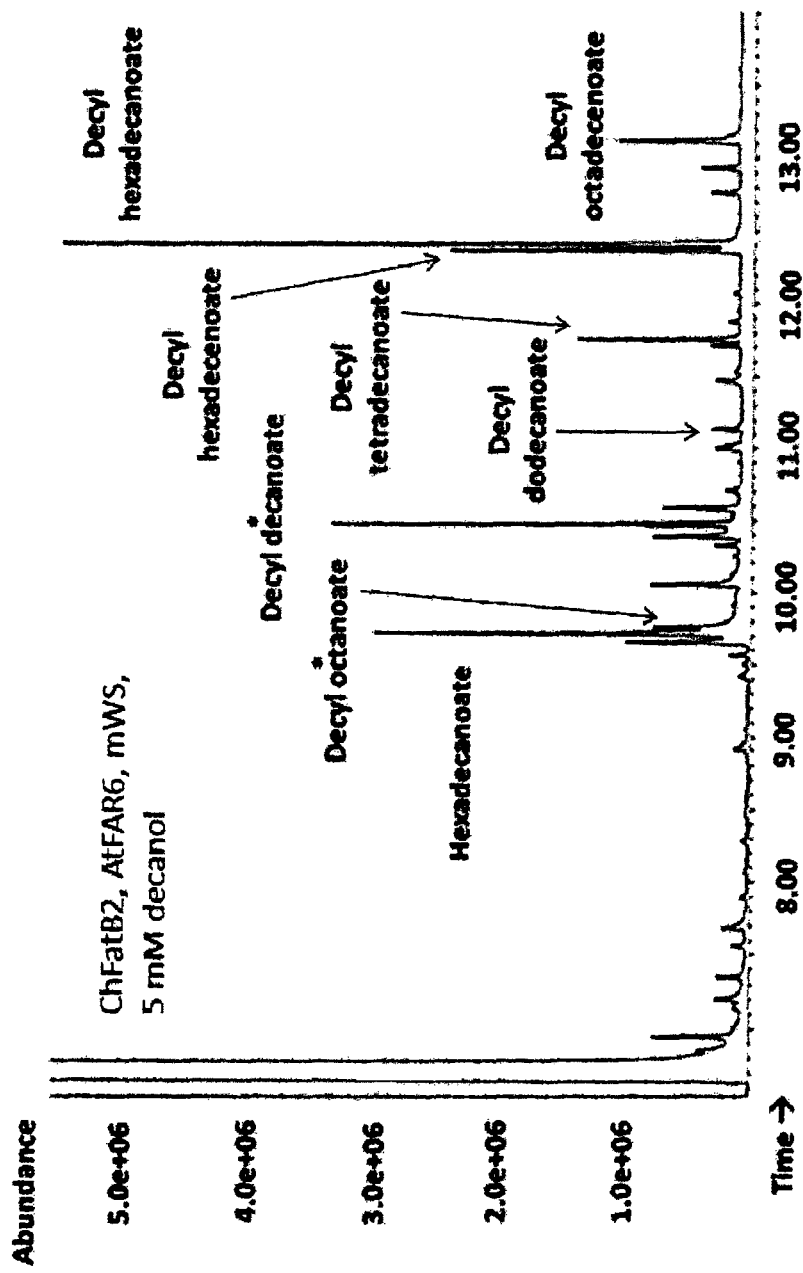
FIG. 14B depicts the results of gas chromatography analysis of wax ester products extracted from *E. coli* cells transformed with the *Mus musculus* wax synthase gene and *C. hookeriana* thioesterase ChFatB2.

The results are depicted in FIGS. 14A-14B. FIG. 14B shows the analysis of products isolated from *E. coli* cells transformed with the *C. hookeriana* ChFatB2 thioesterase. The wax esters produced by the cells were predominantly decyl octanoate and decyl decanoate (expected from the C10-preference of the ChFatB2 thioesterase) and decyl hexadecanoate (reflecting the preference of the *E. coli* host for generating C16 fatty acids). FIG. 14A shows the analysis of products isolated from the media of *E. coli* cells transformed with the Cc1FatB1 thioesterase, demonstrated in Example 9 to generate free C14 and C16 fatty acids in *E. coli*. Consistent with the substrate preference of this thioesterase, co-expression of the Cc1FatB1 thioesterase with the *Mus musculus* wax synthase resulted in the most prevalent wax ester isolated from the cells being decyl tetradecanoate, followed by decyl hexadecenoate.

What is claimed is:

1. A transgenic organism comprising an exogenous nucleic acid molecule encoding a Class II acyl-ACP thioesterase comprising an amino acid sequence selected from the group consisting of an amino acid sequence having at least 90% identity to amino acid 64 to amino acid 361 of SEQ ID NO:51; the amino acid sequence of amino acid 66 to amino acid 362 of SEQ ID NO:55; an amino acid sequence having at least 96% identity to amino acid 65 to amino acid 356 of SEQ ID NO:69; and the amino acid sequence of amino acid 65 to amino acid 362 of SEQ ID NO:85.

2. A transgenic organism according to claim 1, wherein the acyl-ACP thioesterase has a C12, C14, and/or C16 acyl substrate preference.

3. A transgenic organism according to claim 1, wherein the transgenic organism further comprises at least one exogenous nucleic acid molecule encoding an acetyl-CoA carboxylase, a ketoacyl-CoA synthase, a fatty acid elongase, an acyl-CoA synthetase, a fatty acyl-CoA reductase, a fatty aldehyde reductase, an alcohol acetyl transferase, an acyl-CoA alcohol transacylase, an acyltransferase, a wax synthase, an aldehyde decarbonylase, or a fatty acid decarboxylase.

4. A transgenic organism according to claim 1, wherein the organism is plant.

5. A transgenic organism according to claim 1, wherein the organism is a microorganism.

6. A transgenic organism according to claim 5, wherein the organism is a photosynthetic microorganism.

7. A transgenic organism according to claim 6, wherein the photosynthetic microorganism is a eukaryotic alga.

8. A transgenic organism according to claim 6, wherein the photosynthetic microorganism is a cyanobacterium.

9. A method of making a fatty acid product, comprising:
culturing a transgenic microorganism according to claim 5; and
isolating a fatty acid product from the organism or culture medium.

10. The method of claim 9, wherein the fatty acid product is a free fatty acid.

11. The method of claim 9, wherein the fatty acid product comprises one or more triglycerides, fatty aldehydes, fatty alcohols, fatty esters, hydrocarbons, or fatty acids.

12. The method of claim 9, wherein the microorganism is a photosynthetic microorganism.

13. The method of claim 12, wherein the microorganism is cultured mixotrophically.

14. The method of claim 12, wherein the microorganism is cultured phototrophically.

15. The method of claim 12, wherein the photosynthetic organism is a eukaryotic alga.

16. The method of claim 12, wherein the photosynthetic organism is a cyanobacterium.

17. The method of claim 9, wherein at least 50% of the fatty products isolated from the organism, the culture medium, or both are C12 fatty acid products, C14 fatty acid products, C16 fatty acid products, or a combination thereof.

18. The method of claim 9, wherein at least 20% of the fatty products isolated from the organism, the culture medium, or both are C14 fatty acid products.

19. A vector comprising a recombinant nucleic acid molecule encoding a Class II acyl-ACP thioesterase comprising an amino acid sequence selected from the group consisting of:
 a) an amino acid sequence having at least 90% identity to amino acid 64 to amino acid 361 of SEQ ID NO:51;
 b) the amino acid sequence of amino acid 66 to amino acid 362 of SEQ ID NO:55;
 c) an amino acid sequence having at least 96% identity to amino acid 65 to amino acid 356 of SEQ ID NO:69; and
 d) the amino acid sequence of amino acid 65 to amino acid 362 of SEQ ID NO:85;
wherein the vector further comprises a selectable marker.

20. A vector according to claim 19, encoding a Class II acyl-ACP thioesterase comprising a nucleic acid sequence encoding a thioesterase that comprises an amino acid sequence selected from the group consisting of:
an amino acid sequence having at least 90% identity to SEQ ID NO:51;
the amino acid sequence of SEQ ID NO:55;
an amino acid sequence having at least 96% identity to SEQ ID NO:69; and
the amino acid sequence of SEQ ID NO:85.

* * * * *

SEQUENCE LISTING

```
<160> NUMBER OF SEQ ID NOS: 101

<210> SEQ ID NO 1
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 1
atggtggctr cygmwgcaag                                                    20

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctaagakaym gagtytccak ktsargtc                                           28

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcagcaagtt chgcatkctt cc                                                 22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
caktcttsgg yckccactca g                                                  21

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgtgctgatt gacatccaag tc                                                 22

<210> SEQ ID NO 6
<211> LENGTH: 1943
<212> TYPE: DNA
<213> ORGANISM: Cuphea aequipetala

<400> SEQUENCE: 6
gcagcaagtt ctgcatgctt ccctgttcca tccccaggag cctcccctaa acctgggaag        60
ttaggcaact ggccatcgag tttgagccct tccttgaagc ccaagtcaat ccccaatggc       120
ggatttcagg ttaaggcaaa tgccagtgcc catcctaagg ctaacggttc tgcagtaact       180
ctaaagtctg gcagcctcaa cactcaggaa gacactttgt cgtcgtcccc tcctccccgg       240
gcttttttta accagttgcc tgattggagt atgcttctga ctgcaatcac aaccgtcttc       300
gtggcgccag agaagcggtg gactatgttt gataggaaat ctaagaggcc taacatgctc       360
```

```
atggactcgt ttgggttgga gagggttgtt caggatgggc tcgtgttcag acagagtttt    420
tcgattaggt cttatgaaat atgcgctgat cgaacagcct cactagagac ggtgatgaac    480
cacgtgcagg tactgctttg aaactatcca ttcatcgtat atgctagtga tcagtaaatg    540
agccatgact cgatgatgac atagataaca ccgaattgtc ggtatgacga gctgattgtg    600
tccattataa tttagaggtg cacttttctg ttcatggtga ggttggtaac ttggtatccc    660
ggggtgagag ttgtcaggtt gattcaatga aagctgtaaa ttttcgatta catttacgta    720
ctatgaaagt taaaatactc tccttcgaca gagaaatgac tatgcattct gataagaagt    780
atttcatcta aaatgcttgc attagttttg cttatatttt ctcgttaact ccgttttcct    840
ctaaacagga aacatcactc aatcaatgta aagtatagg tcttctcgat gacggctttg      900
gtcgtagtcc tgagatgtgt aaaagggacc tcatttgggt ggttacaaga atgaagatca    960
tggtgaatcg ctatccaact tggtaagttt gtcactgggct gaatcgcctc ttacaataat  1020
agttgtgaac attgtggaat gtaatggtct gtatgtgatc tatatggtag gggcgatact   1080
atcgaggtca gtacctggct ctcccaatcg gggaaaatcg gtatgggtcg cgattggcta   1140
ataagtgatt gcagcacagg agaaattctt gtaagagcaa cgaggtagga ttttccggtt   1200
ctgagtttac attctcaaaa accttcatcc atgaccttga aagacattt ggcatgtttt    1260
atatgtaaag tggagtcata tcactctcat attatcgcag tgtgtatgcc atgatgaatc   1320
aaaagacgag aagattctca aaacttccac acgaggttcg ccaggaattt gcgcctcatt   1380
ttctggactc tcctcctgcc attgaagaca atgacggtaa attgcagaag tttgatgtga   1440
agactggtga ttccattcgc aagggtctaa ctgtaagtcc ctatccttca ctatgatagt   1500
aggcgttttt atgaaatata atgtctctga cgttcttc ctcttcatgg tttgtagccg     1560
gggtggtatg acttggatgt caatcagcat gtaagcaacg tgaagtacat tgggtggatt   1620
ctcgaggtac ccttttcgtc gcgccaactt cttatatatt tttggattaa tgataataag   1680
atcaatcaag ttagatattg aatctaagta tatgctaatg gaatacttat tgcagagtat   1740
gccaacagaa gttttggaga ctcaggagct atgctctctc acccttgaat ataggaggga   1800
atgcggaagg gacagtgtgc tggagtccgt gacctctatg gatccctcaa aagttggaga   1860
ccggtttcag taccggcacc ttctgcggct tgaggatggg gctgatatca tgaagggcag   1920
gactgagtgg cgaccgaaga atg                                           1943
```

<210> SEQ ID NO 7
<211> LENGTH: 1089
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
atggcgaatg gtagcgcggt gactctgaaa agcggttccc tgaatactca ggaggatacc     60
ctgtccagca gcccaccccc tcgcgcgttc ttcaaccagt tacccgattg gtctatgttg    120
ttaaccgcga tcactacggt gttttgtcgca ccggagaaac gttggaccat gttcgatcgc   180
aagtccaaac gcccgaacat gttgatggac agcttcggtc tggaacgtgt tgttcaggac    240
ggttttggttt ttcgccaatc cttttccatt cgcagctatg agatttgcgc cgatcgtact   300
gcctccttag aaaccgttat gaatcacgtc aggaaaacta gcttgaatca gtgcaagagc    360
atcggcttac tggatgacgg tttcggccgt tctccagaaa tgtgcaagcg tgacttgatt    420
```

```
tgggtcgtta cgcgcatgaa aatcatggtt aatcgctacc cgacctgggg cgacaccatc    480
gaagtgtcca cctggttgtc tcaatctggt aagatcggca tgggtcgtga ctggctgatt    540
tctgattgta gcaccggtga gatcttagtg cgcgctacct ccgtgtatgc gatgatgaac    600
caaaagaccc gtcgcttttc caagttacct cacgaggttc gtcaagagtt cgcgcctcat    660
ttcttagatt ctcctcccgc tattgaggac aacgacggta agctgcagaa gtttgatgtg    720
aaaactggtg acagcattcg caaaggcttg acgccaggct ggtatgattt agatgttaac    780
cagcatgtct ccaacgttaa gtacattggt tggattctgg agagcatgcc aaccgaagtg    840
ttagagactc aagaactgtg ttccttaact ctggaatatc gtcgcgaatg cggccgtgac    900
tctgtgttgg aaagcgtcac tagcatggat ccgtctaaag tcggcgatcg tttcaatac     960
cgtcacttgt tgcgtctgga ggacggtgcg gatatcatga aaggccgcac cgagtggcgc   1020
ccaaagaacg ccggtgcaaa tggtgcaatc tctaccggta aaacttccaa cggtaattct   1080
atttcttaa                                                           1089
```

<210> SEQ ID NO 8
<211> LENGTH: 362
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

```
Met Ala Asn Gly Ser Ala Val Thr Leu Lys Ser Gly Ser Leu Asn Thr
1               5                   10                  15

Gln Glu Asp Thr Leu Ser Ser Ser Pro Pro Arg Ala Phe Phe Asn
            20                  25                  30

Gln Leu Pro Asp Trp Ser Met Leu Leu Thr Ala Ile Thr Thr Val Phe
        35                  40                  45

Val Ala Pro Glu Lys Arg Trp Thr Met Phe Asp Arg Lys Ser Lys Arg
    50                  55                  60

Pro Asn Met Leu Met Asp Ser Phe Gly Leu Glu Arg Val Val Gln Asp
65                  70                  75                  80

Gly Leu Val Phe Arg Gln Ser Phe Ser Ile Arg Ser Tyr Glu Ile Cys
                85                  90                  95

Ala Asp Arg Thr Ala Ser Leu Glu Thr Val Met Asn His Val Gln Glu
            100                 105                 110

Thr Ser Leu Asn Gln Cys Lys Ser Ile Gly Leu Leu Asp Asp Gly Phe
        115                 120                 125

Gly Arg Ser Pro Glu Met Cys Lys Arg Asp Leu Ile Trp Val Val Thr
    130                 135                 140

Arg Met Lys Ile Met Val Asn Arg Tyr Pro Thr Trp Gly Asp Thr Ile
145                 150                 155                 160

Glu Val Ser Thr Trp Leu Ser Gln Ser Gly Lys Ile Gly Met Gly Arg
                165                 170                 175

Asp Trp Leu Ile Ser Asp Cys Ser Thr Gly Glu Ile Leu Val Arg Ala
            180                 185                 190

Thr Ser Val Tyr Ala Met Met Asn Gln Lys Thr Arg Arg Phe Ser Lys
        195                 200                 205

Leu Pro His Glu Val Arg Gln Glu Phe Ala Pro His Phe Leu Asp Ser
    210                 215                 220

Pro Pro Ala Ile Glu Asp Asn Asp Gly Lys Leu Gln Lys Phe Asp Val
225                 230                 235                 240
```

```
Lys Thr Gly Asp Ser Ile Arg Lys Gly Leu Thr Pro Gly Trp Tyr Asp
            245                 250                 255

Leu Asp Val Asn Gln His Val Ser Asn Val Lys Tyr Ile Gly Trp Ile
        260                 265                 270

Leu Glu Ser Met Pro Thr Glu Val Leu Glu Thr Gln Glu Leu Cys Ser
    275                 280                 285

Leu Thr Leu Glu Tyr Arg Arg Glu Cys Gly Arg Asp Ser Val Leu Glu
290                 295                 300

Ser Val Thr Ser Met Asp Pro Ser Lys Val Gly Asp Arg Phe Gln Tyr
305                 310                 315                 320

Arg His Leu Leu Arg Leu Glu Asp Gly Ala Asp Ile Met Lys Gly Arg
                325                 330                 335

Thr Glu Trp Arg Pro Lys Asn Ala Gly Ala Asn Gly Ala Ile Ser Thr
            340                 345                 350

Gly Lys Thr Ser Asn Gly Asn Ser Ile Ser
        355                 360

<210> SEQ ID NO 9
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gattaaataa ggaggaataa accatggcga atggtagcgc ggtg                    44

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ttaagaaata gaattaccgt tggaagtttt accgg                              35

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Leu Gly Cys Phe Gly Gly
1               5

<210> SEQ ID NO 12
<211> LENGTH: 367
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Ala Asn Gly Ser Ala Val Thr Leu Lys Ser Gly Ser Leu Asn Thr
1               5                   10                  15
```

```
Gln Glu Asp Thr Leu Ser Ser Pro Pro Arg Ala Phe Phe Asn
             20                  25                  30

Gln Leu Pro Asp Trp Ser Met Leu Leu Thr Ala Ile Thr Val Phe
         35                  40                  45

Val Ala Pro Glu Lys Arg Trp Thr Met Phe Asp Arg Lys Ser Lys Arg
 50                  55                  60

Pro Asn Met Leu Met Asp Ser Phe Gly Leu Glu Arg Val Val Gln Asp
 65                  70                  75                  80

Gly Leu Val Phe Arg Gln Ser Phe Ser Ile Arg Ser Tyr Glu Ile Cys
                 85                  90                  95

Ala Asp Arg Thr Ala Ser Leu Glu Thr Val Met Asn His Val Gln Glu
             100                 105                 110

Thr Ser Leu Asn Gln Cys Lys Ser Ile Gly Leu Leu Asp Asp Gly Phe
         115                 120                 125

Gly Arg Ser Pro Glu Met Cys Lys Arg Asp Leu Ile Trp Val Val Thr
         130                 135                 140

Arg Met Lys Ile Met Val Asn Arg Tyr Pro Thr Trp Gly Asp Thr Ile
145                 150                 155                 160

Glu Val Ser Thr Trp Leu Ser Gln Ser Gly Lys Ile Gly Met Gly Arg
                 165                 170                 175

Asp Trp Leu Ile Ser Asp Cys Ser Thr Gly Glu Ile Leu Val Arg Ala
             180                 185                 190

Thr Ser Val Tyr Ala Met Met Asn Gln Lys Thr Arg Arg Phe Ser Lys
         195                 200                 205

Leu Pro His Glu Val Arg Gln Glu Phe Ala Pro His Phe Leu Asp Ser
 210                 215                 220

Pro Pro Ala Ile Glu Asp Asn Asp Gly Lys Leu Gln Lys Phe Asp Val
225                 230                 235                 240

Lys Thr Gly Asp Ser Ile Arg Lys Gly Leu Thr Pro Gly Trp Tyr Asp
                 245                 250                 255

Leu Asp Val Asn Gln His Val Ser Asn Val Lys Tyr Ile Gly Trp Ile
             260                 265                 270

Leu Glu Ser Met Pro Thr Glu Val Leu Glu Thr Gln Glu Leu Cys Ser
         275                 280                 285

Leu Thr Leu Glu Tyr Arg Arg Glu Cys Gly Arg Asp Ser Val Leu Glu
 290                 295                 300

Ser Val Thr Ser Met Asp Pro Ser Lys Val Gly Asp Arg Phe Gln Tyr
305                 310                 315                 320

Arg His Leu Leu Arg Leu Glu Asp Gly Ala Asp Ile Met Lys Gly Arg
                 325                 330                 335

Thr Glu Trp Arg Pro Lys Asn Ala Gly Ala Asn Gly Ala Ile Ser Thr
             340                 345                 350

Gly Lys Thr Ser Asn Gly Asn Ser Lys Leu Gly Cys Phe Gly Gly
         355                 360                 365

<210> SEQ ID NO 13
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
atggcgaatg gtagcgcggt gactctgaaa agcggttccc tgaatactca ggaggatacc      60
```

```
ctgtccagca gcccaccccc tcgcgcgttc ttcaaccagt tacccgattg gtctatgttg      120
ttaaccgcga tcactacggt gtttgtcgca ccggagaaac gttggaccat gttcgatcgc      180
aagtccaaac gcccgaacat gttgatggac agcttcggtc tggaacgtgt tgttcaggac      240
ggtttggttt ttcgccaatc cttttccatt cgcagctatg agatttgcgc cgatcgtact      300
gcctccttag aaaccgttat gaatcacgtc caggaaacta gcttgaatca gtgcaagagc      360
atcggcttac tggatgacgg tttcggccgt tctccagaaa tgtgcaagcg tgacttgatt      420
tgggtcgtta cgcgcatgaa aatcatggtt aatcgctacc cgacctgggg cgacaccatc      480
gaagtgtcca cctggttgtc tcaatctggt aagatcggca tgggtcgtga ctggctgatt      540
tctgattgta gcaccggtga gatcttagtg cgcgctacct ccgtgtatgc gatgatgaac      600
caaaagaccc gtcgcttttc caagttacct cacgaggttc gtcaagagtt cgcgcctcat      660
ttcttagatt ctcctcccgc tattgaggac aacgacggta gctgcagaa gtttgatgtg       720 aaaactggtg acagcattcg caaaggcttg acgccaggct ggtatgattt agatgttaac      780
cagcatgtct ccaacgttaa gtacattggt tggattctgg agagcatgcc aaccgaagtg      840
ttagagactc aagaactgtg ttccttaact ctggaatatc gtcgcgaatg cggccgtgac      900
tctgtgttgg aaagcgtcac tagcatggat ccgtctaaag tcggcgatcg tttttcaatac     960 cgtcacttgt tgcgtctgga ggacggtgcg gatatcatga aaggccgcac cgagtggcgc     1020
ccaaagaacg ccggtgcaaa tggtgcaatc tctaccggta aaacttccaa cgggaattcg     1080
aagcttggct gttttggcgg atga                                            1104

<210> SEQ ID NO 14
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtaatacgac tcactatagg gcacgcgtgg tcgacggccc gggctggtt                  49

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aaccagcccg                                                             10

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gtaatacgac tcactatagg gc                                               22

<210> SEQ ID NO 17
<211> LENGTH: 27
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 17 gtacccttttt cgtcgcgcca acttctt                                           27

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
actatagggc acgcgtggt                                                     19

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gctaatggaa tacttattgc agagtatgcc                                         30

<210> SEQ ID NO 20
<211> LENGTH: 2328
<212> TYPE: DNA
<213> ORGANISM: Cuphea aequipetala

<400> SEQUENCE: 20
ctgttccatc cccaggagcc tcccctaaac ctgggaagtt aggcaactgg ccatcgagtt          60
tgagcccttc cttgaagccc aagtcaatcc ccaatggcgg atttcaggtt aaggcaaatg         120
ccagtgccca tcctaaggct aacggttctg cagtaactct aaagtctggc agcctcaaca         180
ctcaggaaga cactttgtcg tcgtcccctc ctccccgggc ttttttaac cagttgcctg          240 attggagtat gcttctgact gcaatcacaa ccgtcttcgt ggcgccagag aagcggtgga         300
ctatgtttga taggaaatct aagaggccta acatgctcat ggactcgttt gggttggaga         360
gggttgttca ggatgggctc gtgttcagac agagttttc gattaggtct tatgaaatat          420
gcgctgatcg aacagcctca ctagagacgg tgatgaacca cgtgcaggta ctgctttgaa         480
actatccatt catcgtatat gctagtgatc agtaaatgag ccatgactcg atgatgacat         540
agataacacc gaattgtcgg tatgacgagc tgattgtgtc cattataatt tagaggtgca         600
cttttctgtt catggtgagg ttggtaactt ggtatcccgg ggtgagagtt gtcaggttga         660
ttcaatgaaa gctgtaaatt ttcgattaca tttacgtact atgaaagtta aaatactctc         720
cttcgacaga gaaatgacta tgcattctga taagaagtat ttcatctaaa atgcttgcat         780
tagttttgct tatatttct cgttaactcc gttttctct aaacaggaaa catcactcaa           840
tcaatgtaaa agtataggtc ttctcgatga cggctttggt cgtagtcctg agatgtgtaa         900
aagggacctc atttgggtgg ttacaagaat gaagatcatg gtgaatcgct atccaacttg         960
gtaagtttgt cactggctga atcgcctctt acaataatag ttgtgaacat tgtggaatgt        1020
aatggtctgt atgtgatcta tatggtaggg gcgatactat cgaggtcagt acctggctct        1080
```

```
cccaatcggg gaaaatcggt atgggtcgcg attggctaat aagtgattgc agcacaggag      1140
aaattcttgt aagagcaacg aggtaggatt ttccggttct gagtttacat tctcaaaaac      1200
cttcatccat gaccttgaga agacatttgg catgttttat atgtaaagtg gagtcatatc      1260
actctcatat tatcgcagtg tgtatgccat gatgaatcaa aagacgagaa gattctcaaa      1320
acttccacac gaggttcgcc aggaatttgc gcctcatttt ctggactctc ctcctgccat      1380
tgaagacaat gacggtaaat tgcagaagtt tgatgtgaag actggtgatt ccattcgcaa      1440
gggtctaact gtaagtccct atccttcact atgatagtag gcgtttttat gaaatataat      1500
gtctctgaga cgttcttcct cttcatggtt tgtagccggg gtggtatgac ttggatgtca      1560
atcagcatgt aagcaacgtg aagtacattg ggtggattct cgaggtaccc ttttcgtcgc      1620
gccaacttct tatatatttt tggattaatg ataataagat caatcaagtt agatattgaa      1680
tctaagtata tgctaatgga atacttattg cagagtatgc aacagaagt tttggagact       1740 caggagctat gctctctcac ccttgaatat aggcgggaat gcggaaggga cagtgtgctg      1800
gagtccgtga cctctatgga tccctcaaaa gttggagacc ggtttcagta ccggcacctt      1860
ctgcggcttg aggatggggc tgatatcatg aagggcagaa ctgagtggcg gccgaagaat      1920
gcaggaacta acggggtgat atcaacagga aagacttgaa atggaaactc tgtctcttag      1980
aataatctcg ggacccttcg ggatgtgcat ttcttttctc ttttttgcatt tcctggtgag     2040 ctgaaagaag agcatgtagt tgcaatcagt aaactgtgta gttcgtttgt tcgctttgct     2100
tcgcacattt gtataataat atgatctgcc gtcgttgtat catctcacgt ttccagtgcc     2160
atattctttt tattctacct gtttcgagat aaggagacgg acagaccaga gcagaactgg     2220
ggaacaagaa aagaaacagc catgtgggga aggccttaat gatacaaaca acaaagccat     2280
ctccttttgt cttccccccaa tctcctcccc aactcaaaat catataaa                 2328
```

<210> SEQ ID NO 21
<211> LENGTH: 1202
<212> TYPE: DNA
<213> ORGANISM: Cuphea aequipetala

<400> SEQUENCE: 21

```
ctgttccatc cccaggagcc tcccctaaac ctgggaagtt aggcaactgg ccatcgagtt       60
tgagcccttc cttgaagccc aagtcaatcc ccaatggcgg atttcaggtt aaggcaaatg      120
ccagtgccca tcctaaggct aacggttctg cagtaactct aaagtctggc agcctcaaca     180
ctcaggaaga cactttgtcg tcgtcccctc ctccccgggc ttttttttaac cagttgcctg    240 attggagtat gcttctgact gcaatcacaa ccgtcttcgt ggcgccagag aagcggtgga     300
ctatgtttga taggaaatct aagaggccta acatgctcat ggactcgttt ggttggaga      360 gggttgttca ggatgggctc gtgttcagac agagtttttc gattaggtct tatgaaatat     420
gcgctgatcg aacagcctca ctagagacgg tgatgaacca cgtgcaggaa acatcactca     480
atcaatgtaa aagtataggt cttctcgatg acggctttgg tcgtagtcct gagatgtgta    540
aaagggacct catttgggtg gttacaagaa tgaagatcat ggtgaatcgc tatccaactt    600
ggggcgatac tatcgaggtc agtacctggc tctcccaatc ggggaaaatc ggtatgggtc    660
gcgattggct aataagtgat tgcagcacag agaaattct tgtaagagca acgagtgtgt     720
atgccatgat gaatcaaaag acgagaagat tctcaaaact tccacacgag gttcgccagg    780
aatttgcgcc tcattttctg gactctcctc ctgccattga agacaatgac ggtaaattgc    840
agaagtttga tgtgaagact ggtgattcca ttcgcaaggg tctaactccg gggtggtatg    900
```

-continued

```
acttggatgt caatcagcat gtaagcaacg tgaagtacat tgggtggatt ctcgagagta    960
tgccaacaga agttttggag actcaggagc tatgctctct caccccttgaa tataggcggg   1020 aatgcggaag ggacagtgtg ctggagtccg tgacctctat ggatccctca aaagttggag   1080
accggtttca gtaccggcac cttctgcggc ttgaggatgg ggctgatatc atgaagggca   1140
gaactgagtg gcggccgaag aatgcaggaa ctaacggggt gatatcaaca ggaaagactt   1200
ga                                                                  1202
```

<210> SEQ ID NO 22
<211> LENGTH: 399
<212> TYPE: PRT
<213> ORGANISM: Cuphea aequipetala
<220> FEATURE:
<221> NAME/KEY: sig_peptide
<222> LOCATION: (1)..(45)
<220> FEATURE:
<221> NAME/KEY: mat_peptide
<222> LOCATION: (45)..(399)

<400> SEQUENCE: 22

```
Val Pro Ser Pro Gly Ala Ser Pro Lys Pro Gly Lys Leu Gly Asn Trp
            -40                 -35                 -30

Pro Ser Ser Leu Ser Pro Ser Leu Lys Pro Lys Ser Ile Pro Asn Gly
        -25                 -20                 -15

Gly Phe Gln Val Lys Ala Asn Ala Ser Ala His Pro Lys Ala Asn Gly
    -10                  -5                  -1   1

Ser Ala Val Thr Leu Lys Ser Gly Ser Leu Asn Thr Gln Glu Asp Thr
5                10                  15                  20

Leu Ser Ser Ser Pro Pro Arg Ala Phe Phe Asn Gln Leu Pro Asp
                25                  30                  35

Trp Ser Met Leu Leu Thr Ala Ile Thr Thr Val Phe Val Ala Pro Glu
                40                  45                  50

Lys Arg Trp Thr Met Phe Asp Arg Lys Ser Lys Arg Pro Asn Met Leu
                55                  60                  65

Met Asp Ser Phe Gly Leu Glu Arg Val Val Gln Asp Gly Leu Val Phe
70                  75                  80

Arg Gln Ser Phe Ser Ile Arg Ser Tyr Glu Ile Cys Ala Asp Arg Thr
85                  90                  95                  100

Ala Ser Leu Glu Thr Val Met Asn His Val Gln Glu Thr Ser Leu Asn
                105                 110                 115

Gln Cys Lys Ser Ile Gly Leu Leu Asp Asp Gly Phe Gly Arg Ser Pro
                120                 125                 130

Glu Met Cys Lys Arg Asp Leu Ile Trp Val Val Thr Arg Met Lys Ile
                135                 140                 145

Met Val Asn Arg Tyr Pro Thr Trp Gly Asp Thr Ile Glu Val Ser Thr
            150                 155                 160

Trp Leu Ser Gln Ser Gly Lys Ile Gly Met Gly Arg Asp Trp Leu Ile
165                 170                 175                 180

Ser Asp Cys Ser Thr Gly Glu Ile Leu Val Arg Ala Thr Ser Val Tyr
                185                 190                 195

Ala Met Met Asn Gln Lys Thr Arg Arg Phe Ser Lys Leu Pro His Glu
                200                 205                 210

Val Arg Gln Glu Phe Ala Pro His Phe Leu Asp Ser Pro Pro Ala Ile
                215                 220                 225

Glu Asp Asn Asp Gly Lys Leu Gln Lys Phe Asp Val Lys Thr Gly Asp
```

```
    Ser Ile Arg Lys Gly Leu Thr Pro Gly Trp Tyr Asp Leu Asp Val Asn
    245                 250                 255                 260

Gln His Val Ser Asn Val Lys Tyr Ile Gly Trp Ile Leu Glu Ser Met
                    265                 270                 275

Pro Thr Glu Val Leu Glu Thr Gln Glu Leu Cys Ser Leu Thr Leu Glu
                280                 285                 290

Tyr Arg Arg Glu Cys Gly Arg Asp Ser Val Leu Glu Ser Val Thr Ser
            295                 300                 305

Met Asp Pro Ser Lys Val Gly Asp Arg Phe Gln Tyr Arg His Leu Leu
    310                 315                 320

Arg Leu Glu Asp Gly Ala Asp Ile Met Lys Gly Arg Thr Glu Trp Arg
    325                 330                 335                 340

Pro Lys Asn Ala Gly Thr Asn Gly Val Ile Ser Thr Gly Lys Thr
                    345                 350                 355

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccttccttga agcccaagtc aatc                                              24

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cgtctcctta tctcgaaaca ggtag                                             25

<210> SEQ ID NO 25
<211> LENGTH: 1071
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atggcgaatg gtagcgcggt gactctgaaa agcggttccc tgaatactca ggaggatacc        60
ctgtccagca gcccaccccc tcgcgcgttc ttcaaccagt tacccgattg gtctatgttg       120
ttaaccgcga tcactacggt gtttgtcgca ccggagaaac gttggaccat gttcgatcgc       180
aagtccaaac gcccgaacat tttgatggac agcttcggtc tggaacgtgt tgttcaggac       240
ggtttggttt ttcgccaatc cttttccatt cgcagctatg agatttgcgc cgatcgtact       300
gcctccattg aaaccgttat gaatcacgtc aggaaactag cttgaatca gtgcaagagc       360 atcggcttac tggatgacgg tttcggccgt tctccagaaa tgtgcaagcg tgacttgatt       420
tgggtcgtta cgcgcatgaa aatcatggtt aatcgctacc gacctgggg cgacaccatc       480 gaagtgtcca cctggtttgtc tcaatctggt aagatcggca tgggtcgtga ctggctgatt       540
tctgattgta gcaccggtga gatcttagtg cgcgctacct ccgtgtatgc gatgatgaac       600
```

```
caaaagaccc gtcgcttttc caagttacct cacgaggttc gtcaagagtt cgcgcctcat    660
ttcttagatt ctcctcccgc tattgaggac aacgacggta agctgcagaa gtttgatgtg    720
aaaactggtg acagcattcg caaaggcttg acgccaggct ggtatgattt agatgttaac    780
cagcatgtct ccaacgttaa gtacattggt tggattctgg agagcatgcc aaccgaagtg    840
ttagagactc aagaactgtg ttccttaact ctggaatatc gtcgcgaatg cggccgtgac    900
tctgtgttgg aaagcgtcac tagcatggat ccgtctaaag tcggcgatcg ttttcaatac    960
cgtcacttgt tgcgtctgga ggacggtgcg gatatcatga aaggccgcac cgagtggcgc   1020
ccaaagaacg ccggtaccaa tggcgtgatt agtaccggca aaacctaata a            1071
```

<210> SEQ ID NO 26
<211> LENGTH: 355
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

```
Met Ala Asn Gly Ser Ala Val Thr Leu Lys Ser Gly Ser Leu Asn Thr
1               5                   10                  15

Gln Glu Asp Thr Leu Ser Ser Ser Pro Pro Arg Ala Phe Phe Asn
            20                  25                  30

Gln Leu Pro Asp Trp Ser Met Leu Leu Thr Ala Ile Thr Thr Val Phe
        35                  40                  45

Val Ala Pro Glu Lys Arg Trp Thr Met Phe Asp Arg Lys Ser Lys Arg
    50                  55                  60

Pro Asn Ile Leu Met Asp Ser Phe Gly Leu Glu Arg Val Val Gln Asp
65                  70                  75                  80

Gly Leu Val Phe Arg Gln Ser Phe Ser Ile Arg Ser Tyr Glu Ile Cys
                85                  90                  95

Ala Asp Arg Thr Ala Ser Ile Glu Thr Val Met Asn His Val Gln Glu
            100                 105                 110

Thr Ser Leu Asn Gln Cys Lys Ser Ile Gly Leu Leu Asp Asp Gly Phe
        115                 120                 125

Gly Arg Ser Pro Glu Met Cys Lys Arg Asp Leu Ile Trp Val Val Thr
    130                 135                 140

Arg Met Lys Ile Met Val Asn Arg Tyr Pro Thr Trp Gly Asp Thr Ile
145                 150                 155                 160

Glu Val Ser Thr Trp Leu Ser Gln Ser Gly Lys Ile Gly Met Gly Arg
                165                 170                 175

Asp Trp Leu Ile Ser Asp Cys Ser Thr Gly Glu Ile Leu Val Arg Ala
            180                 185                 190

Thr Ser Val Tyr Ala Met Met Asn Gln Lys Thr Arg Arg Phe Ser Lys
        195                 200                 205

Leu Pro His Glu Val Arg Gln Glu Phe Ala Pro His Phe Leu Asp Ser
    210                 215                 220

Pro Pro Ala Ile Glu Asp Asn Asp Gly Lys Leu Gln Lys Phe Asp Val
225                 230                 235                 240

Lys Thr Gly Asp Ser Ile Arg Lys Gly Leu Thr Pro Gly Trp Tyr Asp
                245                 250                 255

Leu Asp Val Asn Gln His Val Ser Asn Val Lys Tyr Ile Gly Trp Ile
            260                 265                 270
```

```
Leu Glu Ser Met Pro Thr Glu Val Leu Glu Thr Gln Glu Leu Cys Ser
            275                 280                 285

Leu Thr Leu Glu Tyr Arg Arg Glu Cys Gly Arg Asp Ser Val Leu Glu
        290                 295                 300

Ser Val Thr Ser Met Asp Pro Ser Lys Val Gly Asp Arg Phe Gln Tyr
305                 310                 315                 320

Arg His Leu Leu Arg Leu Glu Asp Gly Ala Asp Ile Met Lys Gly Arg
                325                 330                 335

Thr Glu Trp Arg Pro Lys Asn Ala Gly Thr Asn Gly Val Ile Ser Thr
            340                 345                 350

Gly Lys Thr
        355

<210> SEQ ID NO 27
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tctacaaact ccggatctga tcattattag gttttgccgg tactaatcac gccattggta      60
ccggcgttct tgggcgcc                                                   79

<210> SEQ ID NO 28
<211> LENGTH: 1071
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
atggcgaatg gtagcgcggt gactctgaaa agcggttccc tgaatactca ggaggatacc      60
ctgtccagca gcccaccccc tcgcgcgttc ttcaaccagt tacccgattg gtctatgttg     120
ttaaccgcga tcactacggt gttttgtcgca ccggagaaac gttggaccat gttcgatcgc    180
aagtccaaac gcccgaacat gttgatggac agcttcggtc tggaacgtgt tgttcaggac    240
ggtttggttt ttcgccaatc cttttccatt cgcagctatg agatttgcgc cgatcgtact    300
gcctccttag aaaccgttat gaatcacgtc caggaaacta gcttgaatca gtgcaagagc    360
atcggcttac tggatgacgg tttcggccgt tctccagaaa tgtgcaagcg tgacttgatt    420
tgggtcgtta cgcgcatgaa aatcatggtt aatcgctacc cgacctgggg cgacaccatc    480
gaagtgtcca cctggttgtc tcaatctggt aagatcggca tgggtcgtga ctggctgatt    540
tctgattgta gcaccggtga gatcttagtg cgcgctacct ccgtgtatgc gatgatgaac    600
caaaagaccc gtcgctttc caagttacct cacgaggttc gtcaagagtt cgcgcctcat    660
ttcttagatt ctcctcccgc tattgaggac aacgacggta gctgcagaa gtttgatgtg    720 aaaactggtg acagcattcg caaaggcttg acgccaggct ggtatgattt agatgttaac    780
cagcatgtct ccaacgttaa gtacattggt tggattctgg agagcatgcc aaccgaagtg    840
ttagagactc aagaactgtg ttccttaact ctggaatatc gtcgcgaatg cggccgtgac    900
tctgtgttgg aaagcgtcac tagcatggat ccgtctaaag tcggcgatcg ttttcaatac    960
cgtcacttgt gcgtctgga ggacggtgcg gatatcatga aaggccgcac cgagtggcgc    1020
ccaaagaacg ccggtaccaa tggcgtgatt agtaccggca aaacctaata a              1071
```

```
<210> SEQ ID NO 29
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Ala Asn Gly Ser Ala Val Thr Leu Lys Ser Gly Ser Leu Asn Thr
1               5                   10                  15

Gln Glu Asp Thr Leu Ser Ser Pro Pro Arg Ala Phe Phe Asn
            20                  25                  30

Gln Leu Pro Asp Trp Ser Met Leu Leu Thr Ala Ile Thr Thr Val Phe
        35                  40                  45

Val Ala Pro Glu Lys Arg Trp Thr Met Phe Asp Arg Lys Ser Lys Arg
    50                  55                  60

Pro Asn Met Leu Met Asp Ser Phe Gly Leu Glu Arg Val Val Gln Asp
65                  70                  75                  80

Gly Leu Val Phe Arg Gln Ser Phe Ser Ile Arg Ser Tyr Glu Ile Cys
                85                  90                  95

Ala Asp Arg Thr Ala Ser Leu Glu Thr Val Met Asn His Val Gln Glu
            100                 105                 110

Thr Ser Leu Asn Gln Cys Lys Ser Ile Gly Leu Leu Asp Asp Gly Phe
        115                 120                 125

Gly Arg Ser Pro Glu Met Cys Lys Arg Asp Leu Ile Trp Val Val Thr
    130                 135                 140

Arg Met Lys Ile Met Val Asn Arg Tyr Pro Thr Trp Gly Asp Thr Ile
145                 150                 155                 160

Glu Val Ser Thr Trp Leu Ser Gln Ser Gly Lys Ile Gly Met Gly Arg
                165                 170                 175

Asp Trp Leu Ile Ser Asp Cys Ser Thr Gly Glu Ile Leu Val Arg Ala
            180                 185                 190

Thr Ser Val Tyr Ala Met Met Asn Gln Lys Thr Arg Arg Phe Ser Lys
        195                 200                 205

Leu Pro His Glu Val Arg Gln Glu Phe Ala Pro His Phe Leu Asp Ser
    210                 215                 220

Pro Pro Ala Ile Glu Asp Asn Asp Gly Lys Leu Gln Lys Phe Asp Val
225                 230                 235                 240

Lys Thr Gly Asp Ser Ile Arg Lys Gly Leu Thr Pro Gly Trp Tyr Asp
                245                 250                 255

Leu Asp Val Asn Gln His Val Ser Asn Val Lys Tyr Ile Gly Trp Ile
            260                 265                 270

Leu Glu Ser Met Pro Thr Glu Val Leu Glu Thr Gln Glu Leu Cys Ser
        275                 280                 285

Leu Thr Leu Glu Tyr Arg Arg Glu Cys Gly Arg Asp Ser Val Leu Glu
    290                 295                 300

Ser Val Thr Ser Met Asp Pro Ser Lys Val Gly Asp Arg Phe Gln Tyr
305                 310                 315                 320

Arg His Leu Leu Arg Leu Glu Asp Gly Ala Asp Ile Met Lys Gly Arg
                325                 330                 335

Thr Glu Trp Arg Pro Lys Asn Ala Gly Thr Asn Gly Val Ile Ser Thr
            340                 345                 350

Gly Lys Thr
```

-continued

355

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
acggtttcaa tggaggcagt acgatcggcg caa                                    33

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tgcctccatt gaaaccgtta tgaatcacgt ccagg                                  35

<210> SEQ ID NO 32
<211> LENGTH: 1071
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
atggcgaatg gtagcgcggt gactctgaaa agcggttccc tgaatactca ggaggatacc       60
ctgtccagca gcccaccccc tcgcgcgttc ttcaaccagt tacccgattg gtctatgttg      120
ttaaccgcga tcactacggt gtttgtcgca ccggagaaac gttggaccat gttcgatcgc      180
aagtccaaac gcccgaacat gttgatggac agcttcggtc tggaacgtgt tgttcaggac      240
ggtttggttt ttcgccaatc cttttccatt cgcagctatg agatttgcgc cgatcgtact      300
gcctccattg aaaccgttat gaatcacgtc aggaaaacta gcttgaatca gtgcaagagc      360
atcggcttac tggatgacgg tttcggccgt tctccagaaa tgtgcaagcg tgacttgatt      420
tgggtcgtta cgcgcatgaa aatcatggtt aatcgctacc gacctggggg cgacaccatc      480
gaagtgtcca cctggttgtc tcaatctggt aagatcggca tgggtcgtga ctggctgatt      540
tctgattgta gcaccggtga gatcttagtg cgcgctacct ccgtgtatgc gatgatgaac      600
caaaagaccc gtcgctttc caagttacct cacgaggttc gtcaagagtt cgcgcctcat      660
ttcttagatt ctcctcccgc tattgaggac aacgacggta agctgcagaa gtttgatgtg      720
aaaactggtg acagcattcg caaaggcttg acgccaggct ggtatgattt agatgttaac      780
cagcatgtct ccaacgttaa gtacattggt tggattctgg agagcatgcc aaccgaagtg      840
ttagagactc aagaactgtg ttccttaact ctggaatatc gtcgcgaatg cggccgtgac      900
tctgtgttgg aaagcgtcac tagcatggat ccgtctaaag tcggcgatcg ttttcaatac      960
cgtcacttgt tgcgtctgga ggacggtgcg gatatcatga aaggccgcac cgagtggcgc     1020
ccaaagaacg ccggtaccaa tggcgtgatt agtaccggca aaacctaata a              1071

<210> SEQ ID NO 33
<211> LENGTH: 355
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 33

```
Met Ala Asn Gly Ser Ala Val Thr Leu Lys Ser Gly Ser Leu Asn Thr
1               5                   10                  15

Gln Glu Asp Thr Leu Ser Ser Pro Pro Arg Ala Phe Phe Asn
                20                  25                  30

Gln Leu Pro Asp Trp Ser Met Leu Leu Thr Ala Ile Thr Thr Val Phe
            35                  40                  45

Val Ala Pro Glu Lys Arg Trp Thr Met Phe Asp Arg Lys Ser Lys Arg
50                  55                  60

Pro Asn Met Leu Met Asp Ser Phe Gly Leu Glu Arg Val Val Gln Asp
65                  70                  75                  80

Gly Leu Val Phe Arg Gln Ser Phe Ser Ile Arg Ser Tyr Glu Ile Cys
                85                  90                  95

Ala Asp Arg Thr Ala Ser Ile Glu Thr Val Met Asn His Val Gln Glu
                100                 105                 110

Thr Ser Leu Asn Gln Cys Lys Ser Ile Gly Leu Leu Asp Asp Gly Phe
            115                 120                 125

Gly Arg Ser Pro Glu Met Cys Lys Arg Asp Leu Ile Trp Val Val Thr
130                 135                 140

Arg Met Lys Ile Met Val Asn Arg Tyr Pro Thr Trp Gly Asp Thr Ile
145                 150                 155                 160

Glu Val Ser Thr Trp Leu Ser Gln Ser Gly Lys Ile Gly Met Gly Arg
                165                 170                 175

Asp Trp Leu Ile Ser Asp Cys Ser Thr Gly Glu Ile Leu Val Arg Ala
            180                 185                 190

Thr Ser Val Tyr Ala Met Met Asn Gln Lys Thr Arg Arg Phe Ser Lys
            195                 200                 205

Leu Pro His Glu Val Arg Gln Glu Phe Ala Pro His Phe Leu Asp Ser
210                 215                 220

Pro Pro Ala Ile Glu Asp Asn Asp Gly Lys Leu Gln Lys Phe Asp Val
225                 230                 235                 240

Lys Thr Gly Asp Ser Ile Arg Lys Gly Leu Thr Pro Gly Trp Tyr Asp
                245                 250                 255

Leu Asp Val Asn Gln His Val Ser Asn Val Lys Tyr Ile Gly Trp Ile
            260                 265                 270

Leu Glu Ser Met Pro Thr Glu Val Leu Glu Thr Gln Glu Leu Cys Ser
            275                 280                 285

Leu Thr Leu Glu Tyr Arg Arg Glu Cys Gly Arg Asp Ser Val Leu Glu
290                 295                 300

Ser Val Thr Ser Met Asp Pro Ser Lys Val Gly Asp Arg Phe Gln Tyr
305                 310                 315                 320

Arg His Leu Leu Arg Leu Glu Asp Gly Ala Asp Ile Met Lys Gly Arg
                325                 330                 335

Thr Glu Trp Arg Pro Lys Asn Ala Gly Thr Asn Gly Val Ile Ser Thr
            340                 345                 350

Gly Lys Thr
        355
```

<210> SEQ ID NO 34
<211> LENGTH: 32

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtccatcaaa atgttcgggc gtttggactt gc                                      32

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cgaacatttt gatggacagc ttcggtctgg                                         30

<210> SEQ ID NO 36
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gattaaataa ggaggaataa accatgttac ccgattggtc tatgttgtta acc              53

<210> SEQ ID NO 37
<211> LENGTH: 975
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
atgttacccg attggtctat gttgttaacc gcgatcacta cggtgtttgt cgcaccggag        60
aaacgttgga ccatgttcga tcgcaagtcc aaacgcccga acatgttgat ggacagcttc       120
ggtctggaac gtgttgttca ggacggtttg gtttttcgcc aatccttttc cattcgcagc       180
tatgagattt gcgccgatcg tactgcctcc attgaaaccg ttatgaatca cgtccaggaa       240
actagcttga atcagtgcaa gagcatcggc ttactggatg acggtttcgg ccgttctcca       300
gaaatgtgca agcgtgactt gatttgggtc gttacgcgca tgaaaatcat ggttaatcgc       360
tacccgacct ggggcgacac catcgaagtg tccacctggt tgtctcaatc tggtaagatc       420
ggcatgggtc gtgactggct gatttctgat tgtagcaccg tgagatctt agtgcgcgct       480 acctccgtgt atgcgatgat gaaccaaaag accgtcgct tttccaagtt acctcacgag       540
gttcgtcaag agttcgcgcc tcatttctta gattctcctc ccgctattga ggacaacgac       600
ggtaagctgc agaagtttga tgtgaaaact ggtgacagca ttcgcaaagg cttgacgcca       660
ggctggtatg atttagatgt taaccagcat gtctccaacg ttaagtacat tggttggatt       720
ctggagagca tgccaaccga agtgttagag actcaagaac tgtgttcctt aactctggaa       780
tatcgtcgcg aatgcggccg tgactctgtg ttggaaagcg tcactagcat ggatccgtct       840
aaagtcggcg atcgttttca ataccgtcac ttgttgcgtc tggaggacgg tgcggatatc       900
atgaaaggcc gcaccgagtg cgcccaaaag aacgccggta ccaatggcgt gattagtacc       960
```

```
                                                                           975
ggcaaaacct aataa
```

<210> SEQ ID NO 38
<211> LENGTH: 323
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Leu Pro Asp Trp Ser Met Leu Leu Thr Ala Ile Thr Thr Val Phe
1               5                   10                  15

Val Ala Pro Glu Lys Arg Trp Thr Met Phe Asp Arg Lys Ser Lys Arg
            20                  25                  30

Pro Asn Met Leu Met Asp Ser Phe Gly Leu Glu Arg Val Val Gln Asp
        35                  40                  45

Gly Leu Val Phe Arg Gln Ser Phe Ser Ile Arg Ser Tyr Glu Ile Cys
    50                  55                  60

Ala Asp Arg Thr Ala Ser Ile Glu Thr Val Met Asn His Val Gln Glu
65                  70                  75                  80

Thr Ser Leu Asn Gln Cys Lys Ser Ile Gly Leu Leu Asp Asp Gly Phe
                85                  90                  95

Gly Arg Ser Pro Glu Met Cys Lys Arg Asp Leu Ile Trp Val Val Thr
            100                 105                 110

Arg Met Lys Ile Met Val Asn Arg Tyr Pro Thr Trp Gly Asp Thr Ile
        115                 120                 125

Glu Val Ser Thr Trp Leu Ser Gln Ser Gly Lys Ile Gly Met Gly Arg
    130                 135                 140

Asp Trp Leu Ile Ser Asp Cys Ser Thr Gly Glu Ile Leu Val Arg Ala
145                 150                 155                 160

Thr Ser Val Tyr Ala Met Met Asn Gln Lys Thr Arg Arg Phe Ser Lys
                165                 170                 175

Leu Pro His Glu Val Arg Gln Glu Phe Ala Pro His Phe Leu Asp Ser
            180                 185                 190

Pro Pro Ala Ile Glu Asp Asn Asp Gly Lys Leu Gln Lys Phe Asp Val
        195                 200                 205

Lys Thr Gly Asp Ser Ile Arg Lys Gly Leu Thr Pro Gly Trp Tyr Asp
    210                 215                 220

Leu Asp Val Asn Gln His Val Ser Asn Val Lys Tyr Ile Gly Trp Ile
225                 230                 235                 240

Leu Glu Ser Met Pro Thr Glu Val Leu Glu Thr Gln Glu Leu Cys Ser
                245                 250                 255

Leu Thr Leu Glu Tyr Arg Arg Glu Cys Gly Arg Asp Ser Val Leu Glu
            260                 265                 270

Ser Val Thr Ser Met Asp Pro Ser Lys Val Gly Asp Arg Phe Gln Tyr
        275                 280                 285

Arg His Leu Leu Arg Leu Glu Asp Gly Ala Asp Ile Met Lys Gly Arg
    290                 295                 300

Thr Glu Trp Arg Pro Lys Asn Ala Gly Thr Asn Gly Val Ile Ser Thr
305                 310                 315                 320

Gly Lys Thr

<210> SEQ ID NO 39
<211> LENGTH: 1071
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 39

```
atggcgaatg gtagcgcggt gactctgaaa agcggttccc tgaatactca ggaggatacc      60
ctgtccagca gcccaccccc tcgcgcgttc ttcaaccagt tacccgattg gtctatgttg     120
ttaaccgcga tcactacggt gtttgtcgca ccggagaaac gttggaccat gttcgatcgc     180
aagtccaaac gcccgaacat gttgatggac agcttcggtc tggaacgtgt tgttcaggac     240
ggtttggttt ttcgccaatc cttttccatt cgcagctatg agatttgcgc cgatcgtact     300
gcctccattg aaaccgttat gaatcacgtc caggaaacta gcttgaatca gtgcaagagc     360
atcggcttac tggatgacgg tttcggccgt tctccagaaa tgtgcaagcg tgacttgatt     420
tgggtcgtta cgcgcatgaa atcatggtt aatcgctacc cgacctgggg cgacaccatc     480
gaagtgtcca cctggttgtc tcaatctggt aagatcggca taggtcgtga ctggctgatt     540
tctgattgta ataccggtga gatcttagtg cgcgctacct ccgtgtatgc gatgatgaac     600
caaaagaccc gtcgcttttc caagttacct cacgaggttc gtcaagagtt cgcgcctcat     660
ttcttagatt ctcctcccgc tattgaggac aacgacggta agctgcagaa gtttgatgtg     720
aaaactggtg acagcattcg caaaggcttg acgccaggct ggtatgattt agatgttaac     780
cagcatgtct ccaacgttaa gtacattggt tggattctgg agagcatgcc aaccgaagtg     840
ttagagactc aagaactgtg ttccttaact ctggaatatc gtcgcgaatg cggccgtgac     900
tctgtgttgg aaagcgtcac tagcatggat ccgtctaaag tcggcgatcg tttcaatac     960
cgtcacttgt tgcgtctgga ggacggtgcg gatatcatga aaggccgcac cgagtggcgc    1020
ccaaagaacg ccggtaccaa tggcgtgatt agtaccggca aaacctaata a             1071
```

<210> SEQ ID NO 40
<211> LENGTH: 355
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

```
Met Ala Asn Gly Ser Ala Val Thr Leu Lys Ser Gly Ser Leu Asn Thr
  1               5                  10                  15

Gln Glu Asp Thr Leu Ser Ser Ser Pro Pro Arg Ala Phe Phe Asn
             20                  25                  30

Gln Leu Pro Asp Trp Ser Met Leu Leu Thr Ala Ile Thr Thr Val Phe
         35                  40                  45

Val Ala Pro Glu Lys Arg Trp Thr Met Phe Asp Arg Lys Ser Lys Arg
     50                  55                  60

Pro Asn Met Leu Met Asp Ser Phe Gly Leu Glu Arg Val Val Gln Asp
 65                  70                  75                  80

Gly Leu Val Phe Arg Gln Ser Phe Ser Ile Arg Ser Tyr Glu Ile Cys
                 85                  90                  95

Ala Asp Arg Thr Ala Ser Ile Glu Thr Val Met Asn His Val Gln Glu
            100                 105                 110

Thr Ser Leu Asn Gln Cys Lys Ser Ile Gly Leu Leu Asp Asp Gly Phe
        115                 120                 125

Gly Arg Ser Pro Glu Met Cys Lys Arg Asp Leu Ile Trp Val Val Thr
```

```
                130                 135                 140
Arg Met Lys Ile Met Val Asn Arg Tyr Pro Thr Trp Gly Asp Thr Ile
145                 150                 155                 160

Glu Val Ser Thr Trp Leu Ser Gln Ser Gly Lys Ile Gly Ile Gly Arg
                165                 170                 175

Asp Trp Leu Ile Ser Asp Cys Asn Thr Gly Glu Ile Leu Val Arg Ala
                180                 185                 190

Thr Ser Val Tyr Ala Met Met Asn Gln Lys Thr Arg Arg Phe Ser Lys
                195                 200                 205

Leu Pro His Glu Val Arg Gln Glu Phe Ala Pro His Phe Leu Asp Ser
210                 215                 220

Pro Pro Ala Ile Glu Asp Asn Asp Gly Lys Leu Gln Lys Phe Asp Val
225                 230                 235                 240

Lys Thr Gly Asp Ser Ile Arg Lys Gly Leu Thr Pro Gly Trp Tyr Asp
                245                 250                 255

Leu Asp Val Asn Gln His Val Ser Asn Val Lys Tyr Ile Gly Trp Ile
                260                 265                 270

Leu Glu Ser Met Pro Thr Glu Val Leu Glu Thr Gln Glu Leu Cys Ser
                275                 280                 285

Leu Thr Leu Glu Tyr Arg Arg Glu Cys Gly Arg Asp Ser Val Leu Glu
                290                 295                 300

Ser Val Thr Ser Met Asp Pro Ser Lys Val Gly Asp Arg Phe Gln Tyr
305                 310                 315                 320

Arg His Leu Leu Arg Leu Glu Asp Gly Ala Asp Ile Met Lys Gly Arg
                325                 330                 335

Thr Glu Trp Arg Pro Lys Asn Ala Gly Thr Asn Gly Val Ile Ser Thr
                340                 345                 350

Gly Lys Thr
        355

<210> SEQ ID NO 41
<211> LENGTH: 5
<212> TYPE: PRT
<213> ORGANISM: Cuphea aequipetala

<400> SEQUENCE: 41

Tyr Arg Arg Glu Cys
1               5

<210> SEQ ID NO 42
<211> LENGTH: 1071
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
atggcgaatg gtagcgcggt gactctgaaa agcggttccc tgaatactca ggaggatacc      60
ctgtccagca gcccaccccc tcgcgcgttc ttcaaccagt acccgattg gtctatgttg     120 ttaaccgcga tcactacggt gtttgtcgca ccggagaaac gttggaccat gttcgatcgc     180
aagtccaaac gcccgaacat gttgatggac agcttcggtc tggaacgtgt tgttcaggac     240
ggtttggttt ttcgccaatc ctttccatt cgcagctatg agatttgcgc cgatcgtact     300
gcctccttag aaaccgttat gaatcacgtc caggaaacta gcttgaatca gtgcaagagc     360
atcggcttac tggatgacgg tttcggccgt tctccagaaa tgtgcaagcg tgacttgatt     420
```

```
tgggtcgtta cgcgcatgaa aatcatggtt aatcgctacc cgacctgggg cgacaccatc   480
gaagtgtcca cctggttgtc tcaatctggt aagatcggca taggtcgtga ctggctgatt   540
tctgattgta gcaccggtga gatcttagtg cgcgctacct ccgtgtatgc gatgatgaac   600
caaaagaccc gtcgcttttc caagttacct cacgaggttc gtcaagagtt cgcgcctcat   660
ttcttagatt ctcctcccgc tattgaggac aacgacggta agctgcagaa gtttgatgtg   720
aaaactggtg acagcattcg caaaggcttg acgccaggct ggtatgattt agatgttaac   780
cagcatgtct ccaacgttaa gtacattggt tggattctgg agagcatgcc aaccgaagtg   840
ttagagactc aagaactgtg ttccttaact ctggaatatc gtcgcgaatg cggccgtgac   900
tctgtgttgg aaagcgtcac tagcatggat ccgtctaaag tcggcgatcg ttttcaatac   960
cgtcacttgt tgcgtctgga ggacggtgcg gatatcatga aaggccgcac cgagtggcgc  1020
ccaaagaacg ccggtaccaa tggcgtgatt agtaccggca aaacctaata a           1071
```

<210> SEQ ID NO 43
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Met Ala Asn Gly Ser Ala Val Thr Leu Lys Ser Gly Ser Leu Asn Thr
1               5                   10                  15

Gln Glu Asp Thr Leu Ser Ser Pro Pro Arg Ala Phe Phe Asn
            20                  25                  30

Gln Leu Pro Asp Trp Ser Met Leu Leu Thr Ala Ile Thr Thr Val Phe
        35                  40                  45

Val Ala Pro Glu Lys Arg Trp Thr Met Phe Asp Arg Lys Ser Lys Arg
    50                  55                  60

Pro Asn Met Leu Met Asp Ser Phe Gly Leu Glu Arg Val Val Gln Asp
65                  70                  75                  80

Gly Leu Val Phe Arg Gln Ser Phe Ser Ile Arg Ser Tyr Glu Ile Cys
                85                  90                  95

Ala Asp Arg Thr Ala Ser Leu Glu Thr Val Met Asn His Val Gln Glu
            100                 105                 110

Thr Ser Leu Asn Gln Cys Lys Ser Ile Gly Leu Leu Asp Asp Gly Phe
        115                 120                 125

Gly Arg Ser Pro Glu Met Cys Lys Arg Asp Leu Ile Trp Val Val Thr
    130                 135                 140

Arg Met Lys Ile Met Val Asn Arg Tyr Pro Thr Trp Gly Asp Thr Ile
145                 150                 155                 160

Glu Val Ser Thr Trp Leu Ser Gln Ser Gly Lys Ile Gly Ile Gly Arg
                165                 170                 175

Asp Trp Leu Ile Ser Asp Cys Ser Thr Gly Glu Ile Leu Val Arg Ala
            180                 185                 190

Thr Ser Val Tyr Ala Met Met Asn Gln Lys Thr Arg Arg Phe Ser Lys
        195                 200                 205

Leu Pro His Glu Val Arg Gln Glu Phe Ala Pro His Phe Leu Asp Ser
    210                 215                 220

Pro Pro Ala Ile Glu Asp Asn Asp Gly Lys Leu Gln Lys Phe Asp Val
225                 230                 235                 240
```

```
Lys Thr Gly Asp Ser Ile Arg Lys Gly Leu Thr Pro Gly Trp Tyr Asp
                245                 250                 255

Leu Asp Val Asn Gln His Val Ser Asn Val Lys Tyr Ile Gly Trp Ile
            260                 265                 270

Leu Glu Ser Met Pro Thr Glu Val Leu Glu Thr Gln Glu Leu Cys Ser
        275                 280                 285

Leu Thr Leu Glu Tyr Arg Arg Glu Cys Gly Arg Asp Ser Val Leu Glu
    290                 295                 300

Ser Val Thr Ser Met Asp Pro Ser Lys Val Gly Asp Arg Phe Gln Tyr
305                 310                 315                 320

Arg His Leu Leu Arg Leu Glu Asp Gly Ala Asp Ile Met Lys Gly Arg
                325                 330                 335

Thr Glu Trp Arg Pro Lys Asn Ala Gly Thr Asn Gly Val Ile Ser Thr
            340                 345                 350

Gly Lys Thr
        355

<210> SEQ ID NO 44
<211> LENGTH: 1071
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
atggcgaatg gtagcgcggt gactctgaaa agcggttccc tgaatactca ggaggatacc      60
ctgtccagca gcccaccccc tcgcgcgttc ttcaaccagt tacccgattg gtctatgttg     120
ttaaccgcga tcactacggt gtttgtcgca ccggagaaac gttggaccat gttcgatcgc     180
aagtccaaac gcccgaacat gttgatggac agcttcggtc tggaacgtgt tgttcaggac     240
ggtttggttt ttcgccaatc cttttccatt cgcagctatg agatttgcgc cgatcgtact     300
gcctccattg aaaccgttat gaatcacgtc caggaaacta gcttgaatca gtgcaagagc     360
atcggcttac tggatgacgg tttcggccgt tctccagaaa tgtgcaagcg tgacttgatt     420
tgggtcgtta cgcgcatgaa aatcatggtt aatcgctacc cgacctgggg cgacaccatc     480
gaagtgtcca cctggttgtc tcaatctggt aagatcggca taggtcgtga ctggctgatt     540
tctgattgta gcaccggtga gatcttagtg cgcgctacct ccgtgtatgc gatgatgaac     600
caaaagaccc gtcgcttttc caagttacct cacgaggttc gtcaagagtt cgcgcctcat     660
ttcttagatt ctcctcccgc tattgaggac aacgacggta agctgcagaa gtttgatgtg     720
aaaactggtg acagcattcg caaaggcttg acgccaggct ggtatgattt agatgttaac     780
cagcatgtct ccaacgttaa gtacattggt tggattctgg agagcatgcc aaccgaagtg     840
ttagagactc aagaactgtg ttccttaact ctggaatatc gtcgcgaatg cggccgtgac     900
tctgtgttgg aaagcgtcac tagcatggat ccgtctaaag tcggcgatcg ttttcaatac     960
cgtcacttgt tgcgtctgga ggacggtgcg gatatcatga aaggccgcac cgagtggcgc    1020
ccaaagaacg ccggtaccaa tggcgtgatt agtaccggca aaacctaata a             1071

<210> SEQ ID NO 45
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 45

```
Met Ala Asn Gly Ser Ala Val Thr Leu Lys Ser Gly Ser Leu Asn Thr
1               5                   10                  15

Gln Glu Asp Thr Leu Ser Ser Pro Pro Arg Ala Phe Phe Asn
            20                  25                  30

Gln Leu Pro Asp Trp Ser Met Leu Leu Thr Ala Ile Thr Thr Val Phe
        35                  40                  45

Val Ala Pro Glu Lys Arg Trp Thr Met Phe Asp Arg Lys Ser Lys Arg
50                  55                  60

Pro Asn Met Leu Met Asp Ser Phe Gly Leu Glu Arg Val Val Gln Asp
65                  70                  75                  80

Gly Leu Val Phe Arg Gln Ser Phe Ser Ile Arg Ser Tyr Glu Ile Cys
                85                  90                  95

Ala Asp Arg Thr Ala Ser Ile Glu Thr Val Met Asn His Val Gln Glu
            100                 105                 110

Thr Ser Leu Asn Gln Cys Lys Ser Ile Gly Leu Leu Asp Asp Gly Phe
        115                 120                 125

Gly Arg Ser Pro Glu Met Cys Lys Arg Asp Leu Ile Trp Val Val Thr
130                 135                 140

Arg Met Lys Ile Met Val Asn Arg Tyr Pro Thr Trp Gly Asp Thr Ile
145                 150                 155                 160

Glu Val Ser Thr Trp Leu Ser Gln Ser Gly Lys Ile Gly Ile Gly Arg
                165                 170                 175

Asp Trp Leu Ile Ser Asp Cys Ser Thr Gly Glu Ile Leu Val Arg Ala
            180                 185                 190

Thr Ser Val Tyr Ala Met Met Asn Gln Lys Thr Arg Arg Phe Ser Lys
        195                 200                 205

Leu Pro His Glu Val Arg Gln Glu Phe Ala Pro His Phe Leu Asp Ser
210                 215                 220

Pro Pro Ala Ile Glu Asp Asn Asp Gly Lys Leu Gln Lys Phe Asp Val
225                 230                 235                 240

Lys Thr Gly Asp Ser Ile Arg Lys Gly Leu Thr Pro Gly Trp Tyr Asp
                245                 250                 255

Leu Asp Val Asn Gln His Val Ser Asn Val Lys Tyr Ile Gly Trp Ile
            260                 265                 270

Leu Glu Ser Met Pro Thr Glu Val Leu Glu Thr Gln Glu Leu Cys Ser
        275                 280                 285

Leu Thr Leu Glu Tyr Arg Arg Glu Cys Gly Arg Asp Ser Val Leu Glu
290                 295                 300

Ser Val Thr Ser Met Asp Pro Ser Lys Val Gly Asp Arg Phe Gln Tyr
305                 310                 315                 320

Arg His Leu Leu Arg Leu Glu Asp Gly Ala Asp Ile Met Lys Gly Arg
                325                 330                 335

Thr Glu Trp Arg Pro Lys Asn Ala Gly Thr Asn Gly Val Ile Ser Thr
            340                 345                 350

Gly Lys Thr
        355
```

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic consensus sequence

<400> SEQUENCE: 46

Ala Asn Gly Ala Ile Ser Thr Gly Lys Thr Ser Asn Gly Asn Ser Ile
1               5                   10                  15

Ser

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 47

Thr Asn Gly Ala Ile Ser Thr Thr Lys Thr Ser Pro Gly Asn Ser Val
1               5                   10                  15

Ser

<210> SEQ ID NO 48
<211> LENGTH: 2320
<212> TYPE: DNA
<213> ORGANISM: Cuphea carthagenensis

<400> SEQUENCE: 48

| | | |
|---|---|---|
| gcagcaagtt ccgcattctt ccccgttaca accccgggaa cctcccgtaa acccgggaag | 60 |
| tttggcaact ggctatcgag cttgagccct cccttcaggc ccaagtcaat ccccagtggc | 120 |
| ggatttcagg ttaaggcaaa cgccagtgcc catcctaagg ctaacggttc tgcagtaagt | 180 |
| ctaaagtctg gcagcctcaa cactcaggag gacacttcgt cgtcccctcc tcctcgggct | 240 |
| ttcattaacc agttgcccga ttggagtatg ctttaaccg cgatcacgac ggtcttcgtg | 300 |
| gcggcagaga agcagtggac tatgcttgat cggaaatcta agaggtctga catgcttgtg | 360 |
| gactcgtttg ggatggagag atagttcag gatgggcttg tgttcagaca gagttttcg | 420 |
| attaggtctt atgaaatagg tgctgatcga agagcctcta tagagacgct gatgaaccac | 480 |
| ttgcaggtac tgctttgaaa ctatacattc atcgaatatg ctagtgatca gtaaatgagc | 540 |
| cacaacttga cgatgacata gataacaccg aattgccggt ataacaagct aattctgtcc | 600 |
| actttgattc aatgaaggaa ccatcagctg taaattttcg attacgttta agtatggtga | 660 |
| aagttaaaac gcattctgat aagtagttcg tccaaaaatg cttgcattag tttgcttata | 720 |
| tttcctcgtt aactgcattg tctttgtttg tgatttttt ttaatctaaa caggaaacat | 780 |
| ctctcaatca ttgtaagagt atccgtcttc taaatgaagg ctttggccgt actcctgaga | 840 |
| tgtgtaaaag ggacctcatt tgggtggtta cgagaatgca tatcatggtg aatcgctatc | 900 |
| caacttggta agtttgtcac tggcttgtct gtcttttggt ccgtgagtgc ctcttaagat | 960 |
| aacagttgta aatatagttg aatgtaatag cctgtatgtg atctgtatgg taggggcgat | 1020 |
| actgtcgaga tcaatacctg ggtctcccag tcgggaaaaa acggtatggg tcgcgattgg | 1080 |
| ctaataagtg attgcaatac aggagaaatt cttataagag caacgaggta ggattttctg | 1140 |
| gttctgagtt tacattctca aaccttctga tgctcgatcc atgagtagac atttggcatg | 1200 |
| tttaatatgt aaagttgagt catgccaatc tcatattatc gcagtgcatg ggctatgatg | 1260 |
| aatcaaaaga cgagaagact gtcaaaactg cctatgagg tttcacagga gatagcgcct | 1320 |
| cattttgtgg actctcctcc tgtcattgaa gacggtgata ggaaattgca caagtttgat | 1380 |

```
gtgaagacgg gtgattccat tcgcaagggt ctaactgtaa gtccctatct ttcactatga    1440
tattagccgt ttttatgaag tatcatgtct ctgagacgat cttcctcttc acggtttgta    1500
gccaaggtgg aatgacttgg atgtcaatca gcacgttaat aacgtgaagt acattgggtg    1560
gattctcgag gtacccttt catcatacga acaactgata tagttttggg ttgatgataa    1620
taaaatcaat aaactgtgat attgcttatt taaatatcat agactagtat ttccccgagt    1680
ttgtcaaagc ttggattccg gttccgctta acaaatctgc aatctatacg aatgcttgtt    1740
gcagagtatg ccaacagaag ttttggagac ccatgagcta tgcttcctga cccttgaata    1800
taggcgggaa tgcggaaggg acagtgtgct ggagtccgtg accgctatgg atccctcaaa    1860
tgagggaggc cggtctcact accaacacct tctgcggctt gaggatggga ctgatatcgt    1920
gaagggaaga actgagtggc ggccgaagaa tgcaagaaat attggggcaa tatcaacagg    1980
aaagacttca aatggaaacc cggcctctta aagggggctc aggatccttc tgagatatgc    2040
atttcttttt cattttctgg tgagctgaaa gaagagcatg tatttgcaat cagtaaattg    2100
tgtggttcgt ttgcagtttc tcgcttcgct cctttgtata ataacatggc cagtcgtctt    2160
tgtatcatct catgttttcc gtttgattta cgccatattc tttgcaatct attcgtttca    2220
agacgaacag cgcatcgcta aatctcgaaa caagtacttg tccaaaatgc atatatgtgc    2280
ctttgaagat cacaatgcag tccgccaaat agacattcaa                         2320
```

```
<210> SEQ ID NO 49
<211> LENGTH: 413
<212> TYPE: PRT
<213> ORGANISM: Cuphea carthagenensis

<400> SEQUENCE: 49

Ala Ala Ser Ser Ala Phe Phe Pro Val Thr Thr Pro Gly Thr Ser Arg
1               5                   10                  15

Lys Pro Gly Lys Phe Gly Asn Trp Leu Ser Ser Leu Ser Pro Pro Phe
            20                  25                  30

Arg Pro Lys Ser Ile Pro Ser Gly Gly Phe Gln Val Lys Ala Asn Ala
        35                  40                  45

Ser Ala His Pro Lys Ala Asn Gly Ser Ala Val Ser Leu Lys Ser Gly
    50                  55                  60

Ser Leu Asn Thr Gln Glu Asp Thr Ser Ser Pro Pro Arg Ala
65                  70                  75                  80

Phe Ile Asn Gln Leu Pro Asp Trp Ser Met Leu Leu Thr Ala Ile Thr
                85                  90                  95

Thr Val Phe Val Ala Ala Glu Lys Gln Trp Thr Met Leu Asp Arg Lys
            100                 105                 110

Ser Lys Arg Ser Asp Met Leu Val Asp Ser Phe Gly Met Glu Arg Ile
        115                 120                 125

Val Gln Asp Gly Leu Val Phe Arg Gln Ser Phe Ser Ile Arg Ser Tyr
    130                 135                 140

Glu Ile Gly Ala Asp Arg Arg Ala Ser Ile Glu Thr Leu Met Asn His
145                 150                 155                 160

Leu Gln Glu Thr Ser Leu Asn His Cys Lys Ser Ile Arg Leu Leu Asn
                165                 170                 175

Glu Gly Phe Gly Arg Thr Pro Glu Met Cys Lys Arg Asp Leu Ile Trp
            180                 185                 190

Val Val Thr Arg Met His Ile Met Val Asn Arg Tyr Pro Thr Trp Gly
        195                 200                 205
```

```
Asp Thr Val Glu Ile Asn Thr Trp Val Ser Gln Ser Gly Lys Asn Gly
    210                 215                 220

Met Gly Arg Asp Trp Leu Ile Ser Asp Cys Asn Thr Gly Glu Ile Leu
225                 230                 235                 240

Ile Arg Ala Thr Ser Ala Trp Ala Met Met Asn Gln Lys Thr Arg Arg
                245                 250                 255

Leu Ser Lys Leu Pro Tyr Glu Val Ser Gln Glu Ile Ala Pro His Phe
            260                 265                 270

Val Asp Ser Pro Pro Val Ile Glu Asp Gly Asp Arg Lys Leu His Lys
        275                 280                 285

Phe Asp Val Lys Thr Gly Asp Ser Ile Arg Lys Gly Leu Thr Pro Arg
290                 295                 300

Trp Asn Asp Leu Asp Val Asn Gln His Val Asn Asn Val Lys Tyr Ile
305                 310                 315                 320

Gly Trp Ile Leu Glu Ser Met Pro Thr Glu Val Leu Glu Thr His Glu
                325                 330                 335

Leu Cys Phe Leu Thr Leu Glu Tyr Arg Arg Glu Cys Gly Arg Asp Ser
            340                 345                 350

Val Leu Glu Ser Val Thr Ala Met Asp Pro Ser Asn Glu Gly Gly Arg
        355                 360                 365

Ser His Tyr Gln His Leu Leu Arg Leu Glu Asp Gly Thr Asp Ile Val
370                 375                 380

Lys Gly Arg Thr Glu Trp Arg Pro Lys Asn Ala Arg Asn Ile Gly Ala
385                 390                 395                 400

Ile Ser Thr Gly Lys Thr Ser Asn Gly Asn Pro Ala Ser
                405                 410

<210> SEQ ID NO 50
<211> LENGTH: 1112
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
atggcgaacg gtagcgctgt ctctctgaag agcggctcct tgaatacgca agaggacact    60
tcttcttccc caccgccacg cgcgttcatc aaccaattac ccgactggtc catgttattg   120
acggcgatta ccactgtctt tgttgccgca gagaaacagt ggactatgtt agaccgcaag   180
agcaagcgct ccgatatgtt agtggattct tttggcatgg aacgcattgt gcaggatggc   240
ttagtgtttc gtcaatcttt tagcattcgt tcttatgaaa tcggtgcaga tcgtcgtgca   300
tccattgaaa ccttaatgaa ccatctgcag gaaactagct tgaatcattg caaatccatt   360
cgcttgttga atgagggttt tggtcgcacc cccgagatgt gcaaacgtga cttgatctgg   420
gtggttaccc gcatgcacat catggtcaac cgctacccta cctggggtga taccgttgag   480
attaacactt gggtttccca agcggcaagg atggtatgg tcgtgattg gctgatttcc    540 gactgtaata ccggcgaaat cctgatccgc gcgacgtctg catgggcgat gatgaaccaa   600
aagacccgtc gtctgtctaa actgccttac gaagtcagcc aagagattgc tccgcacttc   660
gtcgacagcc ctcccgtgat cgaggacggc gaccgtaagt tacacaagtt cgatgtgaaa   720
accggcgaca gcatccgtaa aggtttgact ccgcgtttgga atgacttaga tgttaatcag   780
cacgttaaca acgttaagta tatcggctgg atcttagaga gcatgccgac cgaggtcttg   840
gaaactcatg aactgtgttt cttaactctg gagtatcgtc gcgagtgcgg tcgcgatagc   900
```

```
gtgctggaat ctgtgaccgc gatggatcct tctaatgaag gtggtcgctc ccactaccag      960
catttactgc gcttggagga cggtactgac atcgttaagg ccgcactga gtggcgtcca      1020 aagaatgccc ggaatattgg tgccattagt accggtaaaa ccagtaatgg taatcccgcc    1080
agttaataat gatcagatcc ggagtttgta ga                                  1112
```

```
<210> SEQ ID NO 51
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51
```

Met Ala Asn Gly Ser Ala Val Ser Leu Lys Ser Gly Ser Leu Asn Thr
1               5                   10                  15

Gln Glu Asp Thr Ser Ser Pro Pro Arg Ala Phe Ile Asn Gln
            20                  25                  30

Leu Pro Asp Trp Ser Met Leu Leu Thr Ala Ile Thr Val Phe Val
        35                  40                  45

Ala Ala Glu Lys Gln Trp Thr Met Leu Asp Arg Lys Ser Lys Arg Ser
50                  55                  60

Asp Met Leu Val Asp Ser Phe Gly Met Glu Arg Ile Val Gln Asp Gly
65                  70                  75                  80

Leu Val Phe Arg Gln Ser Phe Ser Ile Arg Ser Tyr Glu Ile Gly Ala
                85                  90                  95

Asp Arg Arg Ala Ser Ile Glu Thr Leu Met Asn His Leu Gln Glu Thr
            100                 105                 110

Ser Leu Asn His Cys Lys Ser Ile Arg Leu Leu Asn Gly Phe Gly
        115                 120                 125

Arg Thr Pro Glu Met Cys Lys Arg Asp Leu Ile Trp Val Val Thr Arg
130                 135                 140

Met His Ile Met Val Asn Arg Tyr Pro Thr Trp Gly Asp Thr Val Glu
145                 150                 155                 160

Ile Asn Thr Trp Val Ser Gln Ser Gly Lys Asn Gly Met Gly Arg Asp
                165                 170                 175

Trp Leu Ile Ser Asp Cys Asn Thr Gly Glu Ile Leu Ile Arg Ala Thr
            180                 185                 190

Ser Ala Trp Ala Met Met Asn Gln Lys Thr Arg Arg Leu Ser Lys Leu
        195                 200                 205

Pro Tyr Glu Val Ser Gln Glu Ile Ala Pro His Phe Val Asp Ser Pro
210                 215                 220

Pro Val Ile Glu Asp Gly Asp Arg Lys Leu His Lys Phe Asp Val Lys
225                 230                 235                 240

Thr Gly Asp Ser Ile Arg Lys Gly Leu Thr Pro Arg Trp Asn Asp Leu
                245                 250                 255

Asp Val Asn Gln His Val Asn Asn Val Lys Tyr Ile Gly Trp Ile Leu
            260                 265                 270

Glu Ser Met Pro Thr Glu Val Leu Glu Thr His Glu Leu Cys Phe Leu
        275                 280                 285

Thr Leu Glu Tyr Arg Arg Glu Cys Gly Arg Asp Ser Val Leu Glu Ser
290                 295                 300

Val Thr Ala Met Asp Pro Ser Asn Glu Gly Gly Arg Ser His Tyr Gln
305                 310                 315                 320

His Leu Leu Arg Leu Glu Asp Gly Thr Asp Ile Val Lys Gly Arg Thr
          325                 330                 335

Glu Trp Arg Pro Lys Asn Ala Arg Asn Ile Gly Ala Ile Ser Thr Gly
          340                 345                 350

Lys Thr Ser Asn Gly Asn Pro Ala Ser
          355                 360

<210> SEQ ID NO 52
<211> LENGTH: 2050
<212> TYPE: DNA
<213> ORGANISM: Cuphea aequipetala

<400> SEQUENCE: 52

| | | | | | |
|---|---|---|---|---|---|
| gcagcaagtt | ctgcatgctt | ctccgtcgca | accccgcgaa | caaacatttc | gccatcgagc | 60 |
| ttgagcgtcc | ccttcaagcc | caaatcaaac | cacaatgttg | gctttcaggt | taaggcaaac | 120 |
| gccagtgccc | atcctaaggc | taacggttct | gcagtaagtc | taaagtctgg | cagcatcgag | 180 |
| actcaggagg | acaaaacttc | atcgtcgtcc | cctcctcctc | ggactttcat | taaccagttg | 240 |
| cccgtctgga | gtatgcttct | gtccgcagtc | acgactgtct | tcggggtggc | tgagaagcag | 300 |
| tggccaatgc | ttgatcggaa | atctaagagg | cccgacatgc | ttgtggaacc | gcttggggtt | 360 |
| gacaggattg | tttatgatgg | ggttagtttc | agacagagtt | tttcgattag | atcttacgaa | 420 |
| ataggcgctg | atcgaacagc | ctcgatagag | accctgatga | acatgttcca | ggtactgcat | 480 |
| tgaatctatg | caaccatagc | attgctagtg | acatagataa | cacctagttg | ccagtataat | 540 |
| tgtgtccatt | ttaatttaga | ggtgccattt | tttttctcta | aacaggaaac | atctcttaat | 600 |
| cattgtaaga | ttatcggtct | tctcaatgac | ggctttggtc | gaactcctga | gatgtgtaag | 660 |
| agggacctca | tttgggtggt | tacgaaaatg | cagatcgagg | tgaatcgcta | tcctacttgg | 720 |
| taagtttgtc | tcttatttgt | ctttggtctg | caaatgcctc | ttactataac | acttgtaaac | 780 |
| atagtggaat | gtgatctata | tggcaggggt | gatactatag | aggtcaatac | ttgggtctca | 840 |
| gcgtcgggga | aacacggtat | gggtcgtgac | tggcttataa | gtgattgcca | tacaggagaa | 900 |
| attcttataa | gagcaacgag | gtagaatttt | tctggttctg | aatttacatt | ctcaaacctt | 960 |
| ctggtgtttg | atatgagagc | aggcatttgg | tatgttttat | attgaaagtt | gagtgaagtc | 1020 |
| agtctaatat | tatcgcagcg | tgtgggctat | gatgaatcaa | aagacgagaa | gattgtcaaa | 1080 |
| aattccatat | gaggttcgac | aggagataga | gcctcagttt | gtggactctg | ctcctgtcat | 1140 |
| tgaagacgat | cgaaaattgc | acaagcttga | tttgaagacg | gtatttccatttgcaatgg | 1200 |
| tctaactgta | agtccctata | tttcgtatga | tatatgtcgt | gtttatgaaa | tatctcgtct | 1260 |
| ctgaggcgat | ctttatcttc | gcgcggtttg | tagccaaggt | ggaccgactt | ggatgtcaat | 1320 |
| cagcacgtta | acaatgtgaa | atacattggg | tggattctcc | aggtaccctt | aataagatca | 1380 |
| ataaacttcg | atattggccc | gaatatctgc | tagctagcac | ttgagatatt | acatatacat | 1440 |
| cgtggattag | tattgcaccg | aagtttgtca | atgcttgatt | taccaatgct | tgttgcagag | 1500 |
| tgttcccaca | gaagttttcg | agaagcagga | gctatgtggc | ctcacccttg | agtataggcg | 1560 |
| agaatgcgga | agggacagtg | tgctggagtc | cgtgaccgct | atggatccat | caaaagaggg | 1620 |
| tgaccggtct | ctttaccagc | accttctccg | actcgaggac | ggggctgata | tcgtcaaggg | 1680 |
| cagaaccgag | tggcggccga | agaatgcagg | aggagccaag | gggccaatat | caaccggaaa | 1740 |
| gacctcaaat | ggaaaatcta | tctcttagaa | ggagcaaggg | accttccgga | gttgtgtagt | 1800 |
| tcgtttgcag | tttctcgctt | tgctttgatt | cactccattg | tataataata | ttatggtcag | 1860 |

```
ccgtctttgt atttgaaaaa aattattaaa aatacaactt catctactaa tgattatttc   1920
atatttaaac taaacaaaaa aattattaaa aataaaatct tataaaatat tctaaccatt   1980
ttaatcttat acaaaataaa atcgaccatt aaaatgagaa aatattaaat aatttaaatt   2040
agaaaacgaa                                                          2050

<210> SEQ ID NO 53
<211> LENGTH: 408
<212> TYPE: PRT
<213> ORGANISM: Cuphea aequipetala

<400> SEQUENCE: 53
```

| | | | | | | | | | | | | | | |
|---|---|---|---|---|---|---|---|---|---|---|---|---|---|---|
|Ala|Ala|Ser|Ser|Ala|Cys|Phe|Ser|Val|Ala|Thr|Pro|Arg|Thr|Asn|Ile|
|1| | | |5| | | | |10| | | | |15| |

Ala Ala Ser Ser Ala Cys Phe Ser Val Ala Thr Pro Arg Thr Asn Ile
1               5                   10                  15

Ser Pro Ser Ser Leu Ser Val Pro Phe Lys Pro Lys Ser Asn His Asn
            20                  25                  30

Val Gly Phe Gln Val Lys Ala Asn Ala Ser Ala His Pro Lys Ala Asn
        35                  40                  45

Gly Ser Ala Val Ser Leu Lys Ser Gly Ser Ile Glu Thr Gln Glu Asp
    50                  55                  60

Lys Thr Ser Ser Ser Pro Pro Arg Thr Phe Ile Asn Gln Leu
65                  70                  75                  80

Pro Val Trp Ser Met Leu Leu Ser Ala Val Thr Thr Val Phe Gly Val
                85                  90                  95

Ala Glu Lys Gln Trp Pro Met Leu Asp Arg Lys Ser Lys Arg Pro Asp
            100                 105                 110

Met Leu Val Glu Pro Leu Gly Val Asp Arg Ile Val Tyr Asp Gly Val
        115                 120                 125

Ser Phe Arg Gln Ser Phe Ser Ile Arg Ser Tyr Glu Ile Gly Ala Asp
    130                 135                 140

Arg Thr Ala Ser Ile Glu Thr Leu Met Asn Met Phe Gln Glu Thr Ser
145                 150                 155                 160

Leu Asn His Cys Lys Ile Ile Gly Leu Leu Asn Asp Gly Phe Gly Arg
                165                 170                 175

Thr Pro Glu Met Cys Lys Arg Asp Leu Ile Trp Val Val Thr Lys Met
            180                 185                 190

Gln Ile Glu Val Asn Arg Tyr Pro Thr Trp Gly Asp Thr Ile Glu Val
        195                 200                 205

Asn Thr Trp Val Ser Ala Ser Gly Lys His Gly Met Gly Arg Asp Trp
    210                 215                 220

Leu Ile Ser Asp Cys His Thr Gly Glu Ile Leu Ile Arg Ala Thr Ser
225                 230                 235                 240

Val Trp Ala Met Met Asn Gln Lys Thr Arg Arg Leu Ser Lys Ile Pro
                245                 250                 255

Tyr Glu Val Arg Gln Glu Ile Glu Pro Gln Phe Val Asp Ser Ala Pro
            260                 265                 270

Val Ile Glu Asp Asp Arg Lys Leu His Lys Leu Asp Leu Lys Thr Gly
        275                 280                 285

Ile Ser Ile Cys Asn Gly Leu Thr Pro Arg Trp Thr Asp Leu Asp Val
    290                 295                 300

Asn Gln His Val Asn Asn Val Lys Tyr Ile Gly Trp Ile Leu Gln Ser
305                 310                 315                 320

Val Pro Thr Glu Val Phe Glu Lys Gln Glu Leu Cys Gly Leu Thr Leu
                325                 330                 335

Glu Tyr Arg Arg Glu Cys Gly Arg Asp Ser Val Leu Glu Ser Val Thr
            340                 345                 350

Ala Met Asp Pro Ser Lys Glu Gly Asp Arg Ser Leu Tyr Gln His Leu
            355                 360                 365

Leu Arg Leu Glu Asp Gly Ala Asp Ile Val Lys Gly Arg Thr Glu Trp
    370                 375                 380

Arg Pro Lys Asn Ala Gly Gly Ala Lys Gly Pro Ile Ser Thr Gly Lys
385                 390                 395                 400

Thr Ser Asn Gly Lys Ser Ile Ser
                405

<210> SEQ ID NO 54
<211> LENGTH: 1089
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
atggcgaacg gcagcgcagt gagcctgaaa tccggcagca ttgagactca ggaggataag      60
accagcagct cttcccctcc cccacgcact ttcattaacc aattacccgt ttggagcatg     120
ttactgtccg cagttacgac cgtgttcggt gttgcggaga acaatggcc catgctggat      180 cgcaaatcta aacgtccaga tatgttgatg aaccgttag gcgtcgaccg tatcgtgtac      240
gacggtgtct cctttcgcca gtccttttcc attcgctctt acgagatcgg tgctgatcgt     300
actgcgtcta tcgaaaccct gatgaatatg tttcaagaaa cctccttgaa ccattgtaag     360
attatcggtt tgttaaacga cggctttggt cgcactccgg agatgtgcaa gcgtgacttg     420
atctgggtcg tgactaagat gcagattgag gtgaatcgtt acccgacctg gggtgacact     480
atcgaagtca atacctgggt gtctgccagc ggtaaacatg gcatgggtcg cgattggttg     540
atttccgatt gtcacactgg tgaaatctta atccgcgcca cctccgtgtg ggcgatgatg     600
aaccagaaaa cccgtcgctt gtctaagatc ccatatgagg tgcgtcaaga aattgaaccg     660
caattcgttg acagcgcgcc tgttatcgag acgatcgta aactgcacaa gttggactta      720
aagactggca tttctatttg caatggttta accccacgtt ggaccgacct ggacgttaac     780
cagcacgtca acaatgttaa gtacatcggt tggattttgc aatccgtgcc caccgaggtt     840
ttcgagaaac aggaactgtg tggcttaacc ctggagtatc gtcgcgaatg cggtcgcgac     900
tccgttctgg aaagcgtcac ggcgatggac ccttccaaag aaggcgatcg cagcttgtat     960
caacacctgc tgcgcttaga ggatggcgct gatatcgtga agggtcgcac cgaatggcgt    1020
cccaagaatg caggcgcaaa cggtgcgatt tctaccggta aaacgagcaa tggtaacagc    1080
atctcttaa                                                           1089

<210> SEQ ID NO 55
<211> LENGTH: 362
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Ala Asn Gly Ser Ala Val Ser Leu Lys Ser Gly Ser Ile Glu Thr
1               5                   10                  15

| | | | | | | | | | | | | |
|---|---|---|---|---|---|---|---|---|---|---|---|---|
|Gln|Glu|Asp|Lys|Thr 20|Ser|Ser|Ser|Pro 25|Pro|Pro|Arg|Thr 30|Phe|Ile|

| | | | | | | | | | | | | |
|---|---|---|---|---|---|---|---|---|---|---|---|---|
|Asn|Gln|Leu|Pro 35|Val|Trp|Ser|Met 40|Leu|Leu|Ser|Ala|Val 45|Thr|Thr|Val|

| | | | | | | | | | | | | |
|---|---|---|---|---|---|---|---|---|---|---|---|---|
|Phe|Gly|Val|Ala|Glu 50|Lys|Gln|Trp|Pro 55|Met|Leu|Asp|Arg 60|Lys|Ser|Lys|

| | | | | | | | | | | | | |
|---|---|---|---|---|---|---|---|---|---|---|---|---|
|Arg 65|Pro|Asp|Met|Leu|Met 70|Glu|Pro|Leu|Gly|Val 75|Asp|Arg|Ile|Val|Tyr 80|

Arg Pro Asp Met Leu Met Glu Pro Leu Gly Val Asp Arg Ile Val Tyr
65                  70                  75                  80

Asp Gly Val Ser Phe Arg Gln Ser Phe Ser Ile Arg Ser Tyr Glu Ile
                85                  90                  95

Gly Ala Asp Arg Thr Ala Ser Ile Glu Thr Leu Met Asn Met Phe Gln
                100                 105                 110

Glu Thr Ser Leu Asn His Cys Lys Ile Ile Gly Leu Leu Asn Asp Gly
            115                 120                 125

Phe Gly Arg Thr Pro Glu Met Cys Lys Arg Asp Leu Ile Trp Val Val
130                 135                 140

Thr Lys Met Gln Ile Glu Val Asn Arg Tyr Pro Thr Trp Gly Asp Thr
145                 150                 155                 160

Ile Glu Val Asn Thr Trp Val Ser Ala Ser Gly Lys His Gly Met Gly
                165                 170                 175

Arg Asp Trp Leu Ile Ser Asp Cys His Thr Gly Glu Ile Leu Ile Arg
                180                 185                 190

Ala Thr Ser Val Trp Ala Met Met Asn Gln Lys Thr Arg Arg Leu Ser
            195                 200                 205

Lys Ile Pro Tyr Glu Val Arg Gln Glu Ile Glu Pro Gln Phe Val Asp
210                 215                 220

Ser Ala Pro Val Ile Glu Asp Arg Lys Leu His Lys Leu Asp Leu
225                 230                 235                 240

Lys Thr Gly Ile Ser Ile Cys Asn Gly Leu Thr Pro Arg Trp Thr Asp
                245                 250                 255

Leu Asp Val Asn Gln His Val Asn Val Lys Tyr Ile Gly Trp Ile
                260                 265                 270

Leu Gln Ser Val Pro Thr Glu Val Phe Glu Lys Gln Glu Leu Cys Gly
            275                 280                 285

Leu Thr Leu Glu Tyr Arg Arg Glu Cys Gly Arg Asp Ser Val Leu Glu
290                 295                 300

Ser Val Thr Ala Met Asp Pro Ser Lys Glu Gly Asp Arg Ser Leu Tyr
305                 310                 315                 320

Gln His Leu Leu Arg Leu Glu Asp Gly Ala Asp Ile Val Lys Gly Arg
                325                 330                 335

Thr Glu Trp Arg Pro Lys Asn Ala Gly Ala Asn Gly Ala Ile Ser Thr
                340                 345                 350

Gly Lys Thr Ser Asn Gly Asn Ser Ile Ser
            355                 360

<210> SEQ ID NO 56
<211> LENGTH: 2719
<212> TYPE: DNA
<213> ORGANISM: Cuphea inflate

<400> SEQUENCE: 56
gcagcaagtt ctgcatgctt ccccgtgccg tccccggaca cctcctctag accgggaaag      60
ctcggaaatg ggtcatcaag cttgagcccc ctcaagccca aatttgtcgt caatgccggg     120
ttgaaggtta aggcaagcgc cagtgcccct cctaagatca atggttcctc ggtcggtcta     180

```
aagtccggca gtctcaagac tcaggaagac actcatacgg cgcctcctcc gcggactttt      240
atcaaccagt tgcctgattg gagtatgctt cttgctgcaa tcactactgc cttcttggca      300
gcagagaagc agtggatgat gcttgattgg aaacctaaga ggcctgacat gcttgtggac      360
ccgttcggat tgggaaggat tgtacaggat gggcttgtgt tcaggcagaa ttttttcgatt     420 aggtcttatg aaataggcgc tgatcgcact gcgtctatag agacggtgat gaaccacttg      480
caggtactgc tgcagcctgc attcaaacta ttcaattcat gaaatggtta tgtactgcct      540
tcatctctat tgtcatgagg tgattcaata aggtttacct cgtgttaact tatatgcact      600
catttcatga tcactttggc ttcttatggt gagatttgtc atgtcgagtc tatggaagaa      660
tcatctgctc tactgtatta ttattaaatt taggcatgat gaaattttat gtggaactta      720
gttacttctg tgatataaaa cccagcaagg aaaacttccg cttcccttt aatcttaaaa       780 taaaaataa aaaactaaa gaaggaact ctcatttcaa atgaaaactg gattagtttt         840
ctgatatgta tgtaatgatt aaacatttgc attaggatgc tcataatttt ggttgaattt      900
attgtctttg tcctttgctt ttttttttt cttttacagg aaacggctct caatcatgtt       960
aagagtgctg gccttcttaa tgacggcttt ggtcgtactc gtgagatgta taaaagggac     1020
cttatttggg ttgtcgcgaa aatgcaggtc atggttaacc gctatcctac ttggtaagtt     1080
tgtcactagc tttttacttt acggtactta ggcttcttac aattttgtat caatgtagct     1140
gtaatgtata tatcatattg tttcatttca atataacaac gatgacaaca aatctccttt     1200
gttgtggaac ctaagggtct gtctgtgatc tatattcagg ggtgacacgg ttgaagtgaa     1260
tacttgggtt gccaagtcag ggaaaaatgg tatgcgtcgt gattggctca taagtgattg     1320
caatacagga gaaattctta ctagagcctc aaggtatggt gtactgtttt gtagtttatg     1380
ttcctgtact ttctagtggt caaatttgag agcattcagt ctggagattt tacagtgatt     1440
gtcgaattaa gttaccctta cattcttgca gcgtgtgggt catgatgaat caaaagacga     1500
gaaaattgtc aaaaattcca gatgaggttc gacatgagat agagcctcat tttgtggact     1560
ctcctcccgt cattgaagac gatgaccgga aacttcccaa gctggatgag aagactgctg     1620
actccatccg caagggtcta actgtaaggg catatcttac actttaacag tggcttgctt     1680
tgctatataa aaaattatgc ttcttagacg attttcctct ttgcaatttg tagccaaagt     1740
ggaatgactt ggatgtcaat cagcacgtca acaacgtgaa gtatattggg tggattcttg     1800
aggtaacttt ttaacctgtt agttgaatat gtgtttatgt taataagata tatgaactta     1860
gatattgacc aatgtaactg ctagcacttg agaattactc aaagtccatt tacagttatt     1920
atattgctaa actaattatg ttgttctcga cataaacaat gtgccaatgc ttgttgcaga     1980
gtactccaca agaagttctg gagacccagg agttatgttc ccttaccctg gaatacaggc     2040
gggaatgtgg aagggagagc gtgctggagt ccctcactgc tgtggacccc tctggaaagg     2100
gctttgggtc ccagttccag caccttctga ggcttgagga tggaggtgag atcgtgaagg     2160
ggagaactga gtggcgaccc aagactgcag gtatcaatgg gccgatagca tccggggaga     2220
cctcacctgg agactcttag aagggagccc tggtcccttt ggagttcggc tttgtttatt     2280
gtcggatgag ctgagtgaac gacaggtaag gtagtagcaa tcggtagatt gtgtggtttg     2340
ttttctgttt ttcacttcgg ctctcttgta taatatcatg gtcttctttg tatcttgcat     2400
gtttcgggtt gatttataca ttatattctt tctatttgtt tcaaggtgag taaagagttg     2460
taattatttg ttttgtcgtt acaatgctgt taaattttca tatgaaagta cttatgtgaa     2520
```

```
ctgcatcgcc ttcccttaga aggtatcata atgcattata accatgttac tgcgttgcat    2580
catctgcgag tcctaaatta tcttatgccg gtgtggtttg gtatgctgtg ctgtgctgta    2640
gtggcttaat ccagatacta tatttgtttt atcaccaggg aacacaagaa accgcaaaca    2700
agacactgct gatggctac                                                 2719
```

```
<210> SEQ ID NO 57
<211> LENGTH: 410
<212> TYPE: PRT
<213> ORGANISM: Cuphea inflate

<400> SEQUENCE: 57
```

Ala Ala Ser Ser Ala Cys Phe Pro Val Pro Ser Pro Asp Thr Ser Ser
1               5                   10                  15

Arg Pro Gly Lys Leu Gly Asn Gly Ser Ser Ser Leu Ser Pro Leu Lys
            20                  25                  30

Pro Lys Phe Val Val Asn Ala Gly Leu Lys Val Lys Ala Ser Ala Ser
        35                  40                  45

Ala Pro Pro Lys Ile Asn Gly Ser Ser Val Gly Leu Lys Ser Gly Ser
    50                  55                  60

Leu Lys Thr Gln Glu Asp Thr His Thr Ala Pro Pro Arg Thr Phe
65                  70                  75                  80

Ile Asn Gln Leu Pro Asp Trp Ser Met Leu Leu Ala Ala Ile Thr Thr
                85                  90                  95

Ala Phe Leu Ala Ala Glu Lys Gln Trp Met Met Leu Asp Trp Lys Pro
            100                 105                 110

Lys Arg Pro Asp Met Leu Val Asp Pro Phe Gly Leu Gly Arg Ile Val
        115                 120                 125

Gln Asp Gly Leu Val Phe Arg Gln Asn Phe Ser Ile Arg Ser Tyr Glu
    130                 135                 140

Ile Gly Ala Asp Arg Thr Ala Ser Ile Glu Thr Val Met Asn His Leu
145                 150                 155                 160

Gln Glu Thr Ala Leu Asn His Val Lys Ser Ala Gly Leu Leu Asn Asp
                165                 170                 175

Gly Phe Gly Arg Thr Arg Glu Met Tyr Lys Arg Asp Leu Ile Trp Val
            180                 185                 190

Val Ala Lys Met Gln Val Met Val Asn Arg Tyr Pro Thr Trp Gly Asp
        195                 200                 205

Thr Val Glu Val Asn Thr Trp Val Ala Lys Ser Gly Lys Asn Gly Met
    210                 215                 220

Arg Arg Asp Trp Leu Ile Ser Asp Cys Asn Thr Gly Glu Ile Leu Thr
225                 230                 235                 240

Arg Ala Ser Ser Val Trp Val Met Met Asn Gln Lys Thr Arg Lys Leu
                245                 250                 255

Ser Lys Ile Pro Asp Glu Val Arg His Glu Ile Glu Pro His Phe Val
            260                 265                 270

Asp Ser Pro Pro Val Ile Glu Asp Asp Arg Lys Leu Pro Lys Leu
        275                 280                 285

Asp Glu Lys Thr Ala Asp Ser Ile Arg Lys Gly Leu Thr Pro Lys Trp
    290                 295                 300

Asn Asp Leu Asp Val Asn Gln His Val Asn Asn Val Lys Tyr Ile Gly
305                 310                 315                 320

Trp Ile Leu Glu Ser Thr Pro Gln Glu Val Leu Glu Thr Gln Glu Leu
                325                 330                 335

```
Cys Ser Leu Thr Leu Glu Tyr Arg Arg Glu Cys Gly Arg Glu Ser Val
                340                 345                 350

Leu Glu Ser Leu Thr Ala Val Asp Pro Ser Gly Lys Gly Phe Gly Ser
            355                 360                 365

Gln Phe Gln His Leu Leu Arg Leu Glu Asp Gly Gly Glu Ile Val Lys
        370                 375                 380

Gly Arg Thr Glu Trp Arg Pro Lys Thr Ala Gly Ile Asn Gly Pro Ile
385                 390                 395                 400

Ala Ser Gly Glu Thr Ser Pro Gly Asp Ser
                405                 410

<210> SEQ ID NO 58
<211> LENGTH: 1086
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
atgggcatta atggctccag tgttggtttg aagtccggca gtttgaagac ccaggaagac      60
acccacaccg ctccccctcc ccgcaccttc atcaaccagt acccgattg gtccatgttg     120 ttagccgcta ttactaccgc ttttttggct gccgaaaagc aatggatgat gttagattgg    180
aagcccaaac ggcccgatat gttagtggac ccttttggtt tgggccggat cgtgcaggat    240
ggtttagtgt tccggcagaa ttttttccat tgcagttatg aaattggtgc cgaccggact    300
gccagtattg agaccgttat gaaccattta aagagaccg ctttgaacca tgttaaatcc     360
gccgggttgt taaatgacgg cttcggtcgt acccgggaga tgtataaacg cgatttaatt    420
tgggttgtgg ctaaaatgca ggtgatggtt aatcggtacc ccacctgggg tgacaccgtg    480
gaggtgaaca cctgggttgc caagtccggg aaaaatggca tgcggcgcga ttggttgatc    540
tccgactgta acaccggtga atcttgact cgggcctcct ccgtgtgggt tatgatgaat      600
cagaaaaccc gcaaattatc caagattcct gatgaggtgc gccatgaaat cgaacctcat    660
ttcgtggact cccctcccgt tattgaagac gatgaccgga agttgcctaa attagatgag    720
aaaactgccg actccatccg gaagggctta accctaaat ggaacgattt ggacgtgaac      780
caacacgtga ataacgtgaa atatattggt tggatcttgg aaagtacccc tcaagaggtg    840
ttagaaactc aagagttgtg ctccttaacc ttagagtatc gccgggaatg cggccgtgaa    900
agtgtgttag aatccttgac cgctgtggac ccctccggta aaggttttgg ctcccagttt    960
caacatttat tgcgtttgga agacgggggc gaaatcgtga agggccgcac cgagtggcgc   1020
cccaagaccg ctggcatcaa tggtcccatc gcctccggcg aaaccagtcc cggtgatagt   1080
taataa                                                              1086

<210> SEQ ID NO 59
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Gly Ile Asn Gly Ser Ser Val Gly Leu Lys Ser Gly Ser Leu Lys
1               5                   10                  15

Thr Gln Glu Asp Thr His Thr Ala Pro Pro Pro Arg Thr Phe Ile Asn
```

```
            20                  25                  30
Gln Leu Pro Asp Trp Ser Met Leu Ala Ala Ile Thr Thr Ala Phe
         35                  40                  45
Leu Ala Ala Glu Lys Gln Trp Met Met Leu Asp Trp Lys Pro Lys Arg
 50                  55                  60
Pro Asp Met Leu Val Asp Pro Phe Gly Leu Gly Arg Ile Val Gln Asp
 65                  70                  75                  80
Gly Leu Val Phe Arg Gln Asn Phe Ser Ile Arg Ser Tyr Glu Ile Gly
                 85                  90                  95
Ala Asp Arg Thr Ala Ser Ile Glu Thr Val Met Asn His Leu Gln Glu
                100                 105                 110
Thr Ala Leu Asn His Val Lys Ser Ala Gly Leu Leu Asn Asp Gly Phe
                115                 120                 125
Gly Arg Thr Arg Glu Met Tyr Lys Arg Asp Leu Ile Trp Val Val Ala
                130                 135                 140
Lys Met Gln Val Met Val Asn Arg Tyr Pro Thr Trp Gly Asp Thr Val
145                 150                 155                 160
Glu Val Asn Thr Trp Val Ala Lys Ser Gly Lys Asn Gly Met Arg Arg
                165                 170                 175
Asp Trp Leu Ile Ser Asp Cys Asn Thr Gly Glu Ile Leu Thr Arg Ala
                180                 185                 190
Ser Ser Val Trp Val Met Met Asn Gln Lys Thr Arg Lys Leu Ser Lys
                195                 200                 205
Ile Pro Asp Glu Val Arg His Glu Ile Glu Pro His Phe Val Asp Ser
                210                 215                 220
Pro Pro Val Ile Glu Asp Asp Arg Lys Leu Pro Lys Leu Asp Glu
225                 230                 235                 240
Lys Thr Ala Asp Ser Ile Arg Lys Gly Leu Thr Pro Lys Trp Asn Asp
                245                 250                 255
Leu Asp Val Asn Gln His Val Asn Asn Val Lys Tyr Ile Gly Trp Ile
                260                 265                 270
Leu Glu Ser Thr Pro Gln Glu Val Leu Glu Thr Gln Glu Leu Cys Ser
                275                 280                 285
Leu Thr Leu Glu Tyr Arg Arg Glu Cys Gly Arg Glu Ser Val Leu Glu
                290                 295                 300
Ser Leu Thr Ala Val Asp Pro Ser Gly Lys Gly Phe Gly Ser Gln Phe
305                 310                 315                 320
Gln His Leu Leu Arg Leu Glu Asp Gly Gly Glu Ile Val Lys Gly Arg
                325                 330                 335
Thr Glu Trp Arg Pro Lys Thr Ala Gly Ile Asn Gly Pro Ile Ala Ser
                340                 345                 350
Gly Glu Thr Ser Pro Gly Asp Ser
                355                 360

<210> SEQ ID NO 60
<211> LENGTH: 2266
<212> TYPE: DNA
<213> ORGANISM: Cuphea leptopoda

<400> SEQUENCE: 60
cccttctcct ttccaacccc tggaacctcc cctaaacccg ggaagttcgg gccatcgagc      60
ttgaacgtcc ccttcagtgt ccatcctaag gctaacggtt ctgcagtaag tctaaagtct     120
gacacactcg agactcagga ggacacttca tcgtcgtccc ctcctcctcg gactttcatt     180
```

| | |
|---|---|
| aaccagttgc ccgactggag tatgcttctg tccgcattca cgaatgtctt cgtggcggct | 240 |
| gagaagcagt ggacgatgct tgatcggaaa tataagaggc cagacatgct ggtggaatcg | 300 |
| tctggggttg acaggactga tctggacggg gttttgttca gacagagttt ttcgatcagg | 360 |
| tcttacgaga taggcgctga tcgaacagcc tcgatagaga cactgatgaa catcttccag | 420 |
| gtactgcatt gaaactattc aaaaaccata gcattgctag tgatctgtaa atgagccaca | 480 |
| actcgacgat gacatatata acaccgaatt gccagtataa ttgtgtccat tttaatttag | 540 |
| agctgatgtt ttaagctcat gatgaggttg gaatttgtca ggttaattca agggaggaac | 600 |
| cataagctgt aaattttcga ctatgtttat gtgtgatgat aagtttgttc tatgtattat | 660 |
| ttttctctaa acaggaaaca tctctgaatc attgtaagag taacggtctt ctcaatgacg | 720 |
| gctttggtcg tactcctgag atgtgtaaga gggacctcat ttgggtggtt acgaaaatgc | 780 |
| agatcgaggt gaaccgctat cctacttggt aagttttgtt tgtcttttgg tctgcaaatg | 840 |
| cctcttgcga taatagttgt aaacatagtg gaatgtaatg gcatgtgtga tctatatggt | 900 |
| aggggtgata atatcgaggt cactacctgg gtctccgagt ctgggaaaaa cggtatgggt | 960 |
| cgtcattggc tgataagtga ttgccataca ggagaaattc ttataagagc aacgaggtag | 1020 |
| aattttctgg ttctgatttt acattctcaa accttctggt gttcgatctg agagcagaca | 1080 |
| tttggtatgt tttatattga agttgagtc aagtcactct aaaattatcg cacgtgtggg | 1140 |
| ctatgatgaa tcaaaagacg agaagattgt caaaacttcc atatgaggtt cgacaggaga | 1200 |
| tagctcctca ctttgtggac tctgctcatg tcattgaaga tgatcgaaaa ttgcacaagc | 1260 |
| ttgaagtgaa gacgggtgat tccattcgca atggtctaac tgtaagtccc tatatttcgg | 1320 |
| tataatattt ggcgtgttta tgaaatatca cgtctctgag gcgatctttc ttcacggttt | 1380 |
| gtagccaagg tggaatgact tggatgtcaa tcagcacgtt aacaatgtga agtacattgg | 1440 |
| atggattctc aaggtacccct tcacatcata caaacaactg atatatatac tcgggataag | 1500 |
| atcgataacc ttagaacttg gcccaagtat ctgctagcta gcacttgtga tatttactta | 1560 |
| aatatcgtgg attagtattg ccccgagttt gtcaatgctt gatgtacaca gttcagctaa | 1620 |
| acaaatatgt aatctatacg aatgcttgtt gttgcagagt gttccaacag aagttttcgt | 1680 |
| gacccaggag ctatgtggcc tcacccttga gtataggcgg gaatgcagaa gggacagtgt | 1740 |
| gctggaatcc gtgaccgcta tggatccctc aaaagaggga gaccggtctc tgtaccagca | 1800 |
| ccttcttcgg cttgaaaatg gggctgatat cgccttgggc agaaccgagt ggcgaccgaa | 1860 |
| gaatgcagga gccaatggag caatatcaac agggaagact tcaaatggaa actctgtctc | 1920 |
| ttagaaggga ctcgggacct ttccgagttg tgcgtttatt tttctgtatc aatttctgaa | 1980 |
| agaagggaat gtagttgcaa ttagtaaact gtgtagttcg tttatgcttc gctccatttg | 2040 |
| ctaagacaaa tagcacattc atcgttacaa tatcgttaga tttcgaaaca agtacttgtc | 2100 |
| taaagcatat ataaacccttt gaagatcaca ctacattctg cactgcagtc agctaaatgg | 2160 |
| acattcaaat actatccaag ccgtttgaga tgatgtaatc ctaatccaag aactattccg | 2220 |
| ttcaaagatg tttccacatg aacatgaaag ttgcatcaag gttctc | 2266 |

<210> SEQ ID NO 61
<211> LENGTH: 395
<212> TYPE: PRT
<213> ORGANISM: Cuphea leptopoda

<400> SEQUENCE: 61

Ala Ala Ser Ser Ala Cys Phe Ser Phe Pro Thr Pro Gly Thr Ser Pro

```
1               5                   10                  15
Lys Pro Gly Lys Phe Gly Pro Ser Ser Leu Asn Val Pro Phe Ser Val
                20                  25                  30

His Pro Lys Ala Asn Gly Ser Ala Val Ser Leu Lys Ser Asp Thr Leu
                35                  40                  45

Glu Thr Gln Glu Asp Thr Ser Ser Ser Pro Pro Pro Arg Thr Phe
            50                  55                  60

Ile Asn Gln Leu Pro Asp Trp Ser Met Leu Leu Ser Ala Phe Thr Asn
65                  70                  75                  80

Val Phe Val Ala Ala Glu Lys Gln Trp Thr Met Leu Asp Arg Lys Tyr
                85                  90                  95

Lys Arg Pro Asp Met Leu Val Glu Ser Ser Gly Val Asp Arg Thr Asp
                100                 105                 110

Leu Asp Gly Val Leu Phe Arg Gln Ser Phe Ser Ile Arg Ser Tyr Glu
                115                 120                 125

Ile Gly Ala Asp Arg Thr Ala Ser Ile Glu Thr Leu Met Asn Ile Phe
            130                 135                 140

Gln Glu Thr Ser Leu Asn His Cys Lys Ser Asn Gly Leu Leu Asn Asp
145                 150                 155                 160

Gly Phe Gly Arg Thr Pro Glu Met Cys Lys Arg Asp Leu Ile Trp Val
                165                 170                 175

Val Thr Lys Met Gln Ile Glu Val Asn Arg Tyr Pro Thr Trp Gly Asp
                180                 185                 190

Asn Ile Glu Val Thr Thr Trp Val Ser Glu Ser Gly Lys Asn Gly Met
            195                 200                 205

Gly Arg His Trp Leu Ile Ser Asp Cys His Thr Gly Glu Ile Leu Ile
            210                 215                 220

Arg Ala Thr Arg Val Ala Met Met Asn Gln Lys Thr Arg Arg Leu
225                 230                 235                 240

Ser Lys Leu Pro Tyr Glu Val Arg Gln Glu Ile Ala Pro His Phe Val
                245                 250                 255

Asp Ser Ala His Val Ile Glu Asp Arg Lys Leu His Lys Leu Glu
            260                 265                 270

Val Lys Thr Gly Asp Ser Ile Arg Asn Gly Leu Thr Pro Arg Trp Asn
            275                 280                 285

Asp Leu Asp Val Asn Gln His Val Asn Val Lys Tyr Ile Gly Trp
            290                 295                 300

Ile Leu Lys Ser Val Pro Thr Glu Val Phe Val Thr Gln Glu Leu Cys
305                 310                 315                 320

Gly Leu Thr Leu Glu Tyr Arg Arg Glu Cys Arg Arg Asp Ser Val Leu
                325                 330                 335

Glu Ser Val Thr Ala Met Asp Pro Ser Lys Gly Asp Arg Ser Leu
            340                 345                 350

Tyr Gln His Leu Leu Arg Leu Glu Asn Gly Ala Asp Ile Ala Leu Gly
                355                 360                 365

Arg Thr Glu Trp Arg Pro Lys Asn Ala Gly Ala Asn Gly Ala Ile Ser
            370                 375                 380

Thr Gly Lys Thr Ser Asn Gly Asn Ser Val Ser
385                 390                 395

<210> SEQ ID NO 62
<211> LENGTH: 1083
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 62

```
atggcaaatg gctccgcagt gagcctgaaa tctgatacct agaaaccca ggaggacact      60
tcttccagct cccctccgcc acgtaccttt atcaatcaat tgccggactg gagcatgtta    120
ttgagcgcat tcaccaatgt tttcgttgcc gcggagaaac agtggactat gttggaccgt    180
aagtataagc gcccagacat gctggttgag agcagcggcg ttgaccgtac tgatttggac    240
ggtgtgttat tccgccaaag cttttctatc cgcagctatg aaatcggtgc cgaccgcacc    300
gcgtccatcg agactctgat gaacatcttc caggagactt ctctgaatca ctgcaagtct    360
aacggtttgc tgaacgacgg ctttggccgc actccagaaa tgtgtaaacg cgacttgatt    420
tgggtggtta cgaaaatgca aattgaagtg aaccgctacc ccacctgggg tgataacatt    480
gaggtgacca cgtgggtgtc tgaatctggc aaaaacggca tgggccgtca ctggctgatt    540
tccgattgcc ataccggtga dattttgatc cgcgctactc gccgcgtcgc catgatgaat    600
caaaagaccc gtcgtttaag caaactgccg tacgaagtgc gtcaggaaat tgctcctcat    660
ttcgtcgatt ccgcacacgt gatcgaagat gatcgtaagt acataagct ggaggttaag    720
accggtgact ccattcgcaa cggtttaact ccgcgttgga atgacctgga tgttaaccaa    780
cacgtcaaca acgtcaaata cattggttgg attctgaagt ctgtcccac cgaagtcttt    840
gttacgcagg agttatgcgg tttaaccctg aatatcgtc gcgagtgtcg ccgtgatagc    900
gttttagaat ctgtgactgc aatggatccc tctaaggagg cgatcgcag cttataccag    960
cacttgttgc gtttggagaa tggtgccgac atcgcgctgg gccgtaccga atggcgtccc   1020
aagaacgcgg tgccaatgg cgccattagt accggtaaaa ccagtaatgg taatagttaa   1080
taa                                                                 1083
```

<210> SEQ ID NO 63
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Met Ala Asn Gly Ser Ala Val Ser Leu Lys Ser Asp Thr Leu Glu Thr
1               5                   10                  15

Gln Glu Asp Thr Ser Ser Ser Pro Pro Arg Thr Phe Ile Asn
            20                  25                  30

Gln Leu Pro Asp Trp Ser Met Leu Leu Ser Ala Phe Thr Asn Val Phe
        35                  40                  45

Val Ala Ala Glu Lys Gln Trp Thr Met Leu Asp Arg Lys Tyr Lys Arg
    50                  55                  60

Pro Asp Met Leu Val Glu Ser Ser Gly Val Asp Arg Thr Asp Leu Asp
65                  70                  75                  80

Gly Val Leu Phe Arg Gln Ser Phe Ser Ile Arg Ser Tyr Glu Ile Gly
                85                  90                  95

Ala Asp Arg Thr Ala Ser Ile Glu Thr Leu Met Asn Ile Phe Gln Glu
            100                 105                 110

Thr Ser Leu Asn His Cys Lys Ser Asn Gly Leu Leu Asn Asp Gly Phe
        115                 120                 125
```

```
Gly Arg Thr Pro Glu Met Cys Lys Arg Asp Leu Ile Trp Val Val Thr
        130                 135                 140

Lys Met Gln Ile Glu Val Asn Arg Tyr Pro Thr Trp Gly Asp Asn Ile
145                 150                 155                 160

Glu Val Thr Thr Trp Val Ser Glu Ser Gly Lys Asn Gly Met Gly Arg
                165                 170                 175

His Trp Leu Ile Ser Asp Cys His Thr Gly Glu Ile Leu Ile Arg Ala
            180                 185                 190

Thr Arg Arg Val Ala Met Met Asn Gln Lys Thr Arg Arg Leu Ser Lys
        195                 200                 205

Leu Pro Tyr Glu Val Arg Gln Glu Ile Ala Pro His Phe Val Asp Ser
210                 215                 220

Ala His Val Ile Glu Asp Asp Arg Lys Leu His Lys Leu Glu Val Lys
225                 230                 235                 240

Thr Gly Asp Ser Ile Arg Asn Gly Leu Thr Pro Arg Trp Asn Asp Leu
                245                 250                 255

Asp Val Asn Gln His Val Asn Asn Val Lys Tyr Ile Gly Trp Ile Leu
            260                 265                 270

Lys Ser Val Pro Thr Glu Val Phe Val Thr Gln Glu Leu Cys Gly Leu
        275                 280                 285

Thr Leu Glu Tyr Arg Arg Glu Cys Arg Arg Asp Ser Val Leu Glu Ser
290                 295                 300

Val Thr Ala Met Asp Pro Ser Lys Glu Gly Asp Arg Ser Leu Tyr Gln
305                 310                 315                 320

His Leu Leu Arg Leu Glu Asn Gly Ala Asp Ile Ala Leu Gly Arg Thr
                325                 330                 335

Glu Trp Arg Pro Lys Asn Ala Gly Ala Asn Gly Ala Ile Ser Thr Gly
            340                 345                 350

Lys Thr Ser Asn Gly Asn Ser
        355

<210> SEQ ID NO 64
<211> LENGTH: 2860
<212> TYPE: DNA
<213> ORGANISM: Cuphea leptopoda

<400> SEQUENCE: 64
gcagcaagtt ctgcatgctt ccccctgccg tccccggaca cctcctctag accgggaaag        60
ctcggaaatg ggtcatcgag cttgagcccc tcaagcccaa atttgtcgca caatgccggg       120
ttgaaggtta aggcaaacgc cagtgcccct cctaagatca atggttcctc ggtcggtcta       180
aagtccggca gtctcaagac tcaggaagat actcctttgg cgcctcctcc gcggactttt       240
atcaaccagt tacctgattg gagtatgctt cttgctgcaa tcactactgt ctttctggca       300
gcagagaggc agtggatgat gcttgattgg aaacctaaga ggcctgacat gcttgttgac       360
ccgttcggat tgggaagtat tgtccagaat gggcttgtgt tcaggcagaa ttttttcgatt      420 aggtcctatg aaataggcgc tgatcgcact gcgtctatag agacggtgat gaaccacttg       480
caggtactgg tgcatcctgc atttaaacta ttcaattcat gaaatgctta tgtccagtaa       540
ccaagccata cttgattatg gcttaccaaa tttaatggtg aatttgagaa agaaagggtt       600
gtactgcatt cctctctatt gtcatgaggt gattcaatat aggtttacct cgtgtcagtt       660
ttaacttata tgcactcatt tcatgatcac cttggctttt tatggtgaga tttgtcatgt       720
cgagtcaata atagaatcat ctgctctact atattattct taaatttagg cacgatgaaa       780
```

| | |
|---|---|
| ttttatttgg aacttagtta cttctgtgat agaaaaccca ggaaggaaag cttcctcttg | 840 |
| ctctttaatg taaaaaaata aataaataaa aataaaggaa ctctcatttc aattgaaaac | 900 |
| tggattagtt ttctgatatg catgtaagga ttaaacattt gcattagttt gctgataatt | 960 |
| ttggttgaat tcattgtctt tgtcctgtgt tttttttttt cctttttacag gaaacggctc | 1020 |
| tcaatcatgt taagagtgct gggcttctta atgaaggctt tggtcgtact cctgagatgt | 1080 |
| ataaaaggga ccttatttgg gttgtcgcga aaatgcaggt catggttaac cgctatccta | 1140 |
| cttggtaagt ttgtcactag cttttttactt tatggtactt agaggcttct tacaattttg | 1200 |
| agtcaatgta gctgtaatgt atatcacatt gtaatgagtg ctcgctgtta ccttccttgt | 1260 |
| gatatggtgt ttcatttcaa tataacactg atgactacaa atctccttta tgttgtggaa | 1320 |
| cctaagggcc tgtctgtgat ctatattcag gggtgacacg gttgaagtga atacttgggt | 1380 |
| tgccaagtca gggaaaaatg gtatgcgtcg tgattggctc ataagtgatt gcaatacagg | 1440 |
| agaaattctt actagagctt caaggtatgt actgatttat agtttatgtt cctctacttt | 1500 |
| ctagttgtca aatttgagag catccaatca ggagatttta cggtgaaagt cgaattaagt | 1560 |
| tacccttaca ttattgcagc gtgtgggtca tgatgaatca aaagacaaga agattgtcaa | 1620 |
| aaattccaga tgaggttcga catgagatag aacctcattt tgtggactct gctcccgtca | 1680 |
| ttgaagacga tgaccggaaa cttcccaagc tggatgagaa tactgctgac tccatccgca | 1740 |
| agggtctaac tgtaaggcca tattttacac tttaacagtg gcttgcattg ttatataaaa | 1800 |
| aatcatgctt cttagacgat tttcctcttt gcaatttgta gccgaagtgg aatgacttgg | 1860 |
| atgtcaatca gcatgtcaac aacgtgaagt acatcgggtg gattcttgag gtgacttttt | 1920 |
| aacctgttag ttgaatattt gtgcatctta ataagatata tgaaagtaga tattgaccga | 1980 |
| agtaactgct agcgcttgag aattgctcat atgtccctga agtccattta cagttattat | 2040 |
| attgctaaac tagttatgct gttttgaaat aaacaatgtg ccaatgttcg ttgcagagta | 2100 |
| ctccacaaga agttctggag acccaggagt tatgttccct taccctggaa tacaggcgag | 2160 |
| aatgcggaag ggagagcgtg ctggagtccc tcactgctgt ggaccccttct ggaaagggct | 2220 |
| ttgggtccca gttccaacac cttctgaggc ttgaggatgg aggtgagatc gtgaagggga | 2280 |
| gaactgagtg gcgacccaag actgcaggta tcaatggggc gatagcatcc ggggaaacct | 2340 |
| cacccggaga cttttagaag ggagccctgg tcccctttgga gttctgcttt ctttattttc | 2400 |
| ggatgcgctg agtgaacacg gcaggtaagg ttgcagcaat cagtagattg tgtagtttgt | 2460 |
| ttgctgtttt tcacttcggc tctcttgtat aatatcatgg tcttcttgt atcctcgcat | 2520 |
| atttcgggtt gatttgcaca ttatattctt tctatttgtt tcaaggtgag tagcgagttg | 2580 |
| taattattta tcttgtcgtt ccattgtcgt taaatttca aatgaaagta cttatgtgaa | 2640 |
| cttcatcgcc ttctctcgga aggtatcgta atgcattatt aacatgttgc tgtgttgcat | 2700 |
| catctgcgag tctgtgactt atcttatgcc ggtgtggtat ggtgtgctgt gctgtgctgg | 2760 |
| cttaatccgg atactatatt tgttttatca ccagggaaca caagaaaccg caaacaagat | 2820 |
| aagaaccagc ccgggccgtc gaccacgcgt gccctatagt | 2860 |

<210> SEQ ID NO 65
<211> LENGTH: 410
<212> TYPE: PRT
<213> ORGANISM: Cuphea leptopoda

<400> SEQUENCE: 65

Ala Ala Ser Ser Ala Cys Phe Pro Leu Pro Ser Pro Asp Thr Ser Ser

```
1               5                   10                  15
Arg Pro Gly Lys Leu Gly Asn Gly Ser Ser Leu Ser Pro Leu Lys
                20                  25                  30
Pro Lys Phe Val Ala Asn Ala Gly Leu Lys Val Lys Ala Asn Ala Ser
                35                  40                  45
Ala Pro Pro Lys Ile Asn Gly Ser Ser Val Gly Leu Lys Ser Gly Ser
 50                  55                  60
Leu Lys Thr Gln Glu Asp Thr Pro Leu Ala Pro Pro Arg Thr Phe
 65                  70                  75                  80
Ile Asn Gln Leu Pro Asp Trp Ser Met Leu Leu Ala Ala Ile Thr Thr
                85                  90                  95
Val Phe Leu Ala Ala Glu Arg Gln Trp Met Met Leu Asp Trp Lys Pro
                100                 105                 110
Lys Arg Pro Asp Met Leu Val Asp Pro Phe Gly Leu Gly Ser Ile Val
                115                 120                 125
Gln Asn Gly Leu Val Phe Arg Gln Asn Phe Ser Ile Arg Ser Tyr Glu
                130                 135                 140
Ile Gly Ala Asp Arg Thr Ala Ser Ile Glu Thr Val Met Asn His Leu
145                 150                 155                 160
Gln Glu Thr Ala Leu Asn His Val Lys Ser Ala Gly Leu Leu Asn Glu
                165                 170                 175
Gly Phe Gly Arg Thr Pro Glu Met Tyr Lys Arg Asp Leu Ile Trp Val
                180                 185                 190
Val Ala Lys Met Gln Val Met Val Asn Arg Tyr Pro Thr Trp Gly Asp
                195                 200                 205
Thr Val Glu Val Asn Thr Trp Val Ala Lys Ser Gly Lys Asn Gly Met
210                 215                 220
Arg Arg Asp Trp Leu Ile Ser Asp Cys Asn Thr Gly Glu Ile Leu Thr
225                 230                 235                 240
Arg Ala Ser Ser Val Trp Val Met Met Asn Gln Lys Thr Arg Arg Leu
                245                 250                 255
Ser Lys Ile Pro Asp Glu Val Arg His Glu Ile Glu Pro His Phe Val
                260                 265                 270
Asp Ser Ala Pro Val Ile Glu Asp Asp Arg Lys Leu Pro Lys Leu
                275                 280                 285
Asp Glu Asn Thr Ala Asp Ser Ile Arg Lys Gly Leu Thr Pro Lys Trp
                290                 295                 300
Asn Asp Leu Asp Val Asn Gln His Val Asn Asn Val Lys Tyr Ile Gly
305                 310                 315                 320
Trp Ile Leu Glu Ser Thr Pro Gln Glu Val Leu Glu Thr Gln Glu Leu
                325                 330                 335
Cys Ser Leu Thr Leu Glu Tyr Arg Arg Glu Cys Gly Arg Glu Ser Val
                340                 345                 350
Leu Glu Ser Leu Thr Ala Val Asp Pro Ser Gly Lys Gly Phe Gly Ser
                355                 360                 365
Gln Phe Gln His Leu Leu Arg Leu Glu Asp Gly Gly Glu Ile Val Lys
                370                 375                 380
Gly Arg Thr Glu Trp Arg Pro Lys Thr Ala Gly Ile Asn Gly Ala Ile
385                 390                 395                 400
Ala Ser Gly Glu Thr Ser Pro Gly Asp Phe
                405                 410

<210> SEQ ID NO 66
```

<211> LENGTH: 1967
<212> TYPE: DNA
<213> ORGANISM: Cuphea paucipetala

<400> SEQUENCE: 66

```
gcagcaagtt cagcattctt ctcctttcca gccccgggaa cctcccttaa acccgggaag    60
ttcggcaatt ggccatcgaa cttgagcgtc cccttcaatc ccaaagcaaa ccacaatggt   120
ggctttcatg ttaaggcaaa caccagtgcc catcctaagg ctaacggttc tgcagtaagt   180
ctaaaggatg gcagccttga gactcaggag ggcacttcat cgtcgtccca tcctcctcgg   240
actttcatta accagttgcc cgactggagt atgcttctgt ccgcaatcac aactgtcttt   300
gttgcagctg agaagcagtg gacgatgctt gatcggaaat ctaagaggcc cgacatgctc   360
gtggaaccgt ttgttcagga tggtgtttcg ttcagacaga gttttttcgat aaggtcttat   420
gaaataggcg ctgatcgaac agcctcaata gagacgttga tgaacatctt ccaggtattg   480
cattgaaact attcaaccat agcattgcta gtgatctgta aacgatccac tactcgacga   540
tgacatagat aacaccgaaa gttgtggcca ttttaattta gaggtgctgt tttttgctca   600
tgatgagatt tgtttctcag ggtgagattt gtcaggttga ttcaagggag taaccataag   660
ctgtaaattt tcgactacgt ttaggtgtga tgaaagttaa atactcttat tcgaataaga   720
aaaaaaggct atgcattctt atgataagta tttcttctta gatgcgtgca tctgtttgct   780
tatatttccc cgttaactcc attgtctttg ttctaagttt tttgtttctc taaacaggaa   840
acatctctga atcattgtaa gagtctcggt cttctcaatg acggctttgg tcgtactcct   900
gagatgtgta agagggacct catttgggtg gttacgaaaa tgcagattga ggttaatcgc   960
tatcctactt ggtaagtttg tctctggctt gtttgtcttt cggtccacaa atgcctctta  1020
cggtaatagc tgtaaacata gtggaatgta atggcctgtg tgatctatat ggtaggggcg  1080
atactatcga ggtcactact tgggtctccg agtcgggaaa aacggtatg agtcgagatt   1140
ggctgataag tgattgccat acaggagaaa ttcttataag agcaacgagg tagactttt    1200
ctggttctca ttttacattc tcagaccttc tgatgttcga tctgagagca gacatttggt  1260
atgttttata ttgaaagttg agtcaagtca ctctaatatt atcgcagcgt gtgggctatg  1320
atgaatcaaa agacgagaag attgtcaaaa attccagatg aggttcgaca ggagatagtg  1380
ccttattttg tggactctgc tcctgtcatt gaagacgatc gaaaattgca caagcttgat  1440
gtgaagacgg gtgattccat cgcaatggt ctaactgtaa gtccctatat ttcagtatga   1500
tatttggcat gtttatgaaa catcaagtct ctgaggcgat cttctcttc acggtttgta   1560
gccaaggtgg aatgacttgg atgtcaatca gcacgttaac aatgtgaagt acattgggtg  1620
gattctcaag gtaccttttt catcatacaa acaactgata ataagatcaa taaacttaga  1680
tcttgccccg agtttgtgaa tgcttgattt acacagttcg gctaaacaaa tcagtaatct  1740
atacgaatgc ttgttgcaga gtgttccaac agaagttttc gtgacccagg agctatgtgg  1800
cctcacccctt gagtataggc gggaatgcag aagggacagt gtgctggagt ccgtgaccgc  1860
tatggatcct tcaaaagagg gagaccggtc tctgtaccag caccttcttc ggcttgagaa  1920
tggggctgat atcgccttag gcagaactga gtggagaccg aagactg              1967
```

<210> SEQ ID NO 67
<211> LENGTH: 389
<212> TYPE: PRT
<213> ORGANISM: Cuphea paucipetala

<400> SEQUENCE: 67

-continued

```
Ala Ala Ser Ser Ala Phe Phe Ser Phe Pro Ala Pro Gly Thr Ser Leu
1               5                   10                  15

Lys Pro Gly Lys Phe Gly Asn Trp Pro Ser Asn Leu Ser Val Pro Phe
                20                  25                  30

Asn Pro Lys Ala Asn His Asn Gly Gly Phe His Val Lys Ala Asn Thr
            35                  40                  45

Ser Ala His Pro Lys Ala Asn Gly Ser Ala Val Ser Leu Lys Asp Gly
50                      55                  60

Ser Leu Glu Thr Gln Glu Gly Thr Ser Ser Ser His Pro Pro Arg
65                  70                  75                  80

Thr Phe Ile Asn Gln Leu Pro Asp Trp Ser Met Leu Ser Ala Ile
                85                  90                  95

Thr Thr Val Phe Val Ala Ala Glu Lys Gln Trp Thr Met Leu Asp Arg
                100                 105                 110

Lys Ser Lys Arg Pro Asp Met Leu Val Glu Pro Phe Val Gln Asp Gly
            115                 120                 125

Val Ser Phe Arg Gln Ser Phe Ser Ile Arg Ser Tyr Glu Ile Gly Ala
130                 135                 140

Asp Arg Thr Ala Ser Ile Glu Thr Leu Met Asn Ile Phe Gln Glu Thr
145                 150                 155                 160

Ser Leu Asn His Cys Lys Ser Leu Gly Leu Leu Asn Asp Gly Phe Gly
                165                 170                 175

Arg Thr Pro Glu Met Cys Lys Arg Asp Leu Ile Trp Val Val Thr Lys
            180                 185                 190

Met Gln Ile Glu Val Asn Arg Tyr Pro Thr Trp Gly Asp Thr Ile Glu
        195                 200                 205

Val Thr Thr Trp Val Ser Glu Ser Gly Lys Asn Gly Met Ser Arg Asp
210                 215                 220

Trp Leu Ile Ser Asp Cys His Thr Gly Glu Ile Leu Ile Arg Ala Thr
225                 230                 235                 240

Ser Val Trp Ala Met Met Asn Gln Lys Thr Arg Arg Leu Ser Lys Ile
                245                 250                 255

Pro Asp Glu Val Arg Gln Glu Ile Val Pro Tyr Phe Val Asp Ser Ala
            260                 265                 270

Pro Val Ile Glu Asp Asp Arg Lys Leu His Lys Leu Asp Val Lys Thr
        275                 280                 285

Gly Asp Ser Ile Arg Asn Gly Leu Thr Pro Arg Trp Asn Asp Leu Asp
290                 295                 300

Val Asn Gln His Val Asn Asn Val Lys Tyr Ile Gly Trp Ile Leu Lys
305                 310                 315                 320

Ser Val Pro Thr Glu Val Phe Val Thr Gln Glu Leu Cys Gly Leu Thr
                325                 330                 335

Leu Glu Tyr Arg Arg Glu Cys Arg Arg Asp Ser Val Leu Glu Ser Val
            340                 345                 350

Thr Ala Met Asp Pro Ser Lys Glu Gly Asp Arg Ser Leu Tyr Gln His
        355                 360                 365

Leu Leu Arg Leu Glu Asn Gly Ala Asp Ile Ala Leu Gly Arg Thr Glu
370                 375                 380

Trp Arg Pro Lys Thr
385
```

<210> SEQ ID NO 68
<211> LENGTH: 1097

<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 68

```
atggctaatg gttctgccgt gagcttgaaa gatggtagct tagaaactca agagggtact      60
tcttcttcct cccatccacc acgcaccttt atcaatcagc tgcctgattg gtccatgctg     120
ctgtccgcga tcacgaccgt ctttgtcgct gcggagaaac agtggaccat gttagaccgc     180
aagagcaaac gtcccgatat gctggtggag ccctttgtgc aagatggtgt ctctttccgc     240
cagtctttca gcatccgttc ctatgagatt ggcgccgatc gtaccgcaag cattgaaacc     300
ttaatgaata tcttccaaga aacctctttg aaccactgca agtctttagg cttattgaat     360
gacggtttcg gtcgcactcc ggagatgtgt aagcgtgatt tgatttgggt tgtcaccaag     420
atgcagattg aggttaaccg ttacccgact tggggcgaca ccatcgaggt taccacttgg     480
gtgtctgaat ccggtaagaa cggcatgtcc cgcgattggt tgatttccga ctgtcacacc     540
ggcgagatct taatccgcgc aacttccgtt tgggcgatga tgaatcagaa aactcgccgc     600
ttatctaaga tccctgacga agtgcgtcaa gaaatcgtgc cctatttcgt tgactctgcg     660
cctgttatcg aggacgaccg caaactgcat aagttggatg tgaaaactgg tgactccatt     720
cgtaatggct tgacgccacg ttggaacgac ctggacgtca accacacgt caacaacgtc      780
aagtacatcg gttggattct gaaaagcgtg cctaccgaag tgtttgttac ccaggagttg     840
tgcggcttaa ctttggaata ccgtcgcgag tgtcgtcgtg attccgtctt ggaaagcgtt     900
accgcgatgg atcctagcaa agaaggtgat cgtagcttgt accaacactt actgcgcctg     960
gagaacggtg cggacattgc attaggtcgc accgaatggc gtccgaagaa tgcaggcacc    1020
aacggtgcca tctctaccac caagacgtcc ccaggtaata gcgtgagcta ataatgatca    1080
gatccggagt ttgtaga                                                   1097
```

<210> SEQ ID NO 69
<211> LENGTH: 356
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 69

Met Ala Asn Gly Ser Ala Val Ser Leu Lys Asp Gly Ser Leu Glu Thr
1               5                   10                  15

Gln Glu Gly Thr Ser Ser Ser His Pro Pro Arg Thr Phe Ile Asn
                20                  25                  30

Gln Leu Pro Asp Trp Ser Met Leu Leu Ser Ala Ile Thr Thr Val Phe
        35                  40                  45

Val Ala Ala Glu Lys Gln Trp Thr Met Leu Asp Arg Lys Ser Lys Arg
    50                  55                  60

Pro Asp Met Leu Val Glu Pro Phe Val Gln Asp Gly Val Ser Phe Arg
65                  70                  75                  80

Gln Ser Phe Ser Ile Arg Ser Tyr Glu Ile Gly Ala Asp Arg Thr Ala
                85                  90                  95

Ser Ile Glu Thr Leu Met Asn Ile Phe Gln Glu Thr Ser Leu Asn His
                100                 105                 110

Cys Lys Ser Leu Gly Leu Leu Asn Asp Gly Phe Gly Arg Thr Pro Glu

|     |     |     |     | 115 |     |     |     | 120 |     |     |     | 125 |     |     |
| --- | --- | --- | --- | --- | --- | --- | --- | --- | --- | --- | --- | --- | --- | --- |

Met Cys Lys Arg Asp Leu Ile Trp Val Val Thr Lys Met Gln Ile Glu
130                     135                     140

Val Asn Arg Tyr Pro Thr Trp Gly Asp Thr Ile Glu Val Thr Thr Trp
145                 150                     155                 160

Val Ser Glu Ser Gly Lys Asn Gly Met Ser Arg Asp Trp Leu Ile Ser
                165                     170                     175

Asp Cys His Thr Gly Glu Ile Leu Ile Arg Ala Thr Ser Val Trp Ala
            180                     185                     190

Met Met Asn Gln Lys Thr Arg Arg Leu Ser Lys Ile Pro Asp Glu Val
        195                     200                     205

Arg Gln Glu Ile Val Pro Tyr Phe Val Asp Ser Ala Pro Val Ile Glu
    210                     215                     220

Asp Asp Arg Lys Leu His Lys Leu Asp Val Lys Thr Gly Asp Ser Ile
225                     230                     235                     240

Arg Asn Gly Leu Thr Pro Arg Trp Asn Asp Leu Asp Val Asn Gln His
                245                     250                     255

Val Asn Asn Val Lys Tyr Ile Gly Trp Ile Leu Lys Ser Val Pro Thr
            260                     265                     270

Glu Val Phe Val Thr Gln Glu Leu Cys Gly Leu Thr Leu Glu Tyr Arg
        275                     280                     285

Arg Glu Cys Arg Arg Asp Ser Val Leu Glu Ser Val Thr Ala Met Asp
    290                     295                     300

Pro Ser Lys Glu Gly Asp Arg Ser Leu Tyr Gln His Leu Leu Arg Leu
305                     310                     315                     320

Glu Asn Gly Ala Asp Ile Ala Leu Gly Arg Thr Glu Trp Arg Pro Lys
                325                     330                     335

Asn Ala Gly Thr Asn Gly Ala Ile Ser Thr Thr Lys Thr Ser Pro Gly
            340                     345                     350

Asn Ser Val Ser
        355

<210> SEQ ID NO 70
<211> LENGTH: 2546
<212> TYPE: DNA
<213> ORGANISM: Cuphea leptodpoda

<400> SEQUENCE: 70
gcagcaagtt ctgcatgctt cccccctgcca tccccggaca gcacctctag gccgggaaag    60
ctcggaaatg ggtcatcgag cttgagcccc ctcaagccca aatttgtcgc caatgccggg   120
ttgaaggtta aggcaaacgc cactgcccct cctaagatca atggttcctc ggtcggtcta   180
aaatccggca gtctcaagac tcaggaagac actccttcgg cgcctcctcc gcggactttt   240
atcaaccagt tgcctgattg gagtatgctt cttgctgcaa tcactactgt cttcctggca   300
gcagagaagc agtggatgat gcttgattgg aaacctaaga ggcctgacat gcttgtcgac   360
ccgttcggat tgggaagtat tgtccagaat gggcttgtgt tcaggcagaa cttttcgatt   420
aggtcctatg aaataggcgc tgatcgcact gcatctatag agacggtgat gaaccacttg   480
caggtactgg tgcatcctgc atttaaactt ttgaatacat gaaatgctta tgtccagtaa   540
ccgagccata tttgactatg cttactaaa ttaaatggtg aatttgagaa agaagggccg   600
tgctgccttc ctctcttatt gtcatgagtt gattcaatat aggttaccct cgtgtcagat   660
tttaacttat atgctttggc ttcttatggt gagatttgtc atgtcgagtc aatggaagga   720

```
tcatctgctc aactatatta ttattgaatt taggcatgat gaacttttac gttgaactta      780
gtttcttctg tgatagaaaa cccaggaagg aaagcttcct cttgcccttt aatctaaaaa      840
aaaaaaaaac taaaggaact ctcatttcaa ttgaaaactg gattagtttt ctgatatgta      900
tgtaaggatt aaacatttgc attagtttgc tgataatttt ggttgaattc attgtctttg      960
ttatgtgctt ttttttttct tttacaggaa acggctctca atcatgttaa gagtgctgga     1020
cttcttaatg acggctttgg tcgtactcct gagatgtata aaagggacct tatttgggtt     1080
gtcgcgaaaa tgcaggtcat ggttaaccgc tatcctactt ggtaagtttg tcactagctt     1140
tttactttac ggtacttaga ggcttcttac aattttgtgt caatgtagct gtaatgtata     1200
tcacattgta ttgagtgctc attgttacat tccttgtgat atggtgtttc atttcaacac     1260
cgatgactac aaatctcctt tatgttgtgg aacctaaggg cctgtctgtg atctatattt     1320
aggggtgaca cggttgaagt gaatacttgg gttgccaagt cagggaaaaa tggtatgcgt     1380
cgtgattggc tcataagtga ttgcaatact ggagaaattc ttactagagc ttcaaggtat     1440
gatgtactgt tttgtagttt atgttcctgt actttctggt tgtcaaattt gagagcattc     1500
aatcagggga ttttaaggtg aaagtcgaat gaagttaccc ttacattatt gcagcgtgtg     1560
ggtcatgatg aatcaaaaga caagaagact gtcaaaaatt ccagatgagg ttcgacatga     1620
gatagagcct cattttgtgg actctgctcc cgtcattgaa gacgatgacc ggaaacttcc     1680
caagctggat gagaatactg ctgactccat ccgcaagggt ctaactgtaa ggccatattt     1740
tacactttaa cagtggcttg cattgctata taaaaaatca tgcttcttag atgattttcc     1800
tctttgcaat ttgtagccga agtggaacga cttggatgtc aatcagcatg tcaacaacgt     1860
gaagtacatc gggtggattc ttgaggtaag ttttttaacct gttagttgag tatgtgtgta     1920
tcttaataag atatatgaac ttagatattg acccaagtaa ctgctagccc tcgagaatta     1980
ctcatatttc cctgaagtcc acttacagtt attatattgc taaactaaat atgctgtttt     2040
cgacataaac aatgtgccaa tgttcgttgc agagtactcc acaagaagtt ctggagaccc     2100
aggagttatg ttcccttacc ctggagtaca ggcgggaatg cggaagggag agcgtgctag     2160
agtccctcac tgctgtggac ccctctgaaa agggctttgg gtcccagttc aacaccttc     2220 tgaggcttga ggatggaggt gagatcgtga aggggagaac tgagtggcga cccaagactg     2280
caggtatcaa tggcgcgata gcatccaggg agacctcacc tggagacttt tagaagggag     2340
ccctggtccc tttggagttc tgctttcttt attgtcggat gagctgagtg aacatggcag     2400
gtaaggttgc agcaatcagt agattgtgta gtttgtttgc tgttttcac tttggctctc      2460 ttgtataata tcatggtctt ctttgtatcc tcgcatattt cggtttgata accagcccgg     2520
gccgtcgacc acgcgtgccc tatagt                                           2546
```

<210> SEQ ID NO 71
<211> LENGTH: 410
<212> TYPE: PRT
<213> ORGANISM: Cuphea leptodpoda

<400> SEQUENCE: 71

Ala Ala Ser Ser Ala Cys Phe Pro Leu Pro Ser Pro Asp Ser Thr Ser
1               5                   10                  15

Arg Pro Gly Lys Leu Gly Asn Gly Ser Ser Ser Leu Ser Pro Leu Lys
            20                  25                  30

Pro Lys Phe Val Ala Asn Ala Gly Leu Lys Val Lys Ala Asn Ala Thr
        35                  40                  45

Ala Pro Pro Lys Ile Asn Gly Ser Ser Val Gly Leu Lys Ser Gly Ser
50                  55                      60

Leu Lys Thr Gln Glu Asp Thr Pro Ser Ala Pro Pro Arg Thr Phe
65              70                  75                  80

Ile Asn Gln Leu Pro Asp Trp Ser Met Leu Leu Ala Ala Ile Thr Thr
                85                  90                  95

Val Phe Leu Ala Ala Glu Lys Gln Trp Met Met Leu Asp Trp Lys Pro
            100                 105                 110

Lys Arg Pro Asp Met Leu Val Asp Pro Phe Gly Leu Gly Ser Ile Val
            115                 120                 125

Gln Asn Gly Leu Val Phe Arg Gln Asn Phe Ser Ile Arg Ser Tyr Glu
130                 135                 140

Ile Gly Ala Asp Arg Thr Ala Ser Ile Glu Thr Val Met Asn His Leu
145                 150                 155                 160

Gln Glu Thr Ala Leu Asn His Val Lys Ser Ala Gly Leu Leu Asn Asp
                165                 170                 175

Gly Phe Gly Arg Thr Pro Glu Met Tyr Lys Arg Asp Leu Ile Trp Val
            180                 185                 190

Val Ala Lys Met Gln Val Met Val Asn Arg Tyr Pro Thr Trp Gly Asp
            195                 200                 205

Thr Val Glu Val Asn Thr Trp Val Ala Lys Ser Gly Lys Asn Gly Met
210                 215                 220

Arg Arg Asp Trp Leu Ile Ser Asp Cys Asn Thr Gly Glu Ile Leu Thr
225                 230                 235                 240

Arg Ala Ser Ser Val Trp Val Met Met Asn Gln Lys Thr Arg Arg Leu
                245                 250                 255

Ser Lys Ile Pro Asp Glu Val Arg His Glu Ile Glu Pro His Phe Val
            260                 265                 270

Asp Ser Ala Pro Val Ile Glu Asp Asp Arg Lys Leu Pro Lys Leu
            275                 280                 285

Asp Glu Asn Thr Ala Asp Ser Ile Arg Lys Gly Leu Thr Pro Lys Trp
290                 295                 300

Asn Asp Leu Asp Val Asn Gln His Val Asn Asn Val Lys Tyr Ile Gly
305                 310                 315                 320

Trp Ile Leu Glu Ser Thr Pro Gln Glu Val Leu Glu Thr Gln Glu Leu
                325                 330                 335

Cys Ser Leu Thr Leu Glu Tyr Arg Arg Glu Cys Gly Arg Glu Ser Val
            340                 345                 350

Leu Glu Ser Leu Thr Ala Val Asp Pro Ser Lys Gly Phe Gly Ser
            355                 360                 365

Gln Phe Gln His Leu Leu Arg Leu Glu Asp Gly Gly Glu Ile Val Lys
370                 375                 380

Gly Arg Thr Glu Trp Arg Pro Lys Thr Ala Gly Ile Asn Gly Ala Ile
385                 390                 395                 400

Ala Ser Arg Glu Thr Ser Pro Gly Asp Phe
                405                 410

<210> SEQ ID NO 72
<211> LENGTH: 2469
<212> TYPE: DNA
<213> ORGANISM: Cuphea leptodpoda

<400> SEQUENCE: 72
gcagcaagtt cagcatgctt cccttctcca gccccgggat cctcccctaa acccggcaag    60

```
tccggcaatt ggccatcgag cttgagccct tctttcaagc ccaagtcaat ccccaatggc    120
ggttttcatg ttaaggcaaa tgccagtgcc catcctaagg ctaacggttc tgcagtaaat    180
ctaaaatctg gcagcctcaa cactcaggag gacagttcgt cgtccccttc tcctcgggct    240
ttccttaacc agttgcctga ttggagtgtg cttctgactg caatcacgac cgtcttcgtg    300
gcggcagaga agcagtggac aatgcttgat cggaaatcta agaggcctga cgtgctcgtg    360
gactcagttg ggttgaagag tattgttcgg gatgggctcg tgtccagaca gagttttccg    420
attagatctt atgaaatagg cgctgatcga acagcctcta tagagacgct gatgaaccac    480
ttgcaggtac tgctttgaaa ctattcattc atcgcatatg gtagtgatca gtaaatgagc    540
catgactaga tgatgacata gataacaccg attgctggta taacgagcta attgtgtcca    600
tccatcccag ggtgagattt gtggattgat tcatgaaagg gccatcagct gtaaattttc    660
gattacattt acgtatgatg aaagttaaaa tactctcatt cgatcgagaa gtgacaaagc    720
attctgatga gaagtatttc atctaaaatg cttgcattag atttgcttat attttctcgt    780
taactcgatt atctttgtct ttttttttt ttttttctc caaacaggaa acatctatca    840
atcattgtaa gagtctgggt cttctcaatg acggctttgg tcgtactcct gggatgtgta    900
aaaacgacct catttgggtg cttacgaaaa tgcagatcat ggtgaatcgc tacccagctt    960
ggtaagtttg tcactggttg gtttggtttg tcttttggtc cataagtgcc ttttacaata   1020
atagttgtaa acatagtaga atgtaactgt atgtgatctt ttatggtagg ggcgatactg   1080
ttgagatcaa tacctggttc tctcagtcgg ggaaaatcgg tatgggtagt gattggctaa   1140
taagtgattg caacacagga gaaattctta taagagcaac gaggtatgat ttgctggttt   1200
tgagttttca ttctcaaaaa ccttctgatg ctcgatccgt gagcagacat ttggcatgtt   1260
ttatatgtaa aatggagtca tgtcactctc atatgatcgc agcgtgtggg ccatgatgaa   1320
tcaaaagacg agaagattct caagacttcc atacgaggtt cgccaggagt taacgcctca   1380
ttttgtggac tctcctcatg tcattgaaga caatgatcgg aaattgcata agttgatgt   1440 gaagactggt gattcgattc gcaagggtct aactgtaagt ccctatcttt cactatgata   1500
ttaggcgttt ttatgaaata tcatgtctcc gagatgttct ttcacttcgt ggtttgtagc   1560
cgaggtggaa tgacttggat gtcaatcagc atgtaagcaa cgtgaagtac attgggtgga   1620
ttctcgaggt acccttttcg tcgcacaaac aacttatata tttttgggtt aatgatgata   1680
agatcaataa acttagatac tgaatgcaag tctgctagct agcacatgag atattactta   1740
aatatcgtgg attagtattg cccctagttt ttcaaaactt aatttacgat gccgctttac   1800
agatcttcga tctaaccgaa ttattgttgc agagtatgcc aatagaagtt ttggagaccc   1860
aggagctatg ctctctcacc gttgaatata ggcgggaatg tggaatggac agtgtgctgg   1920
agtccgtgac tgctatggat ccctcagaag atggaggccg gtctcagtac aatcaccttc   1980
tgcggcttga ggatgggact gatgtcgtga agggcagaac tgagtggcga ccgaagaatg   2040
caggaacaaa cggggcgata tcaacaacaa agacttcaaa tggaaactcg gtctcttaga   2100
agagtgcatt tcttttctct ttctcatttt ctggtttgct gaaagaagag cacttggttg   2160
caatcagtaa attgtgtagt tcgtttgttc cctttgcttc gctcctttgt ataataacat   2220
ggtcagtcgt ctttgtatca tctcacgttt tcagttgatt tacgccatat tctatctcga   2280
aactagtagt tgtccaaaat gcatgtatat gcctttgaag atcacactgc agtccgccaa   2340
atagagattt tcaaatattt cccaaaacca agagctttac catttaatgg tgttcccaca   2400
tgaacttgta tgttgcatcc tcggcaactc caacagccag cctggacgac ccatcaaaca   2460
``` aacagataa					2469

<210> SEQ ID NO 73
<211> LENGTH: 413
<212> TYPE: PRT
<213> ORGANISM: Cuphea leptodpoda

<400> SEQUENCE: 73

```
Ala Ala Ser Ser Ala Cys Phe Pro Ser Pro Ala Pro Gly Ser Ser Pro
1               5                   10                  15

Lys Pro Gly Lys Ser Gly Asn Trp Pro Ser Ser Leu Ser Pro Ser Phe
            20                  25                  30

Lys Pro Lys Ser Ile Pro Asn Gly Gly Phe His Val Lys Ala Asn Ala
        35                  40                  45

Ser Ala His Pro Lys Ala Asn Gly Ser Ala Val Asn Leu Lys Ser Gly
    50                  55                  60

Ser Leu Asn Thr Gln Glu Asp Ser Ser Ser Pro Ser Pro Arg Ala
65                  70                  75                  80

Phe Leu Asn Gln Leu Pro Asp Trp Ser Val Leu Leu Thr Ala Ile Thr
                85                  90                  95

Thr Val Phe Val Ala Ala Glu Lys Gln Trp Thr Met Leu Asp Arg Lys
                100                 105                 110

Ser Lys Arg Pro Asp Val Leu Val Asp Ser Val Gly Leu Lys Ser Ile
            115                 120                 125

Val Arg Asp Gly Leu Val Ser Arg Gln Ser Phe Ser Ile Arg Ser Tyr
130                 135                 140

Glu Ile Gly Ala Asp Arg Thr Ala Ser Ile Glu Thr Leu Met Asn His
145                 150                 155                 160

Leu Gln Glu Thr Ser Ile Asn His Cys Lys Ser Leu Gly Leu Leu Asn
                165                 170                 175

Asp Gly Phe Gly Arg Thr Pro Gly Met Cys Lys Asn Asp Leu Ile Trp
            180                 185                 190

Val Leu Thr Lys Met Gln Ile Met Val Asn Arg Tyr Pro Ala Trp Gly
        195                 200                 205

Asp Thr Val Glu Ile Asn Thr Trp Phe Ser Gln Ser Gly Lys Ile Gly
    210                 215                 220

Met Gly Ser Asp Trp Leu Ile Ser Asp Cys Asn Thr Gly Glu Ile Leu
225                 230                 235                 240

Ile Arg Ala Thr Ser Val Trp Ala Met Met Asn Gln Lys Thr Arg Arg
                245                 250                 255

Phe Ser Arg Leu Pro Tyr Glu Val Arg Gln Glu Leu Thr Pro His Phe
            260                 265                 270

Val Asp Ser Pro His Val Ile Glu Asp Asn Asp Arg Lys Leu His Lys
        275                 280                 285

Phe Asp Val Lys Thr Gly Asp Ser Ile Arg Lys Gly Leu Thr Pro Arg
    290                 295                 300

Trp Asn Asp Leu Asp Val Asn Gln His Val Ser Asn Val Lys Tyr Ile
305                 310                 315                 320

Gly Trp Ile Leu Glu Ser Met Pro Ile Glu Val Leu Glu Thr Gln Glu
                325                 330                 335

Leu Cys Ser Leu Thr Val Glu Tyr Arg Arg Glu Cys Gly Met Asp Ser
            340                 345                 350

Val Leu Glu Ser Val Thr Ala Met Asp Pro Ser Glu Asp Gly Gly Arg
        355                 360                 365
```

```
Ser Gln Tyr Asn His Leu Leu Arg Leu Glu Asp Gly Thr Asp Val Val
        370                 375                 380

Lys Gly Arg Thr Glu Trp Arg Pro Lys Asn Ala Gly Thr Asn Gly Ala
385                 390                 395                 400

Ile Ser Thr Thr Lys Thr Ser Asn Gly Asn Ser Val Ser
                405                 410

<210> SEQ ID NO 74
<211> LENGTH: 1089
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
atggcaaacg gctccgccgt taatctgaaa tccggttctt tgaacaccca ggaggatagc     60
tctagctctc cgagccctcg cgcgttttg aaccaactgc ccgactggag cgtcctgtta    120
accgcaatta ccactgtctt tgttgcggcc gagaaacaat ggacgatgtt ggatcgcaag    180
agcaaacgcc cagacgtgtt agtcgattcc gtgggcttga agtccattgt gcgcgacggc    240
ttagttagcc gccagtcctt ctccatccgt tcttatgaga ttggtgcaga ccgcactgca    300
tccattgaaa ccttgatgaa tcatctgcaa gaaacttcca tcaaccactg caaatcctta    360
ggtttgttga atgatggttt tggtcgtacc ccaggtatgt gcaagaatga tctgatctgg    420
gtcttaacca aaatgcagat tatggttaac cgttacccg cttggggcga cactgttgag    480
attaacacct ggttctctca gtccggtaag attggcatgg gctctgactg gctgatctct    540
gattgtaata cgggtgaaat tctgattcgc gcaacctctg tctgggctat gatgaaccaa    600
aagactcgcc gttttagccg tttaccctat gaagtgcgcc aggagttgac ccctcacttc    660
gttgactccc ctcacgtgat cgaagataac gatcgcaaac tgcataagtt cgacgtgaaa    720
accggtgata gcatccgcaa gggcttgacg cctcgttgga cgacttgga tgtcaatcag    780 cacgtgagca atgtgaaata catcggctgg atcttagagt ctatgccgat tgaggtttta    840
gagactcaag aattgtgctc cttaaccgtt gaatatcgtc gtgagtgtgg catggacagc    900
gttttagaat ccgtcaccgc gatggatcca agcgaagatg gtggtcgtag ccagtacaat    960
catttactgc gcctggagga cggtactgac gtggtgaagg tcgtactga gtggcgtccg   1020 aagaatgcgg gcaccaacgg tgccatttct accaccaaaa cctctcccgg caattctgtt   1080
tcttaataa                                                          1089

<210> SEQ ID NO 75
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Met Ala Asn Gly Ser Ala Val Asn Leu Lys Ser Gly Ser Leu Asn Thr
1               5                   10                  15

Gln Glu Asp Ser Ser Ser Pro Ser Pro Arg Ala Phe Leu Asn Gln
            20                  25                  30

Leu Pro Asp Trp Ser Val Leu Leu Thr Ala Ile Thr Val Phe Val
        35                  40                  45
```

-continued

```
Ala Ala Glu Lys Gln Trp Thr Met Leu Asp Arg Lys Ser Lys Arg Pro
 50                  55                  60
Asp Val Leu Val Asp Ser Val Gly Leu Lys Ser Ile Val Arg Asp Gly
 65                  70                  75                  80
Leu Val Ser Arg Gln Ser Phe Ser Ile Arg Ser Tyr Glu Ile Gly Ala
                 85                  90                  95
Asp Arg Thr Ala Ser Ile Glu Thr Leu Met Asn His Leu Gln Glu Thr
            100                 105                 110
Ser Ile Asn His Cys Lys Ser Leu Gly Leu Leu Asn Asp Gly Phe Gly
        115                 120                 125
Arg Thr Pro Gly Met Cys Lys Asn Asp Leu Ile Trp Val Leu Thr Lys
    130                 135                 140
Met Gln Ile Met Val Asn Arg Tyr Pro Ala Trp Gly Asp Thr Val Glu
145                 150                 155                 160
Ile Asn Thr Trp Phe Ser Gln Ser Gly Lys Ile Gly Met Gly Ser Asp
                165                 170                 175
Trp Leu Ile Ser Asp Cys Asn Thr Gly Glu Ile Leu Ile Arg Ala Thr
            180                 185                 190
Ser Val Trp Ala Met Met Asn Gln Lys Thr Arg Arg Phe Ser Arg Leu
        195                 200                 205
Pro Tyr Glu Val Arg Gln Glu Leu Thr Pro His Phe Val Asp Ser Pro
    210                 215                 220
His Val Ile Glu Asp Asn Asp Arg Lys Leu His Lys Phe Asp Val Lys
225                 230                 235                 240
Thr Gly Asp Ser Ile Arg Lys Gly Leu Thr Pro Arg Trp Asn Asp Leu
                245                 250                 255
Asp Val Asn Gln His Val Ser Asn Val Lys Tyr Ile Gly Trp Ile Leu
            260                 265                 270
Glu Ser Met Pro Ile Glu Val Leu Glu Thr Gln Glu Leu Cys Ser Leu
        275                 280                 285
Thr Val Glu Tyr Arg Arg Glu Cys Gly Met Asp Ser Val Leu Glu Ser
    290                 295                 300
Val Thr Ala Met Asp Pro Ser Glu Asp Gly Gly Arg Ser Gln Tyr Asn
305                 310                 315                 320
His Leu Leu Arg Leu Glu Asp Gly Thr Asp Val Val Lys Gly Arg Thr
                325                 330                 335
Glu Trp Arg Pro Lys Asn Ala Gly Thr Asn Gly Ala Ile Ser Thr Thr
            340                 345                 350
Lys Thr Ser Pro Gly Asn Ser Val Ser
        355                 360
```

<210> SEQ ID NO 76
<211> LENGTH: 2738
<212> TYPE: DNA
<213> ORGANISM: Cuphea leptodpoda

<400> SEQUENCE: 76

```
gcagcaagtt cagcatgctt ccccctgcca tccccggaca gcacctctag gccgggaaag    60
ctcggaaatg ggtcatcgag cttgagcccc ctcaagccca aatttgtcgc caatgccggg   120
ttgaaggtta aggcaaacgc cactgcccct cctaagatca atggttcctc ggtcggtcta   180
aaatccggca gtctcaagac tcaggaagac actccttcgg cgcctcctcc gcggactttt   240
atcaaccagt tgcctgattg gagtatgctt cttgctgcaa tcactactgt cttcctggca   300
gcagagaagc agtggatgat gcttgattgg aaacctaaga ggcctgacat gcttgtcgac   360
```

```
ccgttcggat tgggaagtat tgtccagaat gggcttgtgt tcaggcagaa ttttcgatt      420 aggtcctatg aaataggcgc tgatcgcact gcatctatag agacggtgat gaaccacttg     480
caggtactgg tgcatcctgc atttaaactt ttgaatacat gaaatgctta tgtccagtaa     540
ccgagccata tttgactatg gcttactaaa ttaaatggtg aatttgagaa agaagggccg     600
tgctgccttc ctctcttatt gtcatgagtt gattcaatat aggtttacct cgtgtcagat     660
tttaacttat atgcactcat ttcatgatcg ctttggcttc ttatggtgag atttgtcatg     720
tcgagtcaat ggaaggatca tctgctcaac tatattatta ttgaatttag gcatgatgaa     780
cttttacgtt gaacttagtt tcttctgtga tagaaaaccc aggaaggaaa gcttcctctt     840 gcccttttaat ctaaaaaaaa aaaaaaacta aggaactct catttcaatt gaaaactgga     900
ttagttttct gatatgtatg taaggattaa acatttgcat tagtttgctg ataattttgg     960
ttgaattcat tgtctttgtt atgtgctttt ttttttcttt tacaggaaac ggctctcaat    1020
catgttaaga gtgctggact tcttaatgac ggctttggtc gtactcctga gatgtataaa    1080
agggacctta tttgggttgt cgcgaaaatg caggtcatgg ttaaccgcta tcctacttgg    1140
taagtttgtc actagctttt tactttacgg tacttagagg cttcttacaa ttttgtgtca    1200
atgtagctgt aatgtatatc acattgtatt gagtgctcat tgttacattc cttgtgatat    1260
ggtgtttcat ttcaacaccg atgactacaa atctccttta tgttgtggaa cctaagggcc    1320
tgtctgtgat ctatatttag gggtgacacg gttgaagtga atacttgggt tgccaagtca    1380
gggaaaaatg gtatgcgtcg tgattggctc ataagtgatt gcaatactgg agaaattctt    1440
actagagctt caaggtatga tgtactgttt tgtagtttat gttcctgtac tttctggttg    1500
tcaaatttga gagcattcaa tcagggggatt ttaaggtgaa agtcgaatga agttacccctt   1560 acattattgc agcgtgtggg tcatgatgaa tcaaaagaca agaagactgt caaaaattcc    1620
agatgaggtt cgacatgaga tagagcctca ttttgtggac tctgctcccg tcattgaaga    1680
cgatgaccgg aaacttccca agctggatga gaatactgct gactccatcc gcaagggtct    1740
aactgtaagg ccatattta cactttaaca gtggcttgca ttgctatata aaaaatcatg     1800
cttcttagat gattttcctc tttgcaattt gtagccgaag tggaacgact tggatgtcaa    1860
tcagcatgtc aacaacgtga agtacatcgg gtggattctt gaggtaagtt tttaacctgt    1920
tagttgagta tgtgtgtatc ttaataagat atatgaactt agatattgac ccaagtaact    1980
gctagccctc gagaattact catatttccc tgaagtccac ttacagttat tatattgcta    2040
aactaaatat gctgttttcg acataaacaa tgtgccaatg ttcgttgcag agtactccac    2100
aagaagttct ggagacccag gagttatgtt cccttaccct ggagtacagg cgggaatgcg    2160
gaagggagag cgtgctagag tccctcactg ctgtggaccc ctctgaaaag ggctttgggt    2220
cccagttcca acaccttctg aggcttgagg atggaggtga gatcgtgaag gggagaactg    2280
agtggcgacc caagactgca ggtatcaatg gggcgatagc atccagggag acctcacctg    2340 gagacttta gaagggagcc ctggtccctt tggagttctg ctttctttat tgtcggatga    2400
gctgagtgaa catggcaggt aaggttgcag caatcagtag attgtgtagt ttgttgctg    2460 tttttcactt tggctctctt gtataatatc atggtcttct ttgtatcctc gcatatttcg    2520
gtttgattta cacattatat tctttctatt tgtttcaagg tgagtagcga gttgtaatta    2580 tttatccttgt cgttccattg tcgttaaatt ttcaaatgaa agtacttatg tgaactgcat   2640
cgccttctct cagaaggtat cgtaatgcat tattaacatg ttgctgtgtt gcatcacctg    2700
```
tgagtctgtg acttatctta tgcctgtgtg gtatggtg                                2738

<210> SEQ ID NO 77
<211> LENGTH: 410
<212> TYPE: PRT
<213> ORGANISM: Cuphea leptodpoda

<400> SEQUENCE: 77

```
Ala Ala Ser Ser Ala Cys Phe Pro Leu Pro Ser Pro Asp Ser Thr Ser
1               5                   10                  15

Arg Pro Gly Lys Leu Gly Asn Gly Ser Ser Leu Ser Pro Leu Lys
            20                  25                  30

Pro Lys Phe Val Ala Asn Ala Gly Leu Lys Val Lys Ala Asn Ala Thr
        35                  40                  45

Ala Pro Pro Lys Ile Asn Gly Ser Ser Val Gly Leu Lys Ser Gly Ser
    50                  55                  60

Leu Lys Thr Gln Glu Asp Thr Pro Ser Ala Pro Pro Arg Thr Phe
65                  70                  75                  80

Ile Asn Gln Leu Pro Asp Trp Ser Met Leu Ala Ala Ile Thr Thr
                85                  90                  95

Val Phe Leu Ala Ala Glu Lys Gln Trp Met Met Leu Asp Trp Lys Pro
            100                 105                 110

Lys Arg Pro Asp Met Leu Val Asp Pro Phe Gly Leu Gly Ser Ile Val
        115                 120                 125

Gln Asn Gly Leu Val Phe Arg Gln Asn Phe Ser Ile Arg Ser Tyr Glu
    130                 135                 140

Ile Gly Ala Asp Arg Thr Ala Ser Ile Glu Thr Val Met Asn His Leu
145                 150                 155                 160

Gln Glu Thr Ala Leu Asn His Val Lys Ser Ala Gly Leu Leu Asn Asp
                165                 170                 175

Gly Phe Gly Arg Thr Pro Glu Met Tyr Lys Arg Asp Leu Ile Trp Val
            180                 185                 190

Val Ala Lys Met Gln Val Met Val Asn Arg Tyr Pro Thr Trp Gly Asp
        195                 200                 205

Thr Val Glu Val Asn Thr Trp Val Ala Lys Ser Gly Lys Asn Gly Met
    210                 215                 220

Arg Arg Asp Trp Leu Ile Ser Asp Cys Asn Thr Gly Glu Ile Leu Thr
225                 230                 235                 240

Arg Ala Ser Ser Val Trp Val Met Met Asn Gln Lys Thr Arg Arg Leu
                245                 250                 255

Ser Lys Ile Pro Asp Glu Val Arg His Glu Ile Glu Pro His Phe Val
            260                 265                 270

Asp Ser Ala Pro Val Ile Glu Asp Asp Arg Lys Leu Pro Lys Leu
        275                 280                 285

Asp Glu Asn Thr Ala Asp Ser Ile Arg Lys Gly Leu Thr Pro Lys Trp
    290                 295                 300

Asn Asp Leu Asp Val Asn Gln His Val Asn Asn Val Lys Tyr Ile Gly
305                 310                 315                 320

Trp Ile Leu Glu Ser Thr Pro Gln Glu Val Leu Glu Thr Gln Glu Leu
                325                 330                 335

Cys Ser Leu Thr Leu Glu Tyr Arg Arg Glu Cys Gly Arg Glu Ser Val
            340                 345                 350

Leu Glu Ser Leu Thr Ala Val Asp Pro Ser Glu Lys Gly Phe Gly Ser
        355                 360                 365
```

```
Gln Phe Gln His Leu Leu Arg Leu Glu Asp Gly Gly Glu Ile Val Lys
    370                 375                 380

Gly Arg Thr Glu Trp Arg Pro Lys Thr Ala Gly Ile Asn Gly Ala Ile
385                 390                 395                 400

Ala Ser Arg Glu Thr Ser Pro Gly Asp Phe
                405                 410

<210> SEQ ID NO 78
<211> LENGTH: 1092
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
atgtccatgg gtatcaacgg ctccagcgtg ggcttgaagt ccggctccct gaaaacccag      60
gaagacaccc ccagcgcccc ccctccccgc acctttatta accaactccc cgactggagc     120
atgttgctcg ctgccatcac cactgtcttt ttggctgccg aaaaacagtg gatgatgttg     180
gattggaaac ctaaacggcc cgatatgttg gttgatcctt cggcttgggc tccatcgtg      240 cagaatggtc tggtctttcg gcagaacttc agcattcgca gctacgagat ggcgccgac      300 cggactgcct ccattgaaac cgtcatgaac cacctgcaag aaaccgctct caatcacgtt     360
aaaagcgccg gctcctgaa cgacggtttt ggtcggaccc ccgaaatgta taacgggac      420 ttgatctggg ttgtggctaa atgcaagtg atggtgaatc gttatccac ttggggcgat      480 actgtggaag tgaatacctg ggttgccaag tccggcaaaa atggtatgcg ccgggactgg     540
ctgattagcg attgcaacac tggtgaaatt ctgacccgcg ccagctccgt ctgggttatg     600
atgaaccaga aaactcggcg cttgagcaaa atccccgacg aagttcgtca tgaaatcgaa     660
cctcactttg tggactccgc tcccgttatt gaagatgacg accggaaact gcccaagttg     720
gacgaaaata ccgctgatag cattcggaaa ggtttgaccc ccaaatggaa tgatctggat     780
gttaaccagc acgttaacaa tgtgaagtac atcggttgga tcttggagtc cactccccag     840
gaagttctgg agacccagga actgtgtagc ttgactttgg agtaccgccg ggagtgtggc     900
cgggagtccg ttttggagtc cctgaccgct gtcgatccca gcgaaaaggg ttttggtagc     960
caatttcaac atttgctgcg tctggaagac ggtggcgaaa tcgtgaaggg tcgtaccgag    1020
tggcgcccca agaccgccgg tattaacggt gccattgcct cccgtgaaac ctccccccggt    1080 gatttctaat aa                                                        1092

<210> SEQ ID NO 79
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Gly Ile Asn Gly Ser Ser Val Gly Leu Lys Ser Gly Ser Leu Lys
1               5                   10                  15

Thr Gln Glu Asp Thr Pro Ser Ala Pro Pro Arg Thr Phe Ile Asn
            20                  25                  30

Gln Leu Pro Asp Trp Ser Met Leu Leu Ala Ala Ile Thr Thr Val Phe
        35                  40                  45

Leu Ala Ala Glu Lys Gln Trp Met Met Leu Asp Trp Lys Pro Lys Arg
```

```
                50              55              60
Pro Asp Met Leu Val Asp Pro Phe Gly Leu Gly Ser Ile Val Gln Asn
 65                  70                  75                  80

Gly Leu Val Phe Arg Gln Asn Phe Ser Ile Arg Ser Tyr Glu Ile Gly
                 85                  90                  95

Ala Asp Arg Thr Ala Ser Ile Glu Thr Val Met Asn His Leu Gln Glu
            100                 105                 110

Thr Ala Leu Asn His Val Lys Ser Ala Gly Leu Leu Asn Asp Gly Phe
        115                 120                 125

Gly Arg Thr Pro Glu Met Tyr Lys Arg Asp Leu Ile Trp Val Val Ala
    130                 135                 140

Lys Met Gln Val Met Asn Arg Tyr Pro Thr Trp Gly Asp Thr Val
145                 150                 155                 160

Glu Val Asn Thr Trp Val Ala Lys Ser Gly Lys Asn Gly Met Arg Arg
                165                 170                 175

Asp Trp Leu Ile Ser Asp Cys Asn Thr Gly Glu Ile Leu Thr Arg Ala
            180                 185                 190

Ser Ser Val Trp Val Met Met Asn Gln Lys Thr Arg Arg Leu Ser Lys
        195                 200                 205

Ile Pro Asp Glu Val Arg His Glu Ile Glu Pro His Phe Val Asp Ser
    210                 215                 220

Ala Pro Val Ile Glu Asp Asp Arg Lys Leu Pro Lys Leu Asp Glu
225                 230                 235                 240

Asn Thr Ala Asp Ser Ile Arg Lys Gly Leu Thr Pro Lys Trp Asn Asp
                245                 250                 255

Leu Asp Val Asn Gln His Val Asn Asn Val Lys Tyr Ile Gly Trp Ile
            260                 265                 270

Leu Glu Ser Thr Pro Gln Glu Val Leu Glu Thr Gln Glu Leu Cys Ser
        275                 280                 285

Leu Thr Leu Glu Tyr Arg Arg Glu Cys Gly Arg Glu Ser Val Leu Glu
    290                 295                 300

Ser Leu Thr Ala Val Asp Pro Ser Glu Lys Gly Phe Gly Ser Gln Phe
305                 310                 315                 320

Gln His Leu Leu Arg Leu Glu Asp Gly Gly Glu Ile Val Lys Gly Arg
                325                 330                 335

Thr Glu Trp Arg Pro Lys Thr Gly Ile Asn Gly Ala Ile Ala Ser
            340                 345                 350

Arg Glu Thr Ser Pro Gly Asp Phe
        355                 360

<210> SEQ ID NO 80
<211> LENGTH: 2678
<212> TYPE: DNA
<213> ORGANISM: Cuphea leptodpoda

<400> SEQUENCE: 80
gcagcaagtt ccgcatgctt cccttctcca gccccgggat cctcccctaa acccggcaag      60
tccggcaatt ggccatcgag cttgagccct tctttcaagc ccaagtcaat ccccaatggc     120
ggttttcatg ttaaggcaaa tgccagtgcc catcctaagg ctaacggttc tgcagtaaat     180
ctaaaatctg gcagcctcaa cactcaggag gacagttcgt cgtccccttc tcctcgggct     240
ttccttaacc agttgcctga ttggagtgtg cttctgactg caatcacgac cgtcttcgtg     300
gcggcagaga agcagtggac aatgcttgat cggaaatcta agaggcctga cgtgctcgtg     360
```

```
gactcagttg ggttgaagag tattgttcgg gatgggctcg tgtccagaca gagttttcg      420
attagatctt atgaaatagg cgctgatcga acagcctcta tagagacgct gatgaaccac    480
ttgcaggtac tgctttgaaa ctattcattc atcgcatatg gtagtgatca gtaaatgagc    540
catgactaga tgatgacata gataacaccg attgctggta taacgagcta attgtgtcca    600
tccatcccag ggtgagattt gtggattgat tcatgaaagg gccatcagct gtaaattttc    660
gattacattt acgtatgatg aaagttaaaa tactctcatt cgatcgagaa gtgacaaagc    720
attctgatga gaagtatttc atctaaaatg cttgcattag atttgcttat attttctcgt    780
taactcgatt atctttgtct tttttttttt tttttttcc  aaacaggaaa catctatcaa    840
tcattgtaag agtctgggtc ttctcaatga cggctttggt cgtactcctg ggatgtgtaa    900
aaacgacctc atttgggtgc ttacgaaaat gcagatcatg gtgaatcgct acccagcttg    960
gtaagtttgt cactggttgg tttggtttgt cttttggtcc ataagtgcct tttacaataa   1020
tagttgtaaa catagtagaa tgtaactgta tgtgatcttt tatggtaggg gcgatactgt   1080
tgagatcaat acctggttct ctcagtcggg gaaaatcggt atgggtagtg attggctaat   1140
aagtgattgc aacacaggag aaattcttat aagagcaacg aggtatgatt tgctggtttt   1200
gagttttcat tctcaaaaac cttctgatgc tcgatccgtg agcagacatt tggcatgttt   1260
tatatgtaaa atggagtcat gtcactctca tatcatcgca gcgtgtgggc catgatgaat   1320
caaaagacga gaagattctc aagacttcca tacgaggttc gccaggagtt aacgcctcat   1380
tttgtggact ctcctcatgt cattgaagac aatgatcgga aattgcataa gtttgatgtg   1440
aagactggtg attcgattcg caagggtcta actgtaagtc cctatctttc actatgatat   1500
taggcgtttt tatgaaatat catgtctccg agatgttctt tcacttcgtg gtttgtagcc   1560
gaggtggaat gacttggatg tcaatcagca tgtaagcaac gtgaagtaca ttgggtggat   1620
tctcgaggta cccttttcgt cgcacaaaca acttatatat ttttgggtta atgatgataa   1680
gatcaataaa cttagatact gaatgcaagt ctgctagcta gcacatgaga tattacttaa   1740
atatcgtgga ttagtattgc ccctagtttt tcaaagctta atttacgatg ccgctttaca   1800
gatcttcgat ctaaccgaat tattgttgca gagtatgcca atagaagttt tggagaccca   1860
ggagctatgc tctctcaccg ttgaatatag gcgggaatgt ggaatggaca gtgtgctgga   1920
gtccgtgact gctatggatc cctcagaaga tggaggccgg tctcagtaca atcaccttct   1980
gcggcttgag gatgggactg atgtcgtgaa gggcagaact gagtggcgac cgaagaatgc   2040
aggaacaaac ggggcgatat caacaacaaa gacttcaaat ggaaactcgg tctcttagaa   2100
gagtgcattt ctttttctctt tctcattttc tggtttgctg aaagaagagc acttggttgc   2160
aatcagtaaa ttgtgtagtt cgttgttcc  ctttgcttcg ctcctttgta taataacatg   2220
gtcagtcgtc tttgtatcat ctcacgtttt cagttgattt acgccatatt ctatctcgaa   2280
actagtactt gtccaaaatg catgtatatg cctttgaaga tcacactgca gtccgccaaa   2340
tagagatttt caaatatttc ccaaaaccaa gagctttacc atttaatggt gttcccacat   2400
gaacttgtat gttgcatcct cggcaactcc aacagccagc ctggacgacc catcaaacaa   2460
acagataagg agacggacag accagagcag aactggggaa caagaaaaga acaacagcca   2520
tgtggggacg gcctcaatga tacaaacaac aaagccacct ccttttgtct tcccccaccc   2580
aaataccaaa tgggttatga atgagaagag ctgctgtgaa tgatgagaac ttgagaaaca   2640
agagctgtct cttctgtttg ttttgtcttt cttcctgc                           2678
```

```
<210> SEQ ID NO 81
<211> LENGTH: 413
<212> TYPE: PRT
<213> ORGANISM: Cuphea leptodpoda

<400> SEQUENCE: 81
```

| | | | | | | | | | | | | | | | |
|---|---|---|---|---|---|---|---|---|---|---|---|---|---|---|---|
| Ala | Ala | Ser | Ser | Ala | Cys | Phe | Pro | Ser | Pro | Ala | Pro | Gly | Ser | Ser | Pro |
| 1 | | | | 5 | | | | | 10 | | | | | 15 | |
| Lys | Pro | Gly | Lys | Ser | Gly | Asn | Trp | Pro | Ser | Ser | Leu | Ser | Pro | Ser | Phe |
| | | | 20 | | | | | 25 | | | | | 30 | | |
| Lys | Pro | Lys | Ser | Ile | Pro | Asn | Gly | Gly | Phe | His | Val | Lys | Ala | Asn | Ala |
| | | | | 35 | | | | | 40 | | | | | 45 | |
| Ser | Ala | His | Pro | Lys | Ala | Asn | Gly | Ser | Ala | Val | Asn | Leu | Lys | Ser | Gly |
| | 50 | | | | | 55 | | | | | 60 | | | | |
| Ser | Leu | Asn | Thr | Gln | Glu | Asp | Ser | Ser | Ser | Pro | Ser | Pro | Arg | Ala |
| 65 | | | | | 70 | | | | | 75 | | | | | 80 |
| Phe | Leu | Asn | Gln | Leu | Pro | Asp | Trp | Ser | Val | Leu | Leu | Thr | Ala | Ile | Thr |
| | | | | 85 | | | | | 90 | | | | | 95 | |
| Thr | Val | Phe | Val | Ala | Ala | Glu | Lys | Gln | Trp | Thr | Met | Leu | Asp | Arg | Lys |
| | | | 100 | | | | | 105 | | | | | 110 | | |
| Ser | Lys | Arg | Pro | Asp | Val | Leu | Val | Asp | Ser | Val | Gly | Leu | Lys | Ser | Ile |
| | | | 115 | | | | | 120 | | | | | 125 | | |
| Val | Arg | Asp | Gly | Leu | Val | Ser | Arg | Gln | Ser | Phe | Ser | Ile | Arg | Ser | Tyr |
| | 130 | | | | | 135 | | | | | 140 | | | | |
| Glu | Ile | Gly | Ala | Asp | Arg | Thr | Ala | Ser | Ile | Glu | Thr | Leu | Met | Asn | His |
| 145 | | | | | 150 | | | | | 155 | | | | | 160 |
| Leu | Gln | Glu | Thr | Ser | Ile | Asn | His | Cys | Lys | Ser | Leu | Gly | Leu | Leu | Asn |
| | | | | 165 | | | | | 170 | | | | | 175 | |
| Asp | Gly | Phe | Gly | Arg | Thr | Pro | Gly | Met | Cys | Lys | Asn | Asp | Leu | Ile | Trp |
| | | | 180 | | | | | 185 | | | | | 190 | | |
| Val | Leu | Thr | Lys | Met | Gln | Ile | Met | Val | Asn | Arg | Tyr | Pro | Ala | Trp | Gly |
| | | | 195 | | | | | 200 | | | | | 205 | | |
| Asp | Thr | Val | Glu | Ile | Asn | Thr | Trp | Phe | Ser | Gln | Ser | Gly | Lys | Ile | Gly |
| | 210 | | | | | 215 | | | | | 220 | | | | |
| Met | Gly | Ser | Asp | Trp | Leu | Ile | Ser | Asp | Cys | Asn | Thr | Gly | Glu | Ile | Leu |
| 225 | | | | | 230 | | | | | 235 | | | | | 240 |
| Ile | Arg | Ala | Thr | Ser | Val | Trp | Ala | Met | Met | Asn | Gln | Lys | Thr | Arg | Arg |
| | | | | 245 | | | | | 250 | | | | | 255 | |
| Phe | Ser | Arg | Leu | Pro | Tyr | Glu | Val | Arg | Gln | Glu | Leu | Thr | Pro | His | Phe |
| | | | 260 | | | | | 265 | | | | | 270 | | |
| Val | Asp | Ser | Pro | His | Val | Ile | Glu | Asp | Asn | Asp | Arg | Lys | Leu | His | Lys |
| | | | 275 | | | | | 280 | | | | | 285 | | |
| Phe | Asp | Val | Lys | Thr | Gly | Asp | Ser | Ile | Arg | Lys | Gly | Leu | Thr | Pro | Arg |
| | 290 | | | | | 295 | | | | | 300 | | | | |
| Trp | Asn | Asp | Leu | Asp | Val | Asn | Gln | His | Val | Ser | Asn | Val | Lys | Tyr | Ile |
| 305 | | | | | 310 | | | | | 315 | | | | | 320 |
| Gly | Trp | Ile | Leu | Glu | Ser | Met | Pro | Ile | Glu | Val | Leu | Glu | Thr | Gln | Glu |
| | | | | 325 | | | | | 330 | | | | | 335 | |
| Leu | Cys | Ser | Leu | Thr | Val | Glu | Tyr | Arg | Arg | Glu | Cys | Gly | Met | Asp | Ser |
| | | | 340 | | | | | 345 | | | | | 350 | | |
| Val | Leu | Glu | Ser | Val | Thr | Ala | Met | Asp | Pro | Ser | Glu | Asp | Gly | Gly | Arg |
| | | | 355 | | | | | 360 | | | | | 365 | | |
| Ser | Gln | Tyr | Asn | His | Leu | Leu | Arg | Leu | Glu | Asp | Gly | Thr | Asp | Val | Val |
| | 370 | | | | | 375 | | | | | 380 | | | | |

```
Lys Gly Arg Thr Glu Trp Arg Pro Lys Asn Ala Gly Thr Asn Gly Ala
385                 390                 395                 400

Ile Ser Thr Thr Lys Thr Ser Asn Gly Asn Ser Val Ser
                405                 410
```

<210> SEQ ID NO 82
<211> LENGTH: 2246
<212> TYPE: DNA
<213> ORGANISM: Cuphea decandra

<400> SEQUENCE: 82

```
gcagcaagtt ctgcatgctt ccccgtacca tcgccggacg cctcccggaa acccggaaag    60
cacggcaatg gggcatcgag cttgagcccc ttcaagccca aatcgatccc cagtggaggt   120
ttgcaggttc aggcaaacgc cagtgcccct cctaagatta atggttcctc ggtcggtcta   180
aagtccggca gcctcaagac tcaggaagac actccttcat cccctcctcc tcggactttt   240
atcaaccagt tgcccgattg gagtatgctt ctggctgcaa tcactaccgt cttcttagcg   300
gctgagaagc agtggatgat gcttgattgg aaacctaaga ggcctgacat gcttgtggac   360
ccgttcggtt tgggaaggat tgttcaggat gggcttgtgt tcaggcagaa ttttcgatt    420
aggtcatatg aaattggcgc tgatcgcact gcatctatag acactgat gaaccacttg     480
caggtactga tgcatgttgc atttaagcta ttcgattctt gaaatgcttg attccatcaa   540
ctgagaatac ttgactatgg catacataat ataaccgtga atttgacaaa gaaaaggggt   600
gcatcgcatt cctctttcta tttgcacgag gtaatataat acagggttac ctatttcgtg   660
atgattttct cattctcagg gtgagatttg tcatgccgag tctctgaagg aatcatcagc   720
catactttt taatttaat ttacgtgatg aaagtttata tggggctctc tcagacctta     780
atctttggaa aagaaatctc attttaaata acttgtttag ttttagatga tatatacttg   840
atttcttata ttcttgcatt agtttgctta taatttagt tcaattgatt atcattgttc    900
tggtgctctt tttttttttc cttcttttca caggaaacag ctctcaatca cgtgaagagc   960
gctgggcttc tcaatgacgg ctttggtcgt actcccgaga tgtataaaag ggaccttatt  1020
tgggttgtgg caaaaatgca ggtcatggtt aatcgctatc ctacttggtg agtttgccac  1080
cagcctgtct gtctatggtc cccagaagct tcatacggtt ttatctgtca acacagctgt  1140
agtgatggtt ctgttttcat tacttttatgc tatatcacgt tgtaacgggt gctcacctt   1200
acagacctaa cgagatggtg tttctattca ctgtgacacc gataatgcaa atctccttta  1260
tcttgtgcaa cctaaatgct tgtgatctat attcaggggt gacacagttg aagtcaatac  1320
ttgggttgcc aagtcgggga aaaatggcat gcgtcgtgat tggctcataa gtgattgcaa  1380
tactggagaa attcttacta gagcatcgag gtatgatgtt ctgtctagta tttgatcttc  1440
ctgaactttc tagttgtcaa tttgtgagca ttcaagctct agatattaca gtgaaagttg  1500
agttctgtta ccctgacatt atcgcagcgt gtgggtcatg atgaatcaaa agacaagaag  1560
attgtcaaaa attccagatg aggttcgaca tgagatagag cctcattttg tggactctcc  1620
tcctgtcatt gaagatgatg atcgaaaact tcccaagctg gatgagaaaa cagctgactc  1680
catccgcaag ggtctaactg taaggcctta aactttcatt gtgatggtag gtagcatgca  1740
tttgttaatt tcatgtccct tagacgatct ttctcttcac gcttttttagc cgaggtggaa  1800
cgacttggat gtcaatcagc acgttaacaa cgtgaagtac attggatgga ttcttgaggt  1860
aattatttaa cttcttagtc gattatttac tttttataat tagatctata aacatagata  1920
ttgacccgtg taaatgctag caatcaagaa ttaattatat ttccccgagt tttctgcaga  1980
```

```
gtactccaca agaagttctg gagacccagg agttatgttc cctcaccctc gaatacagga    2040
gggagtgcgg gagggacagc gtgctggagt ccctcaccgc tgtagaccac tctggaaagg    2100
gctcagggtc aaatttccag caccttctgc ggcttgagga tggaggtgag atcgtgaagg    2160
ggagaactga gtggcgacct aagaacgcag taatcaatgg ggcagtggca cccggggaga    2220
cttcacctgg aaactctgtc tcttag                                         2246
```

```
<210> SEQ ID NO 83
<211> LENGTH: 412
<212> TYPE: PRT
<213> ORGANISM: Cuphea decandra

<400> SEQUENCE: 83

Ala Ala Ser Ser Ala Cys Phe Pro Val Pro Ser Pro Asp Ala Ser Arg
 1               5                  10                  15

Lys Pro Gly Lys His Gly Asn Gly Ala Ser Ser Leu Ser Pro Phe Lys
            20                  25                  30

Pro Lys Ser Ile Pro Ser Gly Gly Leu Gln Val Gln Ala Asn Ala Ser
        35                  40                  45

Ala Pro Pro Lys Ile Asn Gly Ser Ser Val Gly Leu Lys Ser Gly Ser
    50                  55                  60

Leu Lys Thr Gln Glu Asp Thr Pro Ser Ser Pro Pro Arg Thr Phe
65                  70                  75                  80

Ile Asn Gln Leu Pro Asp Trp Ser Met Leu Leu Ala Ala Ile Thr Thr
                85                  90                  95

Val Phe Leu Ala Ala Glu Lys Gln Trp Met Met Leu Asp Trp Lys Pro
            100                 105                 110

Lys Arg Pro Asp Met Leu Val Asp Pro Phe Gly Leu Gly Arg Ile Val
        115                 120                 125

Gln Asp Gly Leu Val Phe Arg Gln Asn Phe Ser Ile Arg Ser Tyr Glu
    130                 135                 140

Ile Gly Ala Asp Arg Thr Ala Ser Ile Glu Thr Leu Met Asn His Leu
145                 150                 155                 160

Gln Glu Thr Ala Leu Asn His Val Lys Ser Ala Gly Leu Leu Asn Asp
                165                 170                 175

Gly Phe Gly Arg Thr Pro Glu Met Tyr Lys Arg Asp Leu Ile Trp Val
            180                 185                 190

Val Ala Lys Met Gln Val Met Val Asn Arg Tyr Pro Thr Trp Gly Asp
        195                 200                 205

Thr Val Glu Val Asn Thr Trp Val Ala Lys Ser Gly Lys Asn Gly Met
    210                 215                 220

Arg Arg Asp Trp Leu Ile Ser Asp Cys Asn Thr Gly Glu Ile Leu Thr
225                 230                 235                 240

Arg Ala Ser Ser Val Trp Val Met Met Asn Gln Lys Thr Arg Arg Leu
                245                 250                 255

Ser Lys Ile Pro Asp Glu Val Arg His Glu Ile Glu Pro His Phe Val
            260                 265                 270

Asp Ser Pro Pro Val Ile Glu Asp Asp Arg Lys Leu Pro Lys Leu
        275                 280                 285

Asp Glu Lys Thr Ala Asp Ser Ile Arg Lys Gly Leu Thr Pro Arg Trp
    290                 295                 300

Asn Asp Leu Asp Val Asn Gln His Val Asn Asn Val Lys Tyr Ile Gly
305                 310                 315                 320
```

```
Trp Ile Leu Glu Ser Thr Pro Gln Glu Val Leu Glu Thr Gln Glu Leu
                325                 330                 335

Cys Ser Leu Thr Leu Glu Tyr Arg Arg Glu Cys Gly Arg Asp Ser Val
            340                 345                 350

Leu Glu Ser Leu Thr Ala Val Asp His Ser Gly Lys Gly Ser Gly Ser
        355                 360                 365

Asn Phe Gln His Leu Leu Arg Leu Glu Asp Gly Glu Ile Val Lys
    370                 375                 380

Gly Arg Thr Glu Trp Arg Pro Lys Asn Ala Val Ile Asn Gly Ala Val
385                 390                 395                 400

Ala Pro Gly Glu Thr Ser Pro Gly Asn Ser Val Ser
                405                 410
```

<210> SEQ ID NO 84
<211> LENGTH: 1092
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84

```
atgggcatta acggttccag cgtcggcctg aagtccggct ccttgaagac ccaggaagat      60
accccctcca gccctcctcc ccggactttt atcaatcagt tgcccgattg gtccatgctt     120
ctggctgcta tcaccaccgt gttcctggct gccgagaaac agtggatgat gttggactgg     180
aagcccaagc gtcccgacat gctggtggac cccttcggtt tgggccggat cgtccaggat     240
ggtttggtat ttcgccaaaa cttttccatt cgttcctatg agattggtgc cgatcggacc     300
gcttccatcg aaaccctcat gaatcacctc aagagactg ctctgaatca cgttaaaagc     360
gccggcttgt tgaatgacgg ttttggccgc actcctgaaa tgtacaaacg cgatctgatt     420
tgggttgtgg ccaagatgca ggtcatggtg aaccggtacc ctacctgggg cgacaccgtg     480
gaggtgaaca cctgggttgc caagtccggt aaaaacggca tgcgccggga ctggctgatt     540
tccgattgca ataccggtga aattctcacc cgtgcttcca gcgtttgggt tatgatgaac     600
cagaagaccc gccgtttgag caagattccc gatgaggtgc gccatgagat tgaacccat      660
ttcgtggact ccccccccgt tattgaggat gacgatcgca aactccccaa gttggacgaa     720
aagaccgctg actccatccg taagggcctg accccccgt ggaacgatct ggatgtgaac     780
caacacgtca acaatgtgaa atatattggc tggattttgg aatccacccc ccaagaagtg     840
ttggaaaccc aagagttgtg tagcttgacc ttggagtacc gccgcgaatg cggccgggat     900
tccgtgctgg aatccttgac tgccgttgat cactccggta aaggttccgg ttccaacttt     960
cagcatctgt tgcgcttgga ggatggtggc gagattgtga aggtcggac cgaatggcgc    1020
cccaaaaatg ccgtgattaa tggcgccgtg gccccccggcg aaacttcccc tggcaattcc    1080
gtgtcctaat aa                                                         1092
```

<210> SEQ ID NO 85
<211> LENGTH: 362
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Met Gly Ile Asn Gly Ser Ser Val Gly Leu Lys Ser Gly Ser Leu Lys

```
  1               5                   10                  15
Thr Gln Glu Asp Thr Pro Ser Ser Pro Pro Arg Thr Phe Ile Asn
                20                  25                  30
Gln Leu Pro Asp Trp Ser Met Leu Leu Ala Ile Thr Thr Val Phe
                35                  40                  45
Leu Ala Ala Glu Lys Gln Trp Met Met Leu Asp Trp Lys Pro Lys Arg
 50                  55                  60
Pro Asp Met Leu Val Asp Pro Phe Gly Leu Gly Arg Ile Val Gln Asp
 65                  70                  75                  80
Gly Leu Val Phe Arg Gln Asn Phe Ser Ile Arg Ser Tyr Glu Ile Gly
                85                  90                  95
Ala Asp Arg Thr Ala Ser Ile Glu Thr Leu Met Asn His Leu Gln Glu
                100                 105                 110
Thr Ala Leu Asn His Val Lys Ser Ala Gly Leu Leu Asn Asp Gly Phe
                115                 120                 125
Gly Arg Thr Pro Glu Met Tyr Lys Arg Asp Leu Ile Trp Val Val Ala
                130                 135                 140
Lys Met Gln Val Met Val Asn Arg Tyr Pro Thr Trp Gly Asp Thr Val
145                 150                 155                 160
Glu Val Asn Thr Trp Val Ala Lys Ser Gly Lys Asn Gly Met Arg Arg
                165                 170                 175
Asp Trp Leu Ile Ser Asp Cys Asn Thr Gly Glu Ile Leu Thr Arg Ala
                180                 185                 190
Ser Ser Val Trp Val Met Met Asn Gln Lys Thr Arg Arg Leu Ser Lys
                195                 200                 205
Ile Pro Asp Glu Val Arg His Glu Ile Glu Pro His Phe Val Asp Ser
210                 215                 220
Pro Pro Val Ile Glu Asp Asp Arg Lys Leu Pro Lys Leu Asp Glu
225                 230                 235                 240
Lys Thr Ala Asp Ser Ile Arg Lys Gly Leu Thr Pro Arg Trp Asn Asp
                245                 250                 255
Leu Asp Val Asn Gln His Val Asn Asn Val Lys Tyr Ile Gly Trp Ile
                260                 265                 270
Leu Glu Ser Thr Pro Gln Glu Val Leu Glu Thr Gln Glu Leu Cys Ser
                275                 280                 285
Leu Thr Leu Glu Tyr Arg Arg Glu Cys Gly Arg Asp Ser Val Leu Glu
                290                 295                 300
Ser Leu Thr Ala Val Asp His Ser Gly Lys Gly Ser Gly Ser Asn Phe
305                 310                 315                 320
Gln His Leu Leu Arg Leu Glu Asp Gly Gly Glu Ile Val Lys Gly Arg
                325                 330                 335
Thr Glu Trp Arg Pro Lys Asn Ala Val Ile Asn Gly Ala Val Ala Pro
                340                 345                 350
Gly Glu Thr Ser Pro Gly Asn Ser Val Ser
                355                 360

<210> SEQ ID NO 86
<211> LENGTH: 2460
<212> TYPE: DNA
<213> ORGANISM: Cuphea leptodpoda

<400> SEQUENCE: 86
gcagcaagtt ctgcatgctt ccctgctcca gccccgggaa cctcccctaa acccgggaag    60
tccggcaatt ggccatcaag cttgagccct tccttaaagc ccaagtcaat ccccaatggc   120
```

```
ggatttcagg ttaaggcaaa tgccagtgcc catcctaagg ctaacggtgc tgcagtaaat    180
ctaaagtctg gcagcctcaa cactcaggag gacacttcgt cgtcccctcc tcctcgggct    240
ttccttaacc agttgcctga ttggagtatg cttctgactg caatcacgac cgtcttcgtg    300
gcggcagaga agcagtggac tatgcttgat cggaaatcta agaggcctga catgctcgtg    360
gactcggttg ggttgaagaa tattgttcgg gatgggctcg tgtccagaca gagttttcg    420 atcaggtctt atgaaatagg cgctgatcga acagcctcta tagagacgct gatgaaccac    480
ttgcaggtac tgctttgaaa ctattcattc atcggatatg ctagtgatca gtaaatgagc    540
catgactaga tgatgacaaa gataacaccg attgccagta taacatgcta attgtgtcca    600 tttttaattta gaggtgttct tttctgttca tgatgaggtt ggtatccgag ggtgagattt    660
gtcaggttga ttcaatgaaa gggccatcag ctgtaaatat tcgattacat ttccgtatga    720
tgaaagttaa aaatactctc attcgatcga gaaatgacta agcattctga tgtaaagtat    780
ttcatctaaa atgcttgcac tggttttgct tatattttct cgttaactcg gatgtctttg    840 ctctttttt ttctctctct ctaaacagga aacatctatc aatcattgta agagtttggg    900
tcttctcaat gacggctttg gtcgtactcc tgggatgtgt aaaaacgacc tcatttgggt    960
gcttacaaaa atgcagatcc tggtgaatcg ctacccagct tggtaagttt gtcactggct    1020
ggtttgtctt ttggtccgta agtgcctctt acaataatag ttgtaaacat agtggaatgt    1080
aatggcttgt atgtgatctt tatggtaggg gagatactgt tgagatcaat acctggttct    1140
ctcagtcggg gaaaatcggc atgggtagtg attggctaat aagtgattgc aacacaggag    1200
aaattcttat aagagcaacg aggtatgatt ttctggttct gagtttacat tctcaaaaac    1260
cttctgatgc tcgatccgtg agcagacatt tggcatgttt tatatgtaaa gtggagtcat    1320
gtcactctca tattatcgca gcgtgtgggc aatgatgaat caaaagacga aagattctc    1380 aagacttcca tacgaggttc gccaggagtt aacgcctcat tttgtagact cacctcatgt    1440
cattgaagac aatgatcgga aattgcataa gtttgatgtg aagactggtg attctattcg    1500
caagggtcta actgtaagtc cctgtctttc actatgatat tagtcgtttt taggaaatac    1560
catgtctctg agacgttctt ccacttcatg gtttgtagcc gaggtggaat gacttggatg    1620
tcaatcaaca cgtaagcaac gtgaagtaca ttgggtggat tctcgaggta ccctttttat    1680
cgcacgaaca actgatatat ttttgggtta atgatgataa atcaataaa ctaagatgtt    1740 gaatgcaagt atctgcttgc tagcacatga gatattactt aaatatcgtg gataagtgtt    1800
gcctcgagtt tttcaaagct tactttacga ttccgattta cacttctttg atctaaccga    1860
attcttgttg cagagtatgc caatagaagt tttggagact caggagctat gctctctcac    1920
cgttgaatat aggcgggaat gcggaatgga cagtgtgctg gagtccgtga ctgctaggga    1980
tccctcagaa gatggaggcc ggtctcagta caatcacctt ctgcggcttg aggatgggac    2040
tgatgtcgtg aagggcagaa ctgagtggcg atcgaagaat gcaggaacta acggggcgac    2100
atcaacagca aagacttcaa atggaaactc ggtctcttag aagagtctcg ggacccttcc    2160
gagatgtgca tttcttttca ctttctcatt ttctggtgag ctgaaagaag agcatgtgga    2220
tgcaatcagt aaattgtgta gttgtttgtt cgctttgctt ctctcctttg tataataaca    2280
tggtcagtcg tctttgtatc atctcacgtt tcagtttat ttgcgccata ttctatctcg    2340
aaactagtac ttgtccaaaa tgcatgtata tgcctttgaa gatcacactg cagtccgaaa    2400
aatagacatt ttcaaatatt tcccaaatcc tagcgcttta gcattgaatg atgttcccac    2460
```

<210> SEQ ID NO 87
<211> LENGTH: 413
<212> TYPE: PRT
<213> ORGANISM: Cuphea leptodpoda

<400> SEQUENCE: 87

```
Ala Ala Ser Ser Ala Cys Phe Pro Ala Pro Ala Gly Thr Ser Pro
1               5                   10                  15

Lys Pro Gly Lys Ser Gly Asn Trp Pro Ser Ser Leu Ser Pro Ser Leu
            20                  25                  30

Lys Pro Lys Ser Ile Pro Asn Gly Gly Phe Gln Val Lys Ala Asn Ala
            35                  40                  45

Ser Ala His Pro Lys Ala Asn Gly Ala Ala Val Asn Leu Lys Ser Gly
        50                  55                  60

Ser Leu Asn Thr Gln Glu Asp Thr Ser Ser Pro Pro Arg Ala
65              70                  75                  80

Phe Leu Asn Gln Leu Pro Asp Trp Ser Met Leu Leu Thr Ala Ile Thr
                    85                  90                  95

Thr Val Phe Val Ala Ala Glu Lys Gln Trp Thr Met Leu Asp Arg Lys
                100                 105                 110

Ser Lys Arg Pro Asp Met Leu Val Asp Ser Val Gly Leu Lys Asn Ile
            115                 120                 125

Val Arg Asp Gly Leu Val Ser Arg Gln Ser Phe Ser Ile Arg Ser Tyr
130                 135                 140

Glu Ile Gly Ala Asp Arg Thr Ala Ser Ile Glu Thr Leu Met Asn His
145                 150                 155                 160

Leu Gln Glu Thr Ser Ile Asn His Cys Lys Ser Leu Gly Leu Leu Asn
                165                 170                 175

Asp Gly Phe Gly Arg Thr Pro Gly Met Cys Lys Asn Asp Leu Ile Trp
            180                 185                 190

Val Leu Thr Lys Met Gln Ile Leu Val Asn Arg Tyr Pro Ala Trp Gly
            195                 200                 205

Asp Thr Val Glu Ile Asn Thr Trp Phe Ser Gln Ser Gly Lys Ile Gly
210                 215                 220

Met Gly Ser Asp Trp Leu Ile Ser Asp Cys Asn Thr Gly Glu Ile Leu
225                 230                 235                 240

Ile Arg Ala Thr Ser Val Trp Ala Met Met Asn Gln Lys Thr Arg Arg
                245                 250                 255

Phe Ser Arg Leu Pro Tyr Glu Val Arg Gln Glu Leu Thr Pro His Phe
            260                 265                 270

Val Asp Ser Pro His Val Ile Glu Asp Asn Asp Arg Lys Leu His Lys
            275                 280                 285

Phe Asp Val Lys Thr Gly Asp Ser Ile Arg Lys Gly Leu Thr Pro Arg
290                 295                 300

Trp Asn Asp Leu Asp Val Asn Gln His Val Ser Asn Val Lys Tyr Ile
305                 310                 315                 320

Gly Trp Ile Leu Glu Ser Met Pro Ile Glu Val Leu Glu Thr Gln Glu
                325                 330                 335

Leu Cys Ser Leu Thr Val Glu Tyr Arg Arg Glu Cys Gly Met Asp Ser
            340                 345                 350

Val Leu Glu Ser Val Thr Ala Arg Asp Pro Ser Glu Asp Gly Gly Arg
            355                 360                 365

Ser Gln Tyr Asn His Leu Leu Arg Leu Glu Asp Gly Thr Asp Val Val
370                 375                 380
```

Lys Gly Arg Thr Glu Trp Arg Ser Lys Asn Ala Gly Thr Asn Gly Ala
385                 390                 395                 400

Thr Ser Thr Ala Lys Thr Ser Asn Gly Asn Ser Val Ser
            405                 410

<210> SEQ ID NO 88
<211> LENGTH: 1089
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
atggcaaatg gtgcagcggt taatctgaag tctggttctt tgaataccca agaggatacc      60
tcttccagcc ctccacctcg tgcgtttctg aaccaattac ccgactggag catgctgttg     120
accgctatca ctaccgtgtt cgtggcggca gaaaagcaat ggaccatgct ggatcgtaag     180
agcaaacgtc ccgatatgtt agtggactcc gtcggtttga agaatatcgt gcgtgacggc     240
ttagtttctc gccagtcttt ctctattcgc agctatgaaa tcggcgcaga ccgcaccgcc     300
tccattgaaa cgttaatgaa ccacctgcaa gagactagca ttaaccattg taaatccttg     360
ggcctgttga tgatggctt cggccgtact cccggtatgt gcaagaacga tctgatctgg     420
gttttgacta agatgcagat tttggtcaac cgctatccgg cgtggggtga tactgtggag     480
atcaacacct ggtttagcca gtccggtaag attggtatgg gctccgactg gttgattagc     540
gattgcaata ccggtgaaat cctgattcgc gccacgagcg tgtgggcaat gatgaatcag     600
aaaacccgtc gcttcagccg tttaccgtac gaagttcgtc aggaattgac tccgcatttt     660
gtcgacagcc cacacgttat cgaggacaac gaccgcaaac tgcataagtt cgacgtcaag     720
accggtgatt ctatccgcaa aggtttgacc cctcgctgga atgacctgga cgttaaccag     780
cacgtttcta atgtcaaata catcggctgg attctggagt ccatgcctat tgaggtcctg     840
gagactcaag agttgtgttc cttaaccgtc gaatatcgtc gcgaatgcgg tatggacagc     900
gtcttagagt ccgtgactgc ccgtgacccc tctgaagatg gtggccgctc tcagtacaac     960
cacttattgc gtttagagga tggcactgat gttgttaaag gccgtaccga gtggcgctcc    1020
aagaacgctg gcactaatgg tgcgacttct accgcgaaaa cctccaatgg taatagtgtg    1080
agttaataa                                                            1089

<210> SEQ ID NO 89
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Met Ala Asn Gly Ala Ala Val Asn Leu Lys Ser Gly Ser Leu Asn Thr
1               5                   10                  15

Gln Glu Asp Thr Ser Ser Ser Pro Pro Arg Ala Phe Leu Asn Gln
            20                  25                  30

Leu Pro Asp Trp Ser Met Leu Leu Thr Ala Ile Thr Thr Val Phe Val
        35                  40                  45

Ala Ala Glu Lys Gln Trp Thr Met Leu Asp Arg Lys Ser Lys Arg Pro
    50                  55                  60

```
Asp Met Leu Val Asp Ser Val Gly Leu Lys Asn Ile Val Arg Asp Gly
 65                  70                  75                  80

Leu Val Ser Arg Gln Ser Phe Ser Ile Arg Ser Tyr Glu Ile Gly Ala
                 85                  90                  95

Asp Arg Thr Ala Ser Ile Glu Thr Leu Met Asn His Leu Gln Glu Thr
            100                 105                 110

Ser Ile Asn His Cys Lys Ser Leu Gly Leu Leu Asn Asp Gly Phe Gly
        115                 120                 125

Arg Thr Pro Gly Met Cys Lys Asn Asp Leu Ile Trp Val Leu Thr Lys
    130                 135                 140

Met Gln Ile Leu Val Asn Arg Tyr Pro Ala Trp Gly Asp Thr Val Glu
145                 150                 155                 160

Ile Asn Thr Trp Phe Ser Gln Ser Gly Lys Ile Gly Met Gly Ser Asp
                165                 170                 175

Trp Leu Ile Ser Asp Cys Asn Thr Gly Glu Ile Leu Ile Arg Ala Thr
            180                 185                 190

Ser Val Trp Ala Met Met Asn Gln Lys Thr Arg Arg Phe Ser Arg Leu
        195                 200                 205

Pro Tyr Glu Val Arg Gln Glu Leu Thr Pro His Phe Val Asp Ser Pro
    210                 215                 220

His Val Ile Glu Asp Asn Asp Arg Lys Leu His Lys Phe Asp Val Lys
225                 230                 235                 240

Thr Gly Asp Ser Ile Arg Lys Gly Leu Thr Pro Arg Trp Asn Asp Leu
                245                 250                 255

Asp Val Asn Gln His Val Ser Asn Val Lys Tyr Ile Gly Trp Ile Leu
            260                 265                 270

Glu Ser Met Pro Ile Glu Val Leu Glu Thr Gln Glu Leu Cys Ser Leu
        275                 280                 285

Thr Val Glu Tyr Arg Arg Glu Cys Gly Met Asp Ser Val Leu Glu Ser
    290                 295                 300

Val Thr Ala Arg Asp Pro Ser Glu Asp Gly Gly Arg Ser Gln Tyr Asn
305                 310                 315                 320

His Leu Leu Arg Leu Glu Asp Gly Thr Asp Val Val Lys Gly Arg Thr
                325                 330                 335

Glu Trp Arg Ser Lys Asn Ala Gly Thr Asn Gly Ala Thr Ser Thr Ala
            340                 345                 350

Lys Thr Ser Asn Gly Asn Ser Val Ser
        355                 360

<210> SEQ ID NO 90
<211> LENGTH: 2225
<212> TYPE: DNA
<213> ORGANISM: Cuphea leptodpoda

<400> SEQUENCE: 90
gcagcaagtt ctgcatgctt ccccatacca tccgccgaca ccacctcgag acccggaaag      60
cttggcaatg gtccatcgag cttcagcccc ttcaagccca atctatcccc caatggtggg     120
ttgcaggtta aggcaaacgc cagtgcccct cctaagatca atggttcctc ggtcggtcta     180
aagtcaggta gtctcaagac tcaggaagac gctccatcgg cccctcctcc gcggactttt     240
atcaaccagt tgcctgattg gagtatgctt cttgctgcaa tcactactgt cttttttggca    300 gcagagaagc agtggatgat gcttgattgg aaacctaaga ggcctgacat gcttgaggac     360
cctttcgggt tgggaaggat tattcagaat gggcttgtgt tcaggcagaa ttttttcgatt   420
```

```
aggtcctatg aaataggcgc cgatcgcact gcgtctatag agacggtgat gaatcatttg      480
caggtacccg tgcatgctgc tttttaaacta ctcaattcat gaaatgctta tgtccagtaa    540
ctgagccaaa ctttattatg gccggccgaa ttccattgcg aatttgagaa agagaagggt     600
tgtattgcat gcattcctct ctctattgtc atagaggtga ttcagtatag gtttacctca     660
tgtcagtttt atcttatatg cactcgtttc atgatcactt tggcttctta tggcgagatt    720
tgccatgtcg aatcaatgaa agaatcatct gctctactat attttttatga aatttacgca   780
ttatgaaatt ttatgtggaa cttttttact tctgtgatag aaaacgcagg aactcttgtt   840
tcatttgaaa attggattag tcctatgata tttatgtaat atttcttaaa catttgaatt   900
agtttgttta aagtttggt tgaattcatt gtcttttttt ctggggtttt tttttttctt     960
ttacaggaaa cagctctcaa tcatgttaag agtgctgggc ttcttaatga cggctttggt  1020
cggactcctg agatgtataa aagggacctt atttgggttg ttgcgaaaat gcaggtcatg   1080
gttaaccgct atcctacttg gtgagtttgt caatagattg ttagtttacg gaccttagag   1140
gcttataatt ttatgtgtca atgtagttgt agtgtatatc acattgtaat gcgtgctcat   1200
tgttacctac cttgtgagat ggtgttcat ttcaatgtaa caccaatgac tacgaatctg    1260
ctgtatgttg tggaacctaa aggcctgtct gtgatctttg ttcaggggtg acacggttga  1320
agtgaatact tgggttgcca ggtcagggaa aaatggtatg cgtcgtgact ggctcataag  1380
tgattgcaat accggagaga ttcttacaag ggcatcaagg tatgatgtat tgtttcgtag  1440
ttatgttcct atactttcca gtggtcaaat ttgagagcat caaccgggga gatcttacag  1500
tgaaattgga attctgtcgc ccttgtatta ttgcagtgtg tgggtcatga tgaatcaaaa  1560
aacaagaaga ttgtcaaaaa ttccagatga ggttcgacat gagatagagc ctcatttgt   1620
ggactctgct cccgtcatcg aagacgatga ccggaaactt cccaagctgg atgaggagac   1680
tgctgactcc atccgcaagg gtctaactgt aaggccacat tttacaattt aacagtggat   1740
tgcgttgcta tataaaaaat tgtgtttctt aaattatttt cctcttcgcg atttgtagcc   1800
gaagtggaat gacttggacg tcaatcagca cgtcaacaac gtgaagtaca tcgggtggat  1860
ccttgaggta acttttaatc tgttagtgaa tatgtgtttta tcgtaataag atatatgaac  1920
ttagatattg agcacttgag aattactcgt atatccctga actacaatta cagttgttat  1980
atcgctcaaa ttttgctgtt ttcatgtgtt gcagagtact ccaccagaag ttttggagac   2040
acaggagtta tgttccctta ccctggaata caggcaggaa tgtggaaggg agagcgtgct   2100
ggagtccctc actgctgcgg acccctctgg agaggggggc tatggatccc aatttcagca  2160
ccttctgcgg cttgaggatg gaggtgagat cgtgaagggg agaactgagt ggcggcccaa  2220
gactg                                                                2225
```

<210> SEQ ID NO 91
<211> LENGTH: 394
<212> TYPE: PRT
<213> ORGANISM: Cuphea leptodpoda
<400> SEQUENCE: 91

```
Ala Ala Ser Ser Ala Cys Phe Pro Ile Pro Ser Ala Asp Thr Thr Ser
1               5                   10                  15

Arg Pro Gly Lys Leu Gly Asn Gly Pro Ser Ser Phe Ser Pro Phe Lys
            20                  25                  30

Pro Lys Ser Ile Pro Asn Gly Gly Leu Gln Val Lys Ala Asn Ala Ser
        35                  40                  45
```

```
Ala Pro Pro Lys Ile Asn Gly Ser Ser Val Gly Leu Lys Ser Gly Ser
         50                  55                  60

Leu Lys Thr Gln Glu Asp Ala Pro Ser Ala Pro Pro Arg Thr Phe
 65              70                  75                  80

Ile Asn Gln Leu Pro Asp Trp Ser Met Leu Leu Ala Ala Ile Thr Thr
                 85                  90                  95

Val Phe Leu Ala Ala Glu Lys Gln Trp Met Met Leu Asp Trp Lys Pro
                100                 105                 110

Lys Arg Pro Asp Met Leu Glu Asp Pro Phe Gly Leu Gly Arg Ile Ile
                115                 120                 125

Gln Asn Gly Leu Val Phe Arg Gln Asn Phe Ser Ile Arg Ser Tyr Glu
        130                 135                 140

Ile Gly Ala Asp Arg Thr Ala Ser Ile Glu Thr Val Met Asn His Leu
145                 150                 155                 160

Gln Glu Thr Ala Leu Asn His Val Lys Ser Ala Gly Leu Leu Asn Asp
                165                 170                 175

Gly Phe Gly Arg Thr Pro Glu Met Tyr Lys Arg Asp Leu Ile Trp Val
                180                 185                 190

Val Ala Lys Met Gln Val Met Val Asn Arg Tyr Pro Thr Trp Gly Asp
                195                 200                 205

Thr Val Glu Val Asn Thr Trp Val Ala Arg Ser Gly Lys Asn Gly Met
210                 215                 220

Arg Arg Asp Trp Leu Ile Ser Asp Cys Asn Thr Gly Glu Ile Leu Thr
225                 230                 235                 240

Arg Ala Ser Ser Val Trp Val Met Met Asn Gln Lys Thr Arg Arg Leu
                245                 250                 255

Ser Lys Ile Pro Asp Glu Val Arg His Glu Ile Glu Pro His Phe Val
                260                 265                 270

Asp Ser Ala Pro Val Ile Glu Asp Asp Arg Lys Leu Pro Lys Leu
                275                 280                 285

Asp Glu Glu Thr Ala Asp Ser Ile Arg Lys Gly Leu Thr Pro Lys Trp
                290                 295                 300

Asn Asp Leu Asp Val Asn Gln His Val Asn Asn Val Lys Tyr Ile Gly
305                 310                 315                 320

Trp Ile Leu Glu Ser Thr Pro Pro Glu Val Leu Glu Thr Gln Glu Leu
                325                 330                 335

Cys Ser Leu Thr Leu Glu Tyr Arg Gln Glu Cys Gly Arg Glu Ser Val
                340                 345                 350

Leu Glu Ser Leu Thr Ala Ala Asp Pro Ser Gly Glu Gly Tyr Gly
                355                 360                 365

Ser Gln Phe Gln His Leu Leu Arg Leu Glu Asp Gly Gly Glu Ile Val
370                 375                 380

Lys Gly Arg Thr Glu Trp Arg Pro Lys Thr
385                 390

<210> SEQ ID NO 92
<211> LENGTH: 2236
<212> TYPE: DNA
<213> ORGANISM: Cuphea leptodpoda

<400> SEQUENCE: 92
gcagcaagtt ctgcatgctt ccccatacca tccgtcgaca ccacctcgag acccggaaag      60
ctcggcaatg gtccatcgag cttcagcccc ttcaaaccca aatccatccc caatggtggg     120
ttgcaggtta aggcaaacgc cagtgcccct cctaagatca atggttcctc ggtcggtcta     180
```

```
aagtcaggcg gtctcaaaac tcaggaagac gctccttcgg cccctcctcc gcggactttt      240
atcaaccagt tgcctgattg gagtatgctt cttgctgcaa tcactactgt cttcttggct      300
gcagagaagc agtggatgat gcttgattgg aaacccaaga ggcctgacat gcttgaggac      360
cctttcgggt tgggaaggat tgttcagaat gggcttgtct tcaggcagaa ttttttcgatt     420 aggtcctatg aaataggcgc cgatcgcact gcgtctatag agacggtgat gaatcatttg      480
caggtaccgg tgcatgatgc ttttaaacta ctcaattcat gaaatgctta tgtccagtaa      540
ttgagccata cttgactatg gcctgccgaa ttccattgcg aatttgagaa agagaatggt      600
tgtattgcat gcattcctct ctctattgtc atagagttga ttcagtatag gtttacctcg      660
tgttagtttt atcttatatg cactcgtttc atgatcactt ggcttcttat ggcgagattt      720
gccatgtcga atcaatgaaa gaatcatctg ctctactata tatttatgaa atttacgcat      780
tatgaaattt tatgtggaac ttttttactt ctgtgataga aaacacagga actctcgttt      840
catttgaaaa ctggattagt cttctgatat ttatgtaata tttcttaaac atttgaatta      900
gtttgtttat aagtttggtt gaattcattg tctttttcct ggttttttttt tcttttacag      960 gaaacagctc tcaatcatgt taagagtgct gggcttctta atgaaggctt tggtcggact      1020
ctcgagatgt ataaaaggga ccttatttgg gttgttgcga aaatgcaggt catggttaac      1080
cgctatccta cttggtgagt ttgtcactag attgttagtt tacggacctt agaggcttac      1140
aattttatgt gtcaatgtag ttgtagtgta tatcacattg taatgcgtgc tcactgttac      1200
ctgccatgtg agatggtgtt tcatttcaat gtaacaccaa tgactacgaa tctgttgtat      1260
gtcgtggaac ctaaaggcct gtctgtgatc tttgttcagg ggtgacacgg ttgaagtgaa      1320
tacttgggtt gccaggtcag ggaaaaatgg tatgcgtcgt gactggctca taagtgattg      1380
caataccgga gagattctta caagagcatc aaggtatgat gtactgtttc gtagttatgt      1440
tcctatactt tcgtgtggtc aaagttgaga gcattcaacc gggagatctt acagtgaaat      1500
tggaattgtg tcacccttgt attattgcag tgtgtgggtc atgatgaatc aaaagacaag      1560
aagattgtca aaaattccag atgaggttcg acatgagata gagcctcatt tgtggactc      1620 tgctcccgtc atcgaagacg atgaccggaa acttcccaag ctggatgagg agactgctga      1680
ctccatccgc aagggtctaa ctgtaaggcc acatttttaca cttttaacagt ggattgcgtt     1740 gctatataaa aaaatttatg tttcttaaat tattttcctc ttcgcgattt gtagccgaag      1800
tggaatgact tggacgtcaa tcagcacgtc aacaacgtga agtacatcgg gtggatcctt      1860
gaggtaactt ttaatctgtt agtgaatatg tgtttatcgt aataagatat atgaacttag      1920
atattgaacc aagtaactgc tagcacttga gaattactcg tatttccctg aactacaatt      1980
acagttgtta tatcgctcaa attttgatgt tttcatgtgt tgcagagtac tccaccagaa      2040
gttttggaga cccaggagtt atgttccctt accctggaat acaggcggga atgtggaagg      2100
gagagcgtgt tggagtccct cactgttgtg gaccccctctg gagaggggggg ctatggatcc     2160 cagtttcagc accttctgcg gcttgaggat ggaggtgaga ttgtgaaggg gagaactgag      2220
tggagaccga agactg                                                      2236
```

<210> SEQ ID NO 93
<211> LENGTH: 394
<212> TYPE: PRT
<213> ORGANISM: Cuphea leptodpoda
<400> SEQUENCE: 93

-continued

```
Ala Ala Ser Ser Ala Cys Phe Pro Ile Pro Ser Val Asp Thr Thr Ser
1               5                   10                  15

Arg Pro Gly Lys Leu Gly Asn Gly Pro Ser Ser Phe Ser Pro Phe Lys
            20                  25                  30

Pro Lys Ser Ile Pro Asn Gly Gly Leu Gln Val Lys Ala Asn Ala Ser
        35                  40                  45

Ala Pro Pro Lys Ile Asn Gly Ser Ser Val Gly Leu Lys Ser Gly Gly
    50                  55                  60

Leu Lys Thr Gln Glu Asp Ala Pro Ser Ala Pro Pro Arg Thr Phe
65                  70                  75                  80

Ile Asn Gln Leu Pro Asp Trp Ser Met Leu Leu Ala Ala Ile Thr Thr
                85                  90                  95

Val Phe Leu Ala Ala Glu Lys Gln Trp Met Met Leu Asp Trp Lys Pro
            100                 105                 110

Lys Arg Pro Asp Met Leu Glu Asp Pro Phe Gly Leu Gly Arg Ile Val
            115                 120                 125

Gln Asn Gly Leu Val Phe Arg Gln Asn Phe Ser Ile Arg Ser Tyr Glu
    130                 135                 140

Ile Gly Ala Asp Arg Thr Ala Ser Ile Glu Thr Val Met Asn His Leu
145                 150                 155                 160

Gln Glu Thr Ala Leu Asn His Val Lys Ser Ala Gly Leu Leu Asn Glu
                165                 170                 175

Gly Phe Gly Arg Thr Leu Glu Met Tyr Lys Arg Asp Leu Ile Trp Val
            180                 185                 190

Val Ala Lys Met Gln Val Met Val Asn Arg Tyr Pro Thr Trp Gly Asp
            195                 200                 205

Thr Val Glu Val Asn Thr Trp Val Ala Arg Ser Gly Lys Asn Gly Met
210                 215                 220

Arg Arg Asp Trp Leu Ile Ser Asp Cys Asn Thr Gly Glu Ile Leu Thr
225                 230                 235                 240

Arg Ala Ser Ser Val Trp Val Met Met Asn Gln Lys Thr Arg Arg Leu
                245                 250                 255

Ser Lys Ile Pro Asp Glu Val Arg His Glu Ile Glu Pro His Phe Val
            260                 265                 270

Asp Ser Ala Pro Val Ile Glu Asp Asp Arg Lys Leu Pro Lys Leu
    275                 280                 285

Asp Glu Glu Thr Ala Asp Ser Ile Arg Lys Gly Leu Thr Pro Lys Trp
    290                 295                 300

Asn Asp Leu Asp Val Asn Gln His Val Asn Asn Val Lys Tyr Ile Gly
305                 310                 315                 320

Trp Ile Leu Glu Ser Thr Pro Pro Glu Val Leu Glu Thr Gln Glu Leu
                325                 330                 335

Cys Ser Leu Thr Leu Glu Tyr Arg Arg Glu Cys Gly Arg Glu Ser Val
            340                 345                 350

Leu Glu Ser Leu Thr Val Val Asp Pro Ser Gly Glu Gly Gly Tyr Gly
    355                 360                 365

Ser Gln Phe Gln His Leu Leu Arg Leu Glu Asp Gly Gly Glu Ile Val
    370                 375                 380

Lys Gly Arg Thr Glu Trp Arg Pro Lys Thr
385                 390
```

<210> SEQ ID NO 94
<211> LENGTH: 2173
<212> TYPE: DNA

<213> ORGANISM: Cuphea avigera

<400> SEQUENCE: 94

```
gcagcaagtt cagcatgctt ccacctgcca tccgccgaca cctcctcgag acccggaaag      60
ctcggcaatg ggccatcgag cttgagcccc ctcaagccta aatcgacccc caatggcggc     120
ttgaaggtta aggcaaatgc tagtgcccct cctaagatca atggtcaccc ggtcggtcta     180
aagtcgggcg gtctcaagac tcaggaagac ggtccttcgg cccctcctcc gcggactttt     240
atcaaccagt tgcctgattg gagtatgctt cttgctgcaa tcactactgt cttcttggct     300
gcagagaagc agtggatgat gcttgattgg aaacctaaga ggcctgacat gcttgtggac     360
ccattcggat tgggaagtat tgttcaggat gggcttgtgt tcaggcagaa ttttttcgatt    420
aggtcctacg aaataggtgc cgatcgcact gcgtctatag agacggtgat gaaccatttg     480
caggtactgg tgcatgctga ttttaaacca ttcaagtcat gaaatgctta tgtccattat     540
gccctgccga atttaatggt gaatttgaga aagtggtgaa ttcagtatag gtttacctcg     600
tgtcggtttt atcttatatg cactcatttc atgatcactt tggttcctta tggtgagatt     660
tgtcatgtcg agtcaatgaa ggaatcatct gctatactat attttcctta aatttacgca     720
ttatgaaatt ttatgtggaa ctccttactt ctgtgatata aaactcaggg aggaaagctt     780
cctcttgccc tttaatcttc gaaaataaaa ctaaagaaag gaactctcat ttcaattgaa     840
aactagaata gttatctgat atttatgtaa tttcttaaaa attcgcatta gtttgtttat     900
cagtttggtt gaattcattg tctttgtcct gttttttttt tttttctttt tacaggaaac     960
agctctcaat catgttaaga gtgctgggct ttctaatgat ggctttggtc gtactcccga    1020
gatgtataaa agggacctta tttggggttgt gcgaaaatg caggtcatgg ttaatcgcta    1080
tcctacatgg tgagtttgtc actagattgt atcacattgt aatgcgggct cacagttacc    1140
tgccttgtga gacggtgttt catttcaatg taacactgat aactgtgaat ctcctttatg    1200
ctgtggaacc taacgcctg ctgtgatctt tattcagggg tgacacggtt gaagtgaata     1260
cttgggttgc caagtcaggg aaaaatggta tgcgtcgtga ctggctcata agtgattgca    1320
atactggcga gattcttaca agagcatcaa ggtatgatgt actgtttcgt atttatgttc    1380
ctgtactttc tagtggtcaa atttgagagc attcaatcgg gatatcttac ggttaaattg    1440
gaatttgtca cccttgcatt attgcagcgt gtgggtcatg atgaatcaaa agacaagaag    1500
actgtcaaaa attccagatg aggttcgaaa tgagatagag cctcattttg tggactctcc    1560
tcccgtcatt gaagacgatg accgcaaact tcccaagctg gatgagaaga atgctgactc    1620
catccgcaag ggtctaactg taaggccata ttttacactt ttaacactgg attgcattgc    1680
tatttaaaaa attatgtgtc ttagatgatt ttcctcttgc gatttgtagc cgaggtggaa    1740
tgacttggat gtcaatcagc acgtcaacaa cgtgaagtac atcggatgga ttcttgaggt    1800
aacttttaat ctgttaattg aatgtgttta tcgtaataag atatatgaac ttcaatagtg    1860
acccaagtaa ctgttagcac ttgagaattg atcgtatttc cctgaattac aattacaatt    1920
attgtagtgc taaacaaata atgttgtttt cacgcattgc agagtactcc accggaagtt    1980
ctggagaccc aggagttatg ttcccttacc ctggaataca ggcggaatg tggaagggag     2040
agcgtgctgg agtccctcac tgctgtggat ccctctggag agggaggcta tgggtcccag    2100
tttcagcacc ttctgcggct tgaggatgga ggtgagattg tgaaggggag aactgagtgg    2160
cggccgaaga atg                                                       2173
```

```
<210> SEQ ID NO 95
<211> LENGTH: 394
<212> TYPE: PRT
<213> ORGANISM: Cuphea avigera

<400> SEQUENCE: 95
```

| | | | | | | | | | | | | | | | |
|---|---|---|---|---|---|---|---|---|---|---|---|---|---|---|---|
| Ala | Ala | Ser | Ser | Ala | Cys | Phe | His | Leu | Pro | Ser | Ala | Asp | Thr | Ser | Ser |
| 1 | | | | 5 | | | | | 10 | | | | | 15 | |
| Arg | Pro | Gly | Lys | Leu | Gly | Asn | Gly | Pro | Ser | Ser | Leu | Ser | Pro | Leu | Lys |
| | | | 20 | | | | | 25 | | | | | 30 | | |
| Pro | Lys | Ser | Thr | Pro | Asn | Gly | Gly | Leu | Lys | Val | Lys | Ala | Asn | Ala | Ser |
| | | | 35 | | | | | 40 | | | | 45 | | | |
| Ala | Pro | Pro | Lys | Ile | Asn | Gly | His | Pro | Val | Gly | Leu | Lys | Ser | Gly | Gly |
| | 50 | | | | | 55 | | | | | 60 | | | | |
| Leu | Lys | Thr | Gln | Glu | Asp | Gly | Pro | Ser | Ala | Pro | Pro | Arg | Thr | Phe | |
| 65 | | | | | 70 | | | | | 75 | | | | | 80 |
| Ile | Asn | Gln | Leu | Pro | Asp | Trp | Ser | Met | Leu | Leu | Ala | Ala | Ile | Thr | Thr |
| | | | | 85 | | | | | 90 | | | | | 95 | |
| Val | Phe | Leu | Ala | Ala | Glu | Lys | Gln | Trp | Met | Met | Leu | Asp | Trp | Lys | Pro |
| | | | | 100 | | | | | 105 | | | | | 110 | |
| Lys | Arg | Pro | Asp | Met | Leu | Val | Asp | Pro | Phe | Gly | Leu | Gly | Ser | Ile | Val |
| | | | 115 | | | | | 120 | | | | | 125 | | |
| Gln | Asp | Gly | Leu | Val | Phe | Arg | Gln | Asn | Phe | Ser | Ile | Arg | Ser | Tyr | Glu |
| | 130 | | | | | 135 | | | | | 140 | | | | |
| Ile | Gly | Ala | Asp | Arg | Thr | Ala | Ser | Ile | Glu | Thr | Val | Met | Asn | His | Leu |
| 145 | | | | | 150 | | | | | 155 | | | | | 160 |
| Gln | Glu | Thr | Ala | Leu | Asn | His | Val | Lys | Ser | Ala | Gly | Leu | Ser | Asn | Asp |
| | | | | 165 | | | | | 170 | | | | | 175 | |
| Gly | Phe | Gly | Arg | Thr | Pro | Glu | Met | Tyr | Lys | Arg | Asp | Leu | Ile | Trp | Val |
| | | | 180 | | | | | 185 | | | | | 190 | | |
| Val | Ala | Lys | Met | Gln | Val | Met | Val | Asn | Arg | Tyr | Pro | Thr | Trp | Gly | Asp |
| | | | 195 | | | | | 200 | | | | | 205 | | |
| Thr | Val | Glu | Val | Asn | Thr | Trp | Val | Ala | Lys | Ser | Gly | Lys | Asn | Gly | Met |
| | 210 | | | | | 215 | | | | | 220 | | | | |
| Arg | Arg | Asp | Trp | Leu | Ile | Ser | Asp | Cys | Asn | Thr | Gly | Glu | Ile | Leu | Thr |
| 225 | | | | | 230 | | | | | 235 | | | | | 240 |
| Arg | Ala | Ser | Ser | Val | Trp | Val | Met | Met | Asn | Gln | Lys | Thr | Arg | Arg | Leu |
| | | | | 245 | | | | | 250 | | | | | 255 | |
| Ser | Lys | Ile | Pro | Asp | Glu | Val | Arg | Asn | Glu | Ile | Glu | Pro | His | Phe | Val |
| | | | 260 | | | | | 265 | | | | | 270 | | |
| Asp | Ser | Pro | Pro | Val | Ile | Glu | Asp | Asp | Arg | Lys | Leu | Pro | Lys | Leu | |
| | | 275 | | | | | 280 | | | | | 285 | | | |
| Asp | Glu | Lys | Asn | Ala | Asp | Ser | Ile | Arg | Lys | Gly | Leu | Thr | Pro | Arg | Trp |
| | 290 | | | | | 295 | | | | | 300 | | | | |
| Asn | Asp | Leu | Asp | Val | Asn | Gln | His | Val | Asn | Asn | Val | Lys | Tyr | Ile | Gly |
| 305 | | | | | 310 | | | | | 315 | | | | | 320 |
| Trp | Ile | Leu | Glu | Ser | Thr | Pro | Pro | Glu | Val | Leu | Glu | Thr | Gln | Glu | Leu |
| | | | | 325 | | | | | 330 | | | | | 335 | |
| Cys | Ser | Leu | Thr | Leu | Glu | Tyr | Arg | Arg | Glu | Cys | Gly | Arg | Glu | Ser | Val |
| | | | 340 | | | | | 345 | | | | | 350 | | |
| Leu | Glu | Ser | Leu | Thr | Ala | Val | Asp | Pro | Ser | Gly | Glu | Gly | Gly | Tyr | Gly |
| | | 355 | | | | | 360 | | | | | 365 | | | |
| Ser | Gln | Phe | Gln | His | Leu | Leu | Arg | Leu | Glu | Asp | Gly | Gly | Glu | Ile | Val |
| | 370 | | | | | 375 | | | | | 380 | | | | |

Lys Gly Arg Thr Glu Trp Arg Pro Lys Asn
385                 390

<210> SEQ ID NO 96
<211> LENGTH: 2535
<212> TYPE: DNA
<213> ORGANISM: Cuphea avigera

<400> SEQUENCE: 96

| | | | | | |
|---|---|---|---|---|---|
| gcagcaagtt | cagcatgctt | ctctgttcca | gtcccgggaa | cctctcctaa | acccgggaag | 60 |
| ttcagaattt | ggccatcgag | cttgagccct | tccttcaagc | ccaagccgat | ccccaatggt | 120 |
| ggattgcagg | ttaaggcaaa | ttccagggca | catccgaagg | ctaacggttc | tgcagttagt | 180 |
| ctaaagtctg | gcagcctcaa | cactcaggag | gacacttcgt | cgtcccctcc | tcctcggact | 240 |
| ttccttcacc | agttgcctga | ttggagtagg | cttctgactg | caatcacgac | cgtgttcgtg | 300 |
| aaatctaaga | ggcctgacat | gcatgatcgg | aaatctaaga | ggcctgacat | gctgatggac | 360 |
| tcgtttgggt | tggagagtat | tgttcaagaa | gggctcgagt | tcagacagag | ttttcgatt | 420 |
| aggtcttatg | aaataggcac | tgatcgaaca | gcctctatag | agacgctgat | gaactacttg | 480 |
| caggtactgc | tttgaaatta | ttcattcgcc | gcaatgctag | tgatcagtaa | atgagccatg | 540 |
| actgacatag | ataacactga | attgccggta | taacaaggta | taacaagcta | attgtgtcca | 600 |
| ttgtaagttt | gaggtgctct | tttctgttcg | tgatgaggtt | tgtatcctag | gttgagaatt | 660 |
| tgtcaggttg | attcaatgaa | aggaccatca | gctgtaaagt | ttcgtttaca | tttacgcacg | 720 |
| atgaaagtta | aaatactctc | attcgacaga | gaaatgactt | agcattctga | tgataagtat | 780 |
| ttcgtctaaa | atgcttgcat | tgtaactccg | atgtcttttt | cctgggttta | ttttttctcta | 840 |
| aacaggaaac | atctctcaat | cattgtaaga | gtaccggtat | tctccttgac | ggctttggtc | 900 |
| gtactcctga | gatgtgtaaa | agggacctca | tttgggtggt | aacaaaaatg | aagatcaagg | 960 |
| tgaatcgcta | tccagcttgg | taagttttctc | gctggctggt | ttgtcttttg | gtccgtaagt | 1020 |
| gcttcttaca | ctaatagttg | taaacatagt | ggaactaatg | gcatgtatgt | gatctatatg | 1080 |
| gtagggggcga | tactgtcgag | atcaatacct | ggttctcccg | gttggggaaa | atcggaaagg | 1140 |
| gtcgcgattg | gctaataagt | gattgcaaca | caggagaaat | tcttataaga | gcaacgaggt | 1200 |
| aggatttttct | gggtctgagt | ttacattctc | aaaaaccttc | tgatgctcca | tctgtgagca | 1260 |
| agacatttgg | catgttttat | atgtaaagtg | gagtcatgtc | actctcatat | tattgcagcg | 1320 |
| cgtatgccac | gatgaatcaa | aagacgagaa | gactctcaaa | acttccatac | gaggttcacc | 1380 |
| aggagatagc | gcctctcttt | gtcgactctc | ctcctgtcat | tgaagacaat | gatctgaaat | 1440 |
| tgcataagtt | tgaagtgaag | actggtgatt | ccattcacaa | gggtctaact | gtacgtccct | 1500 |
| atcttacact | atggcataag | gcattttttt | cgaaatatca | tgtttctgag | acgttcttcc | 1560 |
| tcttcattgt | ttgtagccgg | ggtggaatga | cttggatgtc | aatcagcacg | taagcaacgt | 1620 |
| gaagtacatt | gggtggattc | tcgaggtacc | catttcatcg | cacgaacaac | tgatattttt | 1680 |
| gggttaatga | taataagatc | aataaactta | gaaattgaat | ccaagtatct | gctagctagc | 1740 |
| acatgagaaa | ttacttaaat | atcgtggatt | agtagtgccc | cgagtgtgtt | taagcttact | 1800 |
| ttaacgattc | cgcttaacaa | ataatcttca | atctaatcga | atgattgttg | cagagtatgc | 1860 |
| caacagaagt | tttggagacc | caggagctat | gctctctcgc | ccttgaatat | aggcgggaat | 1920 |
| gcggaaggga | cagtgtgcta | gagtccgtga | cagctatgga | tccacaaaaa | gttggaggcc | 1980 |
| ggtctcagta | ccagcaccct | ctgcgacttg | aggatgggac | tgatatcgtg | aagtgcagaa | 2040 |

-continued

```
ctgagtggcg gccgaagaat ccaggagcta atggggcaat atcaacggga aagacttcaa    2100
atggaaactc ggtctcttag aagagtctcc ggacccttcc gagatgtgca tttctttctc    2160
cttttcattt tgtgtggtga gctgaaagaa gtgcatgtag ttgcaatcag taaattgtgt    2220
agttcgtttg ttcgctcctt tgtataataa catggtcagt cgtcttttcta tcatctcatg    2280 ttttccaaat ttgttatgcc ataaacttt tatattctct gttacaagac gaatagcaca    2340
tctcgaaact aatacttaaa aaaaatacat gtatatgcct cacgccaaat agaacatgcc    2400
tgtaggttaa atacattttt tgtgcatcca tagcacatct cgaaactaga acttgtaaaa    2460
aatacatgta tatgcctcac gccaaataga acatgcctaa tagaggttaa atacattttt    2520
tgtgcatccg gatgc                                                     2535
```

<210> SEQ ID NO 97
<211> LENGTH: 412
<212> TYPE: PRT
<213> ORGANISM: Cuphea avigera

<400> SEQUENCE: 97

```
Ala Ala Ser Ser Ala Cys Phe Ser Val Pro Val Pro Gly Thr Ser Pro
1               5                   10                  15

Lys Pro Gly Lys Phe Arg Ile Trp Pro Ser Ser Leu Ser Pro Ser Phe
            20                  25                  30

Lys Pro Lys Pro Ile Pro Asn Gly Gly Leu Gln Val Lys Ala Asn Ser
        35                  40                  45

Arg Ala His Pro Lys Ala Asn Gly Ser Ala Val Ser Leu Lys Ser Gly
    50                  55                  60

Ser Leu Asn Thr Gln Glu Asp Thr Ser Ser Pro Pro Pro Arg Thr
65                  70                  75                  80

Phe Leu His Gln Leu Pro Asp Trp Ser Arg Leu Leu Thr Ala Ile Thr
                85                  90                  95

Thr Val Phe Val Lys Ser Lys Arg Pro Asp Met His Asp Arg Lys Ser
            100                 105                 110

Lys Arg Pro Asp Met Leu Met Asp Ser Phe Gly Leu Glu Ser Ile Val
        115                 120                 125

Gln Glu Gly Leu Glu Phe Arg Gln Ser Phe Ser Ile Arg Ser Tyr Glu
    130                 135                 140

Ile Gly Thr Asp Arg Thr Ala Ser Ile Glu Thr Leu Met Asn Tyr Leu
145                 150                 155                 160

Gln Glu Thr Ser Leu Asn His Cys Lys Ser Thr Gly Ile Leu Leu Asp
                165                 170                 175

Gly Phe Gly Arg Thr Pro Glu Met Cys Lys Arg Asp Leu Ile Trp Val
            180                 185                 190

Val Thr Lys Met Lys Ile Lys Val Asn Arg Tyr Pro Ala Trp Gly Asp
        195                 200                 205

Thr Val Glu Ile Asn Thr Trp Phe Ser Arg Leu Gly Lys Ile Gly Lys
    210                 215                 220

Gly Arg Asp Trp Leu Ile Ser Asp Cys Asn Thr Gly Glu Ile Leu Ile
225                 230                 235                 240

Arg Ala Thr Ser Ala Tyr Ala Thr Met Asn Gln Lys Thr Arg Arg Leu
                245                 250                 255

Ser Lys Leu Pro Tyr Glu Val His Gln Glu Ile Ala Pro Leu Phe Val
            260                 265                 270

Asp Ser Pro Pro Val Ile Glu Asp Asn Asp Leu Lys Leu His Lys Phe
        275                 280                 285
```

Glu Val Lys Thr Gly Asp Ser Ile His Lys Gly Leu Thr Pro Gly Trp
   290                 295                 300

Asn Asp Leu Asp Val Asn Gln His Val Ser Asn Val Lys Tyr Ile Gly
305                 310                 315                 320

Trp Ile Leu Glu Ser Met Pro Thr Glu Val Leu Glu Thr Gln Glu Leu
                325                 330                 335

Cys Ser Leu Ala Leu Glu Tyr Arg Arg Glu Cys Gly Arg Asp Ser Val
            340                 345                 350

Leu Glu Ser Val Thr Ala Met Asp Pro Thr Lys Val Gly Gly Arg Ser
        355                 360                 365

Gln Tyr Gln His Leu Leu Arg Leu Glu Asp Gly Thr Asp Ile Val Lys
    370                 375                 380

Cys Arg Thr Glu Trp Arg Pro Lys Asn Pro Gly Ala Asn Gly Ala Ile
385                 390                 395                 400

Ser Thr Gly Lys Thr Ser Asn Gly Asn Ser Val Ser
                405                 410

<210> SEQ ID NO 98
<211> LENGTH: 1086
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
atggccaatg gtagcgccgt ttccctgaaa agcggtagct tgaatacccca ggaagacacc      60 agctccagcc ccctccccg cacctttttg catcaactgc ccgattggag ccggctgttg      120
accgccatta ccactgtctt cgttaaatcc aaacgccccg atatgcatga tcgcaaatcc      180
aagcggcccg acatgctgat ggactccttt ggtctggaaa gcattgttca gagggtctg      240 gaatttcggc agtccttttc catccgctcc tacgagattg cactgaccg gactgccagc      300 attgagaccc tgatgaatta cctgcaagag accagcctca atcactgcaa agcaccggc      360 attctgttgg acgttttgg tcgcacccct gaaatgtgca aacgcgatct gatttgggtt      420
gtgactaaaa tgaagattaa ggtgaatcgt tatcccgcct ggggcgatac tgtggagatt      480
aatacctggt tttcccgttt gggcaaaatc ggtaagggtc gcgattggct gattagcgat      540
tgcaacactg gtgagattct gattcgcgcc acttccgctt acgctaccat gaatcaaaag      600
acccgccgtc tgtccaagtt gccttacgag gtccatcaag agattgctcc cctgttcgtt      660
gatagccccc ctgtcatcga agacaacgac ctcaagttgc ataaatttga agttaaaact      720
ggtgactcca tccacaaggg tctgacccct ggttggaatg atctggatgt taaccagcac      780
gtttccaatg tgaagtacat cggttggatc ttggagtcca tgcctaccga ggtgttggag      840
acccaggaac tgtgtagcct cgctttggag taccgccgtg agtgtggccg ggactccgtt      900
ttggagtccg tgactgctat ggaccccact aaagttggtg gccggagcca atatcaacat      960
ttgctgcgtc tggaagacgg tactgacatc gtgaagtgtc gcaccgagtg gcggcctaaa      1020
aatcccggtg ctaatggtgc tatttccacc ggcaaaactt ccaatggtaa ttccgtgagc      1080
taataa      1086

<210> SEQ ID NO 99
<211> LENGTH: 360
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 99

```
Met Ala Asn Gly Ser Ala Val Ser Leu Lys Ser Gly Ser Leu Asn Thr
1               5                   10                  15

Gln Glu Asp Thr Ser Ser Pro Pro Arg Thr Phe Leu His Gln
            20                  25                  30

Leu Pro Asp Trp Ser Arg Leu Leu Thr Ala Ile Thr Thr Val Phe Val
        35                  40                  45

Lys Ser Lys Arg Pro Asp Met His Asp Arg Lys Ser Lys Arg Pro Asp
50                  55                  60

Met Leu Met Asp Ser Phe Gly Leu Glu Ser Ile Val Gln Glu Gly Leu
65                  70                  75                  80

Glu Phe Arg Gln Ser Phe Ser Ile Arg Ser Tyr Glu Ile Gly Thr Asp
                85                  90                  95

Arg Thr Ala Ser Ile Glu Thr Leu Met Asn Tyr Leu Gln Glu Thr Ser
            100                 105                 110

Leu Asn His Cys Lys Ser Thr Gly Ile Leu Leu Asp Gly Phe Gly Arg
        115                 120                 125

Thr Pro Glu Met Cys Lys Arg Asp Leu Ile Trp Val Thr Lys Met
130                 135                 140

Lys Ile Lys Val Asn Arg Tyr Pro Ala Trp Gly Asp Thr Val Glu Ile
145                 150                 155                 160

Asn Thr Trp Phe Ser Arg Leu Gly Lys Ile Gly Lys Gly Arg Asp Trp
                165                 170                 175

Leu Ile Ser Asp Cys Asn Thr Gly Glu Ile Leu Ile Arg Ala Thr Ser
            180                 185                 190

Ala Tyr Ala Thr Met Asn Gln Lys Thr Arg Arg Leu Ser Lys Leu Pro
        195                 200                 205

Tyr Glu Val His Gln Glu Ile Ala Pro Leu Phe Val Asp Ser Pro Pro
            210                 215                 220

Val Ile Glu Asp Asn Asp Leu Lys Leu His Lys Phe Glu Val Lys Thr
225                 230                 235                 240

Gly Asp Ser Ile His Lys Gly Leu Thr Pro Gly Trp Asn Asp Leu Asp
                245                 250                 255

Val Asn Gln His Val Ser Asn Val Lys Tyr Ile Gly Trp Ile Leu Glu
            260                 265                 270

Ser Met Pro Thr Glu Val Leu Glu Thr Gln Glu Leu Cys Ser Leu Ala
        275                 280                 285

Leu Glu Tyr Arg Arg Glu Cys Gly Arg Asp Ser Val Leu Glu Ser Val
    290                 295                 300

Thr Ala Met Asp Pro Thr Lys Val Gly Gly Arg Ser Gln Tyr Gln His
305                 310                 315                 320

Leu Leu Arg Leu Glu Asp Gly Thr Asp Ile Val Lys Cys Arg Thr Glu
                325                 330                 335

Trp Arg Pro Lys Asn Pro Gly Ala Asn Gly Ala Ile Ser Thr Gly Lys
            340                 345                 350

Thr Ser Asn Gly Asn Ser Val Ser
        355                 360
```

<210> SEQ ID NO 100
<211> LENGTH: 2249
<212> TYPE: DNA

<213> ORGANISM: Cuphea avigera

<400> SEQUENCE: 100

```
gcagcaagtt cagcatgctt ccacctgcca tccgccgaca cctcctcgag acccggaaag      60
ctcggcaatg ggccatcgag cttgagcccc ctcaagccta atcgacccc caatggcggc     120
ttgaaggtta aggcaaatgc tagtgcccct cctaagatca atggtcaccc ggtcggtcta     180
aagtcgggcg gtctcaagac tcaggaagac ggtccttcgg cccctcctcc gcggactttt     240
atcaaccagt tgcctgattg gagtatgctt cttgctgcaa tcactactgc cttcttggca     300
gcagagaagc agtggatgat gcttgattgg aaacctaaga ggcctgacat gcttgtggac     360
ccgttcggat tgggaagtat tgtccagcat gggcttgtgt tcaggcagaa ttttttcgatt    420
aggtcctatg aaataggcgc tgatcgcact gcgtctatag acggtgat gaaccacttg       480
caggtactgg tgcatcctgc atttaaacta ttcaattcat gcaatgctta tgtccagtaa     540
ccgagccata cttggctatg cttaccaaa tttaatggtg aatttgagag agaaagggtt      600
gtactgcatt catttcaatt gtcacgaggt gattgaatta cattgtcagt tttagcttac     660
acacactcat tttacgatcg gtttggctta tggtgggatt tgtcatgtcg agtcaatgga     720
agaatcatct gctctactat attattatta aatttaggca taatgaattt tatgtggaac     780
ttagctacat ctgtgataga aacccagga aggaaagctt cctcttgccc tttaatcttc      840
aaaaaaataa acatttaata aaggaactct catttcaatt gaaaattgga ttagttttct     900
gatatgtatg taatgattaa acttttgcat cagtttgctc ataattttgg ttgaattctt     960
tgtctttgtc ctgtgctttt tttcttttac aggaaacggc tctcaatcat gttaagagtg    1020
cggggcttat gaatgacggc tttggtcgta ctccagagat gtataaaaag gaccttattt    1080
gggttgtcgc gaaaatgcag gtcatggtta accgctatcc tacttggtaa gtttgtcact    1140
agctttttac tttacggtac taagaggcgt cttaccatt tgtgtcgatt agctgcaatg     1200
tatatcacat tgtgatgagt gcttgctgtt accttccttg tgatatggtg tttcatttca    1260
atataacatc gatgactaca aatctccttt atgtcgtgga gcctaagggc ctgtctgtga    1320
tctatttca ggggtgacac ggttgaagtg aatacttggg ttgacaagtt agggaaaaat     1380
ggtatgcgtc gtgattggct cattagtgat tgcaatacag gagaaattct tactagagca    1440
tcaaggtatg atgtactgtt ttttagttta tgttcctgta cttctagtg gtcaaatttg     1500
agagcattca ataggtagat tttatagtga aagtcgaatt aagttacctt tacattattg    1560
cagcgtgtgg gtcatgatga atcaaaagac aagaagattg tcaaaaattc cagatgaggt    1620
tcgacgtgag atcgagcctc attttgtgga ctcacctcca gtcattgaag acgatgaccg    1680
aaaacttccc aagctggatg acaagactgc tgactccatc cgcaagggtc taactgtaag    1740
gccatatttt acactttaac agtggcttgc attgctatat aaaaaataaa aaatcatgct    1800
tcttagacga ttttcctctt tgctatttgt agccgaagtg gaatgacttg gatgtcaatc    1860
agcacgtcaa caacgtgaag tacatcggct ggattcttga ggtaacttttt taatttctta   1920
gttgaatatg tgattatctt aataagatat atgaacttag acatcgaccc aaataactaa    1980
ttatgttgct aaaactaatta tgctgttttc gacataaaca atgtgccaat gctcattgca   2040
gagtactcca caagaaattc tggagaccca ggagctatgt tcccttaccc tggaatacag    2100
gcgagaatgc ggaagggaga gcgtgctgga gtccctctct gctgcggacc cctctggaaa    2160
gggctttggg tccagttcc agcaccttct gagacttgag gatggaggtg agatcgtgaa    2220
ggggagaact gagtggcggc ccaagaatg                                      2249
```

<210> SEQ ID NO 101
<211> LENGTH: 393
<212> TYPE: PRT
<213> ORGANISM: Cuphea avigera

<400> SEQUENCE: 101

```
Ala Ala Ser Ser Ala Cys Phe His Leu Pro Ser Ala Asp Thr Ser Ser
1               5                   10                  15

Arg Pro Gly Lys Leu Gly Asn Gly Pro Ser Ser Leu Ser Pro Leu Lys
            20                  25                  30

Pro Lys Ser Thr Pro Asn Gly Gly Leu Lys Val Lys Ala Asn Ala Ser
        35                  40                  45

Ala Pro Pro Lys Ile Asn Gly His Pro Val Gly Leu Lys Ser Gly Gly
    50                  55                  60

Leu Lys Thr Gln Glu Asp Gly Pro Ser Ala Pro Pro Arg Thr Phe
65                  70                  75                  80

Ile Asn Gln Leu Pro Asp Trp Ser Met Leu Leu Ala Ala Ile Thr Thr
                85                  90                  95

Ala Phe Leu Ala Ala Glu Lys Gln Trp Met Met Leu Asp Trp Lys Pro
            100                 105                 110

Lys Arg Pro Asp Met Leu Val Asp Pro Phe Gly Leu Gly Ser Ile Val
        115                 120                 125

Gln His Gly Leu Val Phe Arg Gln Asn Phe Ser Ile Arg Ser Tyr Glu
    130                 135                 140

Ile Gly Ala Asp Arg Thr Ala Ser Ile Glu Thr Val Met Asn His Leu
145                 150                 155                 160

Gln Glu Thr Ala Leu Asn His Val Lys Ser Ala Gly Leu Met Asn Asp
                165                 170                 175

Gly Phe Gly Arg Thr Pro Glu Met Tyr Lys Lys Asp Leu Ile Trp Val
            180                 185                 190

Val Ala Lys Met Gln Val Met Val Asn Arg Tyr Pro Thr Trp Gly Asp
        195                 200                 205

Thr Val Glu Val Asn Thr Trp Val Asp Lys Leu Gly Lys Asn Gly Met
    210                 215                 220

Arg Arg Asp Trp Leu Ile Ser Asp Cys Asn Thr Gly Glu Ile Leu Thr
225                 230                 235                 240

Arg Ala Ser Ser Val Trp Val Met Met Asn Gln Lys Thr Arg Arg Leu
                245                 250                 255

Ser Lys Ile Pro Asp Glu Val Arg Arg Glu Ile Glu Pro His Phe Val
            260                 265                 270

Asp Ser Pro Pro Val Ile Glu Asp Asp Arg Lys Leu Pro Lys Leu
        275                 280                 285

Asp Asp Lys Thr Ala Asp Ser Ile Arg Lys Gly Leu Thr Pro Lys Trp
    290                 295                 300

Asn Asp Leu Asp Val Asn Gln His Val Asn Asn Val Lys Tyr Ile Gly
305                 310                 315                 320

Trp Ile Leu Glu Ser Thr Pro Gln Glu Ile Leu Glu Thr Gln Glu Leu
                325                 330                 335

Cys Ser Leu Thr Leu Glu Tyr Arg Arg Glu Cys Gly Arg Glu Ser Val
            340                 345                 350

Leu Glu Ser Leu Ser Ala Ala Asp Pro Ser Gly Lys Gly Phe Gly Ser
        355                 360                 365

Gln Phe Gln His Leu Leu Arg Leu Glu Asp Gly Gly Glu Ile Val Lys
```

```
            370                 375                 380
Gly Arg Thr Glu Trp Arg Pro Lys Asn
385                 390
```